(12) United States Patent
Wiener et al.

(10) Patent No.: US 11,434,222 B2
(45) Date of Patent: Sep. 6, 2022

(54) MAGL INHIBITORS

(71) Applicant: H. LUNDBECK A/S, Valby (DK)

(72) Inventors: John J. M. Wiener, San Diego, CA (US); Cheryl A. Grice, San Diego, CA (US); Daniel J. Buzard, San Diego, CA (US); Justin S. Cisar, San Diego, CA (US); Olivia Delene Weber, San Diego, CA (US); Amy Allan, San Diego, CA (US); Nicholas Raffaele, San Diego, CA (US); Jeanne Moody, San Diego, CA (US); Michael B. Shaghafi, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 17/524,632

(22) Filed: Nov. 11, 2021

(65) Prior Publication Data
US 2022/0153721 A1    May 19, 2022

Related U.S. Application Data

(60) Provisional application No. 63/113,662, filed on Nov. 13, 2020.

(51) Int. Cl.
| | | |
|---|---|---|
| *C07D 401/12* | (2006.01) | |
| *C07D 405/12* | (2006.01) | |
| *C07D 413/12* | (2006.01) | |
| *C07F 9/6558* | (2006.01) | |
| *C07D 401/14* | (2006.01) | |
| *A61P 25/04* | (2006.01) | |
| *C07D 487/04* | (2006.01) | |
| *C07D 471/04* | (2006.01) | |
| *C07D 417/12* | (2006.01) | |
| *A61P 25/08* | (2006.01) | |
| *C07D 221/20* | (2006.01) | |

(52) U.S. Cl.
CPC ............ *C07D 401/12* (2013.01); *A61P 25/04* (2018.01); *A61P 25/08* (2018.01); *C07D 221/20* (2013.01); *C07D 401/14* (2013.01); *C07D 405/12* (2013.01); *C07D 413/12* (2013.01); *C07D 417/12* (2013.01); *C07D 471/04* (2013.01); *C07D 487/04* (2013.01); *C07F 9/65583* (2013.01)

(58) Field of Classification Search
CPC .................................................... C07D 401/12
USPC ...................................................... 514/249
See application file for complete search history.

(56) References Cited

U.S. PATENT DOCUMENTS

| 9,133,148 B2 | 9/2015 | Cisar et al. |
|---|---|---|
| 10,030,020 B2 | 7/2018 | Cisar et al. |
| 10,781,211 B2 | 9/2020 | Cisar et al. |
| 11,059,822 B2 | 7/2021 | Grice et al. |
| 2011/0172230 A1 | 7/2011 | Ishii et al. |
| 2016/0137649 A1 | 5/2016 | Jones et al. |

FOREIGN PATENT DOCUMENTS

| CN | 110267962 A | 9/2019 |
|---|---|---|
| WO | WO-2010141817 A1 | 12/2010 |
| WO | WO-2014048865 A1 | 4/2014 |
| WO | WO-2015003002 A1 | 1/2015 |
| WO | WO-2015154023 A1 | 10/2015 |
| WO | WO-2016149401 A2 | 9/2016 |
| WO | WO-2017021805 A1 | 2/2017 |
| WO | WO-2017171100 A1 | 10/2017 |
| WO | WO-2017197192 A1 | 11/2017 |
| WO | WO-2018093946 A1 | 5/2018 |
| WO | WO-2018093949 A1 | 5/2018 |
| WO | WO-2019046318 A1 | 3/2019 |
| WO | WO-2019046330 A1 | 3/2019 |

OTHER PUBLICATIONS

Bedse et al. Therapeutic endocannabinoid augmentation for mood and anxiety disorders: comparative profiling of FAAH. Translational Psychiatry 8:92 (2018).
Ben-Ari et al. Electrographic, clinical and pathological alterations following systemic administration of kainic acid, bicuculline or pentetrazole: metabolic mapping using the deoxyglucose method with special reference to the pathology of epilepsy. Neuroscience 6:1361-1391 (1981).
Blankman et al. A comprehensive profile of brain enzymes that hydrolyze the endocannabinoid 2-arachidonoylglycerol. Chem. Biol. 14:1347-1356 (2007).
Burckhardt et al. The fibromyalgia impact questionnaire: development and validation. J Rheumatol 18(5):728-733 (1991).
Collin et al. A double-blind, randomized, placebo-controlled, parallel-group study of Sativex, in subjects with symptoms of spasticity due to multiple sclerosis. Neurol Res 32(5):451-459 (2010).
Collin et al. Randomized controlled trial of cannabis-based medicine in spasticity caused by multiple sclerosis. Eur J Neurol 14(3):290-296 (2007).
Fiz et al. Cannabis use in patients with fibromyalgia: effect on symptoms relief and health-related quality of life. PLoS One 6(4):e18440 (2011).
Gil-Ordonez et al. Monoacylglycerol lipase (MAGL) as a promising therapeutic target. Biochem Pharmacol 157:18-32 (2018).
Grabner et al. Monoglyceride lipase as a drug target: At the crossroads of arachidonic acid metabolism and endocannabinoid signaling. Pharmacol Ther 175:35-46 (2017).

(Continued)

*Primary Examiner* — Kahsay Habte
(74) *Attorney, Agent, or Firm* — Wilson Sonsini Goodrich & Rosati

(57) ABSTRACT

Provided herein are substituted 1,1,1,3,3,3-hexafluoropropan-2-yl 6-azaspiro[2.5]octane-6-carboxylate compounds and pharmaceutical compositions comprising said compounds. The compounds and compositions provided herein are useful as inhibitors of MAGL. Furthermore, the compounds and compositions as provided herein are useful for the treatment of diseases and disorders benefiting from the inhibition of MAGL.

12 Claims, 3 Drawing Sheets

(56) References Cited

OTHER PUBLICATIONS

He et al. Determination of absolute configuration of chiral molecules using vibrational optical activity: a review. Appl. Spectrosc. 65(7):699-723 (2011).
Hill et al. Integrating Endocannabinoid Signaling and Cannabinoids into the Biology and Treatment of Posttraumatic Stress Disorder. Neuropsychopharmacology 43(1):80-102 (2018).
Hill. Medical Marijuana for Treatment of Chronic Pain and Other Medical and Psychiatric Problems: A Clinical Review. JAMA 313(24):2474-2483 (2015).
Ilyasov et al. The endocannabinoid system and oligodendrocytes in health and disease. Front Neurosci 12:733 (2018).
Kano et al. Endocannabinoid-mediated control of synaptic transmission. Physiol Rev 8:309-380 (2009).
Katona et al. Endocannabinoid signalling as a synaptic circuit breaker in neurological disease. Nat Med. 14(9):923-93 (2008).
Langford et al. A double-blind, randomized, placebo-controlled, parallel-group study of THC/CBD oromucosal spray in combination with the existing treatment regimen, in the relief of central neuropathic pain in patients with multiple sclerosis. J Neurol 260(4):984-997 (2013).
Long et al. Selective blockade of 2-arachidonoylglycerol hydrolysis produces cannabinoid behavioral effects. Nat Chem Biol. 5(1):37-44 (2009).
Mease et al. A randomized, double-blind, placebo-controlled, phase III trial of pregabalin in the treatment of patients with fibromyalgia. J Rheumatol 35(3):502-514 (2008).
Mulvihill et al. Therapeutic potential of monoacylglycerol lipase inhibitors. Life Sci 92(8-9):492-497 (2013).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Nomura et al. Endocannabinoid hydrolysis generates brain prostaglandins that promote neuroinflammation. Science 334(6057):809-813 (2011).
Pryce et al. Endocannabinoids in Multiple Sclerosis and Amyotrophic Lateral Sclerosis. Handb Exp Pharmacol 231:213-31 (2015).
Rog et al. Randomized, controlled trial of cannabis-based medicine in central pain in multiple sclerosis. Neurology 65(6):812-819 (2005).
Sarchielli et al. Endocannabinoids in chronic migraine: CSF findings suggest a system failure. Neuropsychopharmacology 32(6):1384-1390 (2007).
Skrabek et al. Nabilone for the treatment of pain in fibromyalgia. J Pain 9(2):164-173 (2008).
Sugaya et al. Crucial Roles of the Endocannabinoid 2-Arachidonoylglycerol in the Suppression of Epileptic Seizures. Cell Rep 16(5):1405-1415 (2016).
Turcotte et al. Nabilone as an adjunctive to gabapentin for multiple sclerosis-induced neuropathic pain: a randomized controlled trial. Pain Med 16(1):149-159 (2015).
Turcotte et al. The CB2 receptor and its role as a regulator of inflammation. Cell. Mol. Life Sci. 73:4449-4470 (2016).
Ware et al. The effects of nabilone on sleep in fibromyalgia: results of a randomized controlled trial. Anesth Analg 110(2):604-610 (2010).
Whiting et al. Cannabinoids for Medical Use: A Systematic Review and Meta-analysis. JAMA 313(24):2456-2473 (2015).
Zajicek et al. Cannabinoids for treatment of spasticity and other symptoms related to multiple sclerosis (CAMS study): multicentre randomised placebo-controlled trial. Lancet 362(9395):1517-1526 (2003).
Berge et al. Pharmaceutical Salts. Journal of Pharmaceutical Sciences 66(1):1-19 (Jan. 1977).
Fleisher et al. Improved oral drug delivery: solubility limitations overcome by the use of prodrugs. Advanced Drug Delivery Reviews 19:115-130 (1996).
Keith et al. Heteroarylureas with spirocyclic diamine cores as inhibitors of fatty acid amide hydrolase. Bioorg Med Chem Lett 24(3):737-41 (2014).
PCT/US2017/032276 International Search Report and Written Opinion dated Sep. 26, 2017.
PCT/US2017/061870 International Search Report and Written Opinion dated Mar. 26, 2018.
PCT/US2017/061870 Invitation to Pay Additional Fees dated Jan. 22, 2018.
PUBCHEM, Substance Database, SID 239803465. Retrieved from Internet: <URL: https://pubchem.ncbi.nlm.nih.gov/substance/239803465> (7pgs.) (Available Date Feb. 13, 2015) (retrieved Jun. 27, 2017).
U.S. Appl. No. 16/349,047 Office Action dated Nov. 27, 2020.
PCT/EP2021/081522 International Search Report and Written Opinion dated Feb. 7, 2022.

MAGL INHIBITORS

CROSS-REFERENCE

This application claims the benefit of U.S. Provisional Patent Application No. 63/113,662, filed Nov. 13, 2020, which is incorporated herein by reference in its entirety.

FIELD OF THE INVENTION

The present invention relates to compounds which are monoacylglycerol lipase (MAGL) inhibitors. Separate aspects of the invention are directed to pharmaceutical compositions comprising said compounds and uses of the compounds to treat diseases and disorders linked to the regulation of the endocannabinoid system signalling activities.

BACKGROUND OF THE INVENTION

MAGL is a member of the serine hydrolase superfamily. MAGL is expressed throughout the brain, in neurons, microglia, astrocytes, and oligodendrocytes. MAGL is the primary enzyme controlling the degradation of 2-arachidonoylglycerol (2-AG) to arachidonic acid (AA) (Blankman et al. Chem Biol. 2007; Nomura et al. Science. 2011).

2-AG is the most abundant endocannabinoid ligand in the brain, where it acts as a retrograde messenger to reduce excessive neurotransmission via the activation of pre-synaptic $CB_1$ receptors (Kano et al. Physiol Rev. 2009; Katona and Freund. Physiol Rev. 2009), regulating immune response via the activation of microglial $CB_2$ receptors (Turcotte et al. Cell Mol Life Sci. 2016), and promotes neuroprotection via e.g., its effects on oligodendrocyte production and survival (Ilyasov et al. Front Neurosci. 2018).

AA is one of the most abundant fatty acids in the brain and the main precursor of eicosanoids such as prostanoids and leukotrienes, which are known inflammatory mediators.

MAGL is at the crossroads between the endocannabinoid and eicosanoid signalling systems. Inhibiting the action or activation of MAGL is a promising therapeutic approach for the prevention or treatment of brain disorders which pathological hallmarks include excessive neurotransmission, neuroinflammation or neurodegeneration such as Alzheimer's disease (AD), Parkinson's disease (PD), Huntington's disease (HD), multiple sclerosis (MS), amyotrophic lateral sclerosis (ALS), traumatic brain injury, stroke, epilepsy, pain, migraine, addiction, anxiety, depression and other stress-related disorders (Grabner et al. Pharmacol Ther. 2017; Mulvihill et al. Life Sci. 2013; Gil-Ordonez et al. Biochem Pharmacol. 2018).

WO2019/046318 discloses spirocyclic compounds, which are MAGL inhibitors.

WO2019/046330 discloses spirocyclic compounds, which are MAGL inhibitors.

Despite advances in MAGL research, there is still a lack of compounds which are potent, efficacious, and selective inhibitors of MAGL and which also are effective in the treatment of neurological and psychiatric disorders associated with diseases or disorders which will benefit from inhibiting the activation of MAGL.

SUMMARY OF THE INVENTION

An objective of the present invention is to provide compounds that inhibit MAGL. Accordingly, the present invention provides a compound of Formula (I):

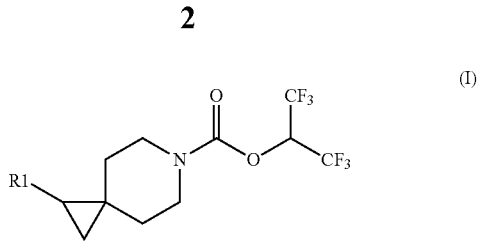

wherein
R1 represents —C(O)NHR2, —C(O)N(CH$_3$)R2, —C(O)NR3R4, —C(O)NHCH2R2, or —C(O)NHC(O)R2;
R2 represents a phenyl, a 5 or 6 membered heteroaryl having one or two heteroatoms independently selected from N, O and S, a 6 membered heterocycle having one or two heteroatoms independently selected from N or O, a $C_3$-$C_7$ cycloalkyl, or a 7 membered bicyclic heterocycle having one or two heteroatoms independently selected from N or O;
R3 and R4 together with the N to which they are attached form a 9 or 10 membered bicyclic heterocycle having 1 to 4 heteroatoms independently selected from N or O, or a 6 membered heterocycle having one or two heteroatoms independently selected from N or O; and
wherein each phenyl, 5 or 6 membered heteroaryl, 6 membered heterocycle, $C_3$-$C_7$ cycloalkyl, 7 membered bicyclic heterocycle, or 9 or 10 membered bicyclic heterocycle are unsubstituted or substituted with 1 or 2 substituents independently selected from halogen, $C_1$-$C_3$ alkyl, $C_1$-$C_3$ haloalkyl, $C_3$-$C_6$ cycloalkyl, $C_1$-$C_3$ alkoxy, cyano, —NHC(O)CH$_3$, —C(O)NH$_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH;
or a pharmaceutically acceptable salt thereof.

In a further aspect of the invention is provided a pharmaceutical composition comprising a compound of Formula (I), or a pharmaceutically acceptable salt thereof, and one or more pharmaceutically acceptable carriers or diluents.

In a further aspect of the invention is provided a compound of Formula (I), or a pharmaceutically acceptable salt thereof, for use in the treatment of a disease or a disorder selected from pain, epilepsy/seizure disorder, Alzheimer's disease, Huntington's chorea, Huntington's disease, multiple sclerosis, obsessive-compulsive disorder, Parkinson's disease, depression, post-traumatic stress disorder, generalized anxiety disorder, and dystonia.

In a further aspect of the invention is provided a method for treating a neurological and/or psychiatric disorder selected from pain, epilepsy/seizure disorder, Alzheimer's disease, Huntington's chorea, Huntington's disease, multiple sclerosis, obsessive-compulsive disorder, Parkinson's disease, depression, post-traumatic stress disorder, generalized anxiety disorder, and dystonia, comprising a step of administering to a patient in need thereof a therapeutically effective amount a compound of Formula (I), or pharmaceutically acceptable salt thereof.

In a further aspect of the invention is provided a use of a compound of Formula (I), or a pharmaceutically acceptable salt thereof in the manufacture of a medicament for the treatment of a disease or disorder selected from pain, epilepsy/seizure disorder, Alzheimer's disease, Huntington's chorea, Huntington's disease, multiple sclerosis, obsessive-compulsive disorder, Parkinson's disease, depression, post-traumatic stress disorder, generalized anxiety disorder, and dystonia.

Other objects and advantages of the compounds described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

INCORPORATION BY REFERENCE

All publications and patent applications mentioned in this specification are herein incorporated by reference to the extent applicable and relevant.

DETAILED DESCRIPTION OF THE INVENTION

Definitions

Figure 1:
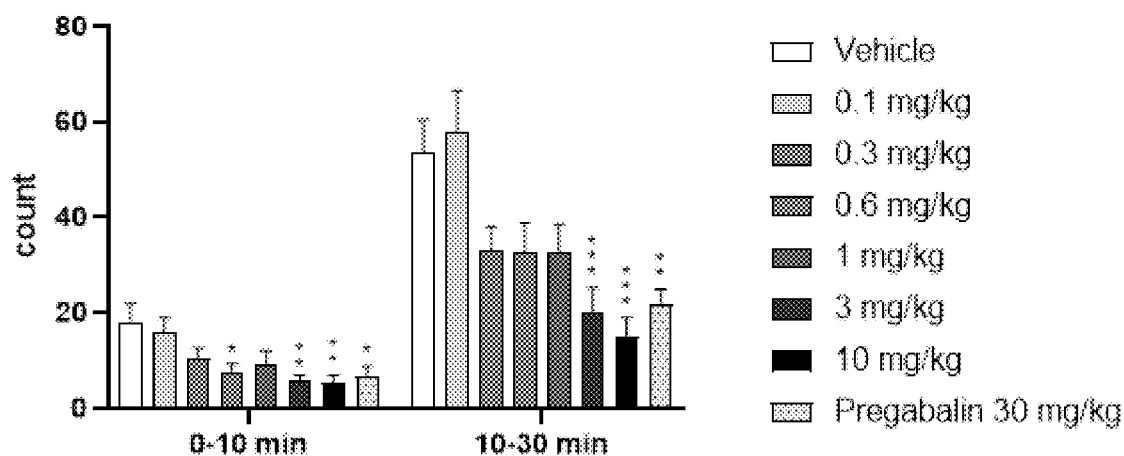
FIG. 1 Anti-nociceptive effects of Example 6 in the rat formalin model; y-axis: count—hind limb licking frequency; x-axis: time period (min). Significance level for post-hoc comparisons (relative to the vehicle group) are indicated: $*p<0.05$, $p<0.01$, $*p<0.001$.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "anti-nociceptive effect" as used herein, pertains to the ability of a compound to increase the tolerance to, treat, delay, and/or reduce pain in a subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effective amount" or "a therapeutically effective amount" can vary from subject to subject, due to variation in metabolism of Compound (I), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "inhibits", "inhibiting", or "inhibitor" of an enzyme, as used herein, refer to inhibition of enzymatic activity.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of MAGL, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the term "alkyl" refer to a linear (i.e. unbranched) or branched saturated hydrocarbon having from one up to eight carbon atoms. The term "$C_1$-$C_3$ alkyl" means a straight or branched chain hydrocarbon containing from 1 to 3 carbon atoms. Representative examples of alkyl include, but are not limited to, methyl, ethyl, 1-propyl, 2-propyl, 1-butyl, 2-butyl, 2-methyl-2-propyl, 2-methyl-1-butyl, n-hexyl, n-heptyl and n-octyl.

The term "alkylene," as used herein, refers to a divalent group derived from a straight or branched chain hydrocarbon of 1 to 10 carbon atoms. Representative examples of alkylene include, but are not limited to, —CH2-, —CH2CH2-, —CH2CH2CH2-, —CH2CH(CH3)CH2-, —CH2CH2CH2CH2-, —CH2CH(CH3)CH2CH2-, —CH(CH3)- and —CH2CH2CH2CH2CH2-.

The term "alkoxy" refers to a moiety of the formula —OR', wherein R' indicates alkyl as defined above. In particular "$C_1$-$C_3$ alkoxy" refers to such a moiety wherein the alkyl part has 1, 2, or 3 carbon atoms. Examples of "$C_1$-$C_3$ alkoxy" include methoxy, ethoxy, n-propoxy, and isopropoxy.

The term "cycloalkyl," as used herein, refers to a saturated ring system containing all carbon atoms as ring members and zero double bonds. A cycloalkyl may be a monocyclic cycloalkyl (e.g., cyclopropyl) and preferably have between 3 to 7 carbon atoms in the ring.

The term "halogen" is intended to indicate a substituent selected from the 7th main group of the periodic table, such as fluoro, chloro or bromo.

The term "haloalkyl" or "haloalkoxy" is intended to refer to an alkyl or alkoxy group as defined hereinabove with 1, 2 or 3 hydrogens replaced by a halogen.

Similarly, the term "fluoroalkyl" is intended to refer to an alkyl group as defined hereinabove, with 1, 2, or 3 hydrogens replaced by fluoro. An example of such group is trifluoromethyl.

The term "hydroxyl" or "hydroxy", as used herein, means an —OH group.

The term "hydroxyalkyl", as used herein, means at least one —OH group is appended to the parent molecular moiety through an alkylene group, as defined herein.

The term "hydroxyhaloalkyl", as used herein, means at least one —OH group is appended to the parent molecular moiety through a haloalkyl group, as defined herein.

The term "hydroxyfluoroalkyl", as used herein, means at least one —OH group is appended to the parent molecular moiety through a fluoroalkyl group, as defined herein.

The term "oxo" as used herein refers to an oxygen atom connected to another atom by a double bond. When the atom to which the oxygen is connected to carbon, the formed carbonyl group is indicated as —(CO)—.

The term "5 membered heteroaryl" refers to a 5 membered aromatic ring wherein 1, 2 or 3 ring atoms are selected from O, N or S. Examples of 5 membered heteroaryls of the present invention include thiophenyl, pyrrolyl, furanyl, oxazolyl, isoxazolyl, thiazolyl, isothiazolyl, pyrazolyl, triazolyl oxadiazolyl, and thiadiazolyl.

The term "6 membered heteroaryl" refers to a 6 membered aromatic ring wherein 1, 2 or 3 ring atoms are selected independently from O, N, or S. Examples of 6 membered heteroaryls of the present inventions include but are not limited to pyridyl, pyridazinyl, pyrimidinyl, pyranyl, diazinyl, and triazinyl.

The terms "monocyclic heterocycle", "mono heterocyclic ring" and "mono heterocycle," as used herein, alone or in combination, refer to saturated or unsaturated nonaromatic rings containing from 5 to 6 ring atoms where one or more of the ring atoms are heteroatoms. In some embodiments of the invention, a heterocyclic ring is intended to mean a 6 membered cyclic ring structure with 1 or 2 heteroatom(s) independently selected from N or O. Examples of a 6 membered heterocycle include but are not limited to tetrahydropyranyl, piperidinyl, and morpholinyl, The term "bicyclic heterocycle", as used herein, refers to a mono heterocyclic ring appended to the parent moiety and forming a fused, spiro or a bridged ring system to a cycloalkyl group, monocyclic heterocycle, benzene ring, or a monocyclic 5 or 6 membered heteroaryl. The term "7 membered bicyclic heterocycle" means a bicycyclic heterocycle as defined above having 7 ringatoms and contains at least 1 heteroatom selected from N, O or S. Examples of a 7 membered bicyclic heterocycle include but are not limited 2-oxaspiro[3.3]heptan-6-yl. The term "9 or 10 membered bicyclic heterocycle" means a bicyclic heterocycle as defined above having 9 or 10 ringatoms and contains at least 1 heteroatom selected from N, O or S. Examples of a 9 or 10 membered bicyclic heterocycle include but are not limited 5,6,7,8-tetrahydroimidazo[1,2-a]pyrazinyl, 5,6,7,8-tetrahydropyrido[3,4-d]pyrimidinyl, 5,6,7,8-tetrahydropyrido[4,3-d]pyrimidinyl, 2-cyclopropyl-5,6,7,8-tetrahydropyrido[4,3-d]pyrimidinyl, 3-cyclopropyl-5,6,7,8-tetrahydro-[1,2,4]triazolo[4,3-a]pyrazinyl, 5,6,7,8-tetrahydroimidazo[1,2-a]pyrazinyl, or 5,6,7,8-tetrahydropyrido[3,4-d]pyrimidinyl.

Embodiments of the Invention

In a first embodiment the present invention relates to a compound of Formula (I):

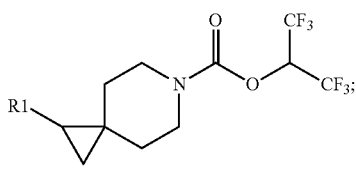

wherein:
R1 represents —C(O)NHR2, —C(O)N(CH$_3$)R2, —C(O)NR3R4, —C(O)NHCH$_2$R2, or —C(O)NHC(O)R2;
R2 represents a phenyl, a 5 or 6 membered heteroaryl having one or two heteroatoms independently selected from N, O and S, a 6 membered heterocycle having one or two heteroatoms independently selected from N or O, a C$_3$-C$_7$ cycloalkyl, or a 7 membered bicyclic heterocycle having one or two heteroatoms independently selected from N or O;
R3 and R4 together with the N to which they are attached form a 9 or 10 membered bicyclic heterocycle having 1 to 4 heteroatoms independently selected from N or O, or a 6 membered heterocycle having one or two heteroatoms independently selected from N or O; and
wherein each phenyl, 5 or 6 membered heteroaryl, 6 membered heterocycle, C$_3$-C$_7$ cycloalkyl, 7 membered bicyclic heterocycle, or 9 or 10 membered bicyclic heterocycle are unsubstituted or substituted with 1 or 2 substituents independently selected from halogen, C$_1$-C$_3$ alkyl, C$_1$-C$_3$ haloalkyl, C$_3$-C$_6$ cycloalkyl, C$_1$-C$_3$ alkoxy, cyano, —NHC(O)CH$_3$, —C(O)NH$_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH;
or a pharmaceutically acceptable salt thereof.

In a further embodiment, the compound of the invention is a compound of Formula (Ia):

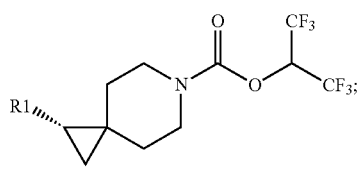

wherein:
R1 represents —C(O)NHR2, —C(O)N(CH$_3$)R2, —C(O)NR3R4, —C(O)NHCH$_2$R2, or —C(O)NHC(O)R2;
R2 represents a phenyl, a 5 or 6 membered heteroaryl having one or two heteroatoms independently selected from N, O and S, a 6 membered heterocycle having one or two heteroatoms independently selected from N or O, a C$_3$-C$_7$ cycloalkyl, or a 7 membered bicyclic heterocycle having one or two heteroatoms independently selected from N or O;
R3 and R4 together with the N to which they are attached form a 9 or 10 membered bicyclic heterocycle having 1 to 4 heteroatoms independently selected from N or O, or a 6 membered heterocycle having one or two heteroatoms independently selected from N or O; and
wherein each phenyl, 5 or 6 membered heteroaryl, 6 membered heterocycle, C$_3$-C$_7$ cycloalkyl, 7 membered bicyclic heterocycle, or 9 or 10 membered bicyclic heterocycle are unsubstituted or substituted with 1 or 2 substituents independently selected from halogen, C$_1$-C$_3$ alkyl, C$_1$-C$_3$ haloalkyl, C$_3$-C$_6$ cycloalkyl, C$_1$-C$_3$ alkoxy, cyano, —NHC(O)CH$_3$, —C(O)NH$_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH;
or a pharmaceutically acceptable salt thereof.

In a further embodiment, the compound of the invention is a compound of Formula (Ib):

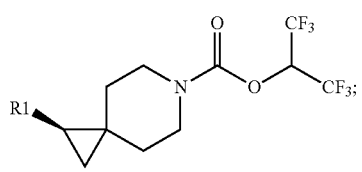

wherein:
R1 represents —C(O)NHR2, —C(O)N(CH$_3$)R2, —C(O)NR3R4, —C(O)NHCH$_2$R2, or —C(O)NHC(O)R2;
R2 represents a phenyl, a 5 or 6 membered heteroaryl having one or two heteroatoms independently selected from N, O and S, a 6 membered heterocycle having one or two heteroatoms independently selected from N or O, a C$_3$-C$_7$ cycloalkyl, or a 7 membered bicyclic heterocycle having one or two heteroatoms independently selected from N or O;

R3 and R4 together with the N to which they are attached form a 9 or 10 membered bicyclic heterocycle having 1 to 4 heteroatoms independently selected from N or O, or a 6 membered heterocycle having one or two heteroatoms independently selected from N or O; and
wherein each phenyl, 5 or 6 membered heteroaryl, 6 membered heterocycle, $C_3$-$C_7$ cycloalkyl, 7 membered bicyclic heterocycle, or 9 or 10 membered bicyclic heterocycle are unsubstituted or substituted with 1 or 2 substituents independently selected from halogen, $C_1$-$C_3$ alkyl, $C_1$-$C_3$ haloalkyl, $C_3$-$C_6$ cycloalkyl, $C_1$-$C_3$ alkoxy, cyano, —NHC(O)CH$_3$, —C(O)NH$_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH;
or a pharmaceutically acceptable salt thereof.

In an embodiment relating to compounds of Formula (I), (Ia) or (Ib), or a pharmaceutically acceptable salt thereof, wherein R1 represents —C(O)NHR2.

In an embodiment relating to compounds of Formula (I), (Ia) or (Ib), or a pharmaceutically acceptable salt thereof, wherein R1 represents —C(O)NHR2; R2 represents a 5 or 6 membered heteroaryl having one or two heteroatoms independently selected from N, O and S or a 6 membered heterocycle having one or two heteroatoms independently selected from N or O; wherein each 5 or 6 membered heteroaryl or 6 membered heterocycle are independently unsubstituted or substituted with 1 substituent selected from halogen, $C_1$-$C_3$ alkyl, $C_1$-$C_3$ haloalkyl, $C_3$-$C_6$ cycloalkyl, $C_1$-$C_3$ alkoxy, cyano, —NHC(O)CH$_3$, —C(O)NH$_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH.

In an embodiment relating to compounds of Formula (I), (Ia) or (Ib), or a pharmaceutically acceptable salt thereof, wherein R2 represents a 5 or 6 membered heteroaryl selected from the group consisting of pyridyl, pyrazinyl, pyridazinyl, pyrimidyl, pyrazolyl, thiazolyl, and isoxazolyl, wherein said 5 or 6 membered heteroaryl is unsubstituted or substituted with 1 substituent selected from the group consisting of halogen, $C_1$-$C_3$ alkyl, $C_1$-$C_3$ haloalkyl, cyclopropyl, $C_1$-$C_3$ alkoxy, cyano, —NHC(O)CH$_3$, —C(O)NH$_2$, —C(O)NHCH$_3$, a 5 membered heteroaryl having 1 or 2 heteroatoms selected independently from N or O, —NHSO$_2$CH$_3$, —P(O)(CH$_3$)$_2$, and —OCH$_2$COOH.

In an embodiment relating to compounds of Formula (I), (Ia) or (Ib), or a pharmaceutically acceptable salt thereof, wherein R2 represents a 6 membered heterocycle selected from the group consisting of tetrahydro-2H-pyran-4-yl, piperazinyl, and piperidinyl, wherein said R2 is unsubstituted or substituted with 1 substituent selected from the group consisting of $C_1$-$C_3$ alkyl, $C_3$-$C_6$ cycloalkyl, and cyano.

In an embodiment relating to compounds of Formula (I), (Ia) or (Ib), or a pharmaceutically acceptable salt thereof, wherein R2 represents a 6 membered heterocycle selected from the group consisting of tetrahydro-2H-pyran-4-yl, piperazinyl, and piperidinyl, wherein said R2 is unsubstituted.

In an embodiment relating to compounds of Formula (I), (Ia) or (Ib), or a pharmaceutically acceptable salt thereof, wherein R2 is selected from the group consisting of:

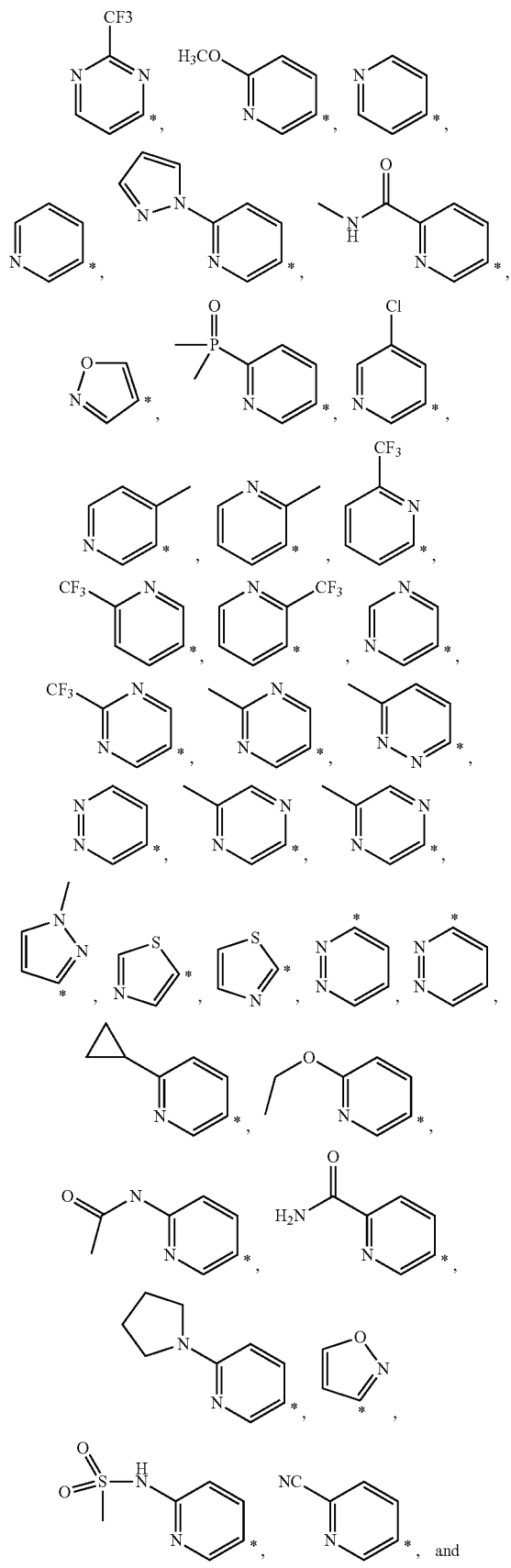

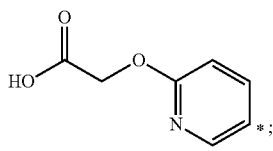

wherein * denotes the point of attachment.

In an embodiment relating to compounds of Formula (I) (Ia) or (Ib), or a pharmaceutically acceptable salt thereof, wherein R2 is selected from the group consisting of:

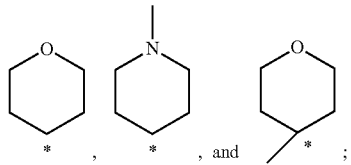

wherein * denotes the point of attachment.

In an embodiment relating to compounds of Formula (I), (Ia) or (Ib), or a pharmaceutically acceptable salt thereof, wherein R3 and R4 together with the N to which they are attached form a 9 or 10 membered bicyclic heterocycle selected from the group consisting of 5,6,7,8-tetrahydro-[1,2,4]triazolo[4,3-a]pyrazinyl, 5,6,7,8-tetrahydroimidazo[1,2-a]pyrazinyl, 5,6,7,8-tetrahydropyrido[3,4-d]pyrimidinyl, and 6,7-dihydro-5H-pyrazolo[5,1-b][1,3]oxazinyl, wherein said 9 to 10 membered bicyclic heterocycle is unsubstituted or substituted with 1 substituent selected from $C_3$-$C_6$ cycloalkyl or $C_1$-$C_3$ haloalkyl.

In an embodiment relating to compounds of Formula (I), (Ia) or (Ib), or a pharmaceutically acceptable salt thereof, wherein R3 and R4 together with the N to which they are attached form a 9 to 10 membered bicyclic heterocycle selected from the group consisting of:

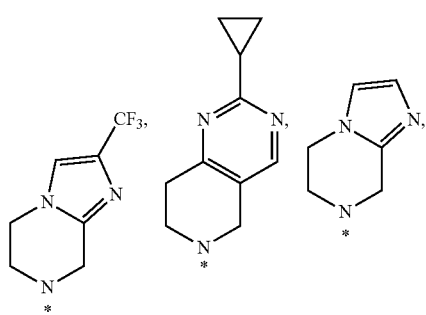

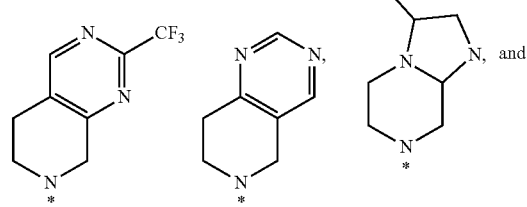

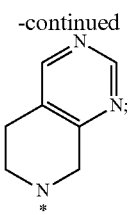

wherein * denotes the point of attachment.

In a further embodiment, the compound of the invention is a compound of Formula (Ic), or a pharmaceutically acceptable salt thereof:

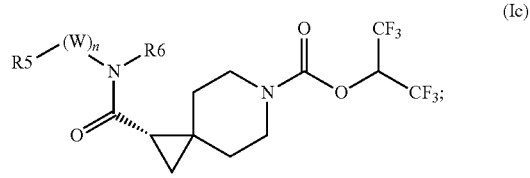

(Ic)

wherein:
R5 represents a phenyl, a 5 or 6 membered heteroaryl having one or two heteroatoms independently selected from N, O and S, a 6 membered heterocycle, a $C_3$-$C_7$ cycloalkyl, or a 7 membered bicyclic heterocycle having one or two heteroatoms independently selected from N or O;
R6 represents a hydrogen or methyl;
W is —$CH_2$— or —C(O)—;
n is 0 or 1; and
wherein each phenyl, 5 or 6 membered heteroaryl, 6 membered heterocycle, $C_3$-$C_7$ cycloalkyl, 7 membered bicyclic heterocycle are unsubstituted or substituted with 1 or 2 substituents independently selected from halogen, $C_1$-$C_3$ alkyl, $C_1$-$C_3$ haloalkyl, $C_3$-$C_6$ cycloalkyl, $C_1$-$C_3$ alkoxy, cyano, —NHC(O)$CH_3$, —C(O)$NH_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH;
or a pharmaceutically acceptable salt thereof.

In a further embodiment, the compound of the invention is a compound of Formula (Id), or a pharmaceutically acceptable salt thereof:

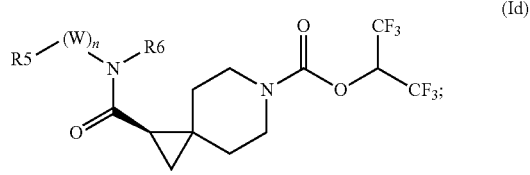

(Id)

wherein:
R5 represents a phenyl, a 5 or 6 membered heteroaryl having one or two heteroatoms independently selected from N, O and S, a 6 membered heterocycle, a $C_3$-$C_7$ cycloalkyl, or a 7 membered bicyclic heterocycle having one or two heteroatoms independently selected from N or O;
R6 represents a hydrogen or methyl;

W is —CH$_2$- or —C(O)—;
n is 0 or 1; and
wherein each phenyl, 5 or 6 membered heteroaryl, 6 membered heterocycle, C$_3$-C$_7$ cycloalkyl, 7 membered bicyclic heterocycle are unsubstituted or substituted with 1 or 2 substituents independently selected from halogen, C$_1$-C$_3$ alkyl, C$_1$-C$_3$ haloalkyl, C$_3$-C$_6$ cycloalkyl, C$_1$-C$_3$ alkoxy, cyano, —NHC(O)CH$_3$, —C(O)NH$_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH;
or a pharmaceutically acceptable salt thereof.

In an embodiment relating to compounds of Formula (Ic) or (Id), or a pharmaceutically acceptable salt thereof, wherein n is 0.

In an embodiment relating to compounds of Formula (Ic) or (Id), or a pharmaceutically acceptable salt thereof, wherein R5 represents a 5 or 6 membered heteroaryl selected from the group consisting of pyridyl, pyrazinyl, pyridazinyl, pyrimidyl, pyrazolyl, thiazolyl, and isoxazolyl, wherein said R5 is unsubstituted or substituted with 1 substituent selected from the group consisting of halogen, C$_1$-C$_3$ alkyl, C$_1$-C$_3$ haloalkyl, cyclopropyl, C$_1$-C$_3$ alkoxy, cyano, —NHC(O)CH$_3$, —C(O)NH$_2$, —C(O)NHCH$_3$, a 5 membered heteroaryl having one or two heteroatoms independently selected from N or O, —NHSO$_2$CH$_3$, —P(O)(CH$_3$)$_2$, and —OCH$_2$COOH.

In an embodiment relating to compounds of Formula (Ic) or (Id), or a pharmaceutically acceptable salt thereof, wherein R5 represents a 6 membered heteroaryl selected from the group consisting of pyridyl, pyrazinyl, pyridazinyl, and pyrimidyl, wherein said 6 membered heteroaryl is unsubstituted.

In an embodiment relating to compounds of Formula (Ic) or (Id), or a pharmaceutically acceptable salt thereof, wherein R5 represents a 6 membered heterocycle selected from the group consisting of tetrahydro-2H-pyran-4-yl, piperazinyl, and piperidinyl, wherein said R5 is unsubstituted or substituted with 1 substituent selected from the group consisting of C$_1$-C$_3$ alkyl, C$_3$-C$_6$ cycloalkyl, and cyano.

In an embodiment relating to compounds of Formula (Ic) or (Id), or a pharmaceutically acceptable salt thereof, wherein R5 is unsubstituted.

In an embodiment relating to compounds of Formula (Ic) or (Id), or a pharmaceutically acceptable salt thereof, wherein R5 is selected from the group consisting of:

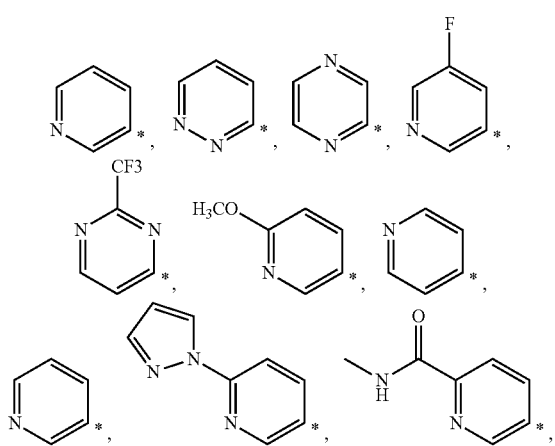

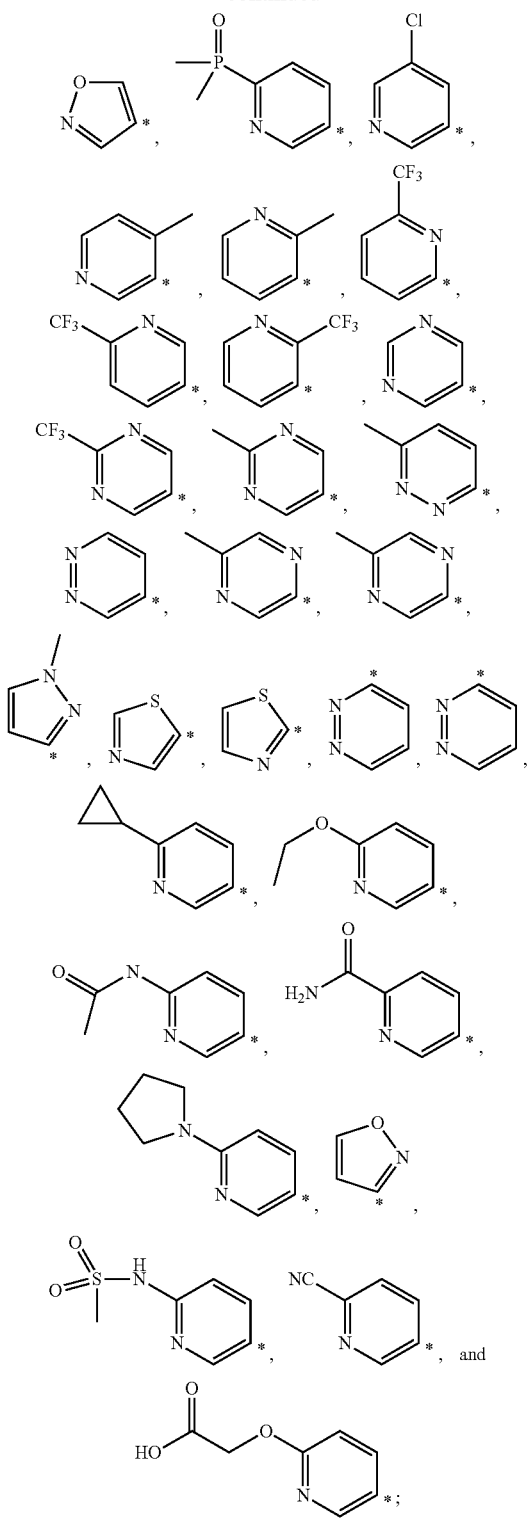

wherein * denotes the point of attachment.

In an embodiment relating to compounds of Formula (Ic) or (Id), or a pharmaceutically acceptable salt thereof, wherein R5 is selected from the group consisting of:

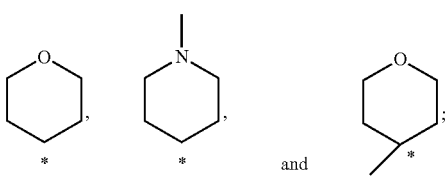

wherein * denotes the point of attachment.

In an embodiment relating to compounds of Formula (Ic) or (Id), or a pharmaceutically acceptable salt thereof, wherein R5 represents a 5,6,7,8-tetrahydropyrido[3,4-d]pyrimidinyl 2-oxaspiro[3.3]heptan-6-yl.

In an embodiment relating to compounds of Formula (Ic) or (Id), or a pharmaceutically acceptable salts thereof, wherein n is 0.

In a further embodiment, the compound of the invention is a compound of Formula (Ie), or a pharmaceutically acceptable salt thereof:

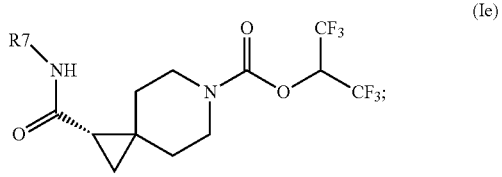

(Ie)

wherein R7 represents a phenyl, a 5 or 6 membered heteroaryl having one or two N atoms, or a 5 or 6 membered heterocycle having one heteroatom atom selected from N or O; and wherein each phenyl, 5 or 6 membered heteroaryl, or 5 or 6 membered heterocycle is unsubstituted or substituted with 1 substituent selected from the group consisting of halogen, $C_1$-$C_3$ alkyl, $C_1$-$C_3$ haloalkyl, cyclopropyl, $C_1$-$C_3$ alkoxy, and cyano.

In a further embodiment, the compound of the invention is a compound of Formula (If), or a pharmaceutically acceptable salt thereof:

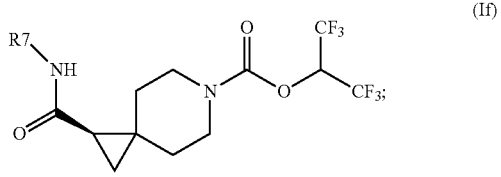

(If)

wherein R7 represents a phenyl, a 5 or 6 membered heteroaryl having one or two N atoms, or a 5 or 6 membered heterocycle having one heteroatom selected from N or O; and wherein each phenyl, 5 or 6 membered heteroaryl, or 5 or 6 membered heterocycle is unsubstituted or substituted with 1 substituent selected from the group consisting of halogen, $C_1$-$C_3$ alkyl, $C_1$-$C_3$ haloalkyl, cyclopropyl, $C_1$-$C_3$ alkoxy, and cyano.

In an embodiment relating to compounds of Formula (Ie) and (If), or a pharmaceutically acceptable salt thereof, wherein R7 represents pyridyl, pyrazinyl, pyridazinyl, pyrimidyl, pyrazolyl, thiazolyl, and isoxazolyl, wherein said R7 is unsubstituted or substituted with 1 substituent selected from the group consisting of halogen, $C_1$-$C_3$ alkyl, $C_1$-$C_3$ haloalkyl, cyclopropyl, $C_1$-$C_3$ alkoxy, and cyano.

In an embodiment relating to compounds of Formula (Ie) and (If), or a pharmaceutically acceptable salt thereof, wherein R7 represents tetrahydro-2H-pyran-4-yl, piperazinyl, and piperidinyl, wherein said R7 is unsubstituted or substituted with 1 substituent selected from the group consisting of $C_1$-$C_3$ alkyl, $C_3$-$C_6$ cycloalkyl, and cyano.

In an embodiment relating to compounds of Formula (Ie) or (If), or a pharmaceutically acceptable salt thereof, wherein R7 represents tetrahydro-2H-pyran-4-yl, piperazinyl or piperidinyl, wherein said R7 is unsubstituted.

In a further embodiment, the compound of the invention is selected from the group consisting of:

1,1,1,3,3,3-hexafluoropropan-2-yl (±)1-(pyridin-3-ylcarbamoyl)-6-azaspiro[2.5]octane-6-carboxylate;

1,1,1,3,3,3-hexafluoropropan-2-yl (±)1-(pyridazin-3-ylcarbamoyl)-6-azaspiro[2.5]octane-6-carboxylate;

1,1,1,3,3,3-hexafluoropropan-2-yl (±)1-((tetrahydro-2H-pyran-4-yl)carbamoyl)-6-azaspiro[2.5]octane-6-carboxylate;

1,1,1,3,3,3-hexafluoropropan-2-yl (±)1-(methyl(pyrazin-2-yl)carbamoyl)-6-azaspiro[2.5]octane-6-carboxylate;

1,1,1,3,3,3-hexafluoropropan-2-yl (±)1-(isoxazol-4-ylcarbamoyl)-6-azaspiro[2.5]octane-6-carboxylate;

1,1,1,3,3,3-hexafluoropropan-2-yl (±)1-((2-(trifluoromethyl)pyrimidin-4-yl)carbamoyl)-6-azaspiro[2.5]octane-6-carboxylate;

1,1,1,3,3,3-hexafluoropropan-2-yl (±)1-((6-(dimethylphosphoryl)pyridin-3-yl)carbamoyl)-6-azaspiro[2.5]octane-6-carboxylate;

1,1,1,3,3,3-hexafluoropropan-2-yl (±)1-(pyridin-4-ylcarbamoyl)-6-azaspiro[2.5]octane-6-carboxylate;

1,1,1,3,3,3-hexafluoropropan-2-yl (±)1-((tetrahydro-2H-pyran-4-carbonyl)carbamoyl)-6-azaspiro[2.5]octane-6-carboxylate;

1,1,1,3,3,3-hexafluoropropan-2-yl (±)1-((6-(1H-pyrazol-1-yl)pyridin-3-yl)carbamoyl)-6-azaspiro[2.5]octane-6-carboxylate;

1,1,1,3,3,3-hexafluoropropan-2-yl (±)1-((6-(methylcarbamoyl)pyridin-3-yl)carbamoyl)-6-azaspiro[2.5]octane-6-carboxylate;

1,1,1,3,3,3-hexafluoropropan-2-yl (±)1-(4-cyclopropylpiperazine-1-carbonyl)-6-azaspiro[2.5]octane-6-carboxylate;

1,1,1,3,3,3-hexafluoropropan-2-yl (±)1-((6-methoxypyridin-3-yl)carbamoyl)-6-azaspiro[2.5]octane-6-carboxylate;

1,1,1,3,3,3-hexafluoropropan-2-yl (±)1-((5-fluoropyridin-3-yl)carbamoyl)-6-azaspiro[2.5]octane-6-carboxylate;

1,1,1,3,3,3-hexafluoropropan-2-yl (±)1-(methyl(pyridin-3-yl)carbamoyl)-6-azaspiro[2.5]octane-6-carboxylate;

1,1,1,3,3,3-hexafluoropropan-2-yl (±)1-(methyl(pyridin-2-yl)carbamoyl)-6-azaspiro[2.5]octane-6-carboxylate;

1,1,1,3,3,3-hexafluoropropan-2-yl (±)1-(pyridin-2-ylcarbamoyl)-6-azaspiro[2.5]octane-6-carboxylate;

1,1,1,3,3,3-hexafluoropropan-2-yl (±)1-((2-(trifluoromethyl)-5,6,7,8-tetrahydroimidazo[1,2-a]pyrazine-7-carbonyl)-6-azaspiro[2.5]octane-6-carboxylate;

1,1,1,3,3,3-hexafluoropropan-2-yl (±)1-(pyrazin-2-ylcarbamoyl)-6-azaspiro[2.5]octane-6-carboxylate;

1,1,1,3,3,3-hexafluoropropan-2-yl (±)1-((2-(trifluoromethyl)-5,6,7,8-tetrahydropyrido[3,4-d]pyrimidine-7-carbonyl)-6-azaspiro[2.5]octane-6-carboxylate;

1,1,1,3,3,3-hexafluoropropan-2-yl (±)1-(5,6,7,8-tetrahydropyrido[4,3-d]pyrimidine-6-carbonyl)-6-azaspiro[2.5]octane-6-carboxylate;

1,1,1,3,3,3-hexafluoropropan-2-yl (±)1-(2-cyclopropyl-5,6,7,8-tetrahydropyrido[4,3-d]pyrimidine-6-carbonyl)-6-azaspiro[2.5]octane-6-carboxylate;
1,1,1,3,3,3-hexafluoropropan-2-yl (±)1-((5-chloropyridin-3-yl)carbamoyl)-6-azaspiro[2.5]octane-6-carboxylate;
1,1,1,3,3,3-hexafluoropropan-2-yl (±)1-((2-methylpyridin-3-yl)carbamoyl)-6-azaspiro[2.5]octane-6-carboxylate;
1,1,1,3,3,3-hexafluoropropan-2-yl (±)1-((6-(trifluoromethyl)pyridin-2-yl)carbamoyl)-6-azaspiro[2.5]octane-6-carboxylate;
1,1,1,3,3,3-hexafluoropropan-2-yl (±)1-((6-(trifluoromethyl)pyridin-2-yl)methyl)carbamoyl)-6-azaspiro[2.5]octane-6-carboxylate;
1,1,1,3,3,3-hexafluoropropan-2-yl (±)1-((6-(trifluoromethyl)pyridin-3-yl)carbamoyl)-6-azaspiro[2.5]octane-6-carboxylate;
1,1,1,3,3,3-hexafluoropropan-2-yl (±)1-((6-methylpyridin-3-yl)carbamoyl)-6-azaspiro[2.5]octane-6-carboxylate;
1,1,1,3,3,3-hexafluoropropan-2-yl (±)1-((2-(trifluoromethyl)pyridin-3-yl)carbamoyl)-6-azaspiro[2.5]octane-6-carboxylate;
1,1,1,3,3,3-hexafluoropropan-2-yl (±)1-((pyridin-3-ylmethyl)carbamoyl)-6-azaspiro[2.5]octane-6-carboxylate;
1,1,1,3,3,3-hexafluoropropan-2-yl (±)1-((cyclohexanecarbonyl)carbamoyl)-6-azaspiro[2.5]octane-6-carboxylate;
1,1,1,3,3,3-hexafluoropropan-2-yl (±)1-(benzoylcarbamoyl)-6-azaspiro[2.5]octane-6-carboxylate;
1,1,1,3,3,3-hexafluoropropan-2-yl (±)1-(pyrimidin-5-ylcarbamoyl)-6-azaspiro[2.5]octane-6-carboxylate;
1,1,1,3,3,3-hexafluoropropan-2-yl (±)1-((2-(trifluoromethyl)pyrimidin-5-yl)carbamoyl)-6-azaspiro[2.5]octane-6-carboxylate;
1,1,1,3,3,3-hexafluoropropan-2-yl (±)1-((2-methylpyrimidin-5-yl)carbamoyl)-6-azaspiro[2.5]octane-6-carboxylate;
1,1,1,3,3,3-hexafluoropropan-2-yl (±)1-((6-methylpyridazin-3-yl)carbamoyl)-6-azaspiro[2.5]octane-6-carboxylate;
1,1,1,3,3,3-hexafluoropropan-2-yl (±)1-(pyridazin-4-ylcarbamoyl)-6-azaspiro[2.5]octane-6-carboxylate;
1,1,1,3,3,3-hexafluoropropan-2-yl (±)1-((5-methylpyrazin-2-yl)carbamoyl)-6-azaspiro[2.5]octane-6-carboxylate;
1,1,1,3,3,3-hexafluoropropan-2-yl (±)1-((1-methylpiperidin-4-yl)carbamoyl)-6-azaspiro[2.5]octane-6-carboxylate;
1,1,1,3,3,3-hexafluoropropan-2-yl (±)1-(((tetrahydro-2H-pyran-4-yl)methyl)carbamoyl)-6-azaspiro[2.5]octane-6-carboxylate;
1,1,1,3,3,3-hexafluoropropan-2-yl (±)1-(morpholine-4-carbonyl)-6-azaspiro[2.5]octane-6-carboxylate;
1,1,1,3,3,3-hexafluoropropan-2-yl (±)1-(4-cyanopiperidine-1-carbonyl)-6-azaspiro[2.5]octane-6-carboxylate;
1,1,1,3,3,3-hexafluoropropan-2-yl (±)1-((1-methyl-1H-pyrazol-3-yl)carbamoyl)-6-azaspiro[2.5]octane-6-carboxylate;
1,1,1,3,3,3-hexafluoropropan-2-yl (±)1-(thiazol-5-ylcarbamoyl)-6-azaspiro[2.5]octane-6-carboxylate;
1,1,1,3,3,3-hexafluoropropan-2-yl (±)1-((4-methyltetrahydro-2H-pyran-4-yl)carbamoyl)-6-azaspiro[2.5]octane-6-carboxylate;
1,1,1,3,3,3-hexafluoropropan-2-yl (±)1-((1-methyl-1H-pyrazol-5-yl)carbamoyl)-6-azaspiro[2.5]octane-6-carboxylate;
1,1,1,3,3,3-hexafluoropropan-2-yl (±)1-(thiazol-2-ylcarbamoyl)-6-azaspiro[2.5]octane-6-carboxylate;
1,1,1,3,3,3-hexafluoropropan-2-yl (±)1-(phenylcarbamoyl)-6-azaspiro[2.5]octane-6-carboxylate;
1,1,1,3,3,3-hexafluoropropan-2-yl (±)1-(p-tolylcarbamoyl)-6-azaspiro[2.5]octane-6-carboxylate;
1,1,1,3,3,3-hexafluoropropan-2-yl (±)-1-((3-fluorophenyl)carbamoyl)-6-azaspiro[2.5]octane-6-carboxylate:
1,1,1,3,3,3-hexafluoropropan-2-yl (±)1-(benzylcarbamoyl)-6-azaspiro[2.5]octane-6-carboxylate;
1,1,1,3,3,3-hexafluoropropan-2-yl (±)1-((pyrimidin-5-ylmethyl)carbamoyl)-6-azaspiro[2.5]octane-6-carboxylate;
1,1,1,3,3,3-hexafluoropropan-2-yl (±)1-((pyridazin-3-ylmethyl)carbamoyl)-6-azaspiro[2.5]octane-6-carboxylate;
1,1,1,3,3,3-hexafluoropropan-2-yl (±)1-((2-oxaspiro[3.3]heptan-6-yl)carbamoyl)-6-azaspiro[2.5]octane-6-carboxylate;
1,1,1,3,3,3-hexafluoropropan-2-yl (±)1-((6-cyclopropylpyridin-3-yl)carbamoyl)-6-azaspiro[2.5]octane-6-carboxylate;
1,1,1,3,3,3-hexafluoropropan-2-yl (±)1-((6-isopropoxypyridin-3-yl)carbamoyl)-6-azaspiro[2.5]octane-6-carboxylate;
1,1,1,3,3,3-hexafluoropropan-2-yl (±)1-((4-methyltetrahydro-2H-pyran-4-yl)methyl)carbamoyl)-6-azaspiro[2.5]octane-6-carboxylate;
1,1,1,3,3,3-hexafluoropropan-2-yl (±)1-((6-acetamidopyridin-3-yl)carbamoyl)-6-azaspiro[2.5]octane-6-carboxylate;
1,1,1,3,3,3-hexafluoropropan-2-yl (±)1-((6-carbamoylpyridin-3-yl)carbamoyl)-6-azaspiro[2.5]octane-6-carboxylate;
1,1,1,3,3,3-hexafluoropropan-2-yl (±)1-(isoxazol-3-ylcarbamoyl)-6-azaspiro[2.5]octane-6-carboxylate;
1,1,1,3,3,3-hexafluoropropan-2-yl (±)1-((6-(methylsulfonamido)pyridin-3-yl)carbamoyl)-6-azaspiro[2.5]octane-6-carboxylate;
(±)2-((5-(6-((((1,1,1,3,3,3-hexafluoropropan-2-yl)oxy)carbonyl)-6-azaspiro[2.5]octane-1-carboxamido)pyridin-2-yl)oxy)acetic acid;
1,1,1,3,3,3-hexafluoropropan-2-yl (±)1-(3-cyclopropyl-5,6,7,8-tetrahydro-[1,2,4]triazolo[4,3-a]pyrazine-7-carbonyl)-6-azaspiro[2.5]octane-6-carboxylate;
1,1,1,3,3,3-hexafluoropropan-2-yl (±)1-(5,6,7,8-tetrahydroimidazo[1,2-a]pyrazine-7-carbonyl)-6-azaspiro[2.5]octane-6-carboxylate;
1,1,1,3,3,3-hexafluoropropan-2-yl (±)1-(5,6,7,8-tetrahydropyrido[3,4-d]pyrimidine-7-carbonyl)-6-azaspiro[2.5]octane-6-carboxylate;
1,1,1,3,3,3-hexafluoropropan-2-yl (±)1-(methyl(pyridazin-3-yl)carbamoyl)-6-azaspiro[2.5]octane-6-carboxylate; and
1,1,1,3,3,3-hexafluoropropan-2-yl (±)1-((6-cyanopyridin-3-yl)carbamoyl)-6-azaspiro[2.5]octane-6-carboxylate; or a pharmaceutically acceptable salt thereof.

In a further embodiment, the compound of the invention is selected from the group consisting of:
1,1,1,3,3,3-hexafluoropropan-2-yl (±)1-(3-cyclopropyl-5,6,7,8-tetrahydro-[1,2,4]triazolo[4,3-a]pyrazine-7-carbonyl)-6-azaspiro[2.5]octane-6-carboxylate;
1,1,1,3,3,3-hexafluoropropan-2-yl (±)1-(5,6,7,8-tetrahydroimidazo[1,2-a]pyrazine-7-carbonyl)-6-azaspiro[2.5]octane-6-carboxylate;
1,1,1,3,3,3-hexafluoropropan-2-yl (±)1-(5,6,7,8-tetrahydropyrido[3,4-d]pyrimidine-7-carbonyl)-6-azaspiro[2.5]octane-6-carboxylate;
1,1,1,3,3,3-hexafluoropropan-2-yl (±)1-(methyl(pyridazin-3-yl)carbamoyl)-6-azaspiro[2.5]octane-6-carboxylate; and 1,1,1,3,3,3-hexafluoropropan-2-yl (±)1-((6-cyanopyridin-3-yl)carbamoyl)-6-azaspiro[2.5]octane-6-carboxylate; or a pharmaceutically acceptable salt thereof.

In a further embodiment, the compound of the invention is selected from the group consisting of:

1,1,1,3,3,3-hexafluoropropan-2-yl (R)-1-(pyridin-3-ylcarbamoyl)-6-azaspiro[2.5]octane-6-carboxylate 1,1,1,3,3,3-hexafluoropropan-2-yl (S)-1-(pyridin-3-ylcarbamoyl)-6-azaspiro[2.5]octane-6-carboxylate;

1,1,1,3,3,3-hexafluoropropan-2-yl (R)-1-(pyridazin-3-ylcarbamoyl)-6-azaspiro[2.5]octane-6-carboxylate 1,1,1,3,3,3-hexafluoropropan-2-yl (S)-1-(pyridazin-3-ylcarbamoyl)-6-azaspiro[2.5]octane-6-carboxylate;

1,1,1,3,3,3-hexafluoropropan-2-yl (R)-1-((tetrahydro-2H-pyran-4-yl)carbamoyl)-6-azaspiro[2.5]octane-6-carboxylate;

1,1,1,3,3,3-hexafluoropropan-2-yl (S)-1-((tetrahydro-2H-pyran-4-yl)carbamoyl)-6-azaspiro[2.5]octane-6-carboxylate;

1,1,1,3,3,3-hexafluoropropan-2-yl (R)-1-(methyl(pyrazin-2-yl)carbamoyl)-6-azaspiro[2.5]octane-6-carboxylate;

1,1,1,3,3,3-hexafluoropropan-2-yl (S)-1-(methyl(pyrazin-2-yl)carbamoyl)-6-azaspiro[2.5]octane-6-carboxylate;

1,1,1,3,3,3-hexafluoropropan-2-yl (R)-1-(isoxazol-4-ylcarbamoyl)-6-azaspiro[2.5]octane-6-carboxylate;

1,1,1,3,3,3-hexafluoropropan-2-yl (S)-1-(isoxazol-4-ylcarbamoyl)-6-azaspiro[2.5]octane-6-carboxylate;

1,1,1,3,3,3-hexafluoropropan-2-yl (R)-1-((2-(trifluoromethyl)pyrimidin-4-yl)carbamoyl)-6-azaspiro[2.5]octane-6-carboxylate;

1,1,1,3,3,3-hexafluoropropan-2-yl (S)-1-((2-(trifluoromethyl)pyrimidin-4-yl)carbamoyl)-6-azaspiro[2.5]octane-6-carboxylate;

1,1,1,3,3,3-hexafluoropropan-2-yl (R)-1-((6-(dimethylphosphoryl)pyridin-3-yl)carbamoyl)-6-azaspiro[2.5]octane-6-carboxylate;

1,1,1,3,3,3-hexafluoropropan-2-yl (S)-1-((6-(dimethylphosphoryl)pyridin-3-yl)carbamoyl)-6-azaspiro[2.5]octane-6-carboxylate;

1,1,1,3,3,3-hexafluoropropan-2-yl (R)-1-(pyridin-4-ylcarbamoyl)-6-azaspiro[2.5]octane-6-carboxylate;

1,1,1,3,3,3-hexafluoropropan-2-yl (S)-1-(pyridin-4-ylcarbamoyl)-6-azaspiro[2.5]octane-6-carboxylate;

1,1,1,3,3,3-hexafluoropropan-2-yl (R)-1-((tetrahydro-2H-pyran-4-carbonyl)carbamoyl)-6-azaspiro[2.5]octane-6-carboxylate;

1,1,1,3,3,3-hexafluoropropan-2-yl (S)-1-((tetrahydro-2H-pyran-4-carbonyl)carbamoyl)-6-azaspiro[2.5]octane-6-carboxylate;

1,1,1,3,3,3-hexafluoropropan-2-yl (R)-1-((6-(1H-pyrazol-1-yl)pyridin-3-yl)carbamoyl)-6-azaspiro[2.5]octane-6-carboxylate;

1,1,1,3,3,3-hexafluoropropan-2-yl (S)-1-((6-(1H-pyrazol-1-yl)pyridin-3-yl)carbamoyl)-6-azaspiro[2.5]octane-6-carboxylate;

1,1,1,3,3,3-hexafluoropropan-2-yl (R)-1-((6-(methylcarbamoyl)pyridin-3-yl)carbamoyl)-6-azaspiro[2.5]octane-6-carboxylate;

1,1,1,3,3,3-hexafluoropropan-2-yl (S)-1-((6-(methylcarbamoyl)pyridin-3-yl)carbamoyl)-6-azaspiro[2.5]octane-6-carboxylate;

1,1,1,3,3,3-hexafluoropropan-2-yl (R)-1-((6-methoxypyridin-3-yl)carbamoyl)-6-azaspiro[2.5]octane-6-carboxylate;

1,1,1,3,3,3-hexafluoropropan-2-yl (S)-1-((6-methoxypyridin-3-yl)carbamoyl)-6-azaspiro[2.5]octane-6-carboxylate;

1,1,1,3,3,3-hexafluoropropan-2-yl (R)-1-((5-fluoropyridin-3-yl)carbamoyl)-6-azaspiro[2.5]octane-6-carboxylate;

1,1,1,3,3,3-hexafluoropropan-2-yl (S)-1-((5-fluoropyridin-3-yl)carbamoyl)-6-azaspiro[2.5]octane-6-carboxylate;

1,1,1,3,3,3-hexafluoropropan-2-yl (R)-1-(methyl(pyridin-3-yl)carbamoyl)-6-azaspiro[2.5]octane-6-carboxylate;

1,1,1,3,3,3-hexafluoropropan-2-yl (S)-1-(methyl(pyridin-3-yl)carbamoyl)-6-azaspiro[2.5]octane-6-carboxylate;

1,1,1,3,3,3-hexafluoropropan-2-yl (R)-1-(methyl(pyridin-2-yl)carbamoyl)-6-azaspiro[2.5]octane-6-carboxylate;

1,1,1,3,3,3-hexafluoropropan-2-yl (S)-1-(methyl(pyridin-2-yl)carbamoyl)-6-azaspiro[2.5]octane-6-carboxylate;

1,1,1,3,3,3-hexafluoropropan-2-yl (R)-1-(pyridin-2-ylcarbamoyl)-6-azaspiro[2.5]octane-6-carboxylate;

1,1,1,3,3,3-hexafluoropropan-2-yl (S)-1-(pyridin-2-ylcarbamoyl)-6-azaspiro[2.5]octane-6-carboxylate;

1,1,1,3,3,3-hexafluoropropan-2-yl (R)-1-(2-(trifluoromethyl)-5,6,7,8-tetrahydroimidazo[1,2-a]pyrazine-7-carbonyl)-6-azaspiro[2.5]octane-6-carboxylate;

1,1,1,3,3,3-hexafluoropropan-2-yl (S)-1-(2-(trifluoromethyl)-5,6,7,8-tetrahydroimidazo[1,2-a]pyrazine-7-carbonyl)-6-azaspiro[2.5]octane-6-carboxylate;

1,1,1,3,3,3-hexafluoropropan-2-yl (R)-1-(pyrazin-2-ylcarbamoyl)-6-azaspiro[2.5]octane-6-carboxylate;

1,1,1,3,3,3-hexafluoropropan-2-yl (S)-1-(pyrazin-2-ylcarbamoyl)-6-azaspiro[2.5]octane-6-carboxylate;

1,1,1,3,3,3-hexafluoropropan-2-yl (R)-1-(2-(trifluoromethyl)-5,6,7,8-tetrahydropyrido[3,4-d]pyrimidine-7-carbonyl)-6-azaspiro[2.5]octane-6-carboxylate;

1,1,1,3,3,3-hexafluoropropan-2-yl (S)-1-(2-(trifluoromethyl)-5,6,7,8-tetrahydropyrido[3,4-d]pyrimidine-7-carbonyl)-6-azaspiro[2.5]octane-6-carboxylate;

1,1,1,3,3,3-hexafluoropropan-2-yl (R)-1-(5,6,7,8-tetrahydropyrido[4,3-d]pyrimidine-6-carbonyl)-6-azaspiro[2.5]octane-6-carboxylate;

1,1,1,3,3,3-hexafluoropropan-2-yl (S)-1-(5,6,7,8-tetrahydropyrido[4,3-d]pyrimidine-6-carbonyl)-6-azaspiro[2.5]octane-6-carboxylate;

1,1,1,3,3,3-hexafluoropropan-2-yl (R)-1-(2-cyclopropyl-5,6,7,8-tetrahydropyrido[4,3-d]pyrimidine-6-carbonyl)-6-azaspiro[2.5]octane-6-carboxylate;

1,1,1,3,3,3-hexafluoropropan-2-yl (S)-1-(2-cyclopropyl-5,6,7,8-tetrahydropyrido[4,3-d]pyrimidine-6-carbonyl)-6-azaspiro[2.5]octane-6-carboxylate;

1,1,1,3,3,3-hexafluoropropan-2-yl (R)-1-((5-chloropyridin-3-yl)carbamoyl)-6-azaspiro[2.5]octane-6-carboxylate;

1,1,1,3,3,3-hexafluoropropan-2-yl (S)-1-((5-chloropyridin-3-yl)carbamoyl)-6-azaspiro[2.5]octane-6-carboxylate;

1,1,1,3,3,3-hexafluoropropan-2-yl (R)-1-((2-methylpyridin-3-yl)carbamoyl)-6-azaspiro[2.5]octane-6-carboxylate;

1,1,1,3,3,3-hexafluoropropan-2-yl (S)-1-((2-methylpyridin-3-yl)carbamoyl)-6-azaspiro[2.5]octane-6-carboxylate;

1,1,1,3,3,3-hexafluoropropan-2-yl (R)-1-((6-(trifluoromethyl)pyridin-2-yl)carbamoyl)-6-azaspiro[2.5]octane-6-carboxylate;

1,1,1,3,3,3-hexafluoropropan-2-yl (S)-1-((6-(trifluoromethyl)pyridin-2-yl)carbamoyl)-6-azaspiro[2.5]octane-6-carboxylate;

1,1,1,3,3,3-hexafluoropropan-2-yl (R)-1-(((6-(trifluoromethyl)pyridin-2-yl)methyl)carbamoyl)-6-azaspiro[2.5]octane-6-carboxylate;

1,1,1,3,3,3-hexafluoropropan-2-yl (S)-1-((6-(trifluoromethyl)pyridin-2-yl)methyl)carbamoyl)-6-azaspiro[2.5]octane-6-carboxylate;

1,1,1,3,3,3-hexafluoropropan-2-yl (R)-1-((6-(trifluoromethyl)pyridin-3-yl)carbamoyl)-6-azaspiro[2.5]octane-6-carboxylate;

1,1,1,3,3,3-hexafluoropropan-2-yl (S)-1-((6-(trifluoromethyl)pyridin-3-yl)carbamoyl)-6-azaspiro[2.5]octane-6-carboxylate;
1,1,1,3,3,3-hexafluoropropan-2-yl (R)-1-((6-methylpyridin-3-yl)carbamoyl)-6-azaspiro[2.5]octane-6-carboxylate;
1,1,1,3,3,3-hexafluoropropan-2-yl (S)-1-((6-methylpyridin-3-yl)carbamoyl)-6-azaspiro[2.5]octane-6-carboxylate;
1,1,1,3,3,3-hexafluoropropan-2-yl (R)-1-((2-(trifluoromethyl)pyridin-3-yl)carbamoyl)-6-azaspiro[2.5]octane-6-carboxylate;
1,1,1,3,3,3-hexafluoropropan-2-yl (S)-1-((2-(trifluoromethyl)pyridin-3-yl)carbamoyl)-6-azaspiro[2.5]octane-6-carboxylate;
1,1,1,3,3,3-hexafluoropropan-2-yl (R)-1-((pyridin-3-ylmethyl)carbamoyl)-6-azaspiro[2.5]octane-6-carboxylate;
1,1,1,3,3,3-hexafluoropropan-2-yl (S)-1-((pyridin-3-ylmethyl)carbamoyl)-6-azaspiro[2.5]octane-6-carboxylate;
1,1,1,3,3,3-hexafluoropropan-2-yl (R)-1-((cyclohexanecarbonyl)carbamoyl)-6-azaspiro[2.5]octane-6-carboxylate;
1,1,1,3,3,3-hexafluoropropan-2-yl (S)-1-((cyclohexanecarbonyl)carbamoyl)-6-azaspiro[2.5]octane-6-carboxylate;
1,1,1,3,3,3-hexafluoropropan-2-yl (R)-1-(benzoylcarbamoyl)-6-azaspiro[2.5]octane-6-carboxylate;
1,1,1,3,3,3-hexafluoropropan-2-yl (S)-1-(benzoylcarbamoyl)-6-azaspiro[2.5]octane-6-carboxylate;
1,1,1,3,3,3-hexafluoropropan-2-yl (R)-1-(pyrimidin-5-ylcarbamoyl)-6-azaspiro[2.5]octane-6-carboxylate;
1,1,1,3,3,3-hexafluoropropan-2-yl (S)-1-(pyrimidin-5-ylcarbamoyl)-6-azaspiro[2.5]octane-6-carboxylate;
1,1,1,3,3,3-hexafluoropropan-2-yl (R)-1-((2-(trifluoromethyl)pyrimidin-5-yl)carbamoyl)-6-azaspiro[2.5]octane-6-carboxylate;
1,1,1,3,3,3-hexafluoropropan-2-yl (S)-1-((2-(trifluoromethyl)pyrimidin-5-yl)carbamoyl)-6-azaspiro[2.5]octane-6-carboxylate;
1,1,1,3,3,3-hexafluoropropan-2-yl (R)-1-((2-methylpyrimidin-5-yl)carbamoyl)-6-azaspiro[2.5]octane-6-carboxylate;
1,1,1,3,3,3-hexafluoropropan-2-yl (S)-1-((2-methylpyrimidin-5-yl)carbamoyl)-6-azaspiro[2.5]octane-6-carboxylate;
1,1,1,3,3,3-hexafluoropropan-2-yl (R)-1-((6-methylpyridazin-3-yl)carbamoyl)-6-azaspiro[2.5]octane-6-carboxylate;
1,1,1,3,3,3-hexafluoropropan-2-yl (S)-1-((6-methylpyridazin-3-yl)carbamoyl)-6-azaspiro[2.5]octane-6-carboxylate;
1,1,1,3,3,3-hexafluoropropan-2-yl (R)-1-(pyridazin-4-ylcarbamoyl)-6-azaspiro[2.5]octane-6-carboxylate;
1,1,1,3,3,3-hexafluoropropan-2-yl (S)-1-(pyridazin-4-ylcarbamoyl)-6-azaspiro[2.5]octane-6-carboxylate;
1,1,1,3,3,3-hexafluoropropan-2-yl (R)-1-((5-methylpyrazin-2-yl)carbamoyl)-6-azaspiro[2.5]octane-6-carboxylate;
1,1,1,3,3,3-hexafluoropropan-2-yl (S)-1-((5-methylpyrazin-2-yl)carbamoyl)-6-azaspiro[2.5]octane-6-carboxylate;
1,1,1,3,3,3-hexafluoropropan-2-yl (R)-1-((1-methylpiperidin-4-yl)carbamoyl)-6-azaspiro[2.5]octane-6-carboxylate;
1,1,1,3,3,3-hexafluoropropan-2-yl (S)-1-((1-methylpiperidin-4-yl)carbamoyl)-6-azaspiro[2.5]octane-6-carboxylate;
1,1,1,3,3,3-hexafluoropropan-2-yl (R)-1-(((tetrahydro-2H-pyran-4-yl)methyl)carbamoyl)-6-azaspiro[2.5]octane-6-carboxylate;
1,1,1,3,3,3-hexafluoropropan-2-yl (S)-1-(((tetrahydro-2H-pyran-4-yl)methyl)carbamoyl)-6-azaspiro[2.5]octane-6-carboxylate;
1,1,1,3,3,3-hexafluoropropan-2-yl (R)-1-(morpholine-4-carbonyl)-6-azaspiro[2.5]octane-6-carboxylate;
1,1,1,3,3,3-hexafluoropropan-2-yl (S)-1-(morpholine-4-carbonyl)-6-azaspiro[2.5]octane-6-carboxylate;
1,1,1,3,3,3-hexafluoropropan-2-yl (R)-1-(4-cyanopiperidine-1-carbonyl)-6-azaspiro[2.5]octane-6-carboxylate;
1,1,1,3,3,3-hexafluoropropan-2-yl (S)-1-(4-cyanopiperidine-1-carbonyl)-6-azaspiro[2.5]octane-6-carboxylate;
1,1,1,3,3,3-hexafluoropropan-2-yl (R)-1-((1-methyl-1H-pyrazol-3-yl)carbamoyl)-6-azaspiro[2.5]octane-6-carboxylate;
1,1,1,3,3,3-hexafluoropropan-2-yl (S)-1-((1-methyl-1H-pyrazol-3-yl)carbamoyl)-6-azaspiro[2.5]octane-6-carboxylate;
1,1,1,3,3,3-hexafluoropropan-2-yl (R)-1-(thiazol-5-ylcarbamoyl)-6-azaspiro[2.5]octane-6-carboxylate;
1,1,1,3,3,3-hexafluoropropan-2-yl (S)-1-(thiazol-5-ylcarbamoyl)-6-azaspiro[2.5]octane-6-carboxylate;
1,1,1,3,3,3-hexafluoropropan-2-yl (R)-1-((4-methyltetrahydro-2H-pyran-4-yl)carbamoyl)-6-azaspiro[2.5]octane-6-carboxylate;
1,1,1,3,3,3-hexafluoropropan-2-yl (S)-1-((4-methyltetrahydro-2H-pyran-4-yl)carbamoyl)-6-azaspiro[2.5]octane-6-carboxylate;
1,1,1,3,3,3-hexafluoropropan-2-yl (R)-1-((1-methyl-1H-pyrazol-5-yl)carbamoyl)-6-azaspiro[2.5]octane-6-carboxylate;
1,1,1,3,3,3-hexafluoropropan-2-yl (S)-1-((1-methyl-1H-pyrazol-5-yl)carbamoyl)-6-azaspiro[2.5]octane-6-carboxylate;
1,1,1,3,3,3-hexafluoropropan-2-yl (R)-1-(thiazol-2-ylcarbamoyl)-6-azaspiro[2.5]octane-6-carboxylate;
1,1,1,3,3,3-hexafluoropropan-2-yl (S)-1-(thiazol-2-ylcarbamoyl)-6-azaspiro[2.5]octane-6-carboxylate;
1,1,1,3,3,3-hexafluoropropan-2-yl (R)-1-(phenylcarbamoyl)-6-azaspiro[2.5]octane-6-carboxylate;
1,1,1,3,3,3-hexafluoropropan-2-yl (S)-1-(phenylcarbamoyl)-6-azaspiro[2.5]octane-6-carboxylate;
1,1,1,3,3,3-hexafluoropropan-2-yl (R)-1-(p-tolylcarbamoyl)-6-azaspiro[2.5]octane-6-carboxylate;
1,1,1,3,3,3-hexafluoropropan-2-yl (S)-1-(p-tolylcarbamoyl)-6-azaspiro[2.5]octane-6-carboxylate;
1,1,1,3,3,3-hexafluoropropan-2-yl (R)-1-((3-fluorophenyl)carbamoyl)-6-azaspiro[2.5]octane-6-carboxylate;
1,1,1,3,3,3-hexafluoropropan-2-yl (S)-1-((3-fluorophenyl)carbamoyl)-6-azaspiro[2.5]octane-6-carboxylate;
1,1,1,3,3,3-hexafluoropropan-2-yl (R)-1-(benzylcarbamoyl)-6-azaspiro[2.5]octane-6-carboxylate;
1,1,1,3,3,3-hexafluoropropan-2-yl (S)-1-(benzylcarbamoyl)-6-azaspiro[2.5]octane-6-carboxylate;
1,1,1,3,3,3-hexafluoropropan-2-yl (R)-1-((pyrimidin-5-ylmethyl)carbamoyl)-6-azaspiro[2.5]octane-6-carboxylate;
1,1,1,3,3,3-hexafluoropropan-2-yl (S)-1-((pyrimidin-5-ylmethyl)carbamoyl)-6-azaspiro[2.5]octane-6-carboxylate;
1,1,1,3,3,3-hexafluoropropan-2-yl (R)-1-((pyridazin-3-ylmethyl)carbamoyl)-6-azaspiro[2.5]octane-6-carboxylate;
1,1,1,3,3,3-hexafluoropropan-2-yl (S)-1-((pyridazin-3-ylmethyl)carbamoyl)-6-azaspiro[2.5]octane-6-carboxylate;
1,1,1,3,3,3-hexafluoropropan-2-yl (R)-1-((2-oxaspiro[3.3]heptan-6-yl)carbamoyl)-6-azaspiro[2.5]octane-6-carboxylate;
1,1,1,3,3,3-hexafluoropropan-2-yl (S)-1-((2-oxaspiro[3.3]heptan-6-yl)carbamoyl)-6-azaspiro[2.5]octane-6-carboxylate;
1,1,1,3,3,3-hexafluoropropan-2-yl (R)-1-((6-cyclopropylpyridin-3-yl)carbamoyl)-6-azaspiro[2.5]octane-6-carboxylate;

1,1,1,3,3,3-hexafluoropropan-2-yl (S)-1-((6-cyclopropylpyridin-3-yl)carbamoyl)-6-azaspiro[2.5]octane-6-carboxylate;

1,1,1,3,3,3-hexafluoropropan-2-yl (R)-1-((6-isopropoxypyridin-3-yl)carbamoyl)-6-azaspiro[2.5]octane-6-carboxylate;

1,1,1,3,3,3-hexafluoropropan-2-yl (S)-1-((6-isopropoxypyridin-3-yl)carbamoyl)-6-azaspiro[2.5]octane-6-carboxylate;

1,1,1,3,3,3-hexafluoropropan-2-yl (R)-1-(((4-methyltetrahydro-2H-pyran-4-yl)methyl)carbamoyl)-6-azaspiro[2.5]octane-6-carboxylate;

1,1,1,3,3,3-hexafluoropropan-2-yl (S)-1-(((4-methyltetrahydro-2H-pyran-4-yl)methyl)carbamoyl)-6-azaspiro[2.5]octane-6-carboxylate;

1,1,1,3,3,3-hexafluoropropan-2-yl (R)-1-((6-acetamidopyridin-3-yl)carbamoyl)-6-azaspiro[2.5]octane-6-carboxylate;

1,1,1,3,3,3-hexafluoropropan-2-yl (S)-1-((6-acetamidopyridin-3-yl)carbamoyl)-6-azaspiro[2.5]octane-6-carboxylate;

1,1,1,3,3,3-hexafluoropropan-2-yl (R)-1-((6-carbamoylpyridin-3-yl)carbamoyl)-6-azaspiro[2.5]octane-6-carboxylate;

1,1,1,3,3,3-hexafluoropropan-2-yl (S)-1-((6-carbamoylpyridin-3-yl)carbamoyl)-6-azaspiro[2.5]octane-6-carboxylate;

1,1,1,3,3,3-hexafluoropropan-2-yl (R)-1-(isoxazol-3-ylcarbamoyl)-6-azaspiro[2.5]octane-6-carboxylate;

1,1,1,3,3,3-hexafluoropropan-2-yl (S)-1-(isoxazol-3-ylcarbamoyl)-6-azaspiro[2.5]octane-6-carboxylate;

1,1,1,3,3,3-hexafluoropropan-2-yl (R)-1-((6-(methylsulfonamido)pyridin-3-yl)carbamoyl)-6-azaspiro[2.5]octane-6-carboxylate;

1,1,1,3,3,3-hexafluoropropan-2-yl (S)-1-((6-(methylsulfonamido)pyridin-3-yl)carbamoyl)-6-azaspiro[2.5]octane-6-carboxylate;

(R)-2-((5-(6-(((1,1,1,3,3,3-hexafluoropropan-2-yl)oxy)carbonyl)-6-azaspiro[2.5]octane-1-carboxamido)pyridin-2-yl)oxy)acetic acid; and (S)-2-((5-(6-(((1,1,1,3,3,3-hexafluoropropan-2-yl)oxy)carbonyl)-6-azaspiro[2.5]octane-1-carboxamido)pyridin-2-yl)oxy)acetic acid; or a pharmaceutically acceptable salt thereof.

In a further embodiment the compound of the invention is selected from the group consisting of:

1,1,1,3,3,3-hexafluoropropan-2-yl (S)-1-(pyridin-3-ylcarbamoyl)-6-azaspiro[2.5]octane-6-carboxylate;

1,1,1,3,3,3-hexafluoropropan-2-yl (S)-1-(pyridazin-3-ylcarbamoyl)-6-azaspiro[2.5]octane-6-carboxylate;

1,1,1,3,3,3-hexafluoropropan-2-yl (S)-1-((tetrahydro-2H-pyran-4-yl)carbamoyl)-6-azaspiro[2.5]octane-6-carboxylate;

1,1,1,3,3,3-hexafluoropropan-2-yl (S)-1-(methyl(pyrazin-2-yl)carbamoyl)-6-azaspiro[2.5]octane-6-carboxylate;

1,1,1,3,3,3-hexafluoropropan-2-yl (S)-1-(isoxazol-4-ylcarbamoyl)-6-azaspiro[2.5]octane-6-carboxylate;

1,1,1,3,3,3-hexafluoropropan-2-yl (S)-1-((2-(trifluoromethyl)pyrimidin-4-yl)carbamoyl)-6-azaspiro[2.5]octane-6-carboxylate;

1,1,1,3,3,3-hexafluoropropan-2-yl (S)-1-((6-(dimethylphosphoryl)pyridin-3-yl)carbamoyl)-6-azaspiro[2.5]octane-6-carboxylate;

1,1,1,3,3,3-hexafluoropropan-2-yl (S)-1-(pyridin-4-ylcarbamoyl)-6-azaspiro[2.5]octane-6-carboxylate;

1,1,1,3,3,3-hexafluoropropan-2-yl (S)-1-((tetrahydro-2H-pyran-4-carbonyl)carbamoyl)-6-azaspiro[2.5]octane-6-carboxylate;

1,1,1,3,3,3-hexafluoropropan-2-yl (S)-1-((6-(1H-pyrazol-1-yl)pyridin-3-yl)carbamoyl)-6-azaspiro[2.5]octane-6-carboxylate;

1,1,1,3,3,3-hexafluoropropan-2-yl (S)-1-((6-(methylcarbamoyl)pyridin-3-yl)carbamoyl)-6-azaspiro[2.5]octane-6-carboxylate;

1,1,1,3,3,3-hexafluoropropan-2-yl (S)-1-((6-methoxypyridin-3-yl)carbamoyl)-6-azaspiro[2.5]octane-6-carboxylate;

1,1,1,3,3,3-hexafluoropropan-2-yl (S)-1-((5-fluoropyridin-3-yl)carbamoyl)-6-azaspiro[2.5]octane-6-carboxylate;

1,1,1,3,3,3-hexafluoropropan-2-yl (S)-1-(methyl(pyridin-3-yl)carbamoyl)-6-azaspiro[2.5]octane-6-carboxylate;

1,1,1,3,3,3-hexafluoropropan-2-yl (S)-1-(methyl(pyridin-2-yl)carbamoyl)-6-azaspiro[2.5]octane-6-carboxylate;

1,1,1,3,3,3-hexafluoropropan-2-yl (S)-1-(pyridin-2-ylcarbamoyl)-6-azaspiro[2.5]octane-6-carboxylate;

1,1,1,3,3,3-hexafluoropropan-2-yl (S)-1-(2-(trifluoromethyl)-5,6,7,8-tetrahydroimidazo[1,2-a]pyrazine-7-carbonyl)-6-azaspiro[2.5]octane-6-carboxylate;

1,1,1,3,3,3-hexafluoropropan-2-yl (S)-1-(pyrazin-2-ylcarbamoyl)-6-azaspiro[2.5]octane-6-carboxylate;

1,1,1,3,3,3-hexafluoropropan-2-yl (S)-1-(2-(trifluoromethyl)-5,6,7,8-tetrahydropyrido[3,4-d]pyrimidine-7-carbonyl)-6-azaspiro[2.5]octane-6-carboxylate;

1,1,1,3,3,3-hexafluoropropan-2-yl (S)-1-(5,6,7,8-tetrahydropyrido[4,3-d]pyrimidine-6-carbonyl)-6-azaspiro[2.5]octane-6-carboxylate;

1,1,1,3,3,3-hexafluoropropan-2-yl (S)-1-(2-cyclopropyl-5,6,7,8-tetrahydropyrido[4,3-d]pyrimidine-6-carbonyl)-6-azaspiro[2.5]octane-6-carboxylate;

1,1,1,3,3,3-hexafluoropropan-2-yl (S)-1-((5-chloropyridin-3-yl)carbamoyl)-6-azaspiro[2.5]octane-6-carboxylate;

1,1,1,3,3,3-hexafluoropropan-2-yl (S)-1-((2-methylpyridin-3-yl)carbamoyl)-6-azaspiro[2.5]octane-6-carboxylate;

1,1,1,3,3,3-hexafluoropropan-2-yl (S)-1-((6-(trifluoromethyl)pyridin-2-yl)carbamoyl)-6-azaspiro[2.5]octane-6-carboxylate;

1,1,1,3,3,3-hexafluoropropan-2-yl (S)-1-((6-(trifluoromethyl)pyridin-2-yl)methyl)carbamoyl)-6-azaspiro[2.5]octane-6-carboxylate;

1,1,1,3,3,3-hexafluoropropan-2-yl (S)-1-((6-(trifluoromethyl)pyridin-3-yl)carbamoyl)-6-azaspiro[2.5]octane-6-carboxylate;

1,1,1,3,3,3-hexafluoropropan-2-yl (S)-1-((6-methylpyridin-3-yl)carbamoyl)-6-azaspiro[2.5]octane-6-carboxylate;

1,1,1,3,3,3-hexafluoropropan-2-yl (S)-1-((2-(trifluoromethyl)pyridin-3-yl)carbamoyl)-6-azaspiro[2.5]octane-6-carboxylate;

1,1,1,3,3,3-hexafluoropropan-2-yl (S)-1-((pyridin-3-ylmethyl)carbamoyl)-6-azaspiro[2.5]octane-6-carboxylate;

1,1,1,3,3,3-hexafluoropropan-2-yl (S)-1-((cyclohexanecarbonyl)carbamoyl)-6-azaspiro[2.5]octane-6-carboxylate;

1,1,1,3,3,3-hexafluoropropan-2-yl (S)-1-(benzoylcarbamoyl)-6-azaspiro[2.5]octane-6-carboxylate;

1,1,1,3,3,3-hexafluoropropan-2-yl (S)-1-(pyrimidin-5-ylcarbamoyl)-6-azaspiro[2.5]octane-6-carboxylate;

1,1,1,3,3,3-hexafluoropropan-2-yl (S)-1-((2-(trifluoromethyl)pyrimidin-5-yl)carbamoyl)-6-azaspiro[2.5]octane-6-carboxylate;

1,1,1,3,3,3-hexafluoropropan-2-yl (S)-1-((2-methylpyrimidin-5-yl)carbamoyl)-6-azaspiro[2.5]octane-6-carboxylate;

1,1,1,3,3,3-hexafluoropropan-2-yl (S)-1-((6-methylpyridazin-3-yl)carbamoyl)-6-azaspiro[2.5]octane-6-carboxylate;

1,1,1,3,3,3-hexafluoropropan-2-yl (S)-1-(pyridazin-4-ylcarbamoyl)-6-azaspiro[2.5]octane-6-carboxylate;

1,1,1,3,3,3-hexafluoropropan-2-yl (S)-1-((5-methylpyrazin-2-yl)carbamoyl)-6-azaspiro[2.5]octane-6-carboxylate;

1,1,1,3,3,3-hexafluoropropan-2-yl (S)-1-((1-methylpiperidin-4-yl)carbamoyl)-6-azaspiro[2.5]octane-6-carboxylate;

1,1,1,3,3,3-hexafluoropropan-2-yl (S)-1-(((tetrahydro-2H-pyran-4-yl)methyl)carbamoyl)-6-azaspiro[2.5]octane-6-carboxylate;

1,1,1,3,3,3-hexafluoropropan-2-yl (S)-1-(morpholine-4-carbonyl)-6-azaspiro[2.5]octane-6-carboxylate;

1,1,1,3,3,3-hexafluoropropan-2-yl (S)-1-(4-cyanopiperidine-1-carbonyl)-6-azaspiro[2.5]octane-6-carboxylate;

1,1,1,3,3,3-hexafluoropropan-2-yl (S)-1-((1-methyl-1H-pyrazol-3-yl)carbamoyl)-6-azaspiro[2.5]octane-6-carboxylate;

1,1,1,3,3,3-hexafluoropropan-2-yl (S)-1-(thiazol-5-ylcarbamoyl)-6-azaspiro[2.5]octane-6-carboxylate;

1,1,1,3,3,3-hexafluoropropan-2-yl (S)-1-((4-methyltetrahydro-2H-pyran-4-yl)carbamoyl)-6-azaspiro[2.5]octane-6-carboxylate;

1,1,1,3,3,3-hexafluoropropan-2-yl (S)-1-((1-methyl-1H-pyrazol-5-yl)carbamoyl)-6-azaspiro[2.5]octane-6-carboxylate;

1,1,1,3,3,3-hexafluoropropan-2-yl (S)-1-(thiazol-2-ylcarbamoyl)-6-azaspiro[2.5]octane-6-carboxylate;

1,1,1,3,3,3-hexafluoropropan-2-yl (S)-1-(phenylcarbamoyl)-6-azaspiro[2.5]octane-6-carboxylate;

1,1,1,3,3,3-hexafluoropropan-2-yl (S)-1-(p-tolylcarbamoyl)-6-azaspiro[2.5]octane-6-carboxylate;

1,1,1,3,3,3-hexafluoropropan-2-yl (S)-1-((3-fluorophenyl)carbamoyl)-6-azaspiro[2.5]octane-6-carboxylate;

1,1,1,3,3,3-hexafluoropropan-2-yl (S)-1-(benzylcarbamoyl)-6-azaspiro[2.5]octane-6-carboxylate;

1,1,1,3,3,3-hexafluoropropan-2-yl (S)-1-((pyrimidin-5-ylmethyl)carbamoyl)-6-azaspiro[2.5]octane-6-carboxylate;

1,1,1,3,3,3-hexafluoropropan-2-yl (S)-1-((pyridazin-3-ylmethyl)carbamoyl)-6-azaspiro[2.5]octane-6-carboxylate;

1,1,1,3,3,3-hexafluoropropan-2-yl (S)-1-((2-oxaspiro[3.3]heptan-6-yl)carbamoyl)-6-azaspiro[2.5]octane-6-carboxylate;

1,1,1,3,3,3-hexafluoropropan-2-yl (S)-1-((6-cyclopropylpyridin-3-yl)carbamoyl)-6-azaspiro[2.5]octane-6-carboxylate;

1,1,1,3,3,3-hexafluoropropan-2-yl (S)-1-((6-isopropoxypyridin-3-yl)carbamoyl)-6-azaspiro[2.5]octane-6-carboxylate;

1,1,1,3,3,3-hexafluoropropan-2-yl (S)-1-(((4-methyltetrahydro-2H-pyran-4-yl)methyl)carbamoyl)-6-azaspiro[2.5]octane-6-carboxylate;

1,1,1,3,3,3-hexafluoropropan-2-yl (S)-1-((6-acetamidopyridin-3-yl)carbamoyl)-6-azaspiro[2.5]octane-6-carboxylate;

1,1,1,3,3,3-hexafluoropropan-2-yl (S)-1-((6-carbamoylpyridin-3-yl)carbamoyl)-6-azaspiro[2.5]octane-6-carboxylate;

1,1,1,3,3,3-hexafluoropropan-2-yl (S)-1-(isoxazol-3-ylcarbamoyl)-6-azaspiro[2.5]octane-6-carboxylate;

1,1,1,3,3,3-hexafluoropropan-2-yl (S)-1-((6-(methylsulfonamido)pyridin-3-yl)carbamoyl)-6-azaspiro[2.5]octane-6-carboxylate; and (S)-2-((5-(6-(((1,1,1,3,3,3-hexafluoropropan-2-yl)oxy)carbonyl)-6-azaspiro[2.5]octane-1-carboxamido)pyridin-2-yl)oxy)acetic acid; or a pharmaceutically acceptable salt thereof.

In a further embodiment, the compound of the invention is selected from the group consisting of:

1,1,1,3,3,3-hexafluoropropan-2-yl (S)-1-(pyridazin-3-ylcarbamoyl)-6-azaspiro[2.5]octane-6-carboxylate;

1,1,1,3,3,3-hexafluoropropan-2-yl (S)-1-((tetrahydro-2H-pyran-4-yl)carbamoyl)-6-azaspiro[2.5]octane-6-carboxylate;

1,1,1,3,3,3-hexafluoropropan-2-yl (S)-1-(pyridin-4-ylcarbamoyl)-6-azaspiro[2.5]octane-6-carboxylate;

1,1,1,3,3,3-hexafluoropropan-2-yl (S)-1-(pyridin-2-ylcarbamoyl)-6-azaspiro[2.5]octane-6-carboxylate;

1,1,1,3,3,3-hexafluoropropan-2-yl (S)-1-(pyrazin-2-ylcarbamoyl)-6-azaspiro[2.5]octane-6-carboxylate;

1,1,1,3,3,3-hexafluoropropan-2-yl (S)-1-(pyrimidin-5-ylcarbamoyl)-6-azaspiro[2.5]octane-6-carboxylate;

1,1,1,3,3,3-hexafluoropropan-2-yl (S)-1-(pyridazin-4-ylcarbamoyl)-6-azaspiro[2.5]octane-6-carboxylate;

1,1,1,3,3,3-hexafluoropropan-2-yl (S)-1-((1-methylpiperidin-4-yl)carbamoyl)-6-azaspiro[2.5]octane-6-carboxylate; and 1,1,1,3,3,3-hexafluoropropan-2-yl (S)-1-((4-methyltetrahydro-2H-pyran-4-yl)carbamoyl)-6-azaspiro[2.5]octane-6-carboxylate; or a pharmaceutically acceptable salt thereof.

In one embodiment the compound of the invention is 1,1,1,3,3,3-hexafluoropropan-2-yl (S)-1-(pyridazin-3-ylcarbamoyl)-6-azaspiro[2.5]octane-6-carboxylate, or a pharmaceutically acceptable salt thereof.

In one embodiment the compound of the invention is 1,1,1,3,3,3-hexafluoropropan-2-yl (S)-1-((tetrahydro-2H-pyran-4-yl)carbamoyl)-6-azaspiro[2.5]octane-6-carboxylate, or a pharmaceutically acceptable salt thereof.

In one embodiment the compound of the invention is 1,1,1,3,3,3-hexafluoropropan-2-yl (S)-1-(pyridin-4-ylcarbamoyl)-6-azaspiro[2.5]octane-6-carboxylate, or a pharmaceutically acceptable salt thereof.

In one embodiment the compound of the invention is 1,1,1,3,3,3-hexafluoropropan-2-yl (S)-1-(pyridin-2-ylcarbamoyl)-6-azaspiro[2.5]octane-6-carboxylate, or a pharmaceutically acceptable salt thereof.

In one embodiment the compound of the invention is 1,1,1,3,3,3-hexafluoropropan-2-yl (S)-1-(pyrazin-2-ylcarbamoyl)-6-azaspiro[2.5]octane-6-carboxylate, or a pharmaceutically acceptable salt thereof.

In one embodiment the compound of the invention is 1,1,1,3,3,3-hexafluoropropan-2-yl (S)-1-(pyrimidin-5-ylcarbamoyl)-6-azaspiro[2.5]octane-6-carboxylate, or a pharmaceutically acceptable salt thereof.

In one embodiment the compound of the invention is 1,1,1,3,3,3-hexafluoropropan-2-yl (S)-1-(pyridazin-3-ylcarbamoyl)-6-azaspiro[2.5]octane-6-carboxylate, or a pharmaceutically acceptable salt thereof.

In one embodiment the compound of the invention is 1,1,1,3,3,3-hexafluoropropan-2-yl (S)-1-((tetrahydro-2H-pyran-4-yl)carbamoyl)-6-azaspiro[2.5]octane-6-carboxylate.

In one embodiment the compound of the invention is 1,1,1,3,3,3-hexafluoropropan-2-yl (S)-1-(pyridin-4-ylcarbamoyl)-6-azaspiro[2.5]octane-6-carboxylate.

In one embodiment the compound of the invention is 1,1,1,3,3,3-hexafluoropropan-2-yl (S)-1-(pyridin-2-ylcarbamoyl)-6-azaspiro[2.5]octane-6-carboxylate.

In one embodiment the compound of the invention is 1,1,1,3,3,3-hexafluoropropan-2-yl (S)-1-(pyrazin-2-ylcarbamoyl)-6-azaspiro[2.5]octane-6-carboxylate.

In one embodiment the compound of the invention is 1,1,1,3,3,3-hexafluoropropan-2-yl (S)-1-(pyrimidin-5-ylcarbamoyl)-6-azaspiro[2.5]octane-6-carboxylate.

In an embodiment is provided a pharmaceutical composition comprising a compound of Formula (I),(Ia),(Ib),(Id),(Ie), or (If), or a pharmaceutically acceptable salt thereof, and one or more pharmaceutically acceptable carriers or diluents.

In a further embodiment is provided a compound of Formula (I),(Ia),(Ib),(Id),(Ie), or (If), or a pharmaceutically acceptable salt thereof, for use as a medicament.

In an embodiment is provided a compound of Formula (I),(Ia),(Ib),(Id),(Ie), or (If), or a pharmaceutically acceptable salt thereof, for use in the treatment of a disease or disorder selected from the group consisting of: pain, epilepsy/seizure disorder, Alzheimer's disease, Huntington's chorea, Huntington's disease, spacsticity, multiple sclerosis, obsessive-compulsive disorder, Parkinson's disease, depression, post-traumatic stress disorder, generalized anxiety disorder, and dystonia.

In a further embodiment is provided a compound of Formula (I),(Ia),(Ib),(Id),(Ie), or (If), or a pharmaceutically acceptable salt thereof, for use in the treatment pain. In a further embodiment the pain is neuropathic pain. In an embodiment the pain is inflammatory pain. In a further embodiment the pain is selected from the group consisting of: acute pain, cancer pain, chronic pain, pain caused by peripheral neuropathy, central pain, pain caused by spinal cord injury, pain caused by stroke, complex regional pain syndrome, fibromyalgia, migraine, vasoocclussive painful crises in sickle cell disease, pain associated with multiple sclerosis, lower back pain, abdominal pain associated with irritable bowel syndrome functional chest pain, rheumatoid arthritis, osteoarthritis, somatoform disorders, or functional dyspepsia.

In an embodiment is provided a use of a compound of Formula (I),(Ia),(Ib),(Id),(Ie), or (If), or a pharmaceutically acceptable salt thereof, in the manufacture of a medicament for the treatment of a disease or disorder selected from the group consisting of: pain, epilepsy/seizure disorder, Alzheimer's disease, Huntington's chorea, Huntington's disease, spacsticity, multiple sclerosis, obsessive-compulsive disorder, Parkinson's disease, depression, post-traumatic stress disorder, generalized anxiety disorder, and dystonia.

In an embodiment is provided a method for the treatment of a disease or disorder selected from the group consisting of: pain, epilepsy/seizure disorder, Alzheimer's disease, Huntington's chorea, Huntington's disease, spacsticity, multiple sclerosis, obsessive-compulsive disorder, Parkinson's disease, depression, post-traumatic stress disorder, generalized anxiety disorder, and dystonia comprising the administration of a therapeutically effective amount of a compound of Formula (I),(Ia),(Ib),(Id),(Ie), or (If), or a pharmaceutically acceptable salt thereof to a patient in need thereof.

The compounds of this invention are generally utilized as the free substance or as a pharmaceutically acceptable salt thereof. When a compound of formula (I) contains a free base such salts may be prepared in a conventional manner by treating a solution or suspension of a free base of formula (I) with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid and sulfonic acids, such as methanesulfonic acid, ethanesulfonic acid, toluenesulfonic acid and benzene-sulfonic acid.

The compounds of the present invention may have one or more asymmetric centres and it is intended that any optical isomers (i.e. enantiomers or diastereomers) as separated, enantiopure or partially purified optical isomers and any mixtures thereof including racemic mixtures, i.e. a mixture of stereoisomers, are included within the scope of the invention.

In this context is understood that when specifying the enantiomeric form, the compound is in enantiomeric excess, e.g. essentially in an enantiopure form. Accordingly, one embodiment of the invention relates to a compound of the invention having an enantiomeric excess (ee) of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials or by the use of chiral catalysis. Absolutestereochemistry may be determined by methods known to the skilled person, such as by Vibrational Circular Dichroism (VCD) Spectroscopy analysis.

Furthermore, when a double bond or a fully or partially saturated ring system is present in the molecule geometric isomers may be formed. It is intended that any geometric isomers as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

Included in this invention are also isotopically labelled compounds, which are similar to those claimed in Formula (I), (Ia), (Ib), (Ic), (Id), (Ie), or (If), or a pharmaceutically acceptable salt thereof, wherein one or more atoms are represented by an atom of the same element having an atomic mass or mass number different from the atomic mass or mass number usually found in nature (e.g., $^2$H, $^3$H, $^{11}$C, $^{13}$C, $^{15}$N, $^{18}$F and the like). Particular mention is made of $^2$H substituted compounds i.e. compounds wherein one or more H atoms are represented by deuterium.

In one embodiment of the invention one or more of the hydrogen atoms of the compound of Formula (I), (Ia), (Ib), (Ic), (Id), (Ie), or (If), or a pharmaceutically acceptable salt thereof, are represented by deuterium. It is recognized that elements are present in natural isotopic abundances in most synthetic compounds, and result in inherent incorporation of deuterium. However, the natural isotopic abundance of hydrogen isotopes such as deuterium is immaterial (about 0.015%) relative to the degree of stable isotopic substitution of compounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordinarily skilled artisan.

Pharmaceutical Compositions

The above-mentioned compounds or pharmaceutically acceptable salts may be in a composition as the sole active ingredient or in combination with other active ingredients. Additionally, one or more pharmaceutically acceptable carriers or diluents may be in the composition.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragées, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, creams, gels, inhalants, dermal patches, implants, etc.

Conveniently, the compounds of Formula (I), (Ia), (Ib), (Ic), (Id), (Ie), or (If) are administered in a unit dosage form containing said compounds in an amount of about 0.1 to 500 mg, such as 1 mg, 2 mg, 4 mg, 6 mg, 8 mg, 10 mg, 20 mg, 30 mg, 40 mg, 50 mg 100 mg, 150 mg, 200 mg or 250 mg of a compound of the present invention.

For parenteral administration, solutions of the compounds of Formula (I), (Ia), (Ib), (Ic), (Id), (Ie), or (If) in sterile aqueous solution, aqueous propylene glycol may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art. Aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phosphor lipids, polyoxyethylene and water. The pharmaceutical compositions formed by combining the compounds of Formula (I), (Ia), (Ib), (Ic), (Id), (Ie), or (If), or a pharmaceutically acceptable salt thereof and the pharmaceutically acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by compression of the mixture in a conventional tabletting machine. Examples of adjuvants or diluents comprise corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Conditions for Treatment

The compounds of the present invention are intended for treatment of diseases and disorders which are linked to regulation of endocannabinoid system signaling activities where a MAGL inhibitor may be therapeutically beneficial. As described above the compounds of the invention may be beneficial in indications which pathological hallmarks include excessive neurotransmission, neuroinflammation or neurodegeneration. Hence, in one embodiment is provided a compound of Formula (I), (Ia), (Ib), (Ic), (Id), (Ie), or (If), or pharmaceutically acceptable salt thereof, for use in the treatment of a disorder or disease selected from the group consisting of pain, epilepsy/seizure disorder, Alzheimer's disease, Huntington's chorea, Huntington's disease, multiple sclerosis, obsessive-compulsive disorder, Parkinson's disease, depression, post-traumatic stress disorder, generalized anxiety disorder, and dystonia.

Multiple Sclerosis Symptomatic Treatment

Nearly all MS patients of all subtypes have one or more symptoms of spasticity, pain, disturbed sleep, bladder dysfunction, and fatigue. Disease modifying therapies do not improve symptoms. Spasticity affects over 80% of MS patients; 34% have moderate, severe, or total spasticity. Severe spasticity is related to cost and level of care, and is independently related to quality of life in MS. Two recent reviews support the use of exocannabinoids for the treatment of MS spasticity and pain (Whiting et al., JAMA. 2015); (Hill et al., JAMA. 2015).

An exocannabinoid preparation is an approved treatment for spasticity associated with MS. Sativex, an oromucosal spray mixture of the $CB_1$ agonist THC and another *cannabis* plant derived alcohol, cannabidiol, was shown to decrease self-reported spasticity related symptoms. In a pivotal trial of Sativex using a randomized withdrawal design, there was improvement with continuing Sativex in spasm frequency, sleep disruption by spasticity, subject global impression of change, carer global impression of change, and physician global impression of change. Other clinical trials have shown activity of a variety of exocannabinoids in spasticity due to MS (Zajicek et al., Lancet. 2003; Collin et al., Eur J Neurol. 2007; Collin et al., Neurol Res. 2010). These parallel group studies exemplify the clinical trial design and endpoints that could be used to show a MAGL inhibitor benefits spasticity in MS.

In an embodiment is provided a compound of Formula (I), (Ia), (Ib), (Ic), (Id), (Ie), or (If), or pharmaceutically acceptable salt thereof, for use in the treatment of multiple sclerosis.

In an embodiment is provided a compound of Formula (I), (Ia), (Ib), (Ic), (Id), (Ie), or (If), or pharmaceutically acceptable salt thereof, for use in the treatment of one or more symptoms in multiple sclerosis selected from fatigue, spasticity, depression, behavioral disturbance, irritability-agitation, and pain.

It is believed that a MAGL inhibitor will also be beneficial in the treatment of indications related to autoimmune encephalomyelitis. Hence, in a further embodiment is provided a compound of Formula (I), (Ia), (Ib), (Ic), (Id), (Ie), or (If), or pharmaceutically acceptable salt thereof, for use in the treatment of Rasmussen encephalitis, Systemic lupus erythematosus, Behcet's disease, Hashimoto's encephalopathy, and Sydenham's chorea.

Amyotrophic Lateral Sclerosis

In Pryce et al. Handb Exp Pharmacol. 2015; 231: 213-31 it is described how Patients of Amyotrophic Lateral Sclerosis (ALS) typically experience muscle weakness and/or fasciculations which gradually worsen, bulbar symptoms and eventually respiratory problems. In preclinical models of ALS it has been suggested that cannabinoids may have a significant neuroprotective effect.

Hence, in an embodiment is provided a compound of Formula (I), (Ia), (Ib), (Ic), (Id), (Ie), or (If), or pharmaceutically acceptable salt thereof for use in the treatment of amyotrophic lateral sclerosis.

Central Pain

Central pain is neuropathic pain caused by lesion or dysfunction of the central nervous system, for example, post-stroke, multiple sclerosis, neuromyelitis optica, idiopathic inflammatory transverse myelitis, spinal cord injury, brachial-radial pain syndrome, and central craniofacial pain. Exocannabinoids have demonstrated activity in central pain associated with multiple sclerosis. A 4-week randomized double-blind placebo-controlled parallel group trial with MS and central pain using an oromucosal spray, THC/CBD, containing the $CB_1$ agonist delta-9-tetrahydrocannabinol and cannabidiol (another *Cannabis*-derived alcohol) showed that the active agent was superior to placebo in reducing the mean intensity of pain (NRS-11) and of sleep disturbance (Rog et al., Neurology. 2005). The same THC/CBD preparation was studied in a larger group of MS patients with central neuropathic pain utilizing a two-stage design; in the second phase of this study, the time to treatment failure (primary endpoint) statistically favored THC/CBD, as did an improvement in the Pain NRS-11 and sleep quality (Langford et al., J Neurol. 2013). Additionally, nabilone, a synthetic $CB_1$ agonist structurally related to THC, showed efficacy in MS-induced central neuropathic pain (Turcotte et al., Pain Med. 2015). Studies of exocannabinoids in central pain have indicated activity, suggesting MAGL inhibitors may also have efficacy in treatment of central pain. Hence, in an embodiment is provided a compound of Formula (I), (Ia), (Ib), (Ic), (Id), (Ie), or (If), or pharmaceutically acceptable salt thereof, for use in the treatment of central pain.

Fibromyalgia

Fibromyalgia (FM) is a common, chronic, idiopathic condition characterized by diffuse body pain and the presence of pressure allodynia. Duloxetine and pregabalin are specifically labeled for the treatment of pain in FM, and tricyclic antidepressants like amitriptyline, while not specifically labeled for FM treatment, are first-line agents. There is no clear pathological understanding of FM, and no validated preclinical model. However, studies of exocannabinoids in FM have indicated activity, suggesting MAGL inhibitors may also have efficacy in treatment of FM. Measures of pain (e.g., NRS-11, Pain VAS) and the Fibromyalgia Impact Questionnaire (FIQ), which measures limitations in several activities of daily living impacted by FM, have demonstrated activity of drugs in FM clinical trials (Burckhardt et al., The fibromyalgia impact questionnaire: development and validation, J Rheumatol. 1991, 728-33); (Mease et al., The Journal of Rheumatology January 2008, 35 (1) 20-30)). A survey of Spanish FM patients who were *cannabis* users and non-users was performed to identify the effects of *cannabis* on a range of disease symptoms such as pain, stiffness, well-being, relaxation and drowsiness; perceived relief was common for pain, sleep disturbances, stiffness, mood disorders and anxiety (Fiz, PLoS One, 2011, 6(4), e18440). In an 8-week, 40-patient study, compared with placebo the exocannabinoid nabilone improved pain measured on a 10 cm VAS, and improved the FIQ domain of anxiety and the FIQ total score (Skrabek et al., J Pain. 2008). In a 31-patient study, compared with amitriptyline nabilone improved the index of sleep (Insomnia Severity Index) and was judged non-inferior on measures of pain (McGill Pain Questionnaire) and the FIQ (Ware, Anesth Analg, 2010, 110(2), 604-10). Hence, in an embodiment is provided a compound of Formula (I), (Ia), (Ib), (Ic), (Id), (Ie), or (If), or pharmaceutically acceptable salt thereof, for use in the treatment of fibromyalgia.

Migraine

Migraine is a common episodic disorder of head and facial pain. Migraine attacks can be acutely treated with NSAIDs, acetaminophen, a variety of triptans (e.g., sumatriptan), and antiemetics, but some migraine sufferers have pain unresponsive to existing treatment options. Data suggest that endocannabinoid pathways may be relevant in migraine. In patients with chronic migraine and probable analgesic-overuse headache, CSF samples showed higher levels of the endocannabinoid palmitoylethanolamide and lower levels of anandamide compared with healthy controls (Sarchielli et al., Neuropsychopharmacology. 2007). In addition, a retrospective chart review of patients attending a medical marijuana clinic with a primary diagnosis of migraine headaches found a decrease in the frequency of migraine headaches after initiating marijuana therapy (Rhyne et al., Pharmacotherapy. 2016), suggesting MAGL inhibitors may also have efficacy in treatment of migraine. Hence, in an embodiment is provided a compound of Formula (I), (Ia), (Ib), (Ic), (Id), (Ie), or (If), or pharmaceutically acceptable salt thereof, for use in the treatment of migraine.

In a further embodiment, disclosed herein is a compound of Formula (I), (Ia), (Ib), (Ic), (Id), (Ie), or (If), or pharmaceutically acceptable salt thereof, for use in the treatment of prevention of chronic migraine, acute treatment of migraine and hemiplegic migraine.

Mood and Anxiety Disorders

Mood and anxiety disorders are chronic, disabling conditions that impose cost to both patients and society. In relation to mood and anxiety disorders, the endocannabinoid system has received increasingly more intention in recent years. A recent study by Bedse G et al., Transl Psychiatry. 2018 it is suggested that the use of MAGL inhibitors may have a beneficial effect in stress-related psychopathology. Hence, in an embodiment, disclosed herein is provided a compound of Formula (I), (Ia), (Ib), (Ic), (Id), (Ie), or (If), or a pharmaceutically acceptable salt thereof, for use in the treatment of mood and anxiety disorders.

In a further embodiment, disclosed herein, is provided a compound of Formula (I), (Ia), (Ib), (Ic), (Id), (Ie), or (If) or pharmaceutically acceptable salt thereof, for use in the treatment of mood and anxiety disorders selected from depression and GAD.

In a further embodiment disclosed herein, is provided a compound of Formula (I), (Ia), (Ib), (Ic), (Id), (Ie), or (If) or pharmaceutically acceptable salt thereof, for use in the treatment of depression selected from major depressive disorder, treatment-resistant depression, catatonic depression, melancholic depression, atypical depression, psychotic depression, perinatal depression, postpartum depression, bipolar depression, including bipolar I depression and bipolar II depression, and mild, moderate or severe depression. In a further embodiment disclosed herein, a compound of Formula (I), (Ia), (Ib), (Ic), (Id), (Ie), or (If), or pharmaceutically acceptable salt thereof, for use in the treatment of major depressive disorder.

In a further embodiment, disclosed herein, is provided a compound of Formula (I), (Ia), (Ib), (Ic), (Id), (Ie), or (If) or pharmaceutically acceptable salt thereof, for use in the treatment of GAD.

Post-Traumatic Stress Disorder

Post-traumatic stress disorder (PTSD) is a trauma- or stress-related disorder. Patients having PTSD will have the symptoms of flashback of trauma, avoidance, hyperarousal, and negative cognitions/moods. In a review by Hill et al., Neuropsychopharmacology 2018 it is suggested that drugs that affect endocannabinoid signaling (such as MAGL inhibitors) may be beneficial in treating symptoms of PTSD. Hence, in an embodiment, disclosed herein, is provided a compound of Formula (I), (Ia), (Ib), (Ic), (Id), (Ie), or (If) or a pharmaceutically acceptable salt thereof, for use in the treatment of PTSD.

In some embodiments disclosed herein are methods of modulating the activity of MAGL. Contemplated methods, for example, comprise exposing said enzyme to a compound described herein. The ability of compounds described herein to modulate or inhibit MAGL is evaluated by procedures known in the art and/or described herein. Another aspect of this disclosure provides methods of treating a disease associated with expression or activity of MAGL in a patient.

Epilepsy

In a study by Sugaya et al., Cell Rep. 2016, it is suggested 2-AG is crucial for suppressing seizures. Hence, in another embodiment, a compound of Formula (I), (Ia), (Ib), (Ic), (Id), (Ie), or (If) is used in the treatment of a epilepsy/seizure disorder.

In an embodiment, a compound of Formula (I), (Ia), (Ib), (Ic), (Id), (Ie), or (If) is used in the treatment of a epilepsy/seizure disorder selected from acute repetitive seizures, temporal lobe epilepsy, Dravet syndrome, Lennox Gastaut syndrome or Angelman syndrome.

Combination Therapies

Also contemplated herein are combination therapies, for example, co-administering a compound of the invention and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is affected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

For example, e.g., for contemplated treatment of pain, a disclosed compound is co-administered with another therapeutic for pain such as an opioid, a cannabinoid receptor ($CB_1$ or $CB_2$) modulator, a COX-2 inhibitor, acetaminophen, and/or a non-steroidal anti-inflammatory agent. Additional therapeutics e.g., for the treatment of pain that are co-administered, include morphine, pregabalin, gabapentin, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

Experimental Section

General Synthesis

Compounds of Formula (I), (Ia), (Ib), (Ic), (Id), (Ie), and (If) or salts thereof may be prepared by a synthetic process. The following schemes 1-3 and examples 1-34 are representative of methods useful for synthesizing one or more of compounds according to Formula (I), (Ia), (Ib), (Ic), (Id), (Ie), and (If). The provided schemes 1-3 are not intended to restrain the scope of the invention in any way.

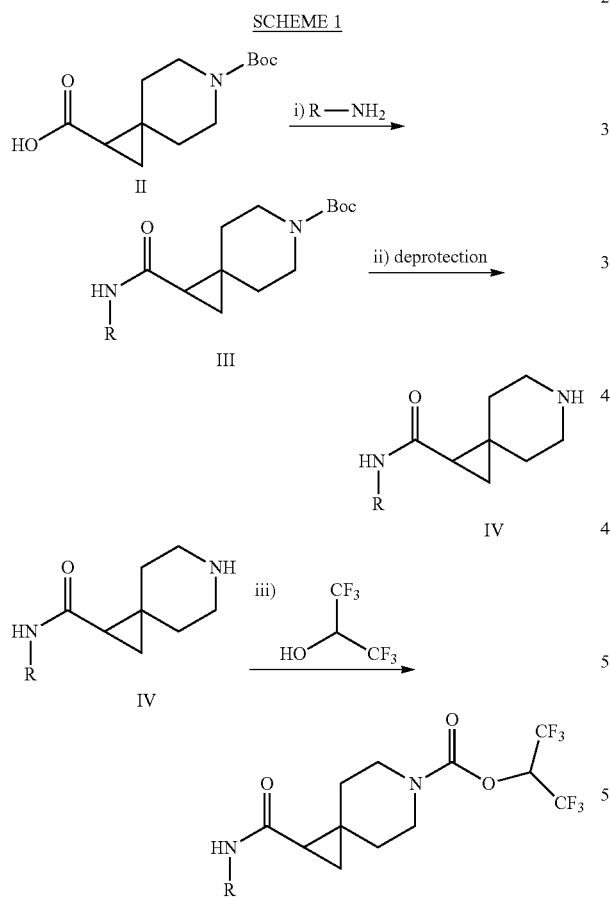

halide. The amide formation step i) is followed by a deprotection in step ii) carried out in a suitable acid and solvent (e.g. TFA and DCM) to provide an intermediate of type IV. The deprotection step is followed coupling reaction in step iii) comprising a reaction with intermediate of type IV with 1,1,1,3,3,3-hexafluoropropan-2-ol carried out in presence of a coupling agent such as CDI in an appropriate solvent (e.g. MeCN) to provide a compound of the present invention.

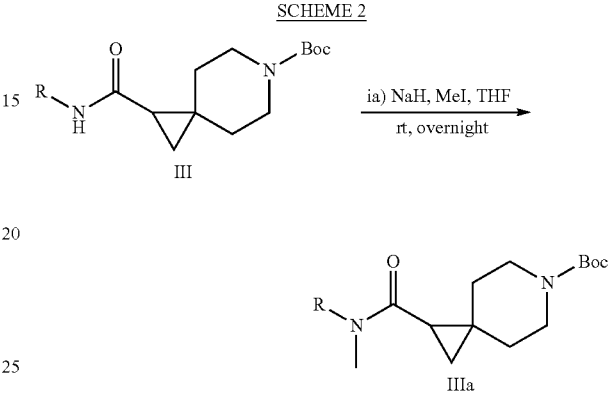

In an alternative synthesis, compounds are provided in which the amide linker is a tertiary amine (R may be a heteroaryl or a heterocycle). As seen in scheme 2 an intermediate of type III is subjected to an alkylation in step ia) to form an intermediate of type IIIa. An intermediate of type IIIa may subsequently be subjected to deprotection step ii) and coupling step iii) as described in scheme 1 to provide a compound of the invention.

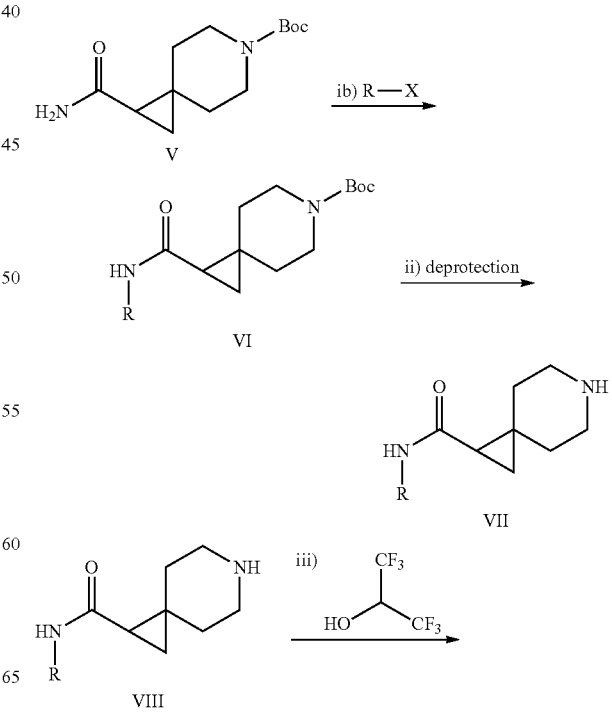

As shown in scheme 1, 6-(tert-butoxycarbonyl)-6-azaspiro[2.5]octane-1-carboxylic acid (II) may be reacted with a primary amine (R may be a heteroaryl or a heterocycle) in the presence of a suitable base and solvent (e.g. DIPEA and THF) to form an intermediate of type III. Alternatively an intermediate of type II may be subjected to an acid halogenation reagent prior to step i) to form an acid

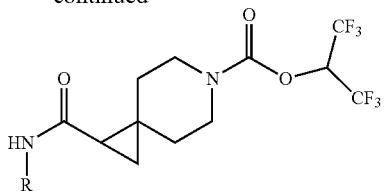

As shown in scheme 3 some compounds of the invention may be made by starting from commercially available t-butyl 1-carbamoyl-6-azaspiro[2.5]octane-6-carboxylate subjected to an aryl halide or a heteroaryl halide (X is a halogen; R is heteroaryl or phenyl) to form an intermediate of type VI. The rest of the synthesis (steps ii) and iii)) follow a similar procedure as shown in scheme 1.

List of Abbreviations

As used above, and throughout the description of the invention, the following abbreviations, unless otherwise indicated, shall be understood to have the following meanings:

| | |
|---|---|
| ACN or MeCN | acetonitrile |
| Bn | benzyl |
| BOC or Boc | tert-butyl carbamate |
| CDI | 1,1'-carbonyldiimidazole |
| Cy | cyclohexyl |
| DCE | dichloroethane (ClCH$_2$CH$_2$Cl) |
| DCM | dichloromethane (CH$_2$Cl$_2$) |
| DIPEA or DIEA | diisopropylethylamine |
| DMAP | 4-(N,N-dimethylamino)pyridine |
| DMF | dimethylformamide |
| DMA | N,N-dimethylacetamide |
| DMSO | dimethylsulfoxide |
| equiv | equivalent(s) |
| Et | ethyl |
| EtOH | ethanol |
| EtOAc | ethyl acetate |
| HATU | 1-[bis(dimethylamino)methylene]-1H-1,2,3-triazolo[4,5-b]pyridinium 3-oxid hexafluorophosphate |
| HPLC | high performance liquid chromatography |
| LAH | lithium aluminum hydride |
| Me | methyl |
| MeOH | methanol |
| MS | mass spectroscopy |
| NMM | N-methylmorpholine |
| NMR | nuclear magnetic resonance |
| PMB | para-methoxybenzyl |
| TEA | triethylamine |
| TFA | trifluoroacetic acid |
| THF | tetrahydrofuran |
| TLC | thin layer chromatography |

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (□) and coupling constants (J) are reported in Hertz. For proton spectra the solvent peak was used as the reference peak.

Analytical Methods
LC-MS Methods

The analytical LC-MS system is equipped with Shimadzu LCMS-2020, PDA detector (operating at 254 nm), ELSD detector, and ESI-source operating in positive ion mode.
LC-conditions:

Method A: The column is Kinetex EVO C18 50*3.0 mm, 2.6 µm operating at 40° C. with 1.2 mL/min of a binary gradient consisting of water+5 mM NH$_4$HCO$_3$ (A) and ACN (B). The retention times ($t_R$) are expressed in minutes based on UV-trace at 254 nm.

| Gradient: | 0.01 min | 10% B |
|---|---|---|
| | 2.00 min | 95% B |
| | 2.70 min | 95% B |
| | 2.75 min | 10% B |
| Total run time: | 3.00 min | |

Method B: The column is Kinetex EVO C18 50*3.0 mm, 2.6 µm operating at 40° C. with 1.2 mL/min of a binary gradient consisting of water+5 mM NH$_4$HCO$_3$ (A) and ACN (B). The retention times ($t_R$) are expressed in minutes based on UV-trace at 254 nm.

| Gradient: | 0.01 min | 10% B |
|---|---|---|
| | 3.20 min | 60% B |
| | 4.00 min | 95% B |
| | 4.80 min | 95% B |
| | 4.90 min | 10% B |
| Total run time: | 5.00 min | |

Method C: The column is Express C18 50*3.0 mm operating at 40° C. with 1.5 mL/min of a binary gradient consisting of water+0.05% TFA (A) and ACN+0.05% TFA (B). The retention times ($t_R$) are expressed in minutes based on UV-trace at 254 nm.

| Gradient: | 0.01 min | 20% B |
|---|---|---|
| | 3.50 min | 50% B |
| | 4.30 min | 95% B |
| | 4.00 min | 95% B |
| | 5.10 min | 5% B |
| Total run time: | 5.30 min | |

Method D: The column is HALO C18 30*3.0 mm, 2 µm operating at 40° C. with 1.5 mL/min of a binary gradient consisting of water+0.05 TFA (A) and ACN+0.05% TFA (B). The retention times ($t_R$) are expressed in minutes based on UV-trace at 200 nm.

| Gradient: | 0.01 min | 5% B |
|---|---|---|
| | 1.20 min | 100% B |
| | 1.80 min | 100% B |
| | 1.82 min | 5% B |
| Total run time: | 2.0 min | |

Method E: The column is Poroshell HPH-C18 50*3.0 mm, 2.7 µm operating at 40° C. with 1.2 mL/min of a binary gradient consisting of water+6.5 mM NH$_4$HCO$_3$+Ammonia (pH=10) (A) and ACN (B). The retention times ($t_R$) are expressed in minutes based on UV-trace at 254 nm.

| Gradient: | 0.01 min | 10% B |
|---|---|---|
| | 2.00 min | 95% B |

-continued

|  | 2.70 min | 95% B |
|---|---|---|
|  | 2.75 min | 10% B |
| Total run time: | 3.00 min |  |

Method F: The column is Express C18 50*3.0 mm operating at 40° C. with 1.5 mL/min of a binary gradient consisting of water+0.05 TFA (A) and ACN+0.05% TFA (B). The retention times ($t_R$) are expressed in minutes based on UV-trace at 254 nm.

| Gradient: | 0.01 min | 5% B |
|---|---|---|
|  | 2.00 min | 95% B |
|  | 2.70 min | 95% B |
|  | 2.80 min | 5% B |
| Total run time: | 3.0 min |  |

Method G: The column is Kinetex EVO C18 50*3.0 mm, 2.6 µm operating at 40° C. with 1.2 mL/min of a binary gradient consisting of water+5 mM $NH_4HCO_3$ (A) and ACN (B). The retention times ($t_R$) are expressed in minutes based on UV-trace at 254 nm.

| Gradient: | 0.01 min | 30% B |
|---|---|---|
|  | 3.20 min | 70% B |
|  | 4.00 min | 95% B |
|  | 4.80 min | 95% B |
|  | 4.90 min | 10% B |
| Total run time: | 5.00 min |  |

Method H: The column is Poroshell HPH-C18 50*3.0 mm, 2.7 µm operating at 40° C. with 1.2 mL/min of a binary gradient consisting of water+5 mM $NH_4HCO_3$ (A) and acetonitrile (B). The retention times ($t_R$) are expressed in minutes based on UV-trace at 254 nm.

| Gradient: | 0.01 min | 10% B |
|---|---|---|
|  | 3.20 min | 60% B |
|  | 4.00 min | 95% B |
|  | 4.80 min | 95% B |
|  | 4.90 min | 10% B |
| Total run time: | 5.00 min |  |

Method I: The column is CORTECS C18 50*2.1 mm, 2.7 µm operating at 40° C. with 1.5 mL/min of a binary gradient consisting of water+0.05% trifluoroacetic acid (A) and acetonitrile+0.05% trifluoroacetic acid (B). The retention times ($t_R$) are expressed in minutes based on UV-trace at 254 nm.

| Gradient: | 0.01 min | 5% B |
|---|---|---|
|  | 2.00 min | 100% B |
|  | 2.80 min | 100% B |
|  | 2.90 min | 5% B |
| Total run time: | 3.00 min |  |

Method J: The column is CORTECS C18 50*2.1 mm, 2.7 µm operating at 40° C. with 1.0 mL/min of a binary gradient consisting of water+0.05% trifluoroacetic acid (A) and acetonitrile+0.05% trifluoroacetic acid (B). The retention times ($t_R$) are expressed in minutes based on UV-trace at 254 nm.

| Gradient: | 0.01 min | 5% B |
|---|---|---|
|  | 3.20 min | 60% B |
|  | 4.10 min | 95% B |
|  | 5.00 min | 95% B |
|  | 5.10 min | 5% B |
| Total run time: | 5.30 min |  |

Method K: The column is Express C18 50*3.0 mm operating at 40° C. with 1.5 mL/min of a binary gradient consisting of water+0.05% TFA (A) and ACN+0.05% TFA (B). The retention times ($t_R$) are expressed in minutes based on UV-trace at 254 nm.

| Gradient: | 0.01 min | 30% B |
|---|---|---|
|  | 3.50 min | 60% B |
|  | 4.30 min | 95% B |
|  | 4.00 min | 95% B |
|  | 5.10 min | 5% B |
| Total run time: | 5.30 min |  |

Method L: The column is Kinetex EVO C18 50*3.0 mm, 2.6 µm operating at 40° C. with 1.2 mL/min of a binary gradient consisting of water+5 mM $NH_4HCO_3$ (A) and ACN (B). The retention times ($t_R$) are expressed in minutes based on UV-trace at 254 nm.

| Gradient: | 0.01 min | 30% B |
|---|---|---|
|  | 3.20 min | 50% B |
|  | 4.00 min | 95% B |
|  | 4.80 min | 95% B |
|  | 4.90 min | 10% B |
| Total run time: | 5.00 min |  |

Method M: The column is Poroshell HPH-C18 50*3.0 mm, 2.7 µm operating at 40° C. with 1.2 mL/min of a binary gradient consisting of water+6.5 mM $NH_4HCO_3$+Ammonia (pH=10) (A) and ACN (B). The retention times ($t_R$) are expressed in minutes based on UV-trace at 254 nm.

| Gradient: | 0.01 min | 10% B |
|---|---|---|
|  | 3.00 min | 60% B |
|  | 4.00 min | 95% B |
|  | 4.70 min | 95% B |
|  | 4.90 min | 10% B |
| Total run time: | 5.00 min |  |

Method N: The column is Kinelex XB-C18 50*3.0 mm, 2.6 µm operating at 45° C. with 1.5 mL/min of a binary gradient consisting of water+0.05% TFA (A) and CAN+0.05% TFA (B). The retention times ($t_R$) are expressed in minutes based on UV-trace at 254 nm.

| Gradient: | 0.01 min | 5% B |
|---|---|---|
|  | 3.00 min | 50% B |
|  | 4.00 min | 100% B |
|  | 4.60 min | 100% B |
|  | 4.70 min | 5% B |
| Total run time: | 5.20 min |  |

Method O: The column is HALO C18 30*3.0 mm, 2 µm operating at 40° C. with 1.5 mL/min of a binary gradient consisting of water+0.05 TFA (A) and ACN+0.05 TFA (B). The retention times ($t_R$) are expressed in minutes based on UV-trace at 200 nm.

| Gradient: | 2.20 min | 100% B |
| --- | --- | --- |
|  | 2.70 min | 100% B |
|  | 2.72 min | 5% B |
| Total run time: | 3.0 min | |

Method P: The column is Express C18 50 mm operating at 40° C. with 1.5 mL/min of a binary gradient consisting of water+0.05% TFA (A) and ACN+0.05% TFA (B). The retention times ($t_R$) are expressed in minutes based on UV-trace at 254 nm.

| Gradient: | 0.01 min | 2% B |
| --- | --- | --- |
|  | 2.00 min | 100% B |
|  | 2.70 min | 100% B |
|  | 2.75 min | 2% B |
| Total run time: | 3.0 min | |

$^1$H NMR Method $^1$H NMR spectra were recorded at 300 or 400 MHz on a Bruker Avance HD. Chemical shift values are expressed in ppm-values relative to tetramethylsilane. The following abbreviations or their combinations are used for multiplicity of NMR signals: br=broad, d=doublet, dd=doublet of doublets, dt—doublet of triplets, hept=heptet, m=multiplet, q=quartet, quint=quintet, s=singlet, t=triplet, td=triplet of doublets.

Example 1: 1,1,1,3,3,3-Hexafluoropropan-2-yl (±)1-(pyridin-3-ylcarbamoyl)-6-azaspiro[2.5]octane-6-carboxylate

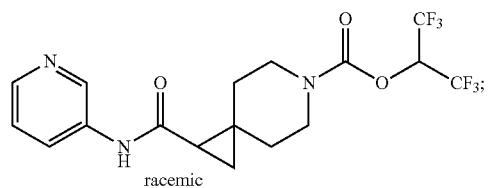 [SMILES: O=C(Nc1cccnc1)C1CC12CCN(C(=O)OC(C(F)(F)F)C(F)(F)F)CC2]

racemic

Step 1: Synthesis of t-butyl 1-(pyridin-3-ylcarbamoyl)-6-azaspiro[2.5]octane-6-carboxylate

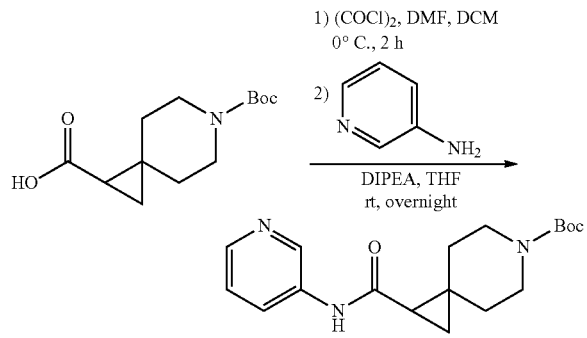

A vial was charged with 6-(t-butoxycarbonyl)-6-azaspiro[2.5]octane-1-carboxylic acid (255 mg) (Nantong MYBio-pharm. Co., Ltd.), DMF (10 mg) and DCM (10 mL). Oxalyl chloride (189 mg) was added dropwise at 0° C. The resulting solution was stirred for 2 h at 0° C. and concentrated under reduced pressure to provide t-butyl 1-(chlorocarbonyl)-6-azaspiro[2.5]octane-6-carboxylate. Another vial was charged with pyridin-3-amine (94.0 mg), THF (5 mL) and DIPEA (258 mg). t-Butyl 1-(chlorocarbonyl)-6-azaspiro[2.5]octane-6-carboxylate in THF (5 mL) was added dropwise at 0° C. The resulting solution was stirred overnight at room temperature and quenched by adding water (10 mL). The mixture was extracted with EtOAc (3×10 mL) and the organic layers were combined, washed with brine (3×10 mL), dried over anhydrous sodium sulfate, filtered and concentrated under reduced pressure. The residue was chromatographed on a silica gel column with EtOAc/petroleum ether (2/1) to provide t-butyl 1-(pyridin-3-ylcarbamoyl)-6-azaspiro[2.5]octane-6-carboxylate (160 mg). LCMS (ESI, m/z): 332 [M+H]$^+$.

Step 2: Synthesis of N-(pyridin-3-yl)-6-azaspiro[2.5]octane-1-carboxamide

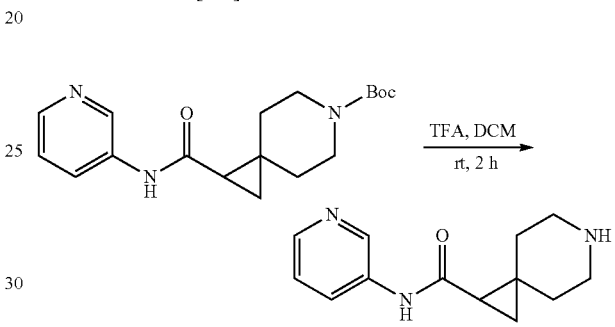

A vial was charged with t-butyl 1-(pyridin-3-ylcarbamoyl)-6-azaspiro[2.5]octane-6-carboxylate (160 mg), DCM (5 mL) and TFA (5 mL). The resulting solution was stirred for 2 h at room temperature and concentrated under reduced pressure. The crude product was dissolved in water (10 mL). The pH value of the solution was adjusted to 8 with sodium bicarbonate saturated solution. The mixture was extracted with DCM (3×10 mL) and the organic layers were combined, washed with brine (2×10 mL), dried over anhydrous sodium sulfate, filtered and concentrated under reduced pressure to provide N-(pyridin-3-yl)-6-azaspiro[2.5]octane-1-carboxamide (112 mg). LCMS (ESI, m/z): 232 [M+H]$^+$.

Step 3: Synthesis of 1,1,1,3,3,3-hexafluoropropan-2-yl (±)1-(pyridin-3-ylcarbamoyl)-6-azaspiro[2.5]octane-6-carboxylate

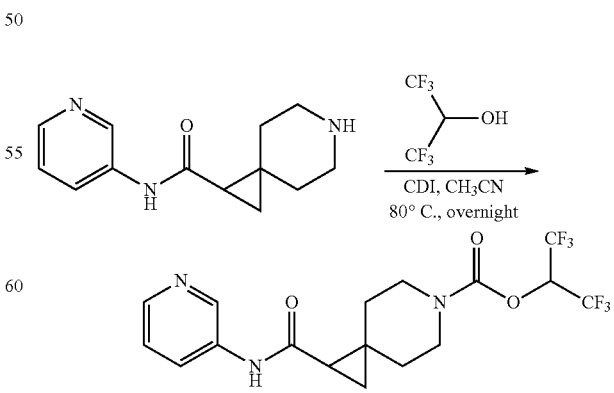

A vial was charged with 1,1,1,3,3,3-hexafluoropropan-2-ol (489 mg), ACN (5 mL), 1,1'-carbonyldiimidazole (94.0 mg) and N-(pyridin-3-yl)-6-azaspiro[2.5]octane-1-carboxamide (112 mg). The resulting solution was stirred overnight at 80° C. and quenched by adding water (10 mL). The mixture was extracted with EtOAc (3×10 mL) and the organic layers were combined, washed with brine (3×10 mL), dried over anhydrous sodium sulfate, filtered and concentrated under reduced pressure. The crude product was purified by preparative HPLC using the following gradient conditions: 40% ACN/60% Phase A increasing to 70% ACN over 7 min, then to 100% ACN over 0.1 min, holding at 100% ACN for 1.9 min, then reducing to 40% ACN over 0.1 min, and holding at 40% for 1.9 min, on a Waters 2767-5 Chromatograph. Column: X-bridge Prep C18, 19*150 mm 5 μm; Mobile phase: Phase A: aqueous $NH_4HCO_3$ (0.05%); Phase B: ACN; Detector, UV220 & 254 nm. Purification afforded 32.7 mg of 1,1,1,3,3,3-hexafluoropropan-2-yl (±)1-(pyridin-3-ylcarbamoyl)-6-azaspiro[2.5]octane-6-carboxylate. $^1$H NMR (300 MHz, Chloroform-d) δ 8.57 (br, 1H), 8.40-8.32 (m, 2H), 8.17 (d, J=7.8 Hz, 1H), 7.30-7.29 (m, 1H), 5.86-5.69 (m, 1H), 3.72-3.49 (m, 4H), 1.97-1.84 (m, 2H), 1.62-1.54 (m, 2H), 1.46-1.39 (m, 2H), 1.03-0.95 (m, 1H). LCMS (ESI, m/z): 426 $[M+H]^+$.

Example 2: 1,1,1,3,3,3-Hexafluoropropan-2-yl (S)-1-(pyridin-3-ylcarbamoyl)-6-azaspiro[2.5]octane-6-carboxylate and Example 3: 1,1,1,3,3,3-Hexafluoropropan-2-yl (R)-1-(pyridin-3-ylcarbamoyl)-6-azaspiro[2.5]octane-6-carboxylate

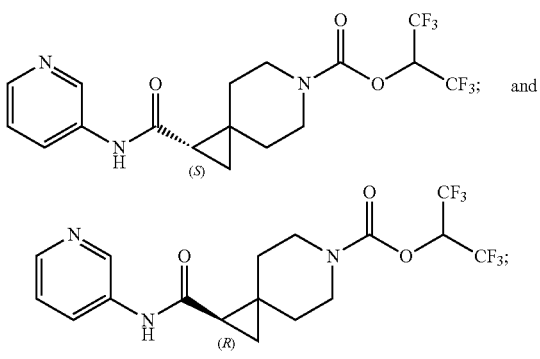

The racemic mixture prepared in Example 1 (32.7 mg) was separated into the two enantiomers by preparative chiral HPLC (Column: CHIRALPAK IG, 2*25 cm, 5 μm; Mobile Phase A: Hex (0.1% DEA)-HPLC, Mobile Phase B: EtOH-HPLC; Flow rate: 20 mL/min; Gradient: 5% B to 5% B over 17 min; UV220/254 nm) to afford:

Example 2 9.0 mg of 1,1,1,3,3,3-hexafluoropropan-2-yl (S)-1-(pyridin-3-ylcarbamoyl)-6-azaspiro[2.5]octane-6-carboxylate. $^1$H NMR (400 MHz, Chloroform-d) δ 8.79 (br, 1H), 8.49 (br, 1H), 8.24 (br, 1H), 8.01 (s, 1H), 7.33 (br, 1H), 5.77 (br, 1H), 3.73-3.63 (m, 1H), 3.59-3.39 (m, 3H), 1.96 (br, 2H), 1.87-1.59 (m, 2H), 1.48 (br, 1H), 1.40 (s, 1H), 1.04 (s, 1H). $t_R$=11.695 min. LCMS (Method A) (ESI, m/z): 426 $[M+H]^+$.
And the corresponding enantiomer Example 3 9.8 mg of 1,1,1,3,3,3-hexafluoropropan-2-yl (R)-1-(pyridin-3-ylcarbamoyl)-6-azaspiro[2.5]octane-6-carboxylate. $^1$H NMR (400 MHz, Chloroform-d) δ 8.72 (br, 1H), 8.35 (br, 1H), 8.22 (br, 1H), 8.04 (s, 1H), 7.32 (br, 1H), 5.87 (br, 1H), 3.80-3.70 (m, 1H), 3.73-3.41 (m, 3H), 1.87 (br, 2H), 1.63-1.59 (m, 2H), 1.48 (br, 1H), 1.40 (s, 1H), 1.04 (s, 1H). $t_R$=14.452 min. LCMS (Method B) (ESI, m/z): 426 $[M+H]^+$.

Determination of the Absolute Configurations of Example 2 and Example 3

The absolute configuration of Example 3 was determined using vibrational circular dichroism (VCD) (Appl. Spectrosc. 65 (7), 699 (2011)). The spectrum was obtained with a ChirallR with DualPEM VCD-spectrometer and was compared with calculated values (methodology and basis set for DFT calculations=B3LYP/6311Gdp with CPCM (chloroform)). VCD spectrum analysis of Example 3 to the calculated VCD spectrum for the (R)-enantiomer establishes Example 3 as the (R)-enantiomer and therefore Example 2 as the (S)-enantiomer. These samples were analyzed by chiral HPLC under the following conditions: Column: CHIRALPAK IC, 3.0*100 mm, 3 mm; mobile phase: Phase A: $CO_2$, Phase B: IPA (0.1% DEA); flow rate: 2 mL/min; gradient: 10% to 50% in 2.0 min, hold 1.0 min at 50%; detection: 220 nm.

Example 2: First Eluting Enantiomer ($t_R$=0.944 Min)

Example 3: Second eluting enantiomer ($t_R$=1.154 min)

Preparation of Intermediates with Known Absolute Configuration: Synthesis

With this information in hand, the building blocks, Intermediate 2A and Intermediate 3A were converted to Example 2 and Example 3 as described below. The absolute configurations of the enantiomers were then determined by comparison of elution order with the known Examples 2 and 3 from above. The details of the synthesis of Example 2 and Example 3 with known absolute configurations are outlined below.

Step 1: Synthesis of 1-benzyl 6-(t-butyl) 6-azaspiro[2.5]octane-1,6-dicarboxylate

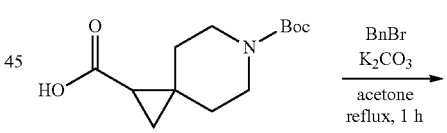

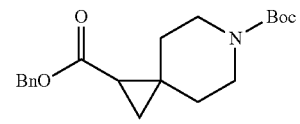

Into a flask purged and maintained with an inert atmosphere of nitrogen, was added a solution of 6-(t-butoxycarbonyl)-6-azaspiro[2.5]octane-1-carboxylic acid (240 g) in acetone (5 L). Benzyl bromide (170.6 g) and $K_2CO_3$ (259.8 g) were added. The resulting solution was refluxed for 2-3 h. The reaction was then cooled to room temperature and filtered. The filter cake was washed with ethyl acetate. The combined filtrate was concentrated under vacuum, resulting in 297 g of crude 1-benzyl 6-(t-butyl) 6-azaspiro[2.5]octane-1,6-dicarboxylate.

Step 2: Synthesis of Benzyl 6-azaspiro[2.5]octane-1-carboxylate Hydrochloride

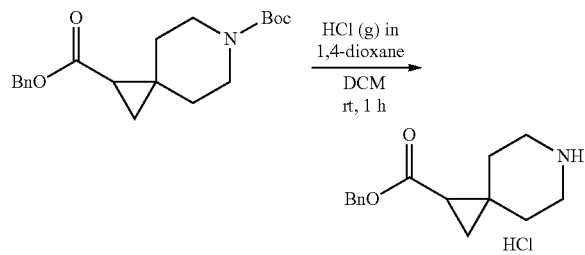

Into a flask purged and maintained with an inert atmosphere of nitrogen, was added a solution of crude 1-benzyl 6-(t-butyl) 6-azaspiro[2.5]octane-1,6-dicarboxylate (297 g) in DCM (1.5 L). HCl (g) in 1,4-dioxane (4M, 1.5 L) was added dropwise. The resulting solution was stirred for 1 h at room temperature and concentrated under vacuum. The crude product was slurried with Et$_2$O (10 V) to provide 198.3 g of benzyl 6-azaspiro[2.5]octane-1-carboxylate.

Step 3: Synthesis of 1-benzyl 6-(1,1,1,3,3,3-hexafluoropropan-2-yl) 6-azaspiro[2.5]octane-1,6-dicarboxylate

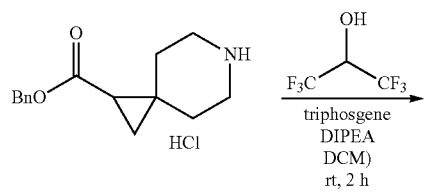

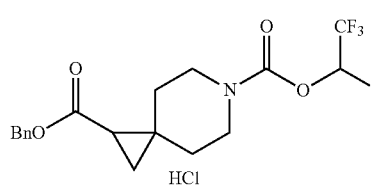

Into a flask purged and maintained with an inert atmosphere of nitrogen, was added a solution of 1,1,1,3,3,3-hexafluoropropan-2-ol (393 g) in DCM (2 L). The mixture was cooled to 0° C. and triphosgene (106.9 g) was added in batches. DIPEA (550 g) was then added dropwise at 0-10° C. The mixture was stirred for 1.5 h at this temperature. A solution of benzyl 6-azaspiro[2.5]octane-1-carboxylate hydrochloride (198 g) in DCM (2 L) was then added dropwise at 0° C. The resulting solution was stirred at room temperature for 2 h. The reaction mixture was quenched by pouring into water (6 L), then extracted with DCM (2×2 L). The combined organic layers were washed with brine (1×3 L), dried over anhydrous sodium sulfate and concentrated under vacuum. The residue was chromatographed on a silica gel column with EtOAc/petroleum ether (1/30), resulting in 265 g of 1-benzyl 6-(1,1,1,3,3,3-hexafluoropropan-2-yl) 6-azaspiro[2.5]octane-1,6-dicarboxylate.

Step 4: Isolation of (S)-1-benzyl 6-(1,1,1,3,3,3-hexafluoropropan-2-yl) 6-azaspiro[2.5]octane-1,6-dicarboxylate (Intermediate 2A) and (R)-1-benzyl 6-(1,1,1,3,3,3-hexafluoropropan-2-yl) 6-azaspiro[2.5]octane-1,6-dicarboxylate (Intermediate 3A)

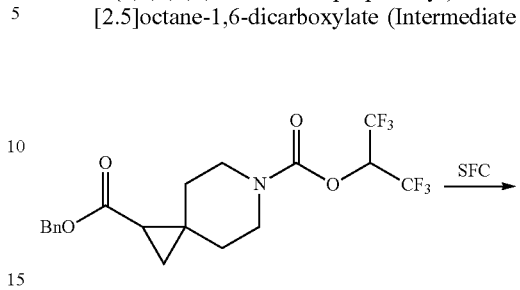

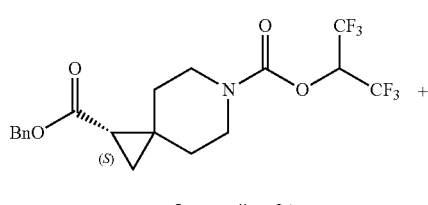

Intermediate 2A

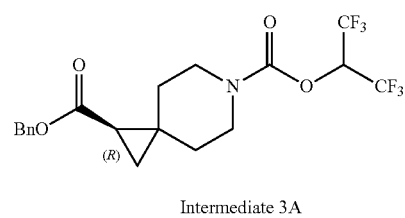

Intermediate 3A

The racemic mixture of 1-benzyl 6-(1,1,1,3,3,3-hexafluoropropan-2-yl) 6-azaspiro[2.5]octane-1,6-dicarboxylate (265 g) prepared in Step 3 was separated by preparative SFC-HPLC (Column: CHIRALPAK IG-3 3.0*50 mm, 3 μm; Mobile Phase: Phase A: CO$_2$, phase B: MeOH (0.1% DEA); Flow rate: 2 mL/min; Gradient: 2% B; 220 nm) to afford the following, whose absolute configurations were determined after preparation of the final products (Example 2 and Example 3) and comparison of elution order on a chiral column:

Intermediate 2A; 110 g of (S)-1-benzyl 6-(1,1,1,3,3,3-hexafluoropropan-2-yl) 6-azaspiro[2.5]octane-1,6-dicarboxylate. $^1$H NMR (300 MHz, Chloroform-d) δ 7.46-7.28 (m, 5H), 5.75 (p, J=6.3 Hz, 1H), 5.13 (s, 2H), 3.57 (m, 3H), 3.28 (m, 1H), 1.86-1.61 (m, 3H), 1.56-1.36 (m, 2H), 1.27-1.19 (m, 1H), 0.99 (dd, J=8.2, 4.7 Hz, 1H). t$_R$=1.572 min. LCMS (Method O) (ESI, m/z): 440 [M+H]$^+$ and Intermediate 3A; 100 g of 1-benzyl 6-(1,1,1,3,3,3-hexafluoropropan-2-yl) (R)-6-azaspiro[2.5]octane-1,6-dicarboxylate. $^1$H NMR (300 MHz, Chloroform-d) δ 7.36 (d, J=2.6 Hz, 5H), 5.75 (p, J=6.3 Hz, 1H), 5.13 (d, J=1.4 Hz, 2H), 3.71-3.40 (m, 3H), 3.39-3.13 (m, 1H), 1.71 (ddd, J=29.4, 9.4, 5.2 Hz, 3H), 1.57-1.36 (m, 2H), 1.23 (d, J=5.2 Hz, 1H), 0.99 (dd, J=8.1, 4.7 Hz, 1H). t$_R$=1.572 min. LCMS (Method O) (ESI, m/z): 440 [M+H]$^+$.

Step 5-1: Synthesis of (S)-6-(((1,1,1,3,3,3-hexafluoropropan-2-yl)oxy)carbonyl)-6-azaspiro[2.5]octane-1-carboxylic Acid (Intermediate 2B)

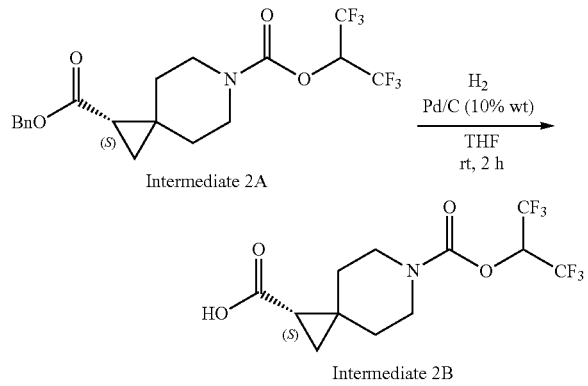

A solution of 1-benzyl 6-(1,1,1,3,3,3-hexafluoropropan-2-yl) (S)-6-azaspiro[2.5]octane-1,6-dicarboxylate (110 g) in THF (2 L) was added to a flask. Wet Pd/C (22 g, 10% wt, 50% $H_2O$) was added to the mixture. The resulting mixture was purged and replaced with $H_2$ three times and then stirred under $H_2$ for 3 h at room temperature. The mixture was filtered, and the filter cake was washed with THF (2×500 mL). The combined filtrate was concentrated under vacuum, and the crude product was co-evaporated with toluene (2×1 L), resulting in 90 g of crude (S)-6-(((1,1,1,3,3,3-hexafluoropropan-2-yl)oxy)carbonyl)-6-azaspiro[2.5]octane-1-carboxylic acid. 0.2 g of crude product was purified by silica column chromatography to provide pure characterization data. $^1$H NMR (300 MHz, Chloroform-d) δ 5.78 (h, J=6.3 Hz, 1H), 3.79-3.40 (m, 4H), 1.85 (q, J=6.1 Hz, 2H), 1.65 (dd, J=8.0, 5.4 Hz, 1H), 1.54 (dq, J=10.9, 5.8, 5.0 Hz, 2H), 1.28 (t, J=5.1 Hz, 1H), 1.09 (dd, J=8.1, 4.8 Hz, 1H). $t_R$=1.441 min. LCMS (Method O) (ESI, m/z): 350 [M+H]$^+$.

Step 6-1: Synthesis of 1,1,1,3,3,3-hexafluoropropan-2-yl (S)-1-(pyridin-3-ylcarbamoyl)-6-azaspiro[2.5]octane-6-carboxylate (Example 2)

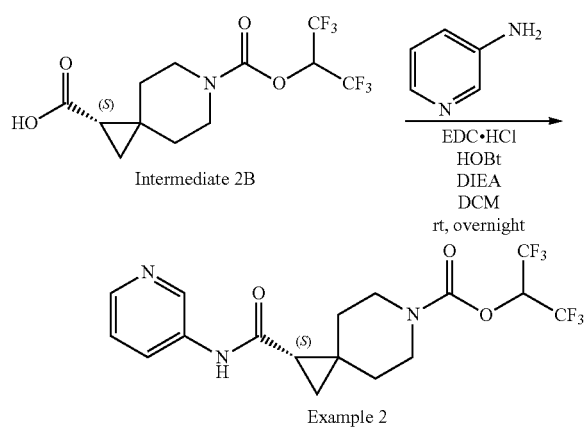

Into a reaction vial was placed a solution of crude (S)-6-(((1,1,1,3,3,3-hexafluoropropan-2-yl)oxy)carbonyl)-6-azaspiro[2.5]octane-1-carboxylic acid (50 mg) in DCM (1 mL). EDC.HCl (30 mg) and HOBt (39 mg) were added, and the resulting mixture was stirred for 15 min. Pyridin-3-amine (18 mg) and DIEA (37 mg) were added. The final reaction mixture was stirred overnight at room temperature. The mixture was diluted with $H_2O$ (10 mL) and extracted with DCM (1×5 mL). The combined organic phases were dried over anhydrous $Na_2SO_4$ and concentrated. The crude product was purified with by preparative HPLC to afford 1,1,1,3,3,3-hexafluoropropan-2-yl (S)-1-(pyridin-3-ylcarbamoyl)-6-azaspiro[2.5]octane-6-carboxylate (35 mg). $^1$H NMR (300 MHz, Chloroform-d) δ 8.59 (s, 1H), 8.27 (dd, J=41.0, 6.5 Hz, 2H), 7.96 (s, 1H), 7.30 (dd, J=8.4, 4.7 Hz, 1H), 5.76 (dd, J=11.6, 6.0 Hz, 1H), 3.79-3.35 (m, 4H), 1.85 (d, J=6.0 Hz, 2H), 1.58 (dd, J=8.0, 5.3 Hz, 2H), 1.51-1.35 (m, 2H), 1.02 (dd, J=8.1, 4.7 Hz, 1H). $t_R$=1.255 min. LCMS (Method O) (ESI, m/z): 426 [M+H]$^+$. CHIRALPAK IC, 3.0*100 mm, 3 um; mobile phase: Phase A: $CO_2$, phase B: IPA (0.1% DEA); flow rate: 2 mL/min; gradient: 10% to 50% in 2.0 min, hold 1.0 min at 50%; detection: 220 nm: $t_R$=1.928 min.

The absolute configuration of Intermediate 2B was determined as the (S)-enantiomer after converting Intermediate 2B to Example 2 and comparing the elution order of Example 2 (made in step 6-1) with Example 3 (made in step 6-2) via chiral chromatography.

Step 5-2: Synthesis of (R)-6-(((1,1,1,3,3,3-hexafluoropropan-2-yl)oxy)carbonyl)-6-azaspiro[2.5]octane-1-carboxylic Acid (Intermediate 3B)

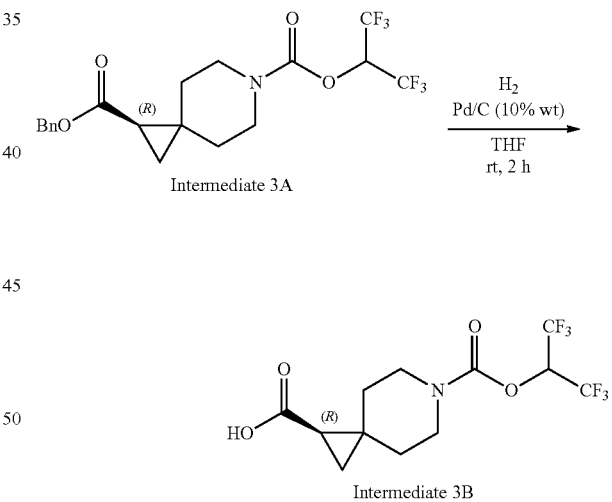

Into a flask was placed a solution of 1-benzyl 6-(1,1,1,3,3,3-hexafluoropropan-2-yl) (R)-6-azaspiro[2.5]octane-1,6-dicarboxylate (1.9 g, 4.3 mmol, 1.0 eq.) in THF (40 mL). Wet Pd/C (0.38 g, 10% wt, 50% $H_2O$) was added to the mixture. The resulting mixture was purged and replaced with $H_2$ three times and stirred under $H_2$ for 2 h at room temperature. The mixture was filtered, and the filter cake was washed with THF (2×50 mL). The combined filtrate was concentrated under vacuum, to provide in 1.5 g of crude (R)-6-(((1,1,1,3,3,3-hexafluoropropan-2-yl)oxy)carbonyl)-6-azaspiro[2.5]octane-1-carboxylic acid that was used directly in the next step without further purification.

Step 6-2: Synthesis of 1,1,1,3,3,3-hexafluoropropan-2-yl (R)-1-(pyridin-3-ylcarbamoyl)-6-azaspiro[2.5]octane-6-carboxylate (Example 3)

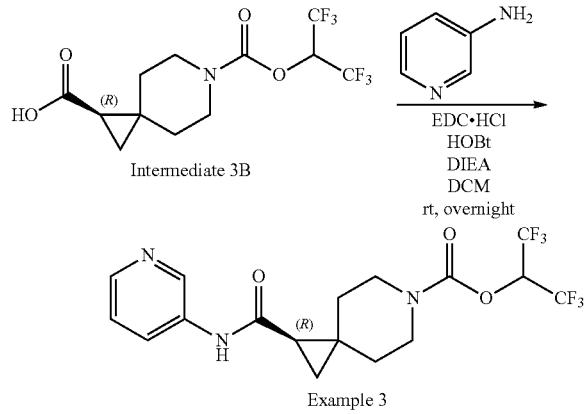

Into a reaction vial was placed a solution of crude (R)-6-(((1,1,1,3,3,3-hexafluoropropan-2-yl)oxy)carbonyl)-6-azaspiro[2.5]octane-1-carboxylic acid (50 mg) in DCM (1 mL). EDC.HCl (30 mg) and HOBt (39 mg) were added, and the resulting mixture was stirred for 15 min. Pyridin-3-amine (18 mg) and DIEA (37 mg) were added. The final reaction mixture was stirred overnight at room temperature. The mixture was diluted with $H_2O$ (10 mL) and extracted with DCM (1×5 mL). The combined organic phases were dried over anhydrous $Na_2SO_4$, filtered, and concentrated. The crude product was purified by preparative HPLC to afford 1,1,1,3,3,3-hexafluoropropan-2-yl (R)-1-(pyridin-3-ylcarbamoyl)-6-azaspiro[2.5]octane-6-carboxylate (50 mg) as a white solid. $^1$H NMR (300 MHz, Chloroform-d) δ 8.59 (t, J=3.2 Hz, 1H), 8.33 (dd, J=4.8, 1.4 Hz, 1H), 8.17 (d, J=8.6 Hz, 2H), 7.32-7.26 (m, 1H), 5.76 (h, J=6.1 Hz, 1H), 3.74-3.35 (m, 4H), 1.86 (t, J=6.0 Hz, 2H), 1.59 (dd, J=8.0, 5.2 Hz, 2H), 1.37 (t, J=5.0 Hz, 2H), 1.00 (dd, J=8.0, 4.6 Hz, 1H). $t_R$=1.266 min. LCMS (ESI, m/z): 426 [M+H]$^+$.

CHIRALPAK IC, 3.0*100 mm, 3 μm; mobile phase: Phase A: $CO_2$, phase B: IPA (0.1% DEA); flow rate: 2 mL/min; gradient: 10% to 50% in 2.0 min, hold 1.0 min at 50%; detection: 220 nm: $t_R$=2.030 min.

The absolute configuration of Intermediate 3B was determined as the (R)-enantiomer after comparing the elution order of Example 2 (made in step 6-1) with Example 3 (made in step 6-2) via chiral chromatography Intermediates 2B and 3B with known absolute configurations were used in the synthesis of examples 5, 6, 8 and 9, as mentioned below.

Example 4: 1,1,1,3,3,3-Hexafluoropropan-2-yl (±)1-(pyridazin-3-ylcarbamoyl)-6-azaspiro[2.5]octane-6-carboxylate

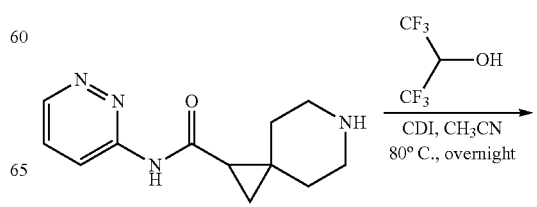

racemic

Step 1: Synthesis of t-butyl 1-(pyridazin-3-ylcarbamoyl)-6-azaspiro[2.5]octane-6-carboxylate

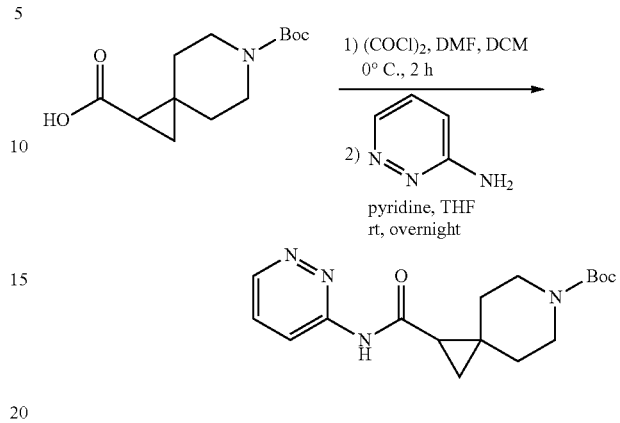

t-Butyl 1-(pyridazin-3-ylcarbamoyl)-6-azaspiro[2.5]octane-6-carboxylate was prepared with 6-[(t-butoxy)carbonyl]-6-azaspiro[2.5]octane-1-carboxylic acid (600 mg), DMF (17.4 mg), oxalyl chloride (386 mg), pyridazin-3-amine (245 mg), and t-butyl 1-(chlorocarbonyl)-6-azaspiro[2.5]octane-6-carboxylate as in Example 1, Step 1 to provide the title compound (360 mg). LCMS (ESI, m/z): 333 [M+H]$^+$.

Step 2: Synthesis of N-(pyridazin-3-yl)-6-azaspiro[2.5]octane-1-carboxamide

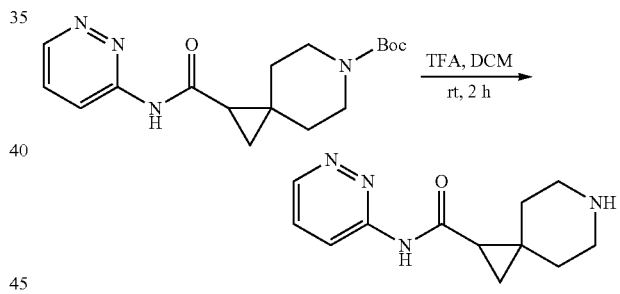

N-(pyridazin-3-yl)-6-azaspiro[2.5]octane-1-carboxamide was prepared with t-butyl 1-(pyridazin-3-ylcarbamoyl)-6-azaspiro[2.5]octane-6-carboxylate (180 mg) and TFA (5 mL) as described in Example 1, Step 2 to provide the title compound (125 mg). LCMS (ESI, m/z): 233 [M+H]$^+$.

Step 3: Synthesis of 1,1,1,3,3,3-hexafluoropropan-2-yl 1-[(pyridazin-3-yl)carbamoyl]-6-azaspiro[2.5]octane-6-carboxylate

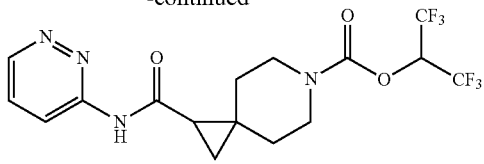

1,1,1,3,3,3-Hexafluoropropan-2-yl 1-[(pyridazin-3-yl)carbamoyl]-6-azaspiro[2.5]octane-6-carboxylate was prepared with N-(pyridazin-3-yl)-6-azaspiro[2.5]octane-1-carboxamide (125 mg), 1, 1'-carbonyldiimidazole (105 mg) and 1,1,1,3,3,3-hexafluoropropan-2-ol (904 mg) as described in Example 1, Step 3 to provide the title compound (33.0 mg).

Example 5: 1,1,1,3,3,3-Hexafluoropropan-2-yl (R)-1-(pyridazin-3-ylcarbamoyl)-6-azaspiro[2.5]octane-6-carboxylate and Example 6: 1,1,1,3,3,3-Hexafluoropropan-2-yl (S)-1-(pyridazin-3-ylcarbamoyl)-6-azaspiro[2.5]octane-6-carboxylate

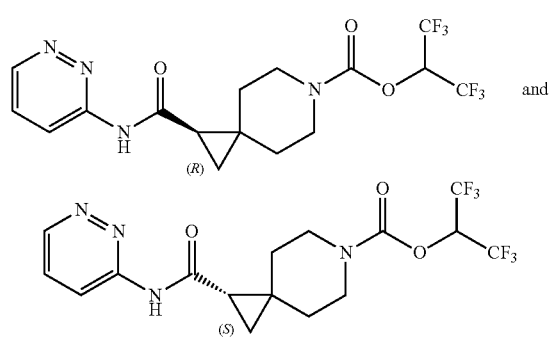

The racemic mixture prepared in Example 4 (33.0 mg) was separated into the two enantiomers by preparative chiral HPLC (Column: CHIRALPAK IC, 2*25 cm, 5 μm; Mobile Phase A: Hex-HPLC, Mobile Phase B: EtOH-HPLC; Flow rate: 20 mL/min; Gradient: 30% B to 30% B over 7 min; UV220/254 nm) to afford:

Example 5: 15.3 mg of 1,1,1,3,3,3-hexafluoropropan-2-yl (R)-1-(pyridazin-3-ylcarbamoyl)-6-azaspiro[2.5]octane-6-carboxylate. ¹H NMR (400 MHz, Chloroform-d) δ 12.2-12.0 (m, 1H), 8.87 (s, 1H), 8.75 (br, 1H), 7.66 (br, 1H), 5.80-5.74 (m, 1H), 3.72-3.64 (m, 3H), 3.43-3.37 (m, 1H), 2.49 (t, J=6.4 Hz, 1H), 1.94-1.86 (m, 2H), 1.70-1.58 (m, 2H), 1.44 (s, 1H), 1.17-1.14 (m, 1H). $t_R$=5.118 min. LCMS (Method C) (ESI, m/z): 427 [M+H]⁺. CHIRALPAK AD, 3.0*100 mm, 3 μm; mobile phase: Phase A: CO₂, phase B: MeOH (0.1% DEA); flow rate: 2 mL/min; gradient: 10% to 50% in 2.0 min, hold 1.0 min at 50%; detection: 220 nm: $t_R$=0.814 min.

And the corresponding enantiomer

Example 6: 10.1 mg of 1,1,1,3,3,3-hexafluoropropan-2-yl (S)-1-(pyridazin-3-ylcarbamoyl)-6-azaspiro[2.5]octane-6-carboxylate. ¹H NMR (400 MHz, Chloroform-d) δ 11.2 (s, 1H), 8.87 (s, 1H), 8.75 (br, 1H), 7.66 (br, 1H), 5.80-5.74 (m, 1H), 3.72-3.64 (m, 3H), 3.43-3.37 (m, 1H), 2.49 (t, J=6.4 Hz, 1H), 1.94-1.86 (m, 2H), 1.70-1.58 (m, 2H), 1.44 (s, 1H), 1.17-1.14 (m, 1H). $t_R$=6.025 min. LCMS (Method C) (ESI, m/z): 427 [M+H]⁺. CHIRALPAK AD, 3.0*100 mm, 3 μm; mobile phase: Phase A: CO₂, phase B: MeOH (0.1% DEA); flow rate: 2 mL/min; gradient: 10% to 50% in 2.0 min, hold 1.0 min at 50%; detection: 220 nm: $t_R$=1.080 min.

Synthesis of Example 5 with known Intermediate 3B

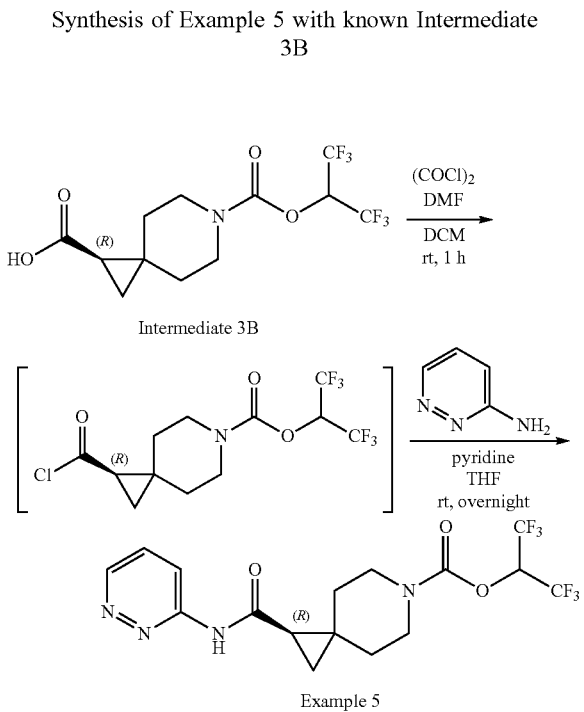

(R)-6-(((1,1,1,3,3,3-hexafluoropropan-2-yl)oxy)carbonyl)-6-azaspiro[2.5]octane-1-carboxylic acid (Intermediate 3B) (200 mg), DMF (5 mg) and THF (10 mL) were added to a flask. (COCl)₂ (100 mg) was added dropwise with stirring at 0° C. over 60 min. The solvent was then removed and THF (2 mL) was added. The resulting solution was added dropwise to a solution of pyridine (90 mg) in THF (2 mL) and pyridazin-3-amine (66 mg). The solution was stirred for 1 hr at room temperature. The reaction was then quenched by the addition of water. The resulting solution was extracted with EtOAc (3×20 mL) and the organic layers combined and dried over anhydrous sodium sulfate, concentrated under vacuum and slurried with hexane/EA (10/1, 10 V) to provide 62 mg of 1,1,1,3,3,3-hexafluoropropan-2-yl (R)-1-(pyridazin-3-ylcarbamoyl)-6-azaspiro[2.5]octane-6-carboxylate. LCMS (ESI, m/z): 427 [M+H]+. 1H NMR (300 MHz, Chloroform-d) δ 10.81 (s, 1H), 8.86 (d, J=4.7 Hz, 1H), 8.61 (d, J=9.1 Hz, 1H), 7.55 (s, 1H), 5.86-5.61 (m, 1H), 3.76-3.27 (m, 4H), 2.28 (dd, J=7.9, 5.4 Hz, 1H), 1.86 (q, J=6.4 Hz, 4H), 1.41 (t, J=4.9 Hz, 1H), 1.10 (dd, J=7.9, 4.6 Hz, 1H). $t_R$=1.439 min. LCMS (Method O) (ESI, m/z): 427 [M+H]⁺. CHIRALPAK AD, 3.0*100 mm, 3 mm; mobile phase: Phase A: CO₂, phase B: MeOH (0.1% DEA); flow rate: 2 mL/min; gradient: 10% to 50% in 2.0 min, hold 1.0 min at 50%; detection: 220 nm: $t_R$=0.805 min.

Note that the retention time of the product prepared here with Intermediate 3B matches the retention time of Example 5 prepared above, in which case the racemic product was separated into its enantiomers by SFC, thus confirming the assigned absolute configuration assigned to Example 5 in the preparation above.

Synthesis of Example 6 with Known Intermediate 2B

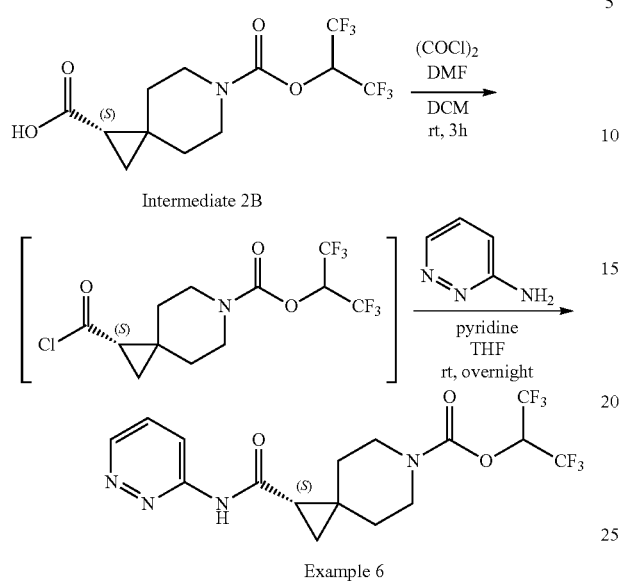

Into a flask purged and maintained with an inert atmosphere of nitrogen, was added (S)-6-(((1,1,1,3,3,3-hexafluoropropan-2-yl)oxy)carbonyl)-6-azaspiro[2.5]octane-1-carboxylic acid (Intermediate 2B) (38.5 g), DCM (800 mL) and DMF (0.40 g). The mixture was cooled to 0° C. and (COCl)$_2$ (11.5 g) was added dropwise. The resulting mixture was stirred at room temperature for 3 h. The mixture was then concentrated under vacuum to obtain crude acyl chloride for later use. Into another flask purged and maintained with an inert atmosphere of nitrogen, was added pyridazin-3-amine (12.6 g), pyridine (17.4 g) and THF (800 mL). The solution of previous acyl chloride in THF (500 mL) was added dropwise at room temperature. The resulting solution was stirred overnight at room temperature. After complete reaction, the mixture was diluted with 3 L of ice water and extracted with EtOAc (2×1 L). The combined organic phases were washed with H2O (1×1 L) and brine (1×1 L), dried over anhydrous Na$_2$SO$_4$ and concentrated under vacuum. The residue was purified by silica gel column chromatography with EtOAc/petroleum ether (1/10), to provide 34.3 g of product. The product was slurried with n-hexane (20 V) and filtered to obtain 26.7 g of 1,1,1,3,3,3-hexafluoropropan-2-yl (S)-1-(pyridazin-3-ylcarbamoyl)-6-azaspiro[2.5]octane-6-carboxylate. The product was isolated by slurry with n-heptane (10 V) to provide 24.13 g of 1,1,1,3,3,3-hexafluoropropan-2-yl (S)-1-[(pyridazin-3-yl)carbamoyl]-6-azaspiro[2.5]octane-6-carboxylate (Example 6). $^1$H NMR (300 MHz, Chloroform-d) δ 10.82 (s, 1H), 8.87 (d, J=4.7 Hz, 1H), 8.61 (d, J=9.1 Hz, 1H), 7.55 (s, 1H), 5.90-5.62 (m, 1H), 3.73-3.27 (m, 4H), 2.26 (dd, J=8.0, 5.4 Hz, 1H), 1.95-1.72 (m, 4H), 1.41 (t, J=5.0 Hz, 1H), 1.11 (dd, J=7.9, 4.6 Hz, 1H). $t_R$=1.443 min. LCMS (Method O) (ESI, m/z): 427 [M+H]$^+$. CHIRALPAK AD, 3.0*100 mm, 3 mm; mobile phase: Phase A: CO$_2$, phase B: MeOH (0.1% DEA); flow rate: 2 mL/min; gradient: 10% to 50% in 2.0 min, hold 1.0 min at 50%; detection: 220 nm: $t_R$=1.032 min.

Note that the retention time of the product prepared here with Intermediate 2B matches the retention time of Example 6 prepared above, in which case the racemic product was separated into its enantiomers by SFC, thus confirming the assigned absolute configuration assigned to Example 6 in the preparation above.

Example 7: 1,1,1,3,3,3-Hexafluoropropan-2-yl (±)-1-((tetrahydro-2H-pyran-4-yl)carbamoyl)-6-azaspiro[2.5]octane-6-carboxylate

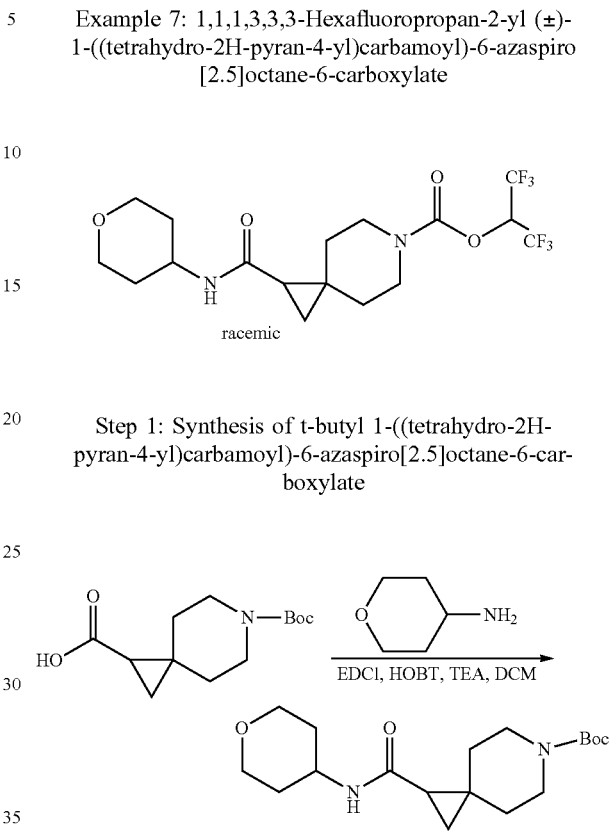

racemic

Step 1: Synthesis of t-butyl 1-((tetrahydro-2H-pyran-4-yl)carbamoyl)-6-azaspiro[2.5]octane-6-carboxylate A flask was charged with 6-(t-butoxycarbonyl)-6-azaspiro [2.5]octane-1-carboxylic acid (300 mg), EDCI (294 mg), HOBT (238 mg), TEA (356 mg), tetrahydro-2H-pyran-4-amine (154 mg) and DCM (5 mL). The reaction mixture was stirred for 12 h at room temperature. The reaction was then quenched with water (10 mL), extracted with DCM (2*15 mL) and concentrated under reduced pressure. The crude product was purified by silica gel chromatography (DCM:MeOH=20:1) to provide t-butyl 1-((tetrahydro-2H-pyran-4-yl)carbamoyl)-6-azaspiro[2.5]octane-6-carboxylate (352 mg). LCMS (ESI, m/z): 339 [M+H]$^+$.

Step 2: Synthesis of N-(tetrahydro-2H-pyran-4-yl)-6-azaspiro[2.5]octane-1-carboxamide

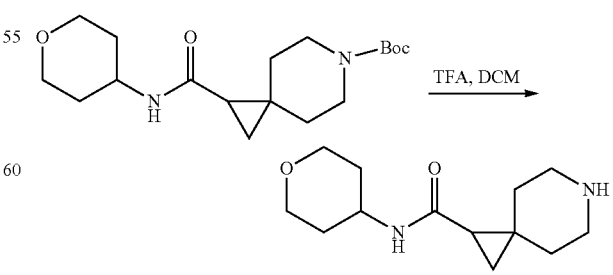

N-(tetrahydro-2H-pyran-4-yl)-6-azaspiro[2.5]octane-1-carboxamide was prepared with t-butyl 1-((tetrahydro-2H- pyran-4-yl)carbamoyl)-6-azaspiro[2.5]octane-6-carboxylate (352 mg), TFA (1.5 mL) and DCM (3 mL) as described in Example 1, Step 2 to provide 500 mg (crude) of the title compound. LCMS (ESI, m/z): 239[M+H]+.

Step 3: Synthesis of 1,1,1,3,3,3-hexafluoropropan-2-yl (±)1-((tetrahydro-2H-pyran-4-yl)carbamoyl)-6-azaspiro[2.5]octane-6-carboxylate

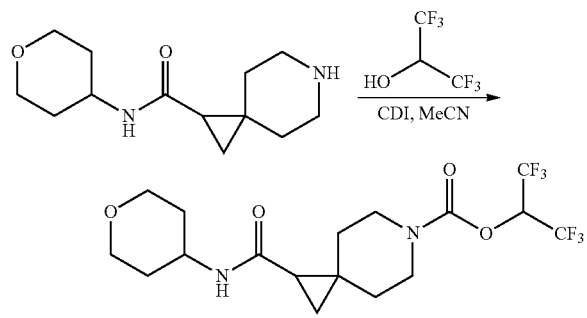

1,1,1,3,3,3-Hexafluoropropan-2-yl 1-((tetrahydro-2H-pyran-4-yl)carbamoyl)-6-azaspiro[2.5]octane-6-carboxylate was prepared from N-(tetrahydro-2H-pyran-4-yl)-6-azaspiro[2.5]octane-1-carboxamide (480 mg), CDI (392 mg) and 1,1,1,3,3,3-hexafluoropropan-2-ol (3389 mg) as described in Example 1, Step 3 to provide the crude product (377 mg). The crude product was purified by reverse phase column chromatography to provide the title compound (88 mg).

Example 8: 1,1,1,3,3,3-Hexafluoropropan-2-yl (S)-1-((tetrahydro-2H-pyran-4-yl)carbamoyl)-6-azaspiro[2.5]octane-6-carboxylate and Example 9: 1,1,1,3,3,3-Hexafluoropropan-2-yl (R)-1-((tetrahydro-2H-pyran-4-yl)carbamoyl)-6-azaspiro[2.5]octane-6-carboxylate

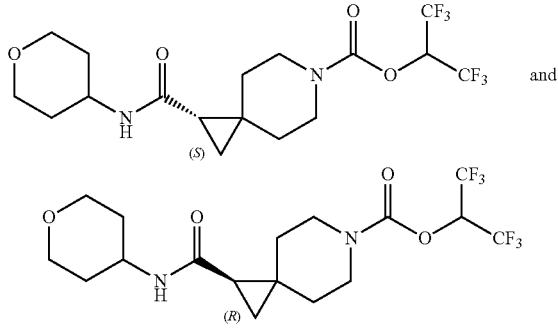

The racemic mixture prepared in Example 7 (88 mg) was separated into the two enantiomers by preparative SFC-HPLC (Column: CHIRAL ART Amylose-C NEO, 3*25 cm, 5 µm; Mobile Phase A: CO2, Mobile Phase B: EtOH (0.5% 2M NH3-MeOH)-HPLC; Flow rate:50 mL/min; Gradient: 15% B; Column Temperature: 35° C.; Back Pressure: 100 bar; UV220 nm) to afford:

Example 8: 13 mg of 1,1,1,3,3,3-hexafluoropropan-2-yl (S)-1-((tetrahydro-2H-pyran-4-yl)carbamoyl)-6-azaspiro [2.5]octane-6-carboxylate 1H NMR (400 MHz, Chloroform-d) δ 5.78 (dq, J=12.0, 6.1 Hz, 1H), 5.52 (d, J=7.9 Hz, 1H), 4.09-3.93 (m, 3H), 3.72-3.40 (m, 6H), 1.97-1.87 (m, 2H), 1.81 (dd, J=10.9, 5.4 Hz, 2H), 1.56-1.50 (m, 2H), 1.50-1.40 (m, 2H), 1.34 (dd, J=8.0, 5.3 Hz, 1H), 1.27 (d, J=4.6 Hz, 1H), 0.88 (dd, J=8.0, 4.5 Hz, 1H). $t_R$=4.32 min. LCMS (Method D) (ESI, m/z): 433 [M+H]+. (S,S) Whelk-01, 4.6*100 mm, 5 µm; mobile phase: Phase A: CO2, phase B: IPA (0.1% DEA); flow rate: 4 mL/min; gradient: 5% to 20% in 2.0 min, hold 1.0 min at 20%; detection: 220 nm: $t_R$=1.568 min.

And the corresponding enantiomer

Example 9: 15.4 mg of 1,1,1,3,3,3-hexafluoropropan-2-yl (R)-1-((tetrahydro-2H-pyran-4-yl)carbamoyl)-6-azaspiro [2.5]octane-6-carboxylate 1H NMR (400 MHz, Chloroform-d) δ 5.78 (m, J=6.0 Hz, 1H), 5.51 (d, J=8.0 Hz, 1H), 4.21-3.87 (m, 3H), 3.87-3.03 (m, 6H), 1.93 (ddd, J=12.9, 4.4, 2.2 Hz, 2H), 1.87-1.70 (m, 2H), 1.55-1.48 (m, 2H), 1.48-1.38 (m, 2H), 1.34 (dd, J=8.0, 5.3 Hz, 1H), 1.27 (d, J=4.6 Hz, 1H), 0.88 (dd, J=8.0, 4.5 Hz, 1H). $t_R$=4.99 min. LCMS (Method A) (ESI, m/z): 433 [M+H]+. (S,S) Whelk-01, 4.6*100 mm, 5 µm; mobile phase: Phase A: CO2, phase B: IPA (0.1% DEA); flow rate: 4 mL/min; gradient: 5% to 20% in 2.0 min, hold 1.0 min at 20%; detection: 220 nm: $t_R$=1.425 min Synthesis of Example 8 with Known Intermediate 2B

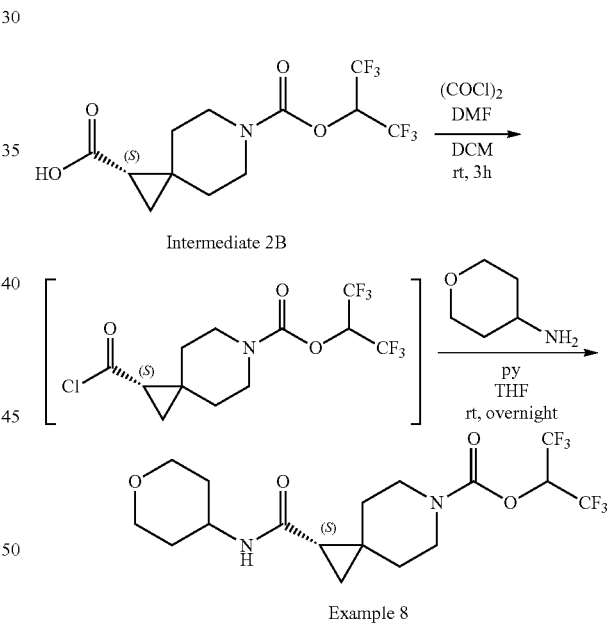

Into a flask purged and maintained with an inert atmosphere of nitrogen, was added (S)-6-[[(1,1,1,3,3,3-hexafluoropropan-2-yl)oxy]carbonyl]-6-azaspiro[2.5]octane-1-carboxylic acid (Intermediate 2B) (21.0 g), DCM (400 mL) and DMF (0.22 g). The mixture was cooled to 0° C. and (COCl)2 (11.5 g) was added dropwise. The resulting mixture was stirred at room temperature for 3 h. The mixture was then concentrated under vacuum to obtain crude acyl chloride for later use. Into another flask purged and maintained with an inert atmosphere of nitrogen was added oxan-4-amine (7.3 g), pyridine (9.5 g) and THF (400 mL). The solution of acyl chloride in THF (200 mL) was added dropwise at room temperature. The resulting solution was stirred overnight at room temperature. After the reaction was complete, the mixture was diluted with ice water (1×3 L) and extracted with EtOAc (2×500 mL). The combined organic phase was washed with H₂O (1×1 L) and brine (1×1 L), dried over anhydrous Na2SO4 and concentrated under vacuum. The residue was purified by silica gel column chromatography with EtOAc/petroleum ether (1/10) to provide 20.7 g of product. The product was further purified by silica gel column chromatography with 0.1% NH₄HCO₃ in H2O-MeCN system to provide 15.2 g of amorphous product. The product was finally recrystallized from MeCN/H2O=1:1 (0.5V/0.5V) to provide 11.97 g of 1,1,1,3,3,3-hexafluoropropan-2-yl (S)-1-[(oxan-4-yl) carbamoyl]-6-azaspiro[2.5]octane-6-carboxylate. ¹H NMR (300 MHz, Chloroform-d) δ 5.76 (s, 1H), 5.49 (d, J=8.0 Hz, 1H), 3.96 (d, J=12.1 Hz, 3H), 3.72-3.34 (m, 6H), 2.00-1.72 (m, 4H), 1.54-1.37 (m, 4H), 1.35-1.20 (m, 2H), 0.86 (dd, J=7.9, 4.4 Hz, 1H). $t_R$=1.442 min. LCMS (Method O) (ESI, m/z): 433 [M+H]⁺. (S,S) Whelk-01, 4.6*100 mm, 5 mm; mobile phase: Phase A: CO₂, phase B: IPA (0.1% DEA); flow rate: 4 mL/min; gradient: 5% to 20% in 2.0 min, hold 1.0 min at 20%; detection: 220 nm: $t_R$=1.525 min.

Note that the retention time of the product prepared here with Intermediate 2B matches the retention time of Example 8 prepared above, in which case the racemic product was separated into its enantiomers by SFC, thus confirming the assigned absolute configuration assigned to Example 8 in the preparation above.

Synthesis of Example 9 with Known Intermediate 3B

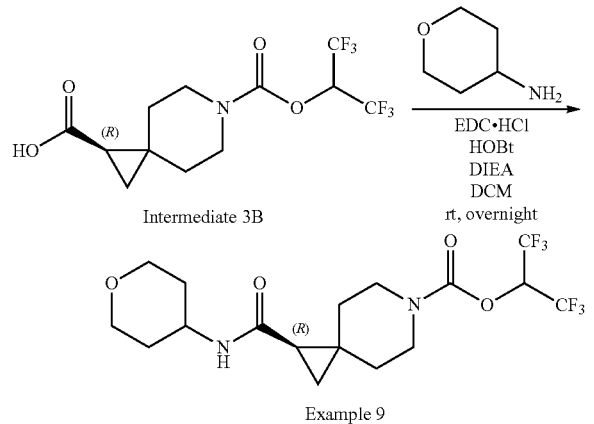

Intermediate 3B

Example 9

Into a reaction vial was placed a solution of crude (R)-6-(((1,1,1,3,3,3-hexafluoropropan-2-yl)oxy)carbonyl)-6-azaspiro[2.5]octane-1-carboxylic acid (Intermediate 3B) (50 mg) and DCM (1 mL). EDC.HCl (30.3 mg) and HOBt (38.7 mg) were added and the resulting mixture was stirred for 15 min. Tetrahydro-2H-pyran-4-amine (18.8 mg) and DIEA (37.0 mg) were added. The reaction mixture was stirred overnight at room temperature. The mixture was diluted with H2O (10 mL) and extracted with DCM (1×5 mL). The combined organic phases were dried over anhydrous Na₂SO4, filtered and concentrated. The crude product was purified by preparative HPLC to afford 1,1,1,3,3,3-hexafluoropropan-2-yl (R)-1-((tetrahydro-2H-pyran-4-yl)carbamoyl)-6-azaspiro[2.5]octane-6-carboxylate (37 mg). 1H NMR (300 MHz, Chloroform-d) δ 5.76 (td, J=6.1, 3.3 Hz, 1H), 5.50 (d, J=8.0 Hz, 1H), 3.96 (d, J=12.5 Hz, 3H), 3.70-3.36 (m, 6H), 1.98-1.72 (m, 4H), 1.55-1.39 (m, 4H), 1.37-1.19 (m, 2H), 0.86 (dd, J=7.9, 4.4 Hz, 1H). $t_R$=1.442 min. LCMS (Method P) (ESI, m/z): 433 [M+H]⁺. (S,S) Whelk-01, 4.6*100 mm, 5 mm; mobile phase: Phase A: CO₂, phase B: IPA (0.1% DEA); flow rate: 4 mL/min; gradient: 5% to 20% in 2.0 min, hold 1.0 min at 20%; detection: 220 nm: $t_R$=1.46 min.

Note that the retention time of the product prepared here with Intermediate 3B matches the retention time of Example 9 prepared above, in which case the racemic product was separated into its enantiomers by SFC, thus confirming the assigned absolute configuration assigned to Example 9 in the preparation above.

Example 10: 1,1,1,3,3,3-Hexafluoropropan-2-yl (±)1-(methyl(pyrazin-2-yl)carbamoyl)-6-azaspiro[2.5]octane-6-carboxylate

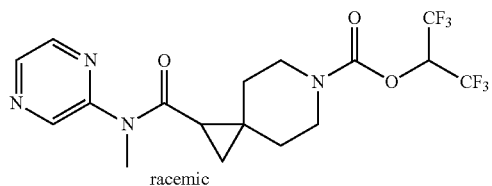 [SMILES: CN(C(=O)C1CC12CCN(C(=O)OC(C(F)(F)F)C(F)(F)F)CC2)c1cnccn1]

racemic

Step 1: Synthesis of t-butyl 1-(pyrazin-2-ylcarbamoyl)-6-azaspiro[2.5]octane-6-carboxylate

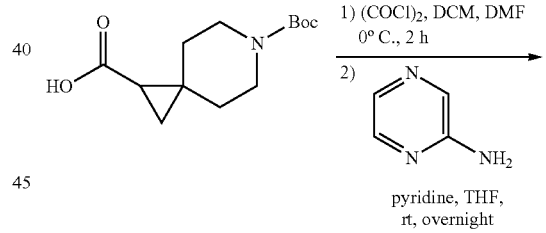

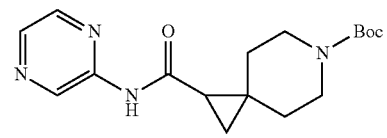

t-Butyl 1-(pyrazin-2-ylcarbamoyl)-6-azaspiro[2.5]octane-6-carboxylate was prepared from 6-(t-butoxycarbonyl)-6-azaspiro[2.5]octane-1-carboxylic acid (500 mg), DCM (10 mL), DMF (14.0 mg), oxalyl chloride (249 mg), pyrazin-2-amine (186 mg), pyridine (464 mg) and t-butyl 1-(carbonochloridoyl)-6-azaspiro[2.5]octane-6-carboxylate as described in Example 1, Step 1 to provide the title compound (190 mg). LCMS (ESI, m/z): 333 [M+H]⁺.

Step 2: Synthesis of t-butyl 1-(methyl(pyrazin-2-yl)carbamoyl)-6-azaspiro[2.5]octane-6-carboxylate

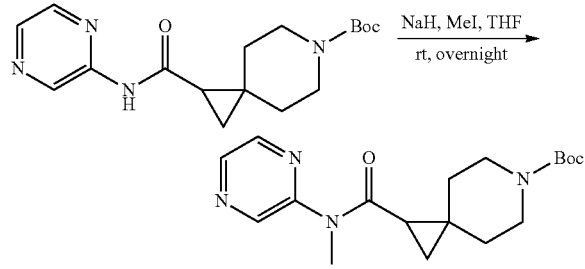

A vial was charged with t-butyl 1-(pyrazin-2-ylcarbamoyl)-6-azaspiro[2.5]octane-6-carboxylate (190 mg) and THF (5 mL). Sodium hydride (34.3 mg, 0.858 mmol, 1.50 equiv, 60% in mineral oil) was added at 0° C. The resulting solution was stirred at 0° C. for 0.5 h, then methyl iodide (97.4 mg) was added. The resulting solution was stirred overnight at room temperature and quenched with water (10 ml). The mixture was extracted with EtOAc (3×10 mL) and the organic layers were combined, washed with brine (3×10 mL), dried over anhydrous sodium sulfate, filtered and concentrated under reduced pressure. The residue was chromatographed on a silica gel column to provide t-butyl 1-(methyl(pyrazin-2-yl)carbamoyl)-6-azaspiro[2.5]octane-6-carboxylate (140 mg). LCMS (ESI, m/z): 347 [M+H]+.

Step 3: Synthesis of N-methyl-N-(pyrazin-2-yl)-6-azaspiro[2.5]octane-1-carboxamide

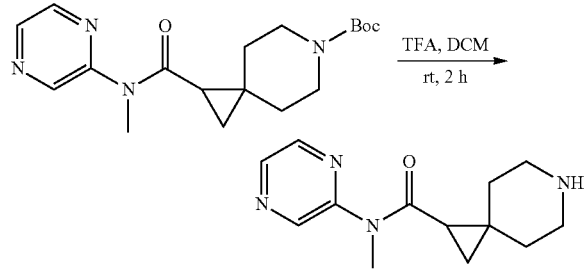

N-methyl-N-(pyrazin-2-yl)-6-azaspiro[2.5]octane-1-carboxamide was prepared from t-butyl 1-(methyl(pyrazin-2-yl)carbamoyl)-6-azaspiro[2.5]octane-6-carboxylate (140 mg), TFA (3 mL) and DCM (3 mL) as described in Example 1, Step 2 to provide the title compound (99.7 mg). LCMS (ESI, m/z): 247 [M+H]+.

Step 4: Synthesis of 1,1,1,3,3,3-hexafluoropropan-2-yl (±)1-(methyl(pyrazin-2-yl)carbamoyl)-6-azaspiro[2.5]octane-6-carboxylate

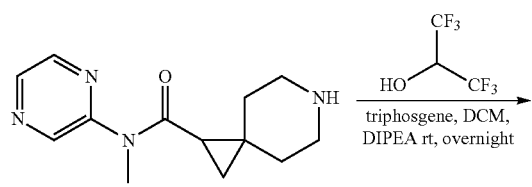

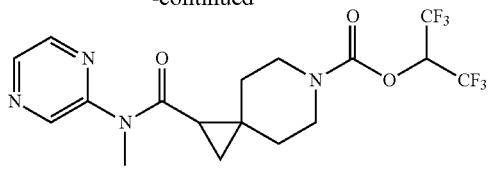

A vial was charged with 1,1,1,3,3,3-hexafluoropropan-2-ol (102 mg, 0.606 mmol, 1.50 equiv), DCM (10 mL) and triphosgene (67.8 mg). DIPEA (156 mg) was added at 0° C. The resulting solution was stirred for 2 h at room temperature, then N-methyl-N-(pyrazin-2-yl)-6-azaspiro[2.5]octane-1-carboxamide (99.7 mg) was added. The resulting solution was stirred overnight at room temperature and then quenched with water (10 mL). The solution was extracted with DCM (3×10 mL) and the organic layers were combined, washed with brine (3×10 mL), dried over anhydrous sodium sulfate, filtered and concentrated under reduced pressure to provide the title compound.

Example 11: 1,1,1,3,3,3-Hexafluoropropan-2-yl (R)-1-(methyl(pyrazin-2-yl)carbamoyl)-6-azaspiro[2.5]octane-6-carboxylate Peak 1 and Example 12: 1,1,1,3,3,3-Hexafluoropropan-2-yl (S)-1-(methyl(pyrazin-2-yl)carbamoyl)-6-azaspiro[2.5]octane-6-carboxylate Peak 2

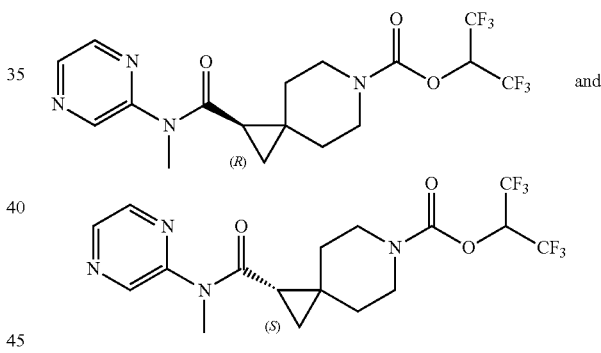

The racemic mixture prepared in Example 10 was separated into the two enantiomers by preparative chiral-HPLC (Column: CHIRALPAK IA Column 2*25 cm, 5 µm; Mobile Phase A: Hex-HPLC, Mobile Phase B: EtOH-HPLC; Flow rate: 20 mL/min; Gradient: 30% B to 30% B over 11 min; Detector, UV220 & 254 nm) to afford:

Example 11: 12.5 mg of 1,1,1,3,3,3-hexafluoropropan-2-yl (R)-1-(methyl(pyrazin-2-yl)carbamoyl)-6-azaspiro[2.5]octane-6-carboxylate peak 1. $^1$H NMR (400 MHz, Chloroform-d) δ 8.79 (s, 1H), 8.45 (d, J=7.31 Hz, 2H), 5.83-5.76 (m, 1H), 3.82-3.75 (m, 2H), 3.52 (s, 3H), 3.46-3.37 (m, 2H), 1.88-1.79 (m, 1H), 1.73-1.62 (m, 3H), 1.48-1.45 (m, 1H), 1.33-1.26 (m, 1H), 0.91-0.88 (m, 1H). $t_R$=7.897 min. LCMS (Method E) (ESI, m/z): 441 [M+H]+.

And the corresponding enantiomer

Example 12: 12.1 mg of 1,1,1,3,3,3-hexafluoropropan-2-yl (S)-1-(methyl(pyrazin-2-yl)carbamoyl)-6-azaspiro[2.5]octane-6-carboxylate peak 2. $^1$H NMR (400 MHz, Chloroform-d) δ 8.79 (s, 1H), 8.46 (d, J=7.50 Hz, 2H), 5.83-5.75 (m, 1H), 3.81-3.76 (m, 2H), 3.52 (s, 3H), 3.45-3.37 (m, 2H), 1.88-1.79 (m, 1H), 1.72-1.59 (m, 3H), 1.47-1.45 (m, 1H), 1.33-1.26 (m, 1H), 0.92-0.88 (m, 1H). $t_R$=9.487 min. LCMS (Method E) (ESI, m/z): 441 [M+H]$^+$.

Determination of the Absolute Configurations of Example 11 and Example 12

The absolute configurations of Examples 11 and 12 were determined in a similar manner as in Example 3, wherein resynthesis of the final compound using an intermediate with known absolute configuration allowed for the assignment of the absolute configuration of the final products (Example 11 and Example 12). In the end it was determined that the first eluting enantiomer was the (R) enantiomer (Example 11), and therefore Example 12 as the (S)-enantiomer.

Example 13: 1,1,1,3,3,3-Hexafluoropropan-2-yl (±)-1-(isoxazol-4-ylcarbamoyl)-6-azaspiro[2.5]octane-6-carboxylate

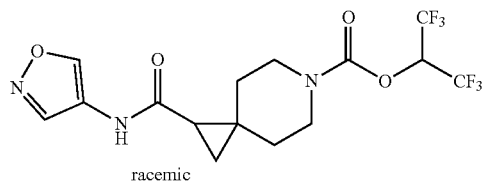 [SMILES: O=C(Nc1cnoc1)C1CC12CCN(C(=O)OC(C(F)(F)F)C(F)(F)F)CC2]

racemic

Step 1: Synthesis of 1-benzyl 6-(t-butyl) 6-azaspiro[2.5]octane-1,6-dicarboxylate

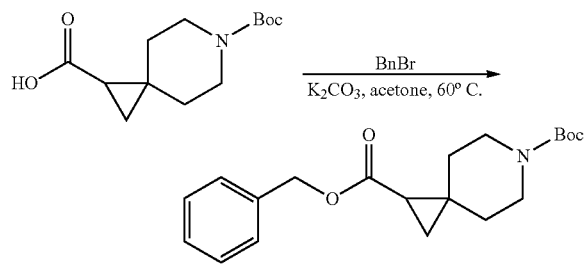

A vial was charged with 6-(t-butoxycarbonyl)-6-azaspiro[2.5]octane-1-carboxylic acid (300 mg), acetone (15 mL), K$_2$CO$_3$ (195 mg) and BnBr (220 mg). The resulting solution was stirred overnight at 60° C. and quenched with water (20 mL). The mixture was extracted with EtOAc (3×20 mL) and the organic layers were combined, washed with brine (3×20 mL), dried over anhydrous sodium sulfate, filtered and concentrated under reduced pressure. The residue was chromatographed on a silica gel column with EtOAc to provide 1-benzyl 6-(t-butyl) 6-azaspiro[2.5]octane-1,6-dicarboxylate (350 mg). LCMS (ESI, m/z): 346 [M+H]$^+$.

Step 2: Synthesis of benzyl 6-azaspiro[2.5]octane-1-carboxylate

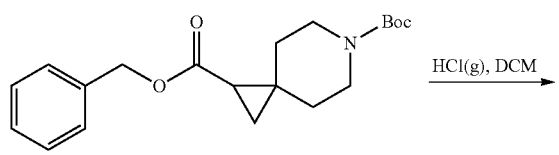

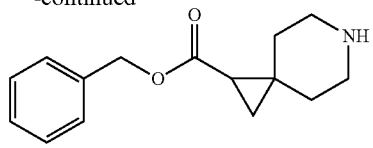

To a solution of 1-benzyl 6-(t-butyl) 6-azaspiro[2.5]octane-1,6-dicarboxylate (350 mg) in DCM (6 mL) was added HCl(g) (3 mL). The resulting solution was stirred for 2 h at room temperature and concentrated under reduced pressure to provide benzyl 6-azaspiro[2.5]octane-1-carboxylate (260 mg). LCMS (ESI, m/z): 246 [M+H]$^+$.

Step 3: Synthesis of 1-benzyl 6-(1,1,1,3,3,3-hexafluoropropan-2-yl) 6-azaspiro[2.5]octane-1,6-dicarboxylate

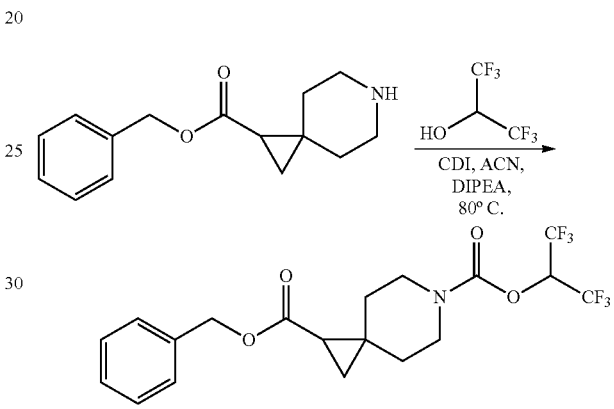

1-Benzyl 6-(1,1,1,3,3,3-hexafluoropropan-2-yl) 6-azaspiro[2.5]octane-1,6-dicarboxylate was prepared from benzyl 6-azaspiro[2.5]octane-1-carboxylate (240 mg), ACN (4 mL), 1,1'-carbonyldiimidazole (205 mg), DIPEA (378 mg) and 1,1,1,3,3,3-hexafluoropropan-2-ol (820 mg) as described in Example 1, Step 3 provide 1-benzyl 6-(1,1,1,3,3,3-hexafluoropropan-2-yl) 6-azaspiro[2.5]octane-1,6-dicarboxylate (350 mg). LCMS (ESI, m/z): 440 [M+H]$^+$.

Step 4: Synthesis of 6-(((1,1,1,3,3,3-hexafluoropropan-2-yl)oxy)carbonyl)-6-azaspiro[2.5]octane-1-carboxylic Acid

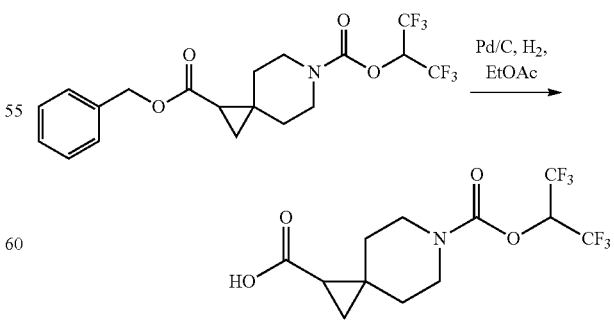

A mixture of 1-benzyl 6-(1,1,1,3,3,3-hexafluoropropan-2-yl) 6-azaspiro[2.5]octane-1,6-dicarboxylate (340 mg) and Pd/C (40 mg, 10% wt) in EtOAc (10 mL) was stirred overnight under H$_2$. The reaction was cooled down to room temperature and filtered. The filtrate was concentrated under reduced pressure to provide 6-(((1,1,1,3,3,3-hexafluoropropan-2-yl)oxy)carbonyl)-6-azaspiro[2.5]octane-1-carboxylic acid (240 mg). LCMS (ESI, m/z): 350 [M+H]$^+$. Step 5: Synthesis of 1,1,1,3,3,3-hexafluoropropan-2-yl (±)1-(isoxazol-4-ylcarbamoyl)-6-azaspiro[2.5]octane-6-carboxylate

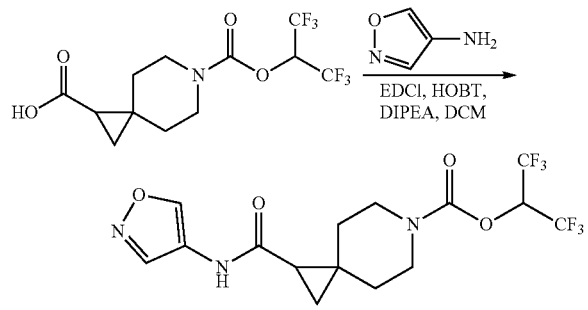

1,1,1,3,3,3-Hexafluoropropan-2-yl (±)1-(isoxazol-4-ylcarbamoyl)-6-azaspiro[2.5]octane-6-carboxylate was prepared from 6-(((1,1,1,3,3,3-hexafluoropropan-2-yl)oxy)carbonyl)-6-azaspiro[2.5]octane-1-carboxylic acid (100 mg), isoxazol-4-amine (44.7 mg), EDCI (60.5 mg), HOBT (38.7 mg) and TEA (86.8 mg) in DCM (2 mL) as described in Example 5, Step 1 to provide the title compound (70 mg).

Example 14: 1,1,1,3,3,3-Hexafluoropropan-2-yl (S)-1-(isoxazol-4-ylcarbamoyl)-6-azaspiro[2.5]octane-6-carboxylate Peak 1 and Example 15: 1,1,1,3,3,3-Hexafluoropropan-2-yl (R)-1-(isoxazol-4-ylcarbamoyl)-6-azaspiro[2.5]octane-6-carboxylate Peak 2

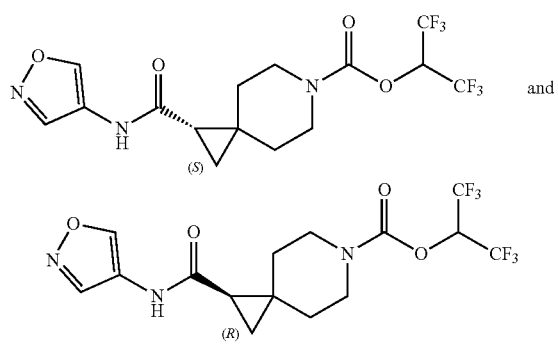

The racemic mixture prepared in Example 10 (70 mg) was separated into the two enantiomers by preparative chiral HPLC (Column: CHIRALPAK IG, 2*25 cm, 5 μm; Mobile Phase A: Hex (0.5% 2M NH$_3$-MeOH)—HPLC, Mobile Phase B: IPA-HPLC; Flow rate: 20 mL/min; Gradient: 20% B to 30% B over 7.5 min; Detector, UV220 & 254 nm) to afford:

Example 14: 15.0 mg of 1,1,1,3,3,3-hexafluoropropan-2-yl (S)-1-(isoxazol-4-ylcarbamoyl)-6-azaspiro[2.5]octane-6-carboxylate peak 1. $^1$H NMR (400 MHz, Chloroform-d) δ 8.96 (s, 1H), 8.37 (s, 1H), 7.48 (s, 1H), 5.86-5.70 (m, 1H), 3.79-3.66 (m, 1H), 3.65-3.43 (m, 3H), 1.93-1.75 (m, 2H), 1.69-1.42 (m, 3H), 1.41-1.34 (m, 1H), 1.11-0.99 (m, 1H). t$_R$=5.612 min. LCMS (Method E) (ESI, m/z): 416 [M+H]$^+$.

And the corresponding enantiomer

Example 15: 9.7 mg of 1,1,1,3,3,3-hexafluoropropan-2-yl (R)-1-(isoxazol-4-ylcarbamoyl)-6-azaspiro[2.5]octane-6-carboxylate peak 2. $^1$H NMR (400 MHz, Chloroform-d) δ 8.96 (s, 1H), 8.37 (s, 1H), 7.48 (s, 1H), 5.84-5.70 (m, 1H), 3.79-3.65 (m, 1H), 3.64-3.42 (m, 3H), 1.93-1.76 (m, 2H), 1.70-1.42 (m, 3H), 1.41-1.35 (m, 1H), 1.10-0.99 (m, 1H). t$_R$=6.706 min. LCMS (Method E) (ESI, m/z): 416 [M+H]$^+$.

Determination of the Absolute Configurations of Example 14 and Example 15

The absolute configurations of Examples 14 and 15 were determined in a similar manner as in Example 3, wherein resynthesis of the final compound using an intermediate with known absolute configuration allowed for the assignment of the absolute configuration of the final products (Example 14 and Example 15). In the end it was determined that the second eluting enantiomer was the (R) enantiomer (Example 15), and therefore Example 14 as the (S)-enantiomer.

Example 16: 1,1,1,3,3,3-Hexafluoropropan-2-yl (±)-1-((2-(trifluoromethyl)pyrimidin-4-yl)carbamoyl)-6-azaspiro[2.5]octane-6-carboxylate

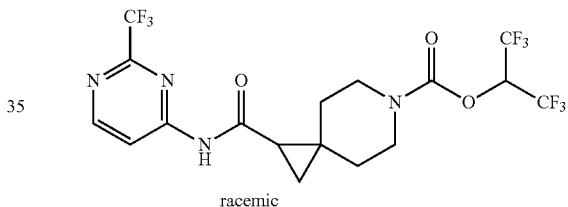

racemic

Step 1: Synthesis of t-butyl 1-(chlorocarbonyl)-6-azaspiro[2.5]octane-6-carboxylate

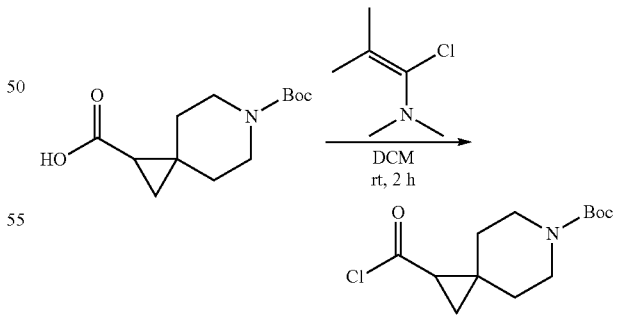

A vial was charged with 6-(t-butoxycarbonyl)-6-azaspiro[2.5]octane-1-carboxylic acid (255 mg) and DCM (10 mL). 1-Chloro-N,N,2-trimethylprop-1-en-1-amine (201 mg) was added dropwise at 0° C. The resulting solution was stirred for 2 h at room temperature and concentrated under reduced pressure to provide of t-butyl 1-(chlorocarbonyl)-6-azaspiro[2.5]octane-6-carboxylate (274 mg).

Step 2: Synthesis of t-butyl 1-((2-(trifluoromethyl)pyrimidin-4-yl)carbamoyl)-6-azaspiro[2.5]octane-6-carboxylate

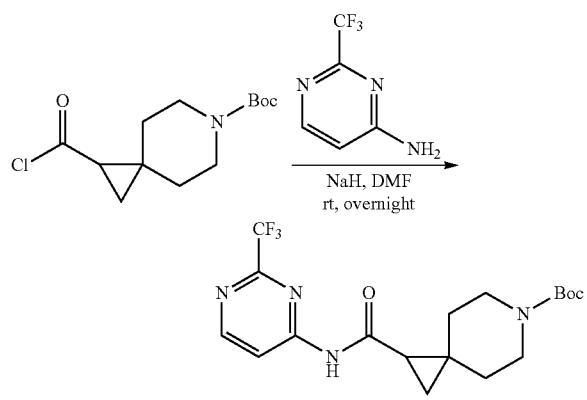

A vial was charged with 2-(trifluoromethyl)pyrimidin-4-amine (200 mg) and THF (15 mL). Sodium hydride (49.0 mg, 1.23 mmol, 2.00 equiv, 60% in mineral oil) was added at 0° C. The resulting suspension was stirred for 0.5 h at room temperature and t-butyl 1-(chlorocarbonyl)-6-azaspiro[2.5]octane-6-carboxylate (252 mg) was added. The resulting solution was stirred overnight at room temperature and quenched by water (10 mL). The mixture was extracted with EtOAc (3×20 mL) and the organic layers were combined, washed with brine (2×20 mL), dried over anhydrous sodium sulfate, filtered and concentrated under reduced pressure. The residue was chromatographed on a silica gel column with EtOAc/petroleum ether (1:3) to provide t-butyl 1-((2-(trifluoromethyl)pyrimidin-4-yl)carbamoyl)-6-azaspiro[2.5]octane-6-carboxylate (240 mg). LCMS (ESI, m/z): 401 [M+H]$^+$.

Step 3: Synthesis of N-(2-(trifluoromethyl)pyrimidin-4-yl)-6-azaspiro[2.5]octane-1-carboxamide

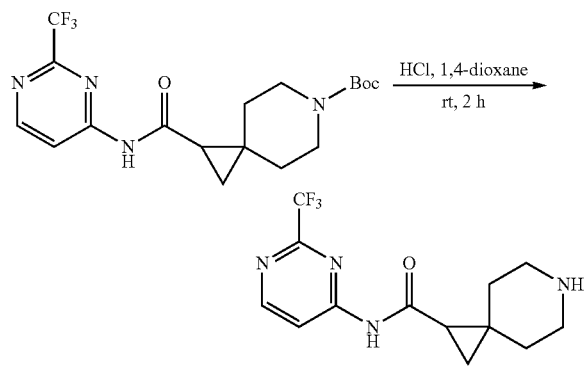

N-(2-(trifluoromethyl)pyrimidin-4-yl)-6-azaspiro[2.5]octane-1-carboxamide was prepared with t-butyl 1-((2-(trifluoromethyl)pyrimidin-4-yl)carbamoyl)-6-azaspiro[2.5]octane-6-carboxylate (240 mg), 1,4-dioxane (4 mL) and concentrated hydrochloric acid (1 mL) as described in Example 13, Step 2 to provide the title compound (180 mg). LCMS (ESI, m/z): 301 [M+H]$^+$.

Step 4: Synthesis of 1,1,1,3,3,3-hexafluoropropan-2-yl (±)-1-((2-(trifluoromethyl)pyrimidin-4-yl)carbamoyl)-6-azaspiro[2.5]octane-6-carboxylate

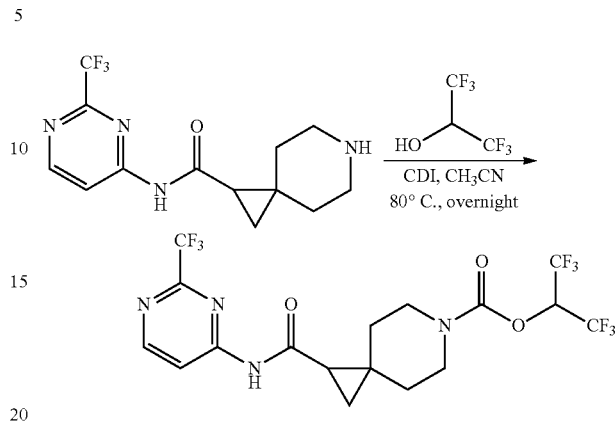

1,1,1,3,3,3-Hexafluoropropan-2-yl (±)-1-((2-(trifluoromethyl)pyrimidin-4-yl)carbamoyl)-6-azaspiro[2.5]octane-6-carboxylate was prepared from N-(2-(trifluoromethyl)pyrimidin-4-yl)-6-azaspiro[2.5]octane-1-carboxamide (0.180 g), carbonyl diimidazole (0.146 g), ACN (15 mL) and 1,1,1,3,3,3-hexafluoropropan-2-ol (1.21 g) as described in Example 1, Step 3 to provide the title compound.

Example 17: 1,1,1,3,3,3-Hexafluoropropan-2-yl (S)-1-((2-(trifluoromethyl)pyrimidin-4-yl)carbamoyl)-6-azaspiro[2.5]octane-6-carboxylate Peak 1 and Example 18: 1,1,1,3,3,3-Hexafluoropropan-2-yl (R)-1-((2-(trifluoromethyl)pyrimidin-4-yl)carbamoyl)-6-azaspiro[2.5]octane-6-carboxylate Peak 2

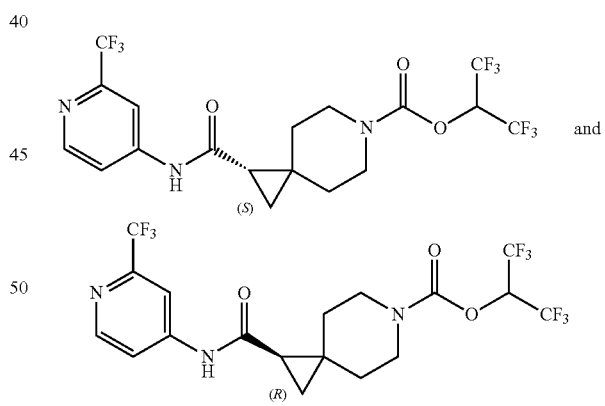

The racemic mixture prepared in Example 16 was separated into the two enantiomers by preparative chiral HPLC (Column: CHIRALPAK AD-H, 2*25 cm, 5 μm; Mobile Phase A:Hex-HPLC, Mobile Phase B: EtOH-HPLC; Flow rate:20 mL/min; Gradient:5% B to 5% B over 11 min; UV220/254 nm) to afford:

Example 17: 15.8 mg 1,1,1,3,3,3-hexafluoropropan-2-yl (S)-1-((2-(trifluoromethyl)pyrimidin-4-yl)carbamoyl)-6-azaspiro[2.5]octane-6-carboxylate peak 1. $^1$H NMR (400 MHz, Chloroform-d) δ 8.78 (d, J=5.6 Hz, 1H), 8.50-8.20 (m, 2H), 5.77 (br, 1H), 3.84-3.68 (m, 1H), 3.68-3.38 (m, 3H), 1.85 (br, 2H), 1.68-1.58 (m, 2H), 1.58-1.40 (m, 2H), 1.22-1.02 (m, 1H). $t_R$=7.674 min. LCMS (Method F) (ESI, m/z): 495 [M+H]⁺.
And the corresponding enantiomer Example 18: 17.2 mg 1,1,1,3,3,3-hexafluoropropan-2-yl (R)-1-((2-(trifluoromethyl)pyrimidin-4-yl)carbamoyl)-6-azaspiro[2.5]octane-6-carboxylate peak 2. ¹H NMR (400 MHz, Chloroform-d) δ 8.78 (d, J=5.6 Hz, 1H), 8.50-8.20 (m, 2H), 5.77 (br, 1H), 3.84-3.68 (m, 1H), 3.68-3.38 (m, 3H), 1.85 (br, 2H), 1.68-1.58 (m, 2H), 1.58-1.40 (m, 2H), 1.22-1.02 (m, 1H). $t_R$=9.747 min. LCMS (Method F) (ESI, m/z): 495 [M+H]⁺.

Determination of the Absolute Configurations of Example 17 and Example 18

The absolute configurations of Examples 17 and 18 were determined in a similar manner as in Example 3, wherein resynthesis of the final compound using an intermediate with known absolute configuration allowed for the assignment of the absolute configuration of the final products (Example 17 and Example 18). In the end it was determined that the second eluting enantiomer was the (R) enantiomer (Example 18), and therefore Example 17 as the (S)-enantiomer.

Example 19: 1,1,1,3,3,3-Hexafluoropropan-2-yl (±)-1-((6-(dimethylphosphoryl)pyridin-3-yl)carbamoyl)-6-azaspiro[2.5]octane-6-carboxylate

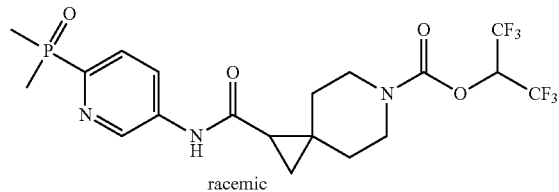 [SMILES: CP(C)(=O)c1ccc(NC(=O)C2CC23CCN(C(=O)OC(C(F)(F)F)C(F)(F)F)CC3)cn1]

racemic

Step 1: Synthesis of t-butyl 1-(((6-iodopyridin-3-yl)carbamoyl)-6-azaspiro[2.5]octane-6-carboxylate

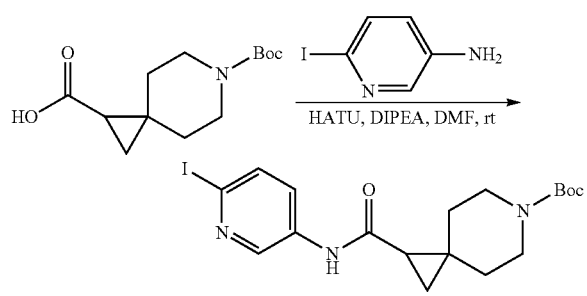

To a stirred solution of 6-(t-butoxycarbonyl)-6-azaspiro[2.5]octane-1-carboxylic acid (500.00 mg), HATU (1116.95 mg) and DIEA (759.32 mg) in DMF (10.00 mL), was added 6-iodopyridin-3-amine (430.87 mg) at room temperature. The resulting mixture was stirred overnight and quenched with water (50 mL). The resulting mixture was extracted with EtOAc (3×50 mL) and the combined organic layers were washed with brine (3×30 mL) and dried over anhydrous Na2SO4. After filtration, the filtrate was concentrated under reduced pressure. The residue was purified by reverse flash chromatography with the following conditions: column, C18 silica gel; mobile phase, MeOH in water, 10% to 50% gradient over 10 min; detector, UV 254/220 nm to afford t-butyl 1-((6-iodopyridin-3-yl)carbamoyl)-6-azaspiro[2.5]octane-6-carboxylate (700 mg). LCMS (ESI, m/z): 458 [M+H]⁺.

Step 2: Synthesis of t-butyl 1-(((6-(dimethylphosphoryl)pyridin-3-yl)carbamoyl)-6-azaspiro[2.5]octane-6-carboxylate

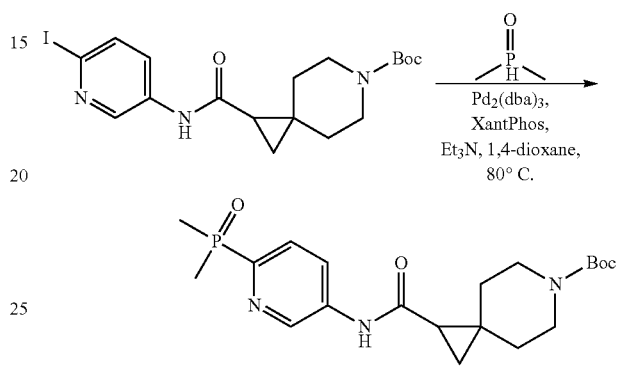

A mixture of t-butyl 1-((6-iodopyridin-3-yl)carbamoyl)-6-azaspiro[2.5]octane-6-carboxylate (700.00 mg), Pd₂(dba)₃ (140.17 mg), XantPhos (88.57 mg), Et₃N (464.67 mg) and (methylphosphonoyl)methane (238.94 mg) in 1,4-dioxane (10.00 mL) was stirred overnight at 80° C. under nitrogen atmosphere. The resulting mixture was cooled to room temperature, quenched with water (50 mL) and extracted with EtOAc (3×50 mL). The combined organic layers were washed with brine (3×30 mL) and dried over anhydrous Na2SO4. After filtration, the filtrate was concentrated under reduced pressure. The residue was purified by reverse flash chromatography with the following conditions: column, C18 silica gel; mobile phase, MeOH in water, 10% to 50% gradient in 10 min; detector, UV254/220 nm to afford t-butyl 1-((6-(dimethylphosphoryl)pyridin-3-yl)carbamoyl)-6-azaspiro[2.5]octane-6-carboxylate (560 mg). LCMS (ESI, m/z): 408 [M+H]⁺.

Step 3: Synthesis of N-(6-(dimethylphosphoryl)pyridin-3-yl)-6-azaspiro[2.5]octane-1-carboxamide Hydrochloride

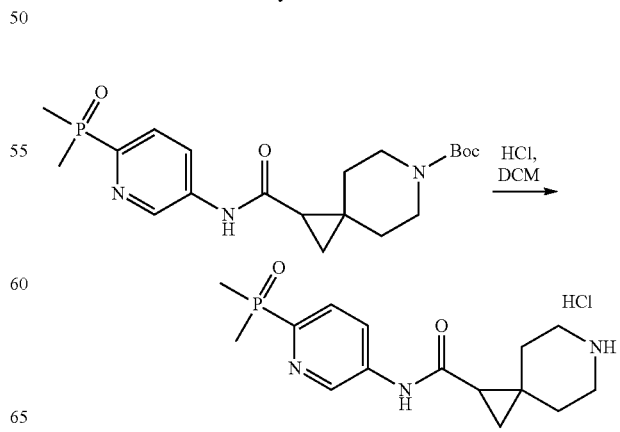

N-(6-(dimethylphosphoryl)pyridin-3-yl)-6-azaspiro[2.5]octane-1-carboxamide hydrochloride was prepared from t-butyl 1-[[6-(dimethylphosphoryl)pyridin-3-yl]carbamoyl]-6-azaspiro[2.5]octane-6-carboxylate (560.00 mg), DCM (5.00 mL), and HCl(g), (4 M in 1,4-dioxane, 5.00 mL, 20 mmol) as described in Example 13, Step 2 to provide the title compound (400 mg). The crude product was used directly in the next step directly without further purification. LCMS (ESI, m/z): 308 [M−HCl+H]⁺.

Step 4: Synthesis of 1,1,1,3,3,3-hexafluoropropan-2-yl (±)-1-((6-(dimethylphosphoryl)pyridin-3-yl)carbamoyl)-6-azaspiro[2.5]octane-6-carboxylate

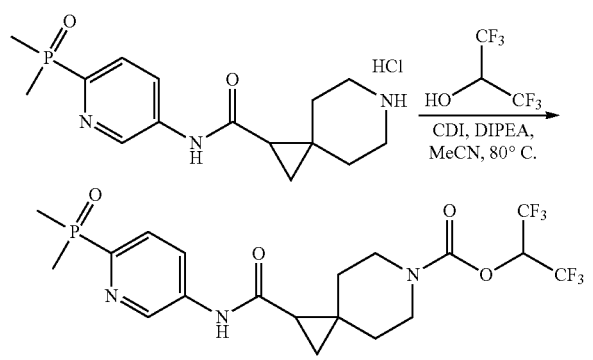

1,1,1,3,3,3-hexafluoropropan-2-yl (±)-1-((6-(dimethylphosphoryl)pyridin-3-yl)carbamoyl)-6-azaspiro[2.5]octane-6-carboxylate was prepared from N-(6-(dimethylphosphoryl)pyridin-3-yl)-6-azaspiro[2.5]octane-1-carboxamide hydrochloride (350.00 mg), DIPEA (525.00 mg) hexafluoroisopropanol (341.86 mg) and CDI (214.33 mg) in MeCN (10.00 mL) as described in Example 1, Step 3 to provide the title compound (400 mg) LCMS (ESI, m/z): 502 [M+H]⁺.

Example 20: 1,1,1,3,3,3-Hexafluoropropan-2-yl (R or S)-1-((6-(dimethylphosphoryl)pyridin-3-yl)carbamoyl)-6-azaspiro[2.5]octane-6-carboxylate Peak 1

Example 21: 1,1,1,3,3,3-Hexafluoropropan-2-yl (R or S)-1-((6-(dimethylphosphoryl)pyridin-3-yl)carbamoyl)-6-azaspiro[2.5]octane-6-carboxylate Peak 2

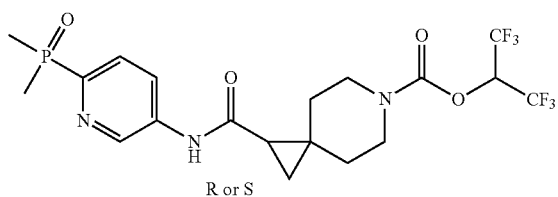 [SMILES: CP(C)(=O)c1ccc(NC(=O)C2CC23CCN(C(=O)OC(C(F)(F)F)C(F)(F)F)CC3)cn1]

R or S

The racemic mixture prepared in Example 19 was separated into the two enantiomers by chiral HPLC (CHIRAL ART Cellulose-SB, 2*25 cm, 5 μm; Mobile Phase A: Hex (0.2% DEA)-HPLC, Mobile Phase B: EtOH:DCM=1:1-HPLC; Flow rate: 20 mL/min; Gradient:10% B to 10% B over 21 min; UV220/254 nm) to afford:

Example 20: 135.2 mg 1,1,1,3,3,3-hexafluoropropan-2-yl (R or S)-1-((6-(dimethylphosphoryl)pyridin-3-yl)carbamoyl)-6-azaspiro[2.5]octane-6-carboxylate peak 1. ¹H NMR (400 MHz, DMSO-d₆) δ 10.67 (s, 1H), 8.89-8.87 (m, 1H), 8.22-8.18 (m, 1H), 7.90-7.86 (m, 1H), 6.59-6.54 (m, 1H), 3.62-3.56 (m, 2H), 3.54-3.49 (m, 1H), 3.33 (s, 1H), 1.87-1.83 (m, 1H), 1.69 (s, 2H), 1.65-1.59 (m, 6H), 1.51 (s, 2H), 1.20-1.11 (m, 1H), 1.06-0.99 (m, 1H). $t_R$=8.88 min. LCMS (Method D) (ESI, m/z): 502 [M+H]⁺.

And the corresponding enantiomer

Example 21: 122.5 mg 1,1,1,3,3,3-hexafluoropropan-2-yl (R or S)-1-((6-(dimethylphosphoryl)pyridin-3-yl)carbamoyl)-6-azaspiro[2.5]octane-6-carboxylate peak 2. ¹H NMR (400 MHz, DMSO-d₆) δ 10.67 (s, 1H), 8.89-8.87 (m, 1H), 8.22-8.18 (m, 1H), 7.90-7.86 (m, 1H), 6.59-6.54 (m, 1H), 3.62-3.56 (m, 2H), 3.55-3.47 (m, 1H), 3.33 (s, 1H), 1.89-1.81 (m, 1H), 1.70 (s, 1H), 1.66-1.59 (m, 7H), 1.51 (s, 2H), 1.21-1.11 (m, 1H), 1.06-0.98 (m, 1H). $t_R$=11.641 min. LCMS (Method D) (ESI, m/z): 502 [M+H]⁺.

Example 22: 1,1,1,3,3,3-Hexafluoropropan-2-yl (±)-1-(pyridin-4-ylcarbamoyl)-6-azaspiro[2.5]octane-6-carboxylate

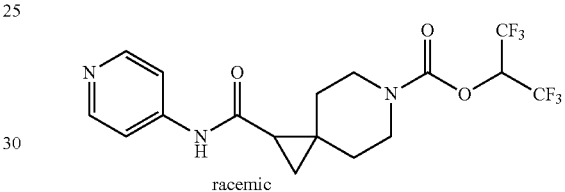

racemic

Step 1: Synthesis of t-butyl 1-carbamoyl-6-azaspiro[2.5]octane-6-carboxylate

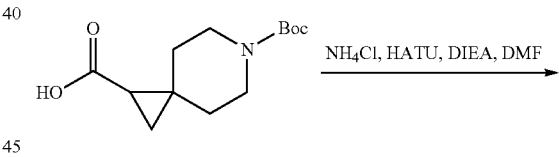

A mixture of 6-(t-butoxycarbonyl)-6-azaspiro[2.5]octane-1-carboxylic acid (600 mg, 2.34 mmol, 1.00 equiv), HATU (1069 mg, 2.80 mmol, 1.20 equiv), DIPEA (15.2 mg, 11.2 mmol, 5.00 equiv), and NH₄Cl (620 mg, 11.7 mmol, 5.00 equiv) in DMF (10 mL) was stirred for overnight at room temperature. The resulting mixture was quenched with water (50 mL). The aqueous layer was extracted with EtOAc (2×200 mL). The resulting mixture was concentrated under reduced pressure. The residue was purified by silica gel column chromatography, eluted with petroleum ether/EtOAc (8:1) to afford t-butyl 1-carbamoyl-6-azaspiro[2.5]octane-6-carboxylate (500 mg). LCMS (ESI, m/z): 255 [M+H]⁺.

Step 2: Synthesis of t-butyl 1-(pyridin-4-ylcarbamoyl)-6-azaspiro[2.5]octane-6-carboxylate

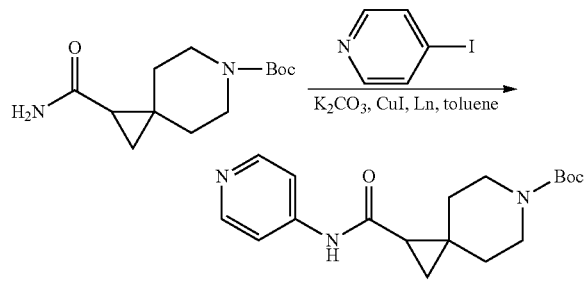

A mixture of t-butyl 1-carbamoyl-6-azaspiro[2.5]octane-6-carboxylate (400 mg), 4-iodopyridine (386 mg), K₂CO₃ (433 mg), Ln (22 mg), and CuI (15 mg) in toluene (30 mL) was stirred for overnight at 100° C. under a nitrogen atmosphere. The resulting mixture was quenched with water (50 mL). The aqueous layer was extracted with EtOAc (2×200 mL) and the resulting mixture was concentrated under reduced pressure. The residue was purified by silica gel column chromatography, eluting with petroleum ether/EtOAc (8:1) to afford t-butyl 1-(pyridin-4-ylcarbamoyl)-6-azaspiro[2.5]octane-6-carboxylate (360 mg). LCMS (ESI, m/z): 332 [M+H]⁺.

Step 3: Synthesis of N-(pyridin-4-yl)-6-azaspiro[2.5]octane-1-carboxamide

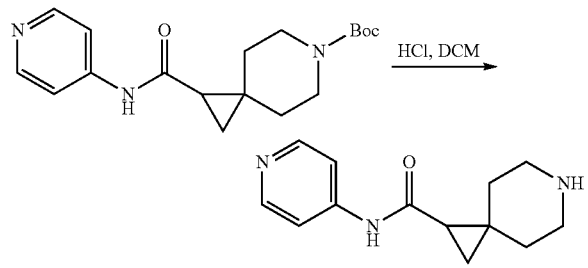

N-(pyridin-4-yl)-6-azaspiro[2.5]octane-1-carboxamide was prepared from t-butyl 1-(pyridin-4-ylcarbamoyl)-6-azaspiro[2.5]octane-6-carboxylate (360 mg), DCM (5 mL), and HCl (gas)/1,4-dioxane (3 mL) as described in Example 13, Step 2 to provide the title compound (200 mg). LCMS (ESI, m/z): 232 [M+H]⁺.

Step 4: Synthesis of 1,1,1,3,3,3-hexafluoropropan-2-yl (±)-1-(pyridin-4-ylcarbamoyl)-6-azaspiro[2.5]octane-6-carboxylate

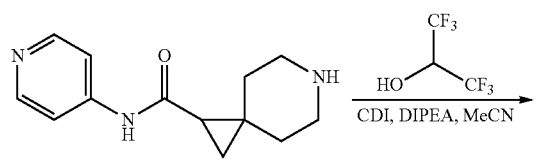

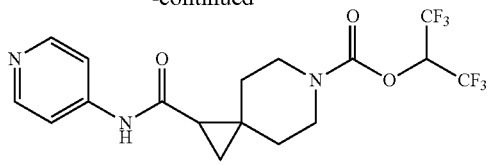

1,1,1,3,3,3-Hexafluoropropan-2-yl (±)-1-(pyridin-4-ylcarbamoyl)-6-azaspiro[2.5]octane-6-carboxylate was prepared from N-(pyridin-4-yl)-6-azaspiro[2.5]octane-1-carboxamide (440 mg), CDI (369 mg), ACN (5 mL), DIPEA (489 mg) and 1,1,1,3,3,3-hexafluoropropan-2-ol (1603 mg) as described in Example 1, Step 3 to provide the title compound (100 mg).

Example 23: 1,1,1,3,3,3-Hexafluoropropan-2-yl (R or S)-1-(pyridin-4-ylcarbamoyl)-6-azaspiro[2.5]octane-6-carboxylate Peak 1 and Example 24: 1,1,1,3,3,3-Hexafluoropropan-2-yl (R or S)-1-(pyridin-4-ylcarbamoyl)-6-azaspiro[2.5]octane-6-carboxylate Peak 2

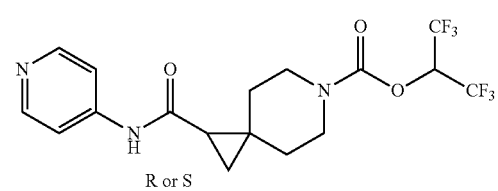 [SMILES: O=C(Nc1ccncc1)C1CC12CCN(C(=O)OC(C(F)(F)F)C(F)(F)F)CC2]

R or S

The racemic mixture prepared in Example 22 was separated into the two enantiomers by chiral HPLC (CHIRALPAK IF, 2*25 cm, 5 μm; Mobile Phase A: Hex (10 mM NH₃-MeOH), Mobile Phase B: EtOH-HPLC; Flow rate:15 mL/min; Gradient:5% B to 5% B over 15 min; UV220/254 nm) to afford:

Example 23: 32.9 mg of 1,1,1,3,3,3-hexafluoropropan-2-yl (R or S)-1-(pyridin-4-ylcarbamoyl)-6-azaspiro[2.5]octane-6-carboxylate peak 1. ¹H NMR (400 MHz, Chloroform-d) δ 9.11-8.88 (m, 1H), 8.59-8.30 (m, 2H), 7.68-7.44 (m, 2H), 5.79-5.60 (m, 1H), 3.80-3.36 (m, 4H), 1.96-1.77 (m, 2H), 1.73-1.51 (m, 2H), 1.50-1.34 (m, 2H), 1.08-0.99 (m, 1H). $t_R$=9.807 min. LCMS (Method E) (ESI, m/z): 426[M+H]⁺.

And the corresponding enantiomer

Example 24: 32.2 mg of 1,1,1,3,3,3-hexafluoropropan-2-yl (R or S)-1-(pyridin-4-ylcarbamoyl)-6-azaspiro[2.5]octane-6-carboxylate peak 2. ¹H NMR (400 MHz, Chloroform-d) δ 9.11-8.88 (m, 1H), 8.59-8.30 (m, 2H), 7.68-7.44 (m, 2H), 5.79-5.60 (m, 1H), 3.80-3.36 (m, 4H), 1.96-1.77 (m, 2H), 1.73-1.51 (m, 2H), 1.50-1.34 (m, 2H), 1.08-0.99 (m, 1H). $t_R$=11.917 min. LCMS (Method E) (ESI, m/z): 426[M+H]⁺.

Example 25: 1,1,1,3,3,3-Hexafluoropropan-2-yl (±)1-((tetrahydro-2H-pyran-4-carbonyl)carbamoyl)-6-azaspiro[2.5]octane-6-carboxylate

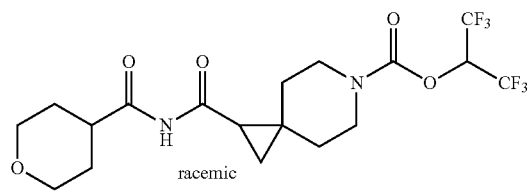 [SMILES: O=C(NC(=O)C1CC12CCN(C(=O)OC(C(F)(F)F)C(F)(F)F)CC2)C1CCOCC1]

Step 1: Synthesis of t-butyl 1-carbamoyl-6-azaspiro[2.5]octane-6-carboxylate

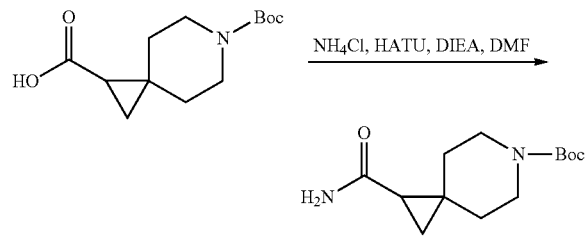

t-Butyl 1-carbamoyl-6-azaspiro[2.5]octane-6-carboxylate was prepared from 6-(t-butoxycarbonyl)-6-azaspiro[2.5]octane-1-carboxylic acid (600 mg, 2.34 mmol, 1.00 equiv), HATU (1069 mg, 2.80 mmol, 1.20 equiv), DIPEA (15.2 mg, 11.2 mmol, 5.00 equiv), NH₄Cl (620 mg, 11.7 mmol, 5.00 equiv) in DMF (10 mL) as described in Example 19, Step 1 to afford t-butyl 1-carbamoyl-6-azaspiro[2.5]octane-6-carboxylate (500 mg). LCMS (ESI, m/z): 255 [M+H]⁺.

Step 2: Synthesis of t-butyl 1-((tetrahydro-2H-pyran-4-carbonyl)carbamoyl)-6-azaspiro[2.5]octane-6-carboxylate

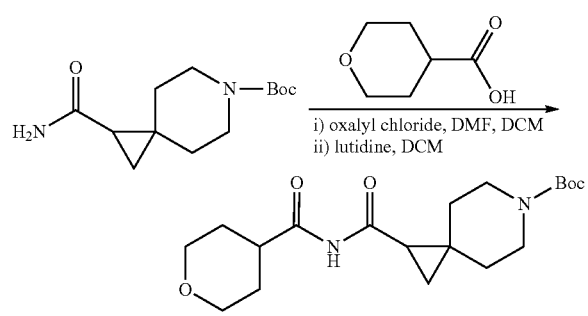

To a mixture of tetrahydro-2H-pyran-4-carboxylic acid (500.00 mg) and oxalyl chloride (961 mg) in DCM (10 mL) was added DMF (30.0 mg) dropwise at room temperature. The reaction mixture was stirred for 1 h at room temperature. The reaction was concentrated under reduced pressure prior to addition of t-butyl 1-carbamoyl-6-azaspiro[2.5]octane-6-carboxylate (150 mg) and lutidine (127 mg) in DCM. The reaction mixture was stirred overnight at room temperature and quenched with water (10 mL). The resulting mixture was extracted with DCM (3×30 mL) and the combined organic layers were washed with brine (2×30 mL), dried over anhydrous Na2SO4, filtered and concentrated under reduced pressure. The residue was purified by flash chromatography to provide t-butyl 1-((tetrahydro-2H-pyran-4-carbonyl)carbamoyl)-6-azaspiro[2.5]octane-6-carboxylate (230 mg). LCMS (ESI, m/z): 367 [M+H]⁺.

Step 3. Synthesis of N-(tetrahydro-2H-pyran-4-carbonyl)-6-azaspiro[2.5]octane-1-carboxamide

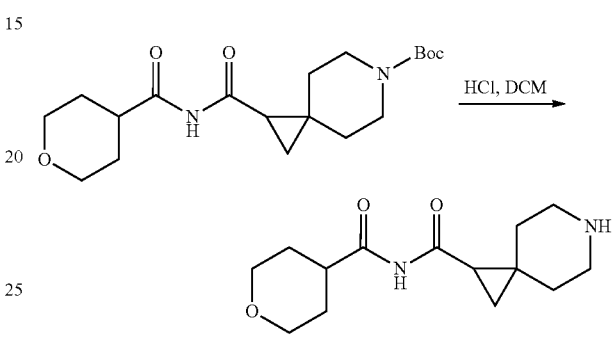

N-(tetrahydro-2H-pyran-4-carbonyl)-6-azaspiro[2.5]octane-1-carboxamide was prepared from t-butyl 1-((tetrahydro-2H-pyran-4-carbonyl)carbamoyl)-6-azaspiro[2.5]octane-6-carboxylate (230 mg), DCM (5 mL), and a solution of HCl (gas)/1,4-dioxane (3 mL) as described in Example 13, Step 2 to provide of N-(tetrahydro-2H-pyran-4-carbonyl)-6-azaspiro[2.5]octane-1-carboxamide (130 mg). LCMS (ESI, m/z): 267[M+H]⁺.

Step 4: Synthesis of 1,1,1,3,3,3-hexafluoropropan-2-yl (±)1-((tetrahydro-2H-pyran-4-carbonyl)carbamoyl)-6-azaspiro[2.5]octane-6-carboxylate

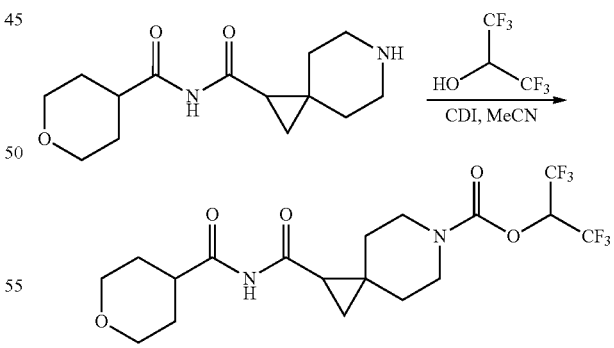

1,1,1,3,3,3-Hexafluoropropan-2-yl (±)1-((tetrahydro-2H-pyran-4-carbonyl)carbamoyl)-6-azaspiro[2.5]octane-6-carboxylate was prepared from N-(tetrahydro-2H-pyran-4-carbonyl)-6-azaspiro[2.5]octane-1-carboxamide (200 mg), CDI (146 mg) ACN (5 mL), DIPEA (489 mg, 3.79 mmol, 2.00 equiv) and 1,1,1,3,3,3-hexafluoropropan-2-ol (634 mg) as described in Example 1, Step 3 to provide the title compound (100 mg).

Example 26: Synthesis of 1,1,1,3,3,3-Hexafluoropropan-2-yl (R or 5)-1-((tetrahydro-2H-pyran-4-carbonyl)carbamoyl)-6-azaspiro[2.5]octane-6-carboxylate Peak 1

Example 27: Synthesis of 1,1,1,3,3,3-Hexafluoropropan-2-yl (R or 5)-1-((tetrahydro-2H-pyran-4-carbonyl)carbamoyl)-6-azaspiro[2.5]octane-6-carboxylate Peak 2

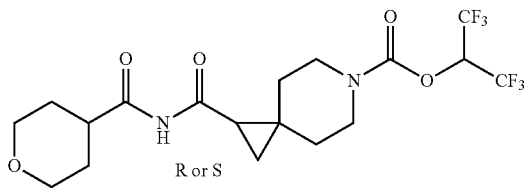 [SMILES: O=C(NC(=O)C1CC12CCN(C(=O)OC(C(F)(F)F)C(F)(F)F)CC2)C1CCOCC1]

R or S

The racemic mixture prepared in Example 25 (100 mg) was separated into the two enantiomers by chiral HPLC (CHIRALPAK IF, 2*25 cm, 5 μm; Mobile Phase A: Hex (10 mM NH₃-MeOH), Mobile Phase B: EtOH-HPLC; Flow rate: 20 mL/min; Gradient:10% B to 10% B over 25 min; UV220/254 nm) to afford:

Example 26: 41.5 mg of 1,1,1,3,3,3-hexafluoropropan-2-yl (R or 5)-1-((tetrahydro-2H-pyran-4-carbonyl)carbamoyl)-6-azaspiro[2.5]octane-6-carboxylate peak 1. $^1$H NMR (400 MHz, Chloroform-d) δ 8.43-8.31 (m, 1H), 5.91-5.69 (m, 1H), 4.15-3.96 (m, 2H), 3.78-3.59 (m, 3H), 3.56-3.39 (m, 2H), 3.34-3.20 (m, 1H), 2.90-2.74 (m, 1H), 2.50-2.40 (m, 1H), 1.90-1.77 (m, 4H), 1.73-1.62 (m, 3H), 1.60-1.51 (m, 1H), 1.48-1.39 (m, 1H), 1.11-1.01 (m, 1H). $t_R$=8.356 min. LCMS (Method A) (ESI, m/z): 461[M+H]$^+$.

And the corresponding enantiomer

Example 27: 24.7 mg of 1,1,1,3,3,3-hexafluoropropan-2-yl (R or 5)-1-((tetrahydro-2H-pyran-4-carbonyl)carbamoyl)-6-azaspiro[2.5]octane-6-carboxylate peak 2. $^1$H NMR (400 MHz, Chloroform-d) δ 8.43-8.31 (m, 1H), 5.91-5.69 (m, 1H), 4.15-3.96 (m, 2H), 3.78-3.59 (m, 3H), 3.56-3.39 (m, 2H), 3.34-3.20 (m, 1H), 2.90-2.74 (m, 1H), 2.50-2.40 (m, 1H), 1.90-1.77 (m, 4H), 1.73-1.62 (m, 3H), 1.60-1.51 (m, 1H), 1.48-1.39 (m, 1H), 1.11-1.01 (m, 1H). $t_R$=16.403 min. LCMS (Method A) (ESI, m/z): 461[M+H]$^+$.

Example 28: 1,1,1,3,3,3-Hexafluoropropan-2-yl (±)1-((6-(1H-pyrazol-1-yl)pyridin-3-yl)carbamoyl)-6-azaspiro[2.5]octane-6-carboxylate

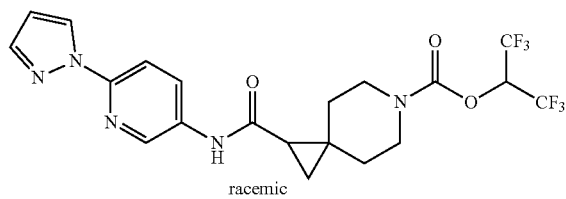 [SMILES: O=C(Nc1ccc(-n2cccn2)nc1)C1CC12CCN(C(=O)OC(C(F)(F)F)C(F)(F)F)CC2]

racemic

Step 1. Synthesis of 5-nitro-2-(1H-pyrazol-1-yl)pyridine

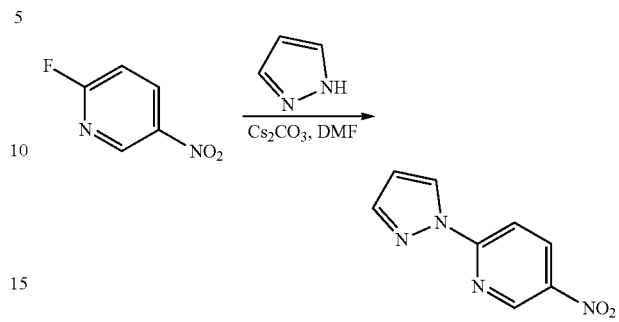

A vial was charged with 2-fluoro-5-nitropyridine (1.00 g, 7.04 mmol, 1.00 equiv), 1H-pyrazole (575 mg), CsCO₃ (5.10 mg) and DMF (10 mL). The resulting solution was stirred overnight at 100° C. and quenched with water (20 mL). The mixture was extracted with EtOAc (3×20 mL) and the organic layers were combined, washed with brine (3×20 mL), dried over anhydrous sodium sulfate, filtered and concentrated under reduced pressure. The residue was purified by flash chromatography to provide of 5-nitro-2-(1H-pyrazol-1-yl)pyridine (1.00 g). LCMS (ESI, m/z): 191 [M+H]$^+$.

Step 2: Synthesis of 6-(1H-pyrazol-1-yl)pyridin-3-amine

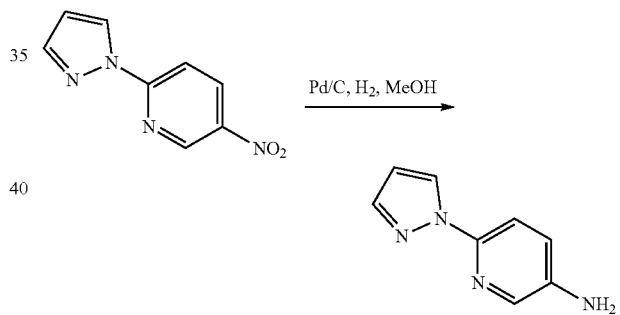

A mixture of 5-nitro-2-(1H-pyrazol-1-yl)pyridine (1.00 g) and Pd/C (20 mg, 10% w.t) in MeOH (10 mL) was stirred overnight under H2. The reaction was cooled to room temperature and filtered. The filtrate was concentrated under reduced pressure to provide 6-(1H-pyrazol-1-yl)pyridin-3-amine (600 mg). LCMS (ESI, m/z): 161 [M+H]$^+$.

Step 3: Synthesis of t-butyl 1-((6-(1H-pyrazol-1-yl)pyridin-3-yl)carbamoyl)-6-azaspiro[2.5]octane-6-carboxylate

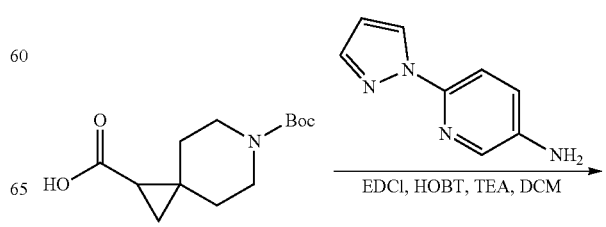

-continued

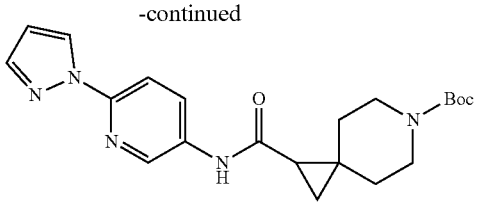

t-butyl 1-((6-(1H-Pyrazol-1-yl)pyridin-3-yl)carbamoyl)-6-azaspiro[2.5]octane-6- was prepared from 6-(t-butoxycarbonyl)-6-azaspiro[2.5]octane-1-carboxylic acid (300 mg), N-(5-aminopyridin-2-yl)acetamide (245 mg), EDCI (248 mg), HOBT (159 mg), and TEA (356 mg) in DCM (3 mL) as described in Example 7, Step 1 to provide t-butyl 14(6-(1H-pyrazol-1-yl)pyridin-3-yl)carbamoyl)-6-azaspiro[2.5]octane-6-carboxylate (300 mg). LCMS (ESI, m/z): 398 [M+H]⁺.

Step 4: Synthesis of N-(6-(1H-pyrazol-1-yl)pyridin-3-yl)-6-azaspiro[2.5]octane-1-carboxamide

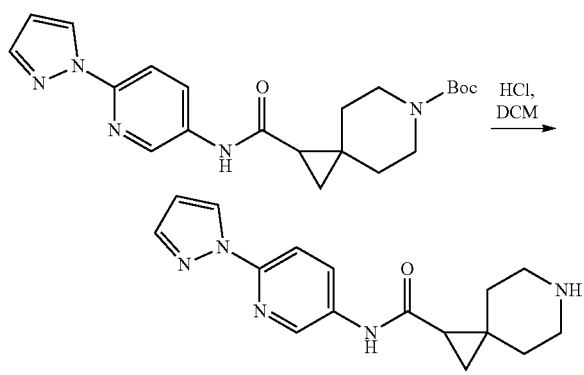

N-(6-(1H-Pyrazol-1-yl)pyridin-3-yl)-6-azaspiro[2.5]octane-1-carboxamide was prepared from t-butyl 1-((6-(1H-pyrazol-1-yl)pyridin-3-yl)carbamoyl)-6-azaspiro[2.5]octane-6-carboxylate (300 mg), DCM (6 mL) and HCl(g) (3 mL) as described in Example 13, Step 2 to provide N-(6-(1H-pyrazol-1-yl)pyridin-3-yl)-6-azaspiro[2.5]octane-1-carboxamide (200 mg). LCMS (ESI, m/z): 298 [M+H]⁺.

Step 5: Synthesis of 1,1,1,3,3,3-hexafluoropropan-2-yl (±)1-((6-(1H-pyrazol-1-yl)pyridin-3-yl)carbamoyl)-6-azaspiro[2.5]octane-6-carboxylate

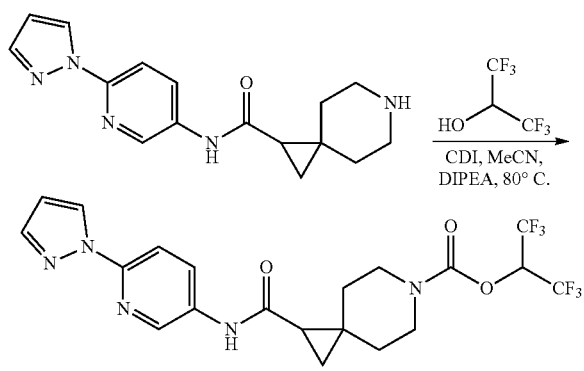

1,1,1,3,3,3-hexafluoropropan-2-yl (±)1-((6-(1H-pyrazol-1-yl)pyridin-3-yl)carbamoyl)-6-azaspiro[2.5]octane-6-carboxylate was prepared from N-(6-(1H-pyrazol-1-yl)pyridin-3-yl)-6-azaspiro[2.5]octane-1-carboxamide (200 mg), ACN (3 mL), 1,1'-carbonyldiimidazole (142 mg), DIPEA (261 mg) and 1,1,1,3,3,3-hexafluoropropan-2-ol (566 mg) as described in Example 1, Step 3 to provide the title compound (240 mg).

Example 29: 1,1,1,3,3,3-Hexafluoropropan-2-yl (R or S)-1-((6-(1H-pyrazol-1-yl)pyridin-3-yl)carbamoyl)-6-azaspiro[2.5]octane-6-carboxylate Peak 1

Example 30: 1,1,1,3,3,3-Hexafluoropropan-2-yl (R or S)-1-((6-(1H-pyrazol-1-yl)pyridin-3-yl)carbamoyl)-6-azaspiro[2.5]octane-6-carboxylate peak 2

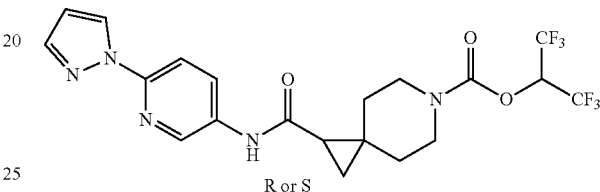

R or S

The racemic mixture prepared in Example 28 was separated into the two enantiomers by chiral HPLC (CHIRALPAK IF, 2*25 cm, 5 μm; Mobile Phase A: Hex (0.5% 2M NH₃-MeOH)-HPLC, Mobile Phase B: EtOH-HPLC; Flow rate:20 mL/min; Gradient:20% B to 20% B over 11 min; UV220/254 nm) to afford:

Example 29: 84.2 mg of 1,1,1,3,3,3-hexafluoropropan-2-yl (R or S)-1-((6-(1H-pyrazol-1-yl)pyridin-3-yl)carbamoyl)-6-azaspiro[2.5]octane-6-carboxylate peak 1. ¹H NMR (400 MHz, Chloroform-d) δ 8.55-8.45 (m, 2H), 8.22 (d, J=8.5 Hz, 2H), 8.00-7.93 (m, 1H), 7.78-7.65 (m, 2H), 6.51-6.46 (m, 1H), 5.84-5.72 (m, 1H), 3.81-3.43 (m, 4H), 1.95-1.81 (m, 2H), 1.72-1.53 (m, 2H), 1.53-1.37 (m, 2H), 1.10-1.00 (m, 1H). t_R=5.29 min. LCMS (Method G) (ESI, m/z): 492[M+H]⁺. And the corresponding enantiomer Example 30: 86.1 mg 1,1,1,3,3,3-hexafluoropropan-2-yl (R or S)-1-((6-(1H-pyrazol-1-yl)pyridin-3-yl)carbamoyl)-6-azaspiro[2.5]octane-6-carboxylate peak 2. ¹H NMR (400 MHz, Chloroform-d) δ 8.55-8.43 (m, 2H), 8.27 (d, J=8.5 Hz, 2H), 8.01-7.93 (m, 1H), 7.79-7.64 (m, 2H), 6.50-6.45 (m, 1H), 5.86-5.70 (m, 1H), 3.80-3.42 (m, 4H), 1.94-1.81 (m, 2H), 1.74-1.53 (m, 2H), 1.55-1.39 (m, 2H), 1.11-0.99 (m, 1H). t_R=7.84 min. LCMS (Method E) (ESI, m/z): 492[M+H]⁺.

Example 31: 1,1,1,3,3,3-Hexafluoropropan-2-yl (±)1-((6-(methylcarbamoyl)pyridin-3-yl)carbamoyl)-6-azaspiro[2.5]octane-6-carboxylate

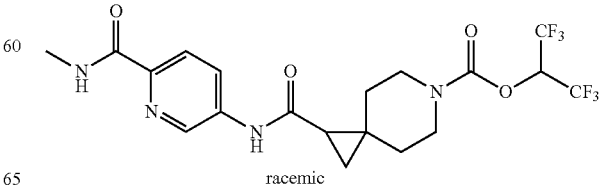

racemic

Step 1: Synthesis of 5-amino-N-methylpicolinamide

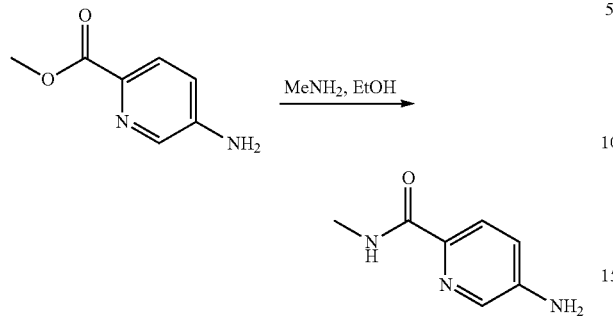

Methyl 5-aminopicolinate (500 mg) was added to a solution of MeNH₂ (204 mg, 6.58 mmol, 2.00 equiv) in EtOH (5 mL). The resulting solution was stirred at 80° C. overnight at room temperature and then quenched with water (10 mL). The resulting solution was extracted with EtOAc (3×20 mL) and the organic layers were combined, washed with brine (1×20 mL), dried over anhydrous Na2SO4, filtered and concentrated under reduced pressure. The residue was purified by column chromatography to provide 5-amino-N-methylpicolinamide (400 mg). LCMS (ESI, m/z): 152 [M+H]⁺.

Step 2: Synthesis of t-butyl 1-((6-(methylcarbamoyl)pyridin-3-yl)carbamoyl)-6-azaspiro[2.5]octane-6-carboxylate

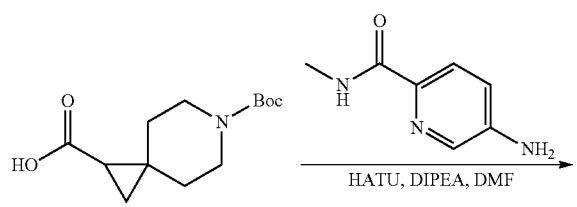

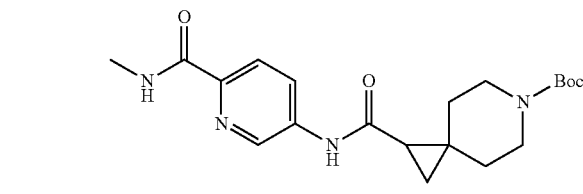

t-Butyl 1-((6-(methylcarbamoyl)pyridin-3-yl)carbamoyl)-6-azaspiro[2.5]octane-6-carboxylate was prepared from 6-(t-butoxycarbonyl)-6-azaspiro[2.5]octane-1-carboxylic acid (300 mg), 5-amino-N-methylpicolinamide (231 mg), HATU (671 mg), and DIPEA (455 mg) in DMF (5 mL) as described in Example 19, Step 1 provide t-butyl 1-((6-(methylcarbamoyl)pyridin-3-yl)carbamoyl)-6-azaspiro[2.5]octane-6-carboxylate (210 mg). LCMS (ESI, m/z): 389 [M+H]⁺.

Step 3: Synthesis of N-(6-(methylcarbamoyl)pyridin-3-yl)-6-azaspiro[2.5]octane-1-carboxamide

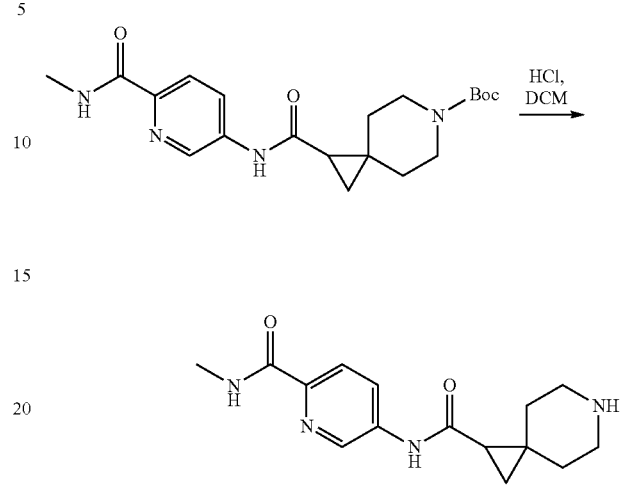

N-(6-(Methylcarbamoyl)pyridin-3-yl)-6-azaspiro[2.5]octane-1-carboxamide was prepared from t-butyl 1-((6-(methylcarbamoyl)pyridin-3-yl)carbamoyl)-6-azaspiro[2.5]octane-6-carboxylate (210 mg) and HCl(g) (2 mL) in DCM (4 mL) as described in Example 13, Step 2 to provide N-(6-(methylcarbamoyl)pyridin-3-yl)-6-azaspiro[2.5]octane-1-carboxamide (140 mg). LCMS (ESI, m/z): 289 [M+H]⁺.

Step 4: Synthesis of 1,1,1,3,3,3-hexafluoropropan-2-yl 1-((6-(methylcarbamoyl)pyridin-3-yl)carbamoyl)-6-azaspiro[2.5]octane-6-carboxylate

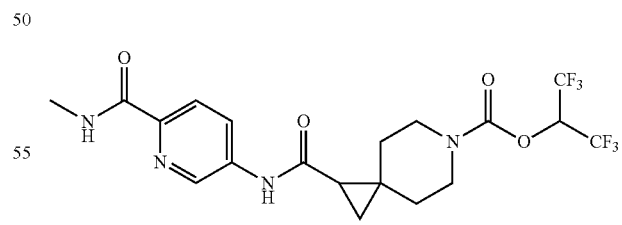

1,1,1,3,3,3-Hexafluoropropan-2-yl 1-((6-(methylcarbamoyl)pyridin-3-yl)carbamoyl)-6-azaspiro[2.5]octane-6-carboxylate was prepared from N-(6-(methylcarbamoyl)pyridin-3-yl)-6-azaspiro[2.5]octane-1-carboxamide (140 mg), ACN (3 mL), 1,1'-carbonyldiimidazole (102 mg), DIPEA (188 mg) and 1,1,1,3,3,3-hexafluoropropan-2-ol (408 mg) as described in Example 1, Step 3 to provide the title compound (160 mg).

Example 32: 1,1,1,3,3,3-Hexafluoropropan-2-yl (R or S)-1-((6-(methylcarbamoyl)pyridin-3-yl)carbamoyl)-6-azaspiro[2.5]octane-6-carboxylate peak 1

Example 33: 1,1,1,3,3,3-Hexafluoropropan-2-yl (R or S)-1-((6-(methylcarbamoyl)pyridin-3-yl)carbamoyl)-6-azaspiro[2.5]octane-6-carboxylate Peak 2

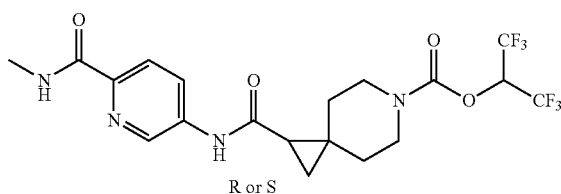 [SMILES: CNC(=O)c1ccc(NC(=O)C2CC23CCN(C(=O)OC(C(F)(F)F)C(F)(F)F)CC3)cn1]

R or S

The racemic mixture prepared in Example 31 was separated into the two enantiomers by chiral HPLC (CHIRALPAK IF, 2*25 cm, 5 μm; Mobile Phase A: Hex (0.5% 2M NH$_3$-MeOH)-HPLC, Mobile Phase B: EtOH-HPLC; Flow rate:20 mL/min; Gradient:30% B to 30% B over 10.5 min; UV220/254 nm) to afford:

Example 32: 33.1 mg of 1,1,1,3,3,3-hexafluoropropan-2-yl (R or S)-1-((6-(methylcarbamoyl)pyridin-3-yl)carbamoyl)-6-azaspiro[2.5]octane-6-carboxylate peak 1. $^1$H NMR (400 MHz, Chloroform-d) δ 8.83 (s, 1H), 8.70-8.46 (m, 1H), 8.39-8.16 (m, 2H), 8.22 (s, 1H), 8.10 (s, 1H), 5.88-5.67 (m, 1H), 3.74 (s, 1H), 3.56 (s, 3H), 3.16-2.97 (m, 3H), 1.87 (s, 2H), 1.79-1.36 (s, 4H), 1.07 (s, 1H). $t_R$=6.605 min. LCMS (Method A) (ESI, m/z): 483 [M+H]$^+$.

Example 33: 31.8 mg of 1,1,1,3,3,3-hexafluoropropan-2-yl (R or S)-1-((6-(methylcarbamoyl)pyridin-3-yl)carbamoyl)-6-azaspiro[2.5]octane-6-carboxylate peak 2. $^1$H NMR (400 MHz, Chloroform-d) δ 8.77 (s, 1H), 8.47 (s, 1H), 8.15 (s, 2H), 8.00 (d, J=5.5 Hz, 1H), 5.86-5.68 (m, 1H), 3.78-3.67 (m, 1H), 3.65-3.47 (m, 3H), 3.04 (d, J=4.8 Hz, 3H), 1.95-1.79 (m, 2H), 1.78-1.38 (m, 4H), 1.09-1.01 (s, 1H). $t_R$=8.899 min. LCMS (Method E) (ESI, m/z): 483 [M+H]$^+$.

Example 34: 1,1,1,3,3,3-Hexafluoropropan-2-yl (±)1-(4-cyclopropylpiperazine-1-carbonyl)-6-azaspiro[2.5]octane-6-carboxylate

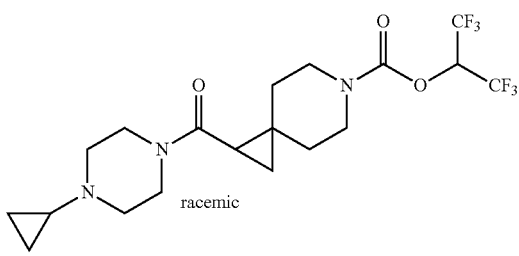 [SMILES: O=C(OC(C(F)(F)F)C(F)(F)F)N1CCC2(CC1)CC2C(=O)N1CCN(C2CC2)CC1]

racemic

Step 1: Synthesis of t-butyl 1-(4-cyclopropylpiperazine-1-carbonyl)-6-azaspiro[2.5]octane-6-carboxylate

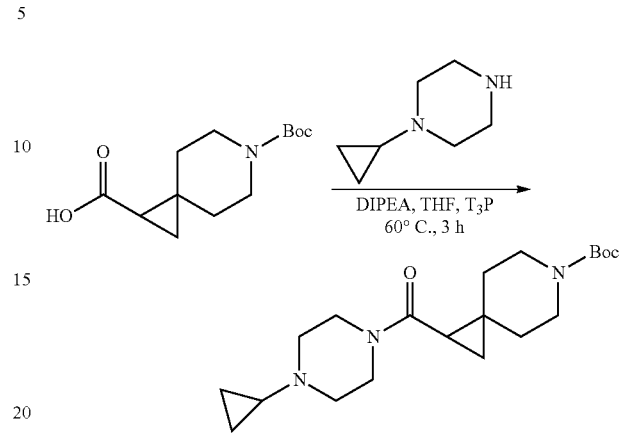

A vial was charged with 6-((t-butoxy)carbonyl)-6-azaspiro[2.5]octane-1-carboxylic acid (150 mg), THF (5 mL), 1-cyclopropylpiperazine (74.0 mg), DIPEA (152 mg) and 2,4,6-tripropyl-1,3,5,2,4,6-trioxatriphosphinane-2,4,6-trione (50% in EtOAc, 563 mg, 0.885 mmol, 1.50 equiv) under nitrogen. The resulting solution was stirred for 3 h at 60° C. and quenched with water (10 mL). The mixture was extracted with EtOAc (3×10 mL) and the organic layers were combined, washed with brine (3×10 mL), dried over anhydrous sodium sulfate, filtered and concentrated under reduced pressure. The residue was chromatographed on a silica gel column with EtOAc/petroleum ether (2/1) to provide t-butyl 1-(4-cyclopropylpiperazine-1-carbonyl)-6-azaspiro[2.5]octane-6-carboxylate (57.0 mg). LCMS (ESI, m/z): 364 [M+H]$^+$.

Step 2: Synthesis of (4-cyclopropylpiperazin-1-yl)(6-azaspiro[2.5]octan-1-yl)methanone

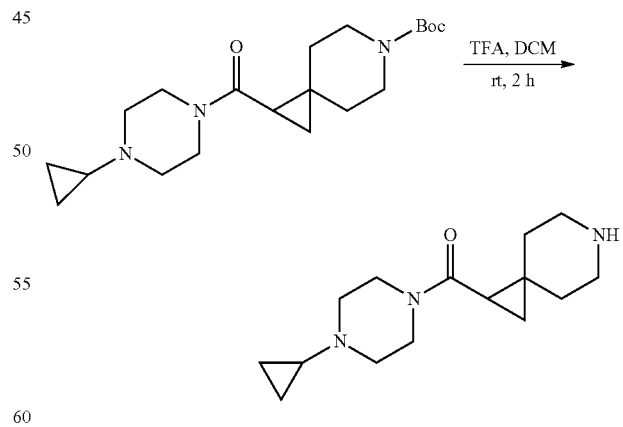

(4-Cyclopropylpiperazin-1-yl)(6-azaspiro[2.5]octan-1-yl)methanone was prepared from t-butyl 1-(4-cyclopropylpiperazin-1-yl)carbonyl)-6-azaspiro[2.5]octane-6-carboxylate (207 mg), DCMe (5 mL) and TFA (5 mL) as described in Example 1, Step 2 to provide the title compound (150 mg). LCMS (ESI, m/z): 264 [M+H]$^+$.

Step 3: Synthesis of 1,1,1,3,3,3-hexafluoropropan-2-yl (±)1-(4-cyclopropylpiperazine-1-carbonyl)-6-azaspiro[2.5]octane-6-carboxylate

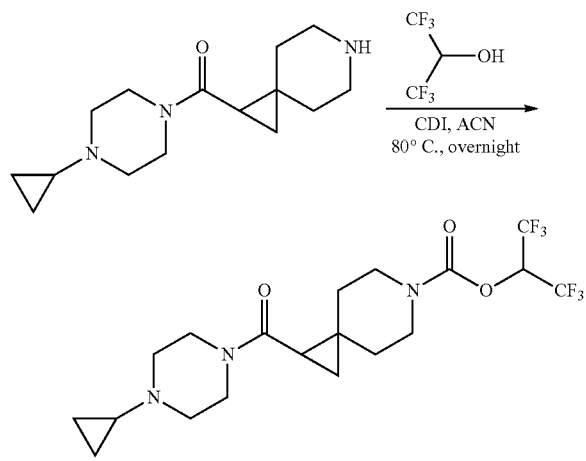

1,1,1,3,3,3-Hexafluoropropan-2-yl (±)1-(4-cyclopropylpiperazine-1-carbonyl)-6-azaspiro[2.5]octane-6-carboxylate was prepared from 1,1,1,3,3,3-hexafluoropropan-2-ol (287 mg), ACN (5 mL), 1,1'-carbonyldiimidazole (111 mg) and (4-cyclopropylpiperazin-1-yl)(6-azaspiro[2.5]octan-1-yl)methanone (150 mg) as described in Example 1, Step 3. The crude product was purified by preparative HPLC using the following gradient conditions: 20% $CH_3CN$/80% Phase A increasing to 80% $CH_3CN$ over 10 min, then to 100% $CH_3CN$ over 0.1 min, holding at 100% $CH_3CN$ for 1.9 min, then reducing to 20% $CH_3CN$ over 0.1 min, and holding at 20% for 1.9 min, on a Waters 2767-5 Chromatograph. Column: X-bridge Prep C18, 19*150 mm 5 μm; Mobile phase: Phase A: aqueous $NH_4HCO_3$ (0.05%); Phase B: $CH_3CN$; Detector, UV220 & 254 nm. Purification resulted in 1,1,1,3,3,3-hexafluoropropan-2-yl (±)1-(4-cyclopropylpiperazine-1-carbonyl)-6-azaspiro[2.5]octane-6-carboxylate (80.7 mg). $^1H$ NMR (300 MHz, Chloroform-d) δ 5.79-5.74 (m, 1H), 3.38-3.81 (m, 8H), 2.71-2.01 (m, 4H), 1.72-1.58 (m, 5H), 1.26-1.53 (m, 2H), 0.85-0.71 (m, 1H), 0.40 (br, 4H). LCMS (Method E) (ESI, m/z): 458 $[M+H]^+$.

Examples 35-189: Examples 35-189 were prepared by similar procedures as described in Examples 1-34. Absolute configuration of Examples 36, 105, 118, 142, 151, 162, and 174 were determined in a similar manner as example 3, wherein resynthesis of the final compound using an intermediate with known absolute configuration allowed for the assignment of the absolute configuration of the final products. The stereochemistry of the corresponding (S)-enantiomers (Examples 37, 106, 117, 141, 150, 163 and 175) were assigned as described above for Example 12, 14, and 17.

| Ex | Name | Structure | NMR ($^1H$ NMR, 300 MHz or 400 MHz, Chloroform-d unless otherwise noted) | MS $[M+H]^+$ |
|---|---|---|---|---|
| 35 | 1,1,1,3,3,3-hexafluoropropan-2-yl (±)1-((6-methoxypyridin-3-yl)carbamoyl)-6-azaspiro[2.5]octane-6-carboxylate | racemic | | |
| 36 | 1,1,1,3,3,3-hexafluoropropan-2-yl (R)-1-((6-methoxypyridin-3-yl)carbamoyl)-6-azaspiro[2.5]octane-6-carboxylate peak 1 | 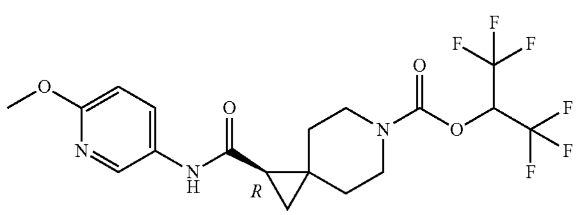 | δ 8.24-8.12 (m, 1H), 8.02-7.88 (m, 1H), 7.66-7.56 (m, 1H), 6.82-6.70 (m, 1H), 5.88-5.69 (m, 1H), 4.02-3.92 (m, 3H), 3.78-3.68 (m, 1H), 3.63-3.46 (m, 3H), 1.89-1.81 (m, 2H), 1.73-1.44 (m, 3H), 1.40-1.32 (m, 1H), 1.01 (dd, J = 8.0, 4.6 Hz, 1H) | 456 |
| 37 | 1,1,1,3,3,3-hexafluoropropan-2-yl (S)-1-((6-methoxypyridin-3-yl)carbamoyl)-6-azaspiro[2.5]octane-6-carboxylate peak 2 | 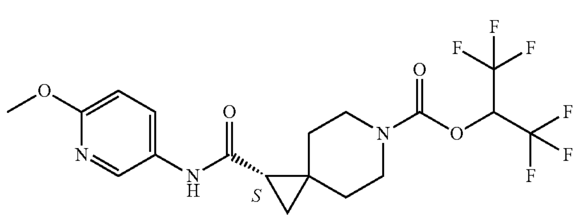 | δ 8.24-8.12 (m, 1H), 8.02-7.88 (m, 1H), 7.66-7.56 (m, 1H), 6.82-6.70 (m, 1H), 5.88-5.69 (m, 1H), 4.02-3.92 (m, 3H), 3.78-3.68 (m, 1H), 3.63-3.46 (m, 3H), 1.89-1.81 (m, 2H), 1.73-1.44 (m, 3H), 1.40-1.32 (m, 1H), 1.01 (dd, J = 8.0, 4.6 Hz, 1H) | 456 |

| Ex | Name | Structure | NMR (¹H NMR, 300 MHz or 400 MHz, Chloroform-d unless otherwise noted) | MS [M + H]⁺ |
|---|---|---|---|---|
| 38 | 1,1,1,3,3,3-hexafluoropropan-2-yl (±)1-((5-fluoropyridin-3-yl)carbamoyl)-6-azaspiro[2.5]octane-6-carboxylate | racemic | | |
| 39 | 1,1,1,3,3,3-hexafluoropropan-2-yl (R or S)-1-((5-fluoropyridin-3-yl)carbamoyl)-6-azaspiro[2.5]octane-6-carboxylate peak 1 | R or S | δ 8.32 (s, 1H), 8.23-8.17 (m, 2H), 7.76 (s, 1H), 5.82-5.74 (m, 1H), 3.77-3.72 (m, 1H), 3.67-3.61 (m, 1H), 3.56-3.47 (m, 2H), 1.87 (br, 2H), 1.70-1.63 (m, 1H), 1.59-1.56 (m, 1H), 1.48 (br, 1H), 1.47-1.41 (m, 1H), 1.09-1.06 (m, 1H) | 444 |
| 40 | 1,1,1,3,3,3-hexafluoropropan-2-yl (R or S)-1-((5-fluoropyridin-3-yl)carbamoyl)-6-azaspiro[2.5]octane-6-carboxylate peak 2 | R or S | δ 8.32-8.17 (m, 3H), 7.76 (s, 1H), 5.82-5.74 (m, 1H), 3.77-3.72 (m, 1H), 3.67-3.61 (m, 1H), 3.56-3.47 (m, 2H), 1.87 (br, 2H), 1.70-1.63 (m, 1H), 1.59-1.56 (m, 1H), 1.48 (br, 1H), 1.47-1.41 (m, 1H), 1.09-1.06 (m, 1H) | 444 |
| 41 | 1,1,1,3,3,3-hexafluoropropan-2-yl (±)1-(methyl(pyridin-3-yl)carbamoyl)-6-azaspiro[2.5]octane-6-carboxylate | racemic | δ 8.61 (m, 1H), 8.55 (s, 1H), 7.58-7.56 (m, 1H), 7.43-7.39 (m, 1H), 5.83-5.71 (m, 1H), 3.84-3.76 (m, 1H), 3.65 (br, 1H), 3.33-3.10 (m, 5H), 1.85-1.75 (m, 2H), 1.59-1.44 (m, 1H), 1.38-1.35 (m, 1H), 1.25 (br, 1H), 1.13-0.99 (m, 1H), 0.77 (br, 1H) | 440 |
| 42 | 1,1,1,3,3,3-hexafluoropropan-2-yl (R or S)-1-(methyl(pyridin-3-yl)carbamoyl)-6-azaspiro[2.5]octane-6-carboxylate peak 1 | R or S | δ 8.61-8.56 (m, 1H), 8.55 (s, 1H), 7.58-7.56 (m, 1H), 7.43-7.39 (m, 1H), 5.83-5.71 (m, 1H), 3.84-3.76 (m, 1H), 3.65 (br, 1H), 3.33-3.10 (m, 5H), 1.85-1.75 (m, 2H), 1.59-1.44 (m, 1H), 1.38-1.35 (m, 1H), 1.25 (br, 1H), 1.13-0.99 (m, 1H), 0.77 (br, 1H) | 440 |
| 43 | 1,1,1,3,3,3-hexafluoropropan-2-yl (R or S)-1-(methyl(pyridin-3-yl)carbamoyl)-6-azaspiro[2.5]octane-6-carboxylate peak 2 | R or S | δ 8.61-8.56 (m, 1H), 8.55 (s, 1H), 7.58-7.56 (m, 1H), 7.43-7.39 (m, 1H), 5.83-5.71 (m, 1H), 3.84-3.76 (m, 1H), 3.65 (br, 1H), 3.33-3.10 (m, 5H), 1.85-1.75 (m, 2H), 1.59-1.44 (m, 1H), 1.38-1.35 (m, 1H), 1.25 (br, 1H), 1.13-0.99 (m, 1H), 0.77 (br, 1H) | 440 |

| Ex | Name | Structure | NMR (¹H NMR, 300 MHz or 400 MHz, Chloroform-d unless otherwise noted) | MS [M + H]⁺ |
|---|---|---|---|---|
| 44 | 1,1,1,3,3,3-hexafluoro-propan-2-yl (±)1-(methyl(pyridin-2-yl)carbamoyl)-6-azaspiro[2.5]octane-6-carboxylate | racemic | | |
| 45 | 1,1,1,3,3,3-hexafluoro-propan-2-yl (R or S)-1-(methyl(pyridin-2-yl)carbamoyl)-6-azaspiro[2.5]octane-6-carboxylate peak 1 | R or S | δ 8.50 (d, J = 4.5 Hz, 1H), 7.81-7.75 (m, 1H), 7.25-7.21 (m, 2H), 5.81-5.75 (m, 1H), 3.77-3.59 (m, 2H), 3.48-3.41 (m, 5H), 1.85-1.81 (m, 1H), 1.76-1.70 (m, 1H), 1.53-1.40 (m, 3H), 1.26-1.21 (m, 1H), 0.79-0.75 (m, 1H) | 440 |
| 46 | 1,1,1,3,3,3-hexafluoro-propan-2-yl (R or S)-1-(methyl(pyridin-2-yl)carbamoyl)-6-azaspiro[2.5]octane-6-carboxylate peak 2 | R or S | δ 8.50 (d, J = 4.5 Hz, 1H), 7.81-7.75 (m, 1H), 7.25-7.21 (m, 2H), 5.81-5.75 (m, 1H), 3.77-3.59 (m, 2H), 3.48-3.41 (m, 5H), 1.85-1.81 (m, 1H), 1.76-1.70 (m, 1H), 1.53-1.40 (m, 3H), 1.26-1.21 (m, 1H), 0.79-0.75 (m, 1H) | 440 |
| 47 | 1,1,1,3,3,3-hexafluoro-propan-2-yl (±)1-(pyridin-2-ylcarbamoyl)-6-azaspiro[2.5]octane-6-carboxylate | racemic | δ 8.62 (d, J = 6.6 Hz, 1H), 8.29-8.13 (m, 2H), 7.78-7.65 (m, 1H), 7.10-6.99 (m, 1H), 5.82-5.72 (m, 1H), 3.71-3.46 (m, 4H), 1.92-1.81 (m, 2H), 1.64-1.45 (m, 3H), 1.38 (t, J = 5.0 Hz, 1H), 1.03-0.99 (m, 1H) | |
| 48 | 1,1,1,3,3,3-hexafluoro-propan-2-yl (R or S)-1-(pyridin-2-ylcarbamoyl)-6-azaspiro[2.5]octane-6-carboxylate peak 1 | R or S | δ 8.46 (d, J = 12.4 Hz, 1H), 8.31-8.23 (m, 1H), 8.16 (d, J = 8.4 Hz, 1H), 7.74-7.67 (m, 1H), 7.07-7.01 (m, 1H), 5.82-5.74 (m, 1H), 3.69-3.51 (m, 4H), 1.87-1.81 (m, 2H), 1.64-1.46 (m, 3H), 1.41-1.34 (m, 1H), 1.03-0.99 (m, 1H) | 426 |
| 49 | 1,1,1,3,3,3-hexafluoro-propan-2-yl (R or S)-1-(pyridin-2-ylcarbamoyl)-6-azaspiro[2.5]octane-6-carboxylate peak 2 | R or S | δ 8.44 (s, 1H), 8.26 (d, J = 3.9 Hz, 1H), 8.16 (d, J = 8.1 Hz, 1H), 7.74-7.68 (m, 1H), 7.10-7.02 (m, 1H), 5.82-5.72 (m, 1H), 3.51-3.69 (m, 4H), 1.94-1.81 (m, 2H), 1.64-1.46 (m, 3H), 1.38 (d, J = 5.0 Hz, 1H), 1.03-0.99 (m, 1H) | 426 |

| Ex | Name | Structure | NMR (¹H NMR, 300 MHz or 400 MHz, Chloroform-d unless otherwise noted) | MS [M + H]⁺ |
|---|---|---|---|---|
| 50 | 1,1,1,3,3,3-hexafluoro-propan-2-yl (±)1-(2-(trifluoromethyl)-5,6,7,8-tetrahydro-imidazo[1,2-a]pyrazine-7-carbonyl)-6-azaspiro[2.5]octane-6-carboxylate | 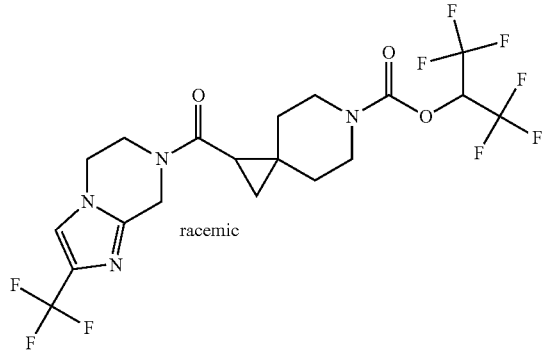 [SMILES: O=C(OC(C(F)(F)F)C(F)(F)F)N1CCC2(CC1)CC2C(=O)N1CCn2cc(C(F)(F)F)nc2C1] racemic | | |
| 51 | 1,1,1,3,3,3-hexafluoro-propan-2-yl (R or S)-1-(2-(trifluoromethyl)-5,6,7,8-tetrahydro-imidazo[1,2-a]pyrazine-7-carbonyl)-6-azaspiro[2.5]octane-6-carboxylate peak 1 | 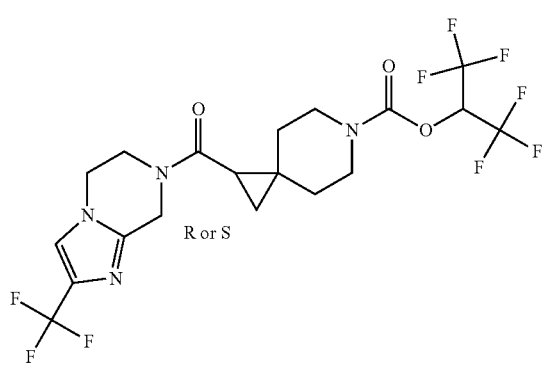 [SMILES: O=C(OC(C(F)(F)F)C(F)(F)F)N1CCC2(CC1)CC2C(=O)N1CCn2cc(C(F)(F)F)nc2C1] R or S | δ 7.28 (s, 1H), 5.79-5.73 (m, 1H), 5.08-4.72 (m, 2H), 4.28-4.18 (m, 1H), 4.11-3.94 (m, 3H), 3.85-3.78 (m, 1H), 3.59-3.53 (m, 1H), 3.47-3.31 (m, 2H), 1.79-1.75 (m, 2H), 1.59-1.54 (m, 2H), 1.42-1.38 (m, 2H), 0.99-0.95 (m, 1H) | 523 |
| 52 | 1,1,1,3,3,3-hexafluoro-propan-2-yl (R or S)-1-(2-(trifluoromethyl)-5,6,7,8-tetrahydro-imidazo[1,2-a]pyrazine-7-carbonyl)-6-aza-spiro[2.5]octane-6-carboxylate peak 2 | 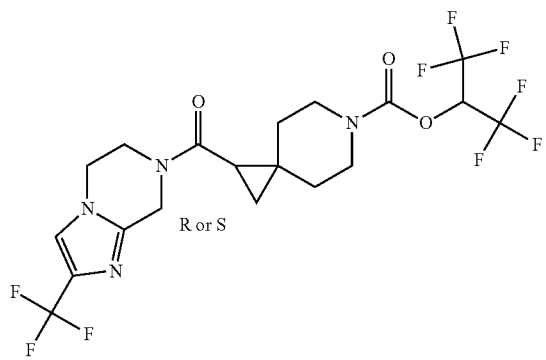 [SMILES: O=C(OC(C(F)(F)F)C(F)(F)F)N1CCC2(CC1)CC2C(=O)N1CCn2cc(C(F)(F)F)nc2C1] R or S | δ 7.28 (s, 1H), 5.79-5.73 (m, 1H), 5.08-4.72 (m, 2H), 4.28-4.18 (m, 1H), 4.10-3.92 (m, 3H), 3.84-3.78 (m, 1H), 3.58-3.52 (m, 1H), 3.47-3.29 (m, 2H), 1.79-1.76 (m, 2H), 1.55-1.47 (m, 2H), 1.45-1.37 (m, 2H), 0.98-0.95 (m, 1H) | 523 |
| 53 | 1,1,1,3,3,3-hexafluoro-propan-2-yl (±)1-(pyrazin-2-ylcarbamoyl)-6-azaspiro[2.5]octane-6-carboxylate | 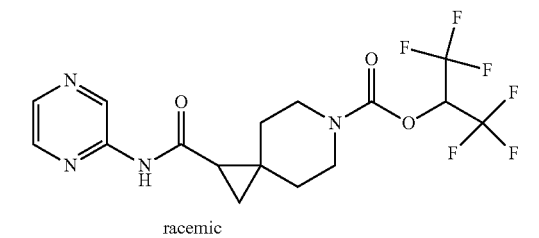 [SMILES: O=C(Nc1cnccn1)C1CC12CCN(C(=O)OC(C(F)(F)F)C(F)(F)F)CC2] racemic | | |

-continued

| Ex | Name | Structure | NMR (¹H NMR, 300 MHz or 400 MHz, Chloroform-d unless otherwise noted) | MS [M + H]⁺ |
|---|---|---|---|---|
| 54 | 1,1,1,3,3,3-hexafluoro-propan-2-yl (R or S)-1-(pyrazin-2-ylcarbamoyl)-6-azaspiro[2.5]octane-6-carboxylate peak 1 | R or S | δ 9.52 (s, 1H), 8.37 (s, 1H), 8.26 (s, 1H), 8.14 (s, 1H), 5.83-5.75 (m, 1H), 3.74-3.68 (m, 1H), 3.62-3.50 (m, 3H), 1.90-1.86 (m, 2H), 1.66-1.61 (m, 2H), 1.55-1.50 (m, 1H), 1.46-1.43 (m, 1H), 1.11-1.07 (m, 1H) | 427 |
| 55 | 1,1,1,3,3,3-hexafluoro-propan-2-yl (R or S)-1-(pyrazin-2-ylcarbamoyl)-6-azaspiro[2.5]octane-6-carboxylate peak 2 | R or S | δ 9.52 (s, 1H), 8.37 (s, 1H), 8.26 (s, 1H), 8.13 (s, 1H), 5.83-5.75 (m, 1H), 3.73-3.68 (m, 1H), 3.61-3.50 (m, 3H), 1.89-1.86 (m, 2H), 1.68-1.61 (m, 2H), 1.55-1.50 (m, 1H), 1.46-1.43 (m, 1H), 1.11-1.08 (m, 1H) | 427 |
| 56 | 1,1,1,3,3,3-hexafluoro-propan-2-yl (±)1-(2-(trifluoromethyl)-5,6,7,8-tetrahydro-pyrido[3,4-d]pyrimidine-7-carbonyl)-6-azaspiro[2.5]octane-6-carboxylate | racemic | ☐ 8.70 (d, J = 10.0 Hz, 1H), 5.77-5.69 (m, 1H), 5.08-4.77 (m, 2H), 4.22-4.06 (m, 1H), 3.84-3.58 (m, 3H), 3.45-3.30 (m, 2H), 3.13-2.95 (m, 2H), 1.82-1.74 (m, 2H), 1.64-1.55 (m, 2H), 1.40 (s, 2H), 0.94 (s, 1H) | 535 |
| 57 | 1,1,1,3,3,3-hexafluoro-propan-2-yl (R or S)-1-(2-(trifluoromethyl)-5,6,7,8-tetrahydro-pyrido[3,4-d]pyrimidine-7-carbonyl)-6-aza-spiro[2.5]octane-6-carboxylate peak 1 | R or S | δ 8.74-8.71 (m, 1H), 5.76 (br, 1H), 5.09-4.80 (m, 2H), 4.19-4.12 (m, 1H), 3.84-3.61 (m, 3H), 3.46-3.24 (m, 2H), 3.14-2.79 (m, 2H), 1.81 (t, J = 6.6 Hz, 2H), 1.72-1.43 (m, 2H), 1.33-1.32 (m, 2H), 0.97 (br, 1H) | 535 |

| Ex | Name | Structure | NMR (¹H NMR, 300 MHz or 400 MHz, Chloroform-d unless otherwise noted) | MS [M + H]⁺ |
|---|---|---|---|---|
| 58 | 1,1,1,3,3,3-hexafluoro-propan-2-yl (R or S)-1-(2-(trifluoromethyl)-5,6,7,8-tetrahydro-pyrido[3,4-d]pyrimidine-7-carbonyl)-6-aza-spiro[2.5]octane-6-carboxylate peak 2 | 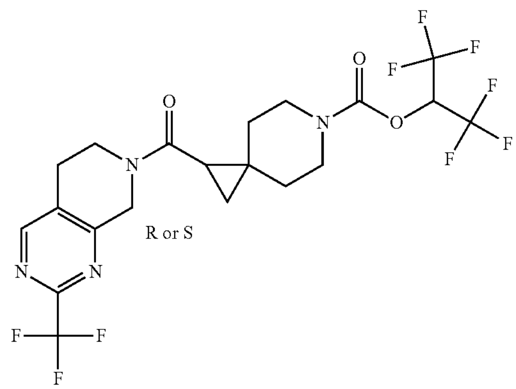 [SMILES: O=C(OC(C(F)(F)F)C(F)(F)F)N1CCC2(CC1)CC2C(=O)N1CCc2cnc(C(F)(F)F)nc2C1] | δ 8.74-8.71 (m, 1H), 5.76 (br, 1H), 5.09-4.80 (m, 2H), 4.19-4.12 (m, 1H), 3.84-3.61 (m, 3H), 3.46-3.24 (m, 2H), 3.14-2.79 (m, 2H), 1.81 (t, J = 6.6 Hz, 2H), 1.72-1.43 (m, 2H), 1.33-1.32 (m, 2H), 0.97 (br, 1H) | 535 |
| 59 | 1,1,1,3,3,3-hexafluoropropan-2-yl (±)1-(5,6,7,8-tetrahydro-pyrido[4,3-d]pyrimidine-6-carbonyl)-6-azaspiro[2.5]octane-6-carboxylate | 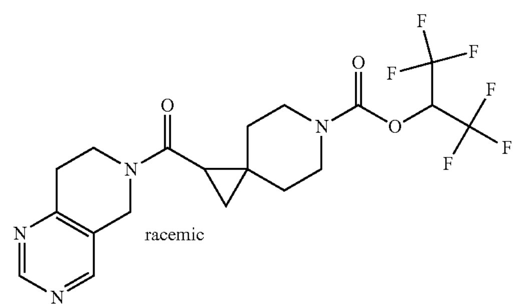 [SMILES: O=C(OC(C(F)(F)F)C(F)(F)F)N1CCC2(CC1)CC2C(=O)N1CCc2ncncc2C1] | | |
| 60 | 1,1,1,3,3,3-hexafluoro-propan-2-yl (R or S)-1-(5,6,7,8-tetrahydro-pyrido[4,3-d]pyrimidine-6-carbonyl)-6-azaspiro[2.5]octane-6-carboxylate peak 1 | 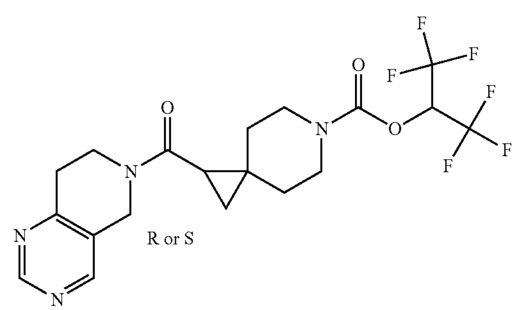 [SMILES: O=C(OC(C(F)(F)F)C(F)(F)F)N1CCC2(CC1)CC2C(=O)N1CCc2ncncc2C1] | δ 9.30 (s, 1H), 8.55 (s, 1H), 5.84 (br, 1H), 5.00-4.55 (m, 2H), 4.15-4.07 (m, 1H), 3.85 (br, 2H), 3.74-3.54 (m, 1H), 3.45-3.34 (m, 2H), 3.22-3.01 (m, 2H), 1.81 (br, 2H), 1.69-1.58 (m, 2H), 1.48 (br, 2H), 0.94 (br, 1H) | 467 |
| 61 | 1,1,1,3,3,3-hexafluoro-propan-2-yl (R or S)-1-(5,6,7,8-tetrahydro-pyrido[4,3-d]pyrimidine-6-carbonyl)-6-azaspiro[2.5]octane-6-carboxylate peak 2 | 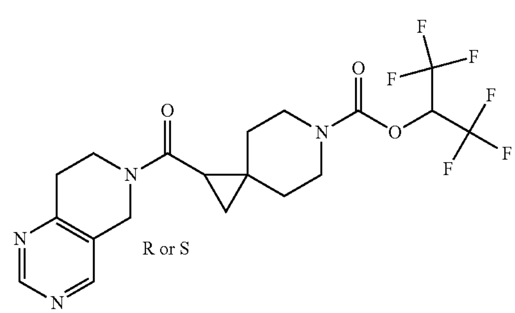 [SMILES: O=C(OC(C(F)(F)F)C(F)(F)F)N1CCC2(CC1)CC2C(=O)N1CCc2ncncc2C1] | δ 9.30 (s, 1H), 8.55 (s, 1H), 5.84 (br, 1H), 5.00-4.55 (m, 2H), 4.15-4.07 (m, 1H), 3.85 (br, 2H), 3.74-3.54 (m, 1H), 3.45-3.34 (m, 2H), 3.22-3.01 (m, 2H), 1.81 (br, 2H), 1.69-1.58 (m, 2H), 1.48 (br, 2H), 0.94 (br, 1H) | 467 |

| Ex | Name | Structure | NMR (¹H NMR, 300 MHz or 400 MHz, Chloroform-d unless otherwise noted) | MS [M + H]⁺ |
|---|---|---|---|---|
| 62 | 1,1,1,3,3,3-hexafluoro-propan-2-yl (±)1-(2-cyclopropyl-5,6,7,8-tetrahydro-pyrido[4,3-d]pyrimidine-6-carbonyl)-6-azaspiro[2.5]octane-6-carboxylate | racemic | | |
| 63 | 1,1,1,3,3,3-hexafluoro-propan-2-yl (R or S)-1-(2-cyclopropyl-5,6,7,8-tetrahydro-pyrido[4,3-d]pyrimidine-6-carbonyl)-6-azaspiro[2.5]octane-6-carboxylate peak 1 | R or S | δ 8.36 (s, 1H), 5.77 (br, 1H), 4.89-4.56 (m, 2H), 4.15-4.05 (m, 1H), 3.84-3.57 (m, 3H), 3.46-3.31 (m, 2H), 3.08-2.89 (m, 2H), 2.23-2.18 (m, 1H), 1.82-1.77 (m, 2H), 1.69-1.63 (m, 1H), 1.58-1.52 (m, 1H), 1.41 (s, 2H), 1.13-1.07 (m, 4H), 0.94-0.90 (m, 1H) | 507 |
| 64 | 1,1,1,3,3,3-hexafluoro-propan-2-yl (R or S)-1-(2-cyclopropyl-5,6,7,8-tetrahydro-pyrido[4,3-d]pyrimidine-6-carbonyl)-6-aza-spiro[2.5]octane-6-carboxylate peak 2 | R or S | δ 8.36 (s, 1H), 5.80-5.74 (m, 1H), 4.89-4.55 (m, 2H), 4.14-4.04 (m, 1H), 3.87-3.58 (m, 3H), 3.45-3.30 (m, 2H), 3.08-2.88 (m, 2H), 2.22-2.19 (m, 1H), 1.81-1.63 (m, 3H), 1.57-1.52 (m, 1H), 1.41 (s, 2H), 1.12-1.06 (m, 4H), 0.93-0.90 (m, 1H) | 507 |
| 65 | 1,1,1,3,3,3-hexafluoro-propan-2-yl (±)1-((5-chloropyridin-3-yl)carbamoyl)-6-azaspiro[2.5]octane-6-carboxylate | racemic | | |
| 66 | 1,1,1,3,3,3-hexafluoro-propan-2-yl (R or S)-1-((5-chloropyridin-3-yl)carbamoyl)-6-azaspiro[2.5]octane-6-carboxylate peak 1 | R or S | δ 8.42 (s, 1H), 8.33-8.32 (m, 2H), 7.84-7.82 (m, 1H), 5.81-5.74 (m, 1H), 3.76-3.70 (m, 1H), 3.66-3.60 (m, 1H), 3.51-3.40 (m, 2H), 1.86 (br, 2H), 1.68-1.55 (m, 2H), 1.46-1.39 (m, 2H), 1.08-1.05 (m, 1H) | 460 |

| Ex | Name | Structure | NMR (¹H NMR, 300 MHz or 400 MHz, Chloroform-d unless otherwise noted) | MS [M + H]⁺ |
|---|---|---|---|---|
| 67 | 1,1,1,3,3,3-hexafluoro-propan-2-yl (R or S)-1-((5-chloropyridin-3-yl)carbamoyl)-6-azaspiro[2.5]octane-6-carboxylate peak 2 | 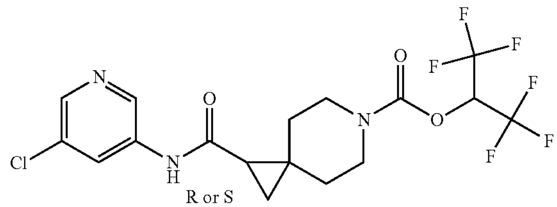 [SMILES: O=C(Nc1cncc(Cl)c1)C1CC12CCN(C(=O)OC(C(F)(F)F)C(F)(F)F)CC2] | δ 8.46 (s, 1H), 8.33 (s, 2H), 7.54 (br, 1H), 5.80-5.76 (m, 1H), 3.76-3.73 (m, 1H), 3.66-3.62 (m, 1H), 3.53-3.49 (m, 2H), 1.87 (br, 2H), 1.68-1.63 (m, 1H), 1.57-1.54 (m, 1H), 1.47-1.35 (m, 2H), 1.09-1.06 (m, 1H) | 460 |
| 68 | 1,1,1,3,3,3-hexafluoro-propan-2-yl (±)1-((2-methylpyridin-3-yl)carbamoyl)-6-azaspiro[2.5]octane-6-carboxylate | 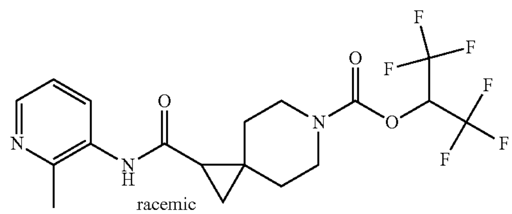 [SMILES: Cc1ncccc1NC(=O)C1CC12CCN(C(=O)OC(C(F)(F)F)C(F)(F)F)CC2] | | |
| 69 | 1,1,1,3,3,3-hexafluoro-propan-2-yl (R or S)-1-((2-methylpyridin-3-yl)carbamoyl)-6-azaspiro[2.5]octane-6-carboxylate peak 1 | 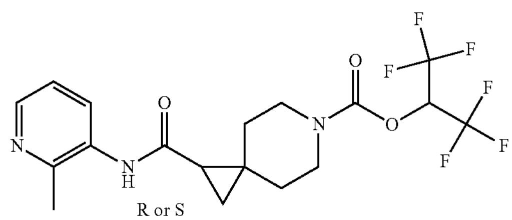 [SMILES: Cc1ncccc1NC(=O)C1CC12CCN(C(=O)OC(C(F)(F)F)C(F)(F)F)CC2] | δ 8.31 (s, 1H), 8.19 (br, 1H), 7.31 (s, 1H), 7.19 (t, J = 5.7 Hz, 1H), 5.81-5.75 (m, 1H), 3.75-3.71 (m, 1H), 3.66-3.52 (m, 3H), 2.56 (s, 3H), 1.88 (br, 2H), 1.65-1.60 (m, 2H), 1.48 (br, 1H), 1.40 (s, 1H), 1.04 (s, 1H) | 440 |
| 70 | 1,1,1,3,3,3-hexafluoro-propan-2-yl (R or S)-1-((2-methylpyridin-3-yl)carbamoyl)-6-azaspiro[2.5]octane-6-carboxylate peak 2 | 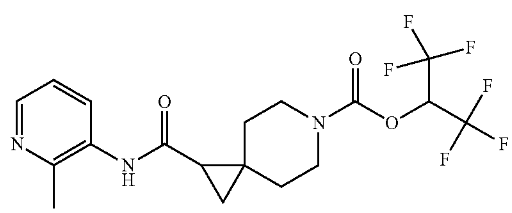 | δ 8.31 (s, 1H), 8.18 (br, 1H), 7.31 (s, 1H), 7.17 (t, J = 5.7 Hz, 1H), 5.81-5.75 (m, 1H), 3.74-3.71 (m, 2H), 3.65-3.52 (m, 2H), 2.56 (s, 3H), 1.89-1.88 (m, 2H), 1.64-1.60 (m, 2H), 1.48-1.39 (s, 2H), 1.04 (s, 1H) | 440 |
| 71 | 1,1,1,3,3,3-hexafluoro-propan-2-yl (±)1-((6-(trifluoro-methyl)pyridin-2-yl)carbamoyl)-6-aza-spiro[2.5]octane-6-carboxylate | 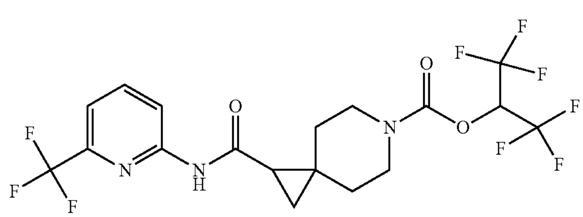 | | |
| 72 | 1,1,1,3,3,3-hexafluoro-propan-2-yl (R or S)-1-((6-(trifluoro-methyl)pyridin-2-yl)car-bamoyl)-6-azaspiro[2.5]octane-6-carboxylate peak 1 | 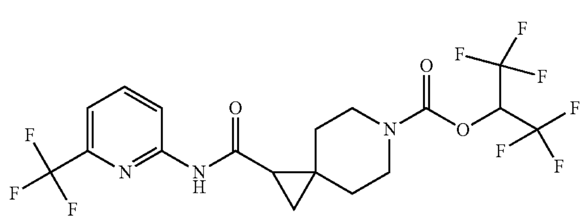 | δ 8.40 (d, J = 8.4 Hz, 1H), 8.28 (s, 1H), 7.89 (t, J = 8.0 Hz, 1H), 7.45 (d, J = 7.6 Hz, 1H), 5.79-5.70 (m, 1H), 3.73-3.67 (m, 1H), 3.61-3.51 (m, 3H), 1.88-1.83 (m, 2H), 1.58-1.53 (m, 3H), 1.44-1.41 (m, 1H), 1.08-1.04 (m, 1H) | 494 |

| Ex | Name | Structure | NMR (¹H NMR, 300 MHz or 400 MHz, Chloroform-d unless otherwise noted) | MS [M + H]⁺ |
|---|---|---|---|---|
| 73 | 1,1,1,3,3,3-hexafluoropropan-2-yl (R or S)-1-(((6-(trifluoromethyl)pyridin-2-yl)carbamoyl)-6-azaspiro[2.5]octane-6-carboxylate peak 2 | R or S | δ 8.40 (d, J = 8.4 Hz, 1H), 8.28 (s, 1H), 7.89 (t, J = 8.0 Hz, 1H), 7.45 (d, J = 7.6 Hz, 1H), 5.79-5.76 (m, 1H), 3.75-3.67 (m, 1H), 3.62-3.51 (m, 3H), 1.88-1.83 (m, 2H), 1.70-1.53 (m, 3H), 1.44-1.41 (m, 1H), 1.09-1.06 (m, 1H) | 494 |
| 74 | 1,1,1,3,3,3-hexafluoropropan-2-yl (±)1-(((6-(trifluoromethyl)pyridin-2-yl)methyl)carbamoyl)-6-azaspiro[2.5]octane-6-carboxylate | racemic | | |
| 75 | 1,1,1,3,3,3-hexafluoropropan-2-yl (R or S)-1-(((6-(trifluoromethyl)pyridin-2-yl)methyl)carbamoyl)-6-azaspiro[2.5]octane-6-carboxylate peak 1 | R or S | δ 8.87 (t, J = 7.8 Hz, 1H), 7.62 (d, J = 8.0 Hz, 1H), 7.49 (d, J = 8.0 Hz, 1H), 6.83 (br, 1H), 5.81-5.74 (m, 1H), 4.74-4.59 (m, 2H), 3.62 (t, J = 5.6 Hz, 2H), 3.54-3.40 (m, 2H), 1.83-1.76 (m, 2H), 1.54-1.49 (m, 3H), 1.29 (br, 1H), 0.94-0.91 (m, 1H) | 508 |
| 76 | 1,1,1,3,3,3-hexafluoropropan-2-yl (R or S)-1-(((6-(trifluoromethyl)pyridin-2-yl)methyl)carbamoyl)-6-azaspiro[2.5]octane-6-carboxylate peak 2 | R or S | δ 8.87 (t, J = 7.8 Hz, 1H), 7.62 (d, J = 8.0 Hz, 1H), 7.48 (d, J = 8.0 Hz, 1H), 6.83 (br, 1H), 5.81-5.74 (m, 1H), 4.73-4.59 (m, 2H), 3.62 (t, J = 5.6 Hz, 2H), 3.54-3.38 (m, 2H), 1.83-1.76 (m, 2H), 1.54-1.49 (m, 3H), 1.29 (br, 1H), 0.94-0.91 (m, 1H) | 508 |

| Ex | Name | Structure | NMR (¹H NMR, 300 MHz or 400 MHz, Chloroform-d unless otherwise noted) | MS [M + H]⁺ |
|---|---|---|---|---|
| 77 | 1,1,1,3,3,3-hexafluoropropan-2-yl (±)1-((6-(trifluoromethyl)pyridin-3-yl)carbamoyl)-6-azaspiro[2.5]octane-6-carboxylate | 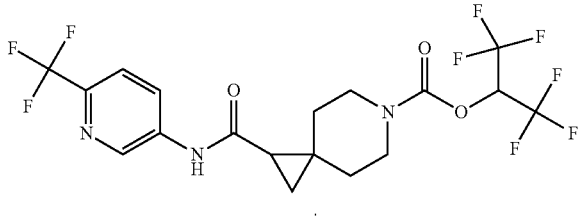 racemic | | |
| 78 | 1,1,1,3,3,3-hexafluoropropan-2-yl (R or S)-1-((6-(trifluoromethyl)pyridin-3-yl)carbamoyl)-6-azaspiro[2.5]octane-6-carboxylate peak 1 | 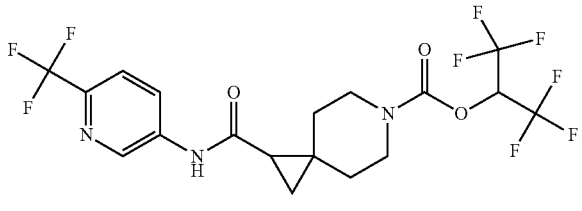 R or S | δ 8.63 (s, 1H), 8.42 (d, J = 8.0 Hz, 1H), 7.72-7.67 (m, 2H), 5.80-5.73 (m, 1H), 3.79-3.73 (m, 1H), 3.69-3.63 (m, 1H), 3.54-3.46 (m, 2H), 1.88 (br, 2H), 1.73-1.64 (m, 1H), 1.61-1.57 (m, 1H), 1.48-1.42 (m, 2H), 1.11-1.08 (m, 1H) | 494 |
| 79 | 1,1,1,3,3,3-hexafluoropropan-2-yl (R or S)-1-((6-(trifluoromethyl)pyridin-3-yl)carbamoyl)-6-azaspiro[2.5]octane-6-carboxylate peak 2 | 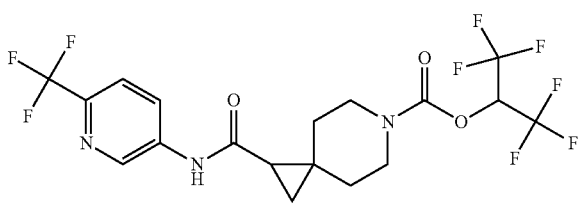 R or S | δ 8.63 (s, 1H), 8.41 (d, J = 8.0 Hz, 1H), 7.76 (s, 1H), 7.68 (d, J = 8.4 Hz, 1H), 5.81-5.73 (m, 1H), 3.78-3.72 (m, 1H), 3.69-3.63 (m, 1H), 3.54-3.45 (m, 2H), 1.88-1.83 (m, 2H), 1.71-1.64 (m, 1H), 1.60-1.57 (m, 1H), 1.47-1.41 (m, 2H), 1.10-1.07 (m, 1H) | 494 |
| 80 | 1,1,1,3,3,3-hexafluoropropan-2-yl (±)1-((6-methylpyridin-3-yl)carbamoyl)-6-azaspiro[2.5]octane-6-carboxylate | 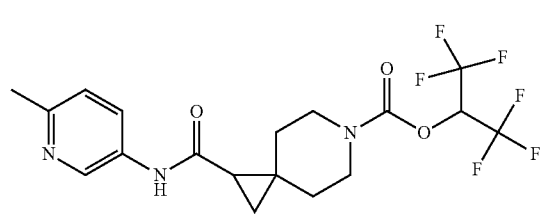 racemic | | |
| 81 | 1,1,1,3,3,3-hexafluoropropan-2-yl (R or S)-1-((6-methylpyridin-3-yl)carbamoyl)-6-azaspiro[2.5]octane-6-carboxylate peak 1 | 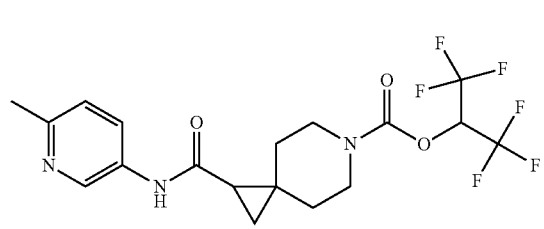 R or S | δ 8.44 (s, 1H), 8.04 (d, J = 8.4 Hz, 1H), 7.92-7.86 (m, 1H), 7.14 (d, J = 8.4 Hz, 1H), 5.81-5.73 (m, 1H), 3.72-3.69 (m, 1H), 3.63-3.50 (m, 3H), 2.53 (s, 3H), 1.88 (br, 2H), 1.62-1.54 (m, 2H), 1.45-1.36 (m, 2H), 1.02-1.00 (m, 1H) | 440 |
| 82 | 1,1,1,3,3,3-hexafluoropropan-2-yl (R or S)-1-((6-methylpyridin-3-yl)carbamoyl)-6-azaspiro[2.5]octane-6-carboxylate peak 2 | 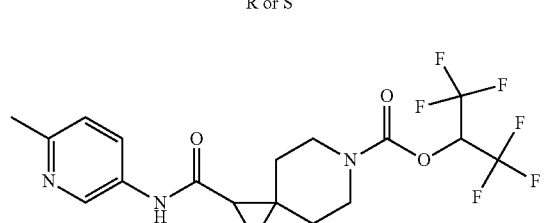 R or S | δ 8.44 (s, 1H), 8.04 (d, J = 8.4 Hz, 1H), 7.97-7.94 (m, 1H), 7.14 (d, J = 8.4 Hz, 1H), 5.81-5.73 (m, 1H), 3.72-3.68 (m, 1H), 3.62-3.50 (m, 3H), 2.53 (s, 3H), 1.88 (br, 2H), 1.62-1.54 (m, 2H), 1.45-1.37 (m, 2H), 1.02-0.99 (m, 1H) | 440 |

| Ex | Name | Structure | NMR (¹H NMR, 300 MHz or 400 MHz, Chloroform-d unless otherwise noted) | MS [M + H]⁺ |
|---|---|---|---|---|
| 83 | 1,1,1,3,3,3-hexafluoropropan-2-yl (±)1-((2-(trifluoromethyl)pyridin-3-yl)carbamoyl)-6-azaspiro[2.5]octane-6-carboxylate | racemic | | |
| 84 | 1,1,1,3,3,3-hexafluoropropan-2-yl (R or S)-1-((2-(trifluoromethyl)pyridin-3-yl)carbamoyl)-6-azaspiro[2.5]octane-6-carboxylate peak 1 | R or S | δ 8.63 (d, J = 8.0 Hz, 1H), 8.46 (d, J = 3.6 Hz, 1H), 7.72 (s, 1H), 7.54-7.51 (m, 1H), 5.82-5.74 (m, 1H), 3.70-3.62 (m, 2H), 3.60-3.50 (m, 2H), 1.87 (br, 2H), 1.68-1.51 (m, 3H), 1.41 (d, J = 9.6 Hz, 1H), 1.12-1.08 (m, 1H) | 494 |
| 85 | 1,1,1,3,3,3-hexafluoropropan-2-yl (R or S)-1-((2-(trifluoromethyl)pyridin-3-yl)carbamoyl)-6-azaspiro[2.5]octane-6-carboxylate peak 2 | R or S | δ 8.63 (d, J = 8.4 Hz, 1H), 8.46 (d, J = 3.6 Hz, 1H), 7.73 (s, 1H), 7.54-7.51 (m, 1H), 5.82-5.74 (m, 1H), 3.70-3.62 (m, 2H), 3.60-3.50 (m, 2H), 1.87 (br, 2H), 1.68-1.51 (m, 3H), 1.41 (d, J = 9.6 Hz, 1H), 1.12-1.08 (m, 1H) | 494 |
| 86 | 1,1,1,3,3,3-hexafluoropropan-2-yl (±)1-((pyridin-3-ylmethyl)carbamoyl)-6-azaspiro[2.5]octane-6-carboxylate | racemic | | |
| 87 | 1,1,1,3,3,3-hexafluoropropan-2-yl (R or S)-1-((pyridin-3-ylmethyl)carbamoyl)-6-azaspiro[2.5]octane-6-carboxylate peak 1 | R or S | δ 8.67 (s, 2H), 7.65 (d, J = 8.0 Hz, 1H), 7.31 (s, 1H), 6.20 (s, 1H), 5.79-5.74 (m, 1H), 4.54-4.43 (m, 2H), 3.67-3.61 (m, 1H), 3.52-3.34 (m, 3H), 1.82 (br, 2H), 1.71-1.49 (m, 1H), 1.45-1.36 (m, 2H), 1.30 (s, 1H), 0.93-0.90 (m, 1H) | 440 |

-continued

| Ex | Name | Structure | NMR (¹H NMR, 300 MHz or 400 MHz, Chloroform-d unless otherwise noted) | MS [M + H]⁺ |
|---|---|---|---|---|
| 88 | 1,1,1,3,3,3-hexafluoropropan-2-yl (R or S)-1-((pyridin-3-ylmethyl)carbamoyl)-6-azaspiro[2.5]octane-6-carboxylate peak 2 | R or S | δ 8.56 (s, 2H), 7.66 (d, J = 8.0 Hz, 1H), 7.32-7.31 (m, 1H), 6.20 (s, 1H), 5.81-5.74 (m, 1H), 4.54-4.43 (m, 2H), 3.70-3.61 (m, 1H), 3.53-3.44 (m, 3H), 1.82 (br, 2H), 1.66-1.49 (m, 1H), 1.42-1.38 (m, 2H), 1.31 (s, 1H), 0.93-0.90 (m, 1H) | 440 |
| 89 | 1,1,1,3,3,3-hexafluoropropan-2-yl (±)1-((cyclohexanecarbonyl)carbamoyl)-6-azaspiro[2.5]octane-6-carboxylate | racemic | | |
| 90 | 1,1,1,3,3,3-hexafluoropropan-2-yl (R or S)-1-((cyclohexanecarbonyl)carbamoyl)-6-azaspiro[2.5]octane-6-carboxylate peak 1 | R or S | δ 8.12 (s, 1H), 5.81-5.74 (m, 1H), 3.78-3.61 (m, 3H), 3.25-3.16 (m, 1H), 2.64 (br, 1H), 2.40 (br, 1H), 1.95-1.93 (m, 2H), 1.87-1.84 (m, 2H), 1.79-1.68 (m, 4H), 1.58-1.44 (m, 4H), 1.38-1.21 (m, 3H), 1.03 (t, J = 5.2 Hz, 1H) | 481 [M + Na]⁺ |
| 91 | 1,1,1,3,3,3-hexafluoropropan-2-yl (R or S)-1-((cyclohexanecarbonyl)carbamoyl)-6-azaspiro[2.5]octane-6-carboxylate peak 2 | R or S | δ 8.02 (s, 1H), 5.81-5.75 (m, 1H), 3.77-3.61 (m, 3H), 3.25-3.16 (m, 1H), 2.64 (br, 1H), 2.39 (br, 1H), 1.95-1.92 (m, 2H), 1.87-1.84 (m, 2H), 1.79-1.67 (m, 4H), 1.57-1.44 (m, 4H), 1.38-1.24 (m, 3H), 1.03 (t, J = 5.2 Hz, 1H) | 481 [M + Na]⁺ |
| 92 | 1,1,1,3,3,3-hexafluoropropan-2-yl (±)1-(benzoylcarbamoyl)-6-azaspiro[2.5]octane-6-carboxylate | racemic | | |
| 93 | 1,1,1,3,3,3-hexafluoropropan-2-yl (R or S)-1-(benzoylcarbamoyl)-6-azaspiro[2.5]octane-6-carboxylate peak 1 | R or S | δ 8.80 (s, 1H), 7.90 (d, J = 7.6 Hz, 2H), 7.67-7.64 (m, 1H), 7.57-7.53 (m, 2H), 5.83-5.74 (m, 1H), 3.87-3.81 (m, 1H), 3.76-3.69 (m, 2H), 3.25-3.15 (m, 1H), 2.98 (t, J = 6.4 Hz, 1H), 1.85-1.72 (m, 3H), 1.61-1.52 (m, 2H), 1.10 (t, J = 6.0 Hz, 1H) | 475 [M + Na]⁺ |

| Ex | Name | Structure | NMR (¹H NMR, 300 MHz or 400 MHz, Chloroform-d unless otherwise noted) | MS [M + H]⁺ |
|---|---|---|---|---|
| 94 | 1,1,1,3,3,3-hexafluoropropan-2-yl (R or S)-1-(benzoylcarbamoyl)-6-azaspiro[2.5]octane-6-carboxylate peak 2 | 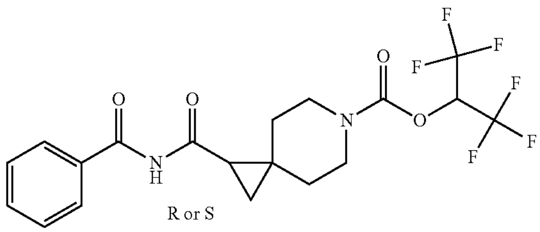 [SMILES: O=C(NC(=O)C1CC12CCN(C(=O)OC(C(F)(F)F)C(F)(F)F)CC2)c1ccccc1] | δ 8.78 (s, 1H), 7.90 (d, J = 7.6 Hz, 2H), 7.67-7.64 (m, 1H), 7.57-7.53 (m, 2H), 5.83-5.74 (m, 1H), 3.87-3.82 (m, 1H), 3.76-3.69 (m, 2H), 3.25-3.15 (m, 1H), 2.98 (t, J = 6.4 Hz, 1H), 1.85-1.72 (m, 3H), 1.61-1.52 (m, 2H), 1.10 (t, J = 6.0 Hz, 1H) | 475 [M + Na]⁺ |
| 95 | 1,1,1,3,3,3-hexafluoropropan-2-yl (±)1-(pyrimidin-5-ylcarbamoyl)-6-azaspiro[2.5]octane-6-carboxylate | 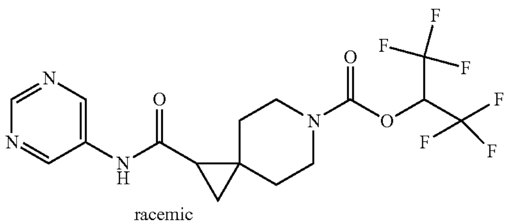 [SMILES: O=C(Nc1cncnc1)C1CC12CCN(C(=O)OC(C(F)(F)F)C(F)(F)F)CC2] | | |
| 96 | 1,1,1,3,3,3-hexafluoropropan-2-yl (R or S)-1-(pyrimidin-5-ylcarbamoyl)-6-azaspiro[2.5]octane-6-carboxylate peak 1 | 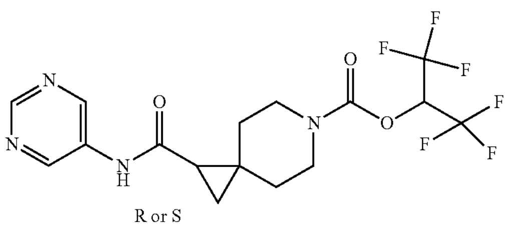 [SMILES: O=C(Nc1cncnc1)C1CC12CCN(C(=O)OC(C(F)(F)F)C(F)(F)F)CC2] | δ 9.00 (br, 3H), 7.48 (s, 1H), 5.90-5.68 (m, 1H), 3.90-3.31 (m, 4H), 1.99-1.71 (m, 3H), 1.67-1.40 (m, 3H), 1.23-1.00 (m, 1H) | 427 |
| 97 | 1,1,1,3,3,3-hexafluoropropan-2-yl (R or S)-1-(pyrimidin-5-ylcarbamoyl)-6-azaspiro[2.5]octane-6-carboxylate peak 2 | 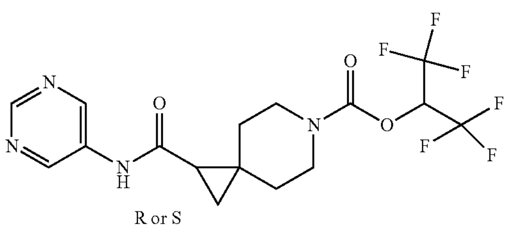 [SMILES: O=C(Nc1cncnc1)C1CC12CCN(C(=O)OC(C(F)(F)F)C(F)(F)F)CC2] | δ 9.00 (br, 3H), 7.57 (s, 1H), 5.90-5.65 (m, 1H), 3.82-3.32 (m, 4H), 1.97-1.40 (m, 6H), 1.30-0.97 (m, 1H) | 427 |
| 98 | 1,1,1,3,3,3-hexafluoropropan-2-yl (±)1-((2-(trifluoromethyl)pyrimidin-5-yl)carbamoyl)-6-azaspiro[2.5]octane-6-carboxylate | 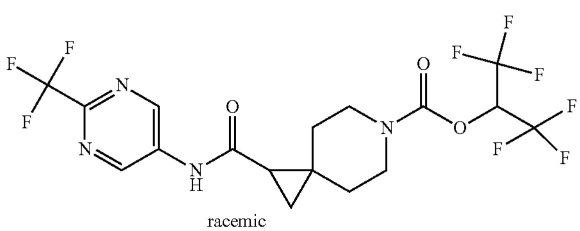 [SMILES: O=C(Nc1cnc(C(F)(F)F)nc1)C1CC12CCN(C(=O)OC(C(F)(F)F)C(F)(F)F)CC2] | | |
| 99 | 1,1,1,3,3,3-hexafluoropropan-2-yl (R or S)-1-((2-(trifluoromethyl)pyrimidin-5-yl)carbamoyl)-6-azaspiro[2.5]octane-6-carboxylate peak 1 | 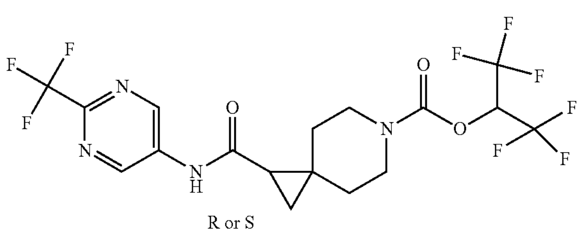 [SMILES: O=C(Nc1cnc(C(F)(F)F)nc1)C1CC12CCN(C(=O)OC(C(F)(F)F)C(F)(F)F)CC2] | δ 9.16 (s, 2H), 7.62 (br, 1H), 5.90-5.60 (m, 1H), 3.92-3.31 (m, 4H), 1.90-1.45 (m, 6H), 1.35-1.00 (m, 1H) | 495 |

| Ex | Name | Structure | NMR (¹H NMR, 300 MHz or 400 MHz, Chloroform-d unless otherwise noted) | MS [M + H]⁺ |
|---|---|---|---|---|
| 100 | 1,1,1,3,3,3-hexafluoro-propan-2-yl (R or S)-1-((2-(trifluoro-methyl)pyrimidin-5-yl)carbamoyl)-6-azaspiro[2.5]octane-6-carboxylate peak 2 | R or S | δ 9.16 (s, 2H), 7.62 (br, 1H), 5.88-5.68 (m, 1H), 3.92-3.60 (m, 2H), 3.60-3.31 (m, 2H), 1.90-1.45 (m, 6H), 1.24-1.07 (m, 1H) | 495 |
| 101 | 1,1,1,3,3,3-hexafluoro-propan-2-yl (±)1-((2-methylpyrimidin-5-yl)carbamoyl)-6-azaspiro[2.5]octane-6-carboxylate | racemic | | |
| 102 | 1,1,1,3,3,3-hexafluoro-propan-2-yl (R or S)-1-((2-methylpyrimidin-5-yl)carbamoyl)-6-azaspiro[2.5]octane-6-carboxylate peak 1 | R or S | δ 9.05-8.82 (m, 2H), 8.02-7.79 (m, 1H), 5.84-5.65 (m, 1H), 3.78-3.41 (m, 4H), 2.80-2.69 | 441 |
| 103 | 1,1,1,3,3,3-hexafluoro-propan-2-yl (R or S)-1-((2-methylpyrimidin-5-yl)carbamoyl)-6-azaspiro[2.5]octane-6-carboxylate peak 2 | R or S | δ 9.05-8.82 (m, 2H), 8.02-7.79 (m, 1H), 5.84-5.65 (m, 1H), 3.78-3.41 (m, 4H), 2.80-2.69 | 441 |
| 104 | 1,1,1,3,3,3-hexafluoro-propan-2-yl (±)1-((6-methylpyridazin-3-yl)carbamoyl)-6-azaspiro[2.5]octane-6-carboxylate | racemic | | |
| 105 | 1,1,1,3,3,3-hexafluoro-propan-2-yl (R)-1-((6-methylpyridazin-3-yl)carbamoyl)-6-azaspiro[2.5]octane-6-carboxylate peak 1 | R | δ 11.90-11.67 (m, 1H), 8.68-8.46 (m, 1H), 7.51-7.38 (m, 1H), 5.82-5.66 (m, 1H), 3.75-3.53 (m, 3H), 3.44-3.24 (m, 1H), 2.67-2.58 (m, 3H), 1.90 (dq, J = 7.8, 5.0, 4.1 Hz, 2H), 1.82-1.54 (m, 2H), 1.45-1.37 (m, 1H), 1.31-1.24 (m, 1H), 1.10 (dd, J = 7.9, 4.5 Hz, 1H) | 441 |

| Ex | Name | NMR (¹H NMR, 300 MHz or 400 MHz, Chloroform-d unless otherwise noted) | MS [M + H]⁺ |
|---|---|---|---|
| 106 | 1,1,1,3,3,3-hexafluoro-propan-2-yl (S)-1-((6-methylpyridazin-3-yl)carbamoyl)-6-azaspiro[2.5]octane-6-carboxylate peak 2 | δ 11.90-11.67 (m, 1H), 8.68-8.46 (m, 1H), 7.51-7.38 (m, 1H), 5.82-5.66 (m, 1H), 3.75-3.53 (m, 3H), 3.44-3.24 (m, 1H), 2.67-2.58 (m, 3H), 1.90 (dq, J = 7.8, 5.0, 4.1 Hz, 2H), 1.82-1.54 (m, 2H), 1.45-1.37 (m, 1H), 1.31-1.24 (m, 1H), 1.10 (dd, J = 7.9, 4.5 Hz, 1H) | 441 |
| 107 | 1,1,1,3,3,3-hexafluoro-propan-2-yl (±)1-(pyridazin-4-ylcarbamoyl)-6-azaspiro[2.5]octane-6-carboxylate | | |
| 108 | 1,1,1,3,3,3-hexafluoro-propan-2-yl (R or S)-1-(pyridazin-4-ylcarbamoyl)-6-azaspiro[2.5]octane-6-carboxylate peak 1 | δ 10.22 (d, J = 33.1 Hz, 1H), 9.48 (s, 1H), 9.02 (d, J = 6.1 Hz, 1H), 8.47 (s, 1H), 5.76 (d, J = 10.5 Hz, 1H), 3.80-3.68 (m, 1H), 3.68-3.54 (m, 2H), 3.49 (s, 1H), 2.07 (d, J = 6.7 Hz, 1H), 1.85 (d, J = 6.8 Hz, 2H), 1.46 (t, J = 5.0 Hz, 1H), 1.14 (dd, J = 7.9, 4.7 Hz, 1H) | 427 |
| 109 | 1,1,1,3,3,3-hexafluoro-propan-2-yl (R or S)-1-(pyridazin-4-ylcarbamoyl)-6-azaspiro[2.5]octane-6-carboxylate peak 2 | δ 10.29 (d, J = 27.8 Hz, 1H), 9.47 (s, 1H), 9.02 (d, J = 6.1 Hz, 1H), 8.46 (s, 1H), 5.81-5.72 (m, 1H), 3.70 (s, 1H), 3.67-3.55 (m, 2H), 3.49 (s, 1H), 2.14-2.02 (m, 1H), 1.86 (s, 2H), 1.59 (d, J = 6.0 Hz, 2H), 1.46 (t, J = 5.0 Hz, 1H), 1.14 (dd, J = 7.8, 4.7 Hz, 1H) | 427 |
| 110 | 1,1,1,3,3,3-hexafluoro-propan-2-yl (±)1-((5-methylpyrazin-2-yl)carbamoyl)-6-azaspiro[2.5]octane-6-carboxylate | | |
| 111 | 1,1,1,3,3,3-hexafluoro-propan-2-yl (R or S)-1-((5-methylpyrazin-2-yl)carbamoyl)-6-azaspiro[2.5]octane-6-carboxylate peak 1 | δ 9.39 (s, 1H), 8.13 (s, 1H), 8.03 (s, 1H), 5.78-5.71 (m, 1H), 3.70 (d, J = 11.5, 1H), 3.56 (d, J = 5.9 Hz, 4H), 2.56 (s, 3H), 1.87 (s, 2H), 1.56 (d, J = 6.3 Hz, 2H), 1.43 (d, J = 5.0 Hz, 1H), 1.08-1.01 (m, 1H) | 441 |

| Ex | Name | Structure | NMR (¹H NMR, 300 MHz or 400 MHz, Chloroform-d unless otherwise noted) | MS [M + H]⁺ |
|---|---|---|---|---|
| 112 | 1,1,1,3,3,3-hexafluoro-propan-2-yl (R or S)-1-((5-methylpyrazin-2-yl)carbamoyl)-6-azaspiro[2.5]octane-6-carboxylate peak 2 | R or S | δ 9.39 (s, 1H), 8.13 (s, 1H), 8.03 (s, 1H), 5.78-5.71 (m, 1H), 3.70 (d, J = 11.5, 1H), 3.56 (d, J = 5.9 Hz, 4H), 2.56 (s, 3H), 1.87 (s, 2H), 1.56 (d, J = 6.3 Hz, 2H), 1.43 (d, J = 5.0 Hz, 1H), 1.08-1.01 (m, 1H) | 441 |
| 113 | 1,1,1,3,3,3-hexafluoro-propan-2-yl (±)1-((1-methylpiperidin-4-yl)carbamoyl)-6-azaspiro[2.5]octane-6-carboxylate | racemic | | |
| 114 | 1,1,1,3,3,3-hexafluoro-propan-2-yl (R or S)-1-((1-methylpiperidin-4-yl)carbamoyl)-6-azaspiro[2.5]octane-6-carboxylate peak 1 | R or S | (Methanol-d₄) δ 6.27-6.00 (m, 1H), 3.93-3.51 (m, 4H), 3.45-3.36 (m, 1H), 3.18-3.02 (m, 2H), 2.56-2.42 (m, 5H), 2.05-1.88 (m, 2H), 1.80-1.69 (m, 2H), 1.66-1.51 (m, 4H), 1.48-1.39 (m, 1H), 1.22-1.13 (m, 1H), 0.95-0.85 (m, 1H) | 446 |
| 115 | 1,1,1,3,3,3-hexafluoro-propan-2-yl (R or S)-1-((1-methylpiperidin-4-yl)carbamoyl)-6-azaspiro[2.5]octane-6-carboxylate peak 2 | R or S | (Methanol-d₄) δ 6.27-6.00 (m, 1H), 3.93-3.51 (m, 4H), 3.45-3.36 (m, 1H), 3.18-3.02 (m, 2H), 2.56-2.42 (m, 5H), 2.05-1.88 (m, 2H), 1.80-1.69 (m, 2H), 1.66-1.51 (m, 4H), 1.48-1.39 (m, 1H), 1.22-1.13 (m, 1H), 0.95-0.85 (m, 1H) | 446 |
| 116 | 1,1,1,3,3,3-hexafluoro-propan-2-yl (±)1-(((tetrahydro-2H-pyran-4-yl)methyl)carbamoyl)-6-azaspiro[2.5]octane-6-carboxylate | racemic | | |
| 117 | 1,1,1,3,3,3-hexafluoro-propan-2-yl (S)-1-(((tetrahydro-2H-pyran-4-yl)methyl)carbamoyl)-6-azaspiro[2.5]octane-6-carboxylate peak 1 | S | δ 5.81-5.67 (m, 2H), 4.06-3.92 (m, 2H), 3.73-3.42 (m, 4H), 3.44-3.33 (m, 2H), 3.27-3.10 (m, 2H), 1.87-1.69 (m, 3H), 1.65-1.49 (m, 3H), 1.45-1.22 (m, 4H), 0.92-0.81 (m, 1H) | 447 |

| Ex | Name | Structure | NMR (¹H NMR, 300 MHz or 400 MHz, Chloroform-d unless otherwise noted) | MS [M + H]⁺ |
|---|---|---|---|---|
| 118 | 1,1,1,3,3,3-hexafluoro-propan-2-yl (R)-1-(((tetrahydro-2H-pyran-4-yl)methyl)car-bamoyl)-6-azaspiro[2.5]octane-6-carboxylate peak 2 | 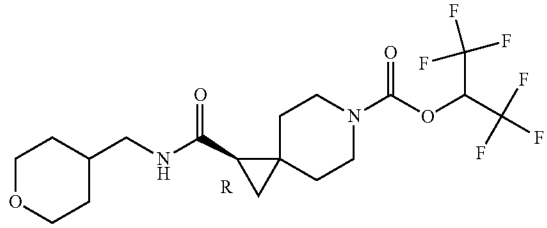 | δ 5.81-5.67 (m, 2H), 4.06-3.92 (m, 2H), 3.73-3.42 (m, 4H), 3.44-3.33 (m, 2H), 3.27-3.10 (m, 2H), 1.87-1.69 (m, 3H), 1.65-1.49 (m, 3H), 1.45-1.22 (m, 4H), 0.92-0.81 (m, 1H) | 447 |
| 119 | 1,1,1,3,3,3-hexafluoropropan-2-yl (±)1-(morpholine-4-carbonyl)-6-azaspiro[2.5]octane-6-carboxylate | 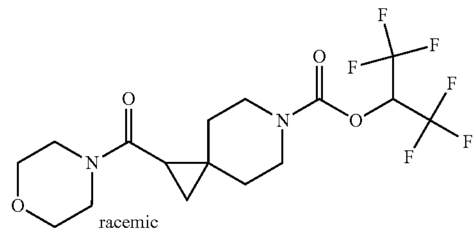 [SMILES: O=C(OC(C(F)(F)F)C(F)(F)F)N1CCC2(CC1)CC2C(=O)N1CCOCC1] | | |
| 120 | 1,1,1,3,3,3-hexafluoro-propan-2-yl (R or S)-1-(morpholine-4-carbonyl)-6-azaspiro[2.5]octane-6-carboxylate peak 1 | 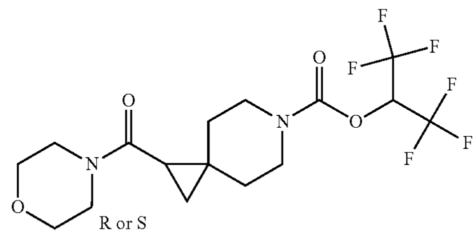 [SMILES: O=C(OC(C(F)(F)F)C(F)(F)F)N1CCC2(CC1)CC2C(=O)N1CCOCC1] | δ 5.85-5.63 (m, 1H), 3.85-3.52 (m, 10H), 3.48-3.28 (m, 2H), 1.79-1.58 (m, 3H), 1.62-1.49 (m, 1H), 1.45-1.29 (m, 2H), 0.94-0.81 (m, 1H) | 419 |
| 121 | 1,1,1,3,3,3-hexafluoro-propan-2-yl (R or S)-1-(morpholine-4-carbonyl)-6-azaspiro[2.5]octane-6-carboxylate peak 2 | 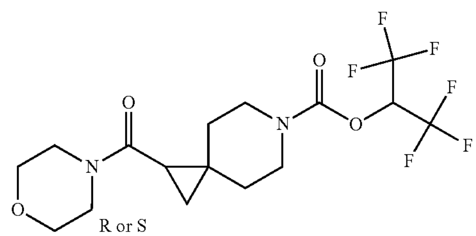 [SMILES: O=C(OC(C(F)(F)F)C(F)(F)F)N1CCC2(CC1)CC2C(=O)N1CCOCC1] | δ 5.85-5.63 (m, 1H), 3.85-3.52 (m, 10H), 3.48-3.28 (m, 2H), 1.79-1.58 (m, 3H), 1.62-1.49 (m, 1H), 1.45-1.29 (m, 2H), 0.94-0.81 (m, 1H) | 419 |
| 122 | 1,1,1,3,3,3-hexafluoro-propan-2-yl (±)1-(4-cyanopiperidine-1-carbonyl)-6-azaspiro[2.5]octane-6-carboxylate | 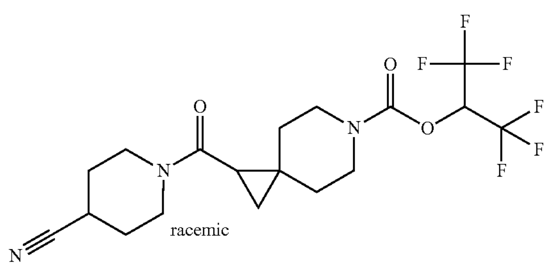 [SMILES: N#CC1CCN(C(=O)C2CC23CCN(C(=O)OC(C(F)(F)F)C(F)(F)F)CC3)CC1] | | |
| 123 | 1,1,1,3,3,3-hexafluoro-propan-2-yl (R or S)-1-(4-cyanopiperidine-1-carbonyl)-6-azaspiro[2.5]octane-6-carboxylate peak 1 | 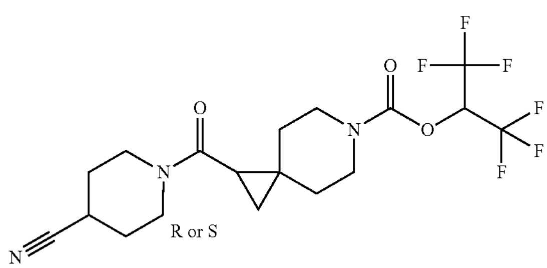 [SMILES: N#CC1CCN(C(=O)C2CC23CCN(C(=O)OC(C(F)(F)F)C(F)(F)F)CC3)CC1] | δ 5.91-5.66 (m, 1H), 3.98-3.49 (m, 6H), 3.49-3.24 (m, 2H), 3.03-2.82 (m, 1H), 2.08-1.81 (m, 4H), 1.81-1.60 (m, 3H), 1.55-1.46 (m, 1H), 1.42-1.27 (m, 2H), 0.95-0.72 (m, 1H) | 442 |

| Ex | Name | Structure | NMR (¹H NMR, 300 MHz or 400 MHz, Chloroform-d unless otherwise noted) | MS [M + H]⁺ |
|---|---|---|---|---|
| 124 | 1,1,1,3,3,3-hexafluoro-propan-2-yl (R or S)-1-(4-cyanopiperidine-1-carbonyl)-6-azaspiro[2.5]octane-6-carboxylate peak 2 | 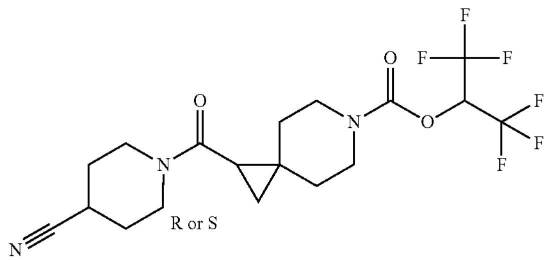 [SMILES: N#CC1CCN(C(=O)C2CC23CCN(C(=O)OC(C(F)(F)F)C(F)(F)F)CC3)CC1] | δ 5.91-5.66 (m, 1H), 3.98-3.49 (m, 6H), 3.49-3.24 (m, 2H), 3.03-2.82 (m, 1H), 2.08-1.81 (m, 4H), 1.81-1.60 (m, 3H), 1.55-1.46 (m, 1H), 1.42-1.27 (m, 2H), 0.95-0.72 (m, 1H) | 442 |
| 125 | 1,1,1,3,3,3-hexafluoro-propan-2-yl (±)1-((1-methyl-1H-pyrazol-3-yl)carbamoyl)-6-azaspiro[2.5]octane-6-carboxylate | 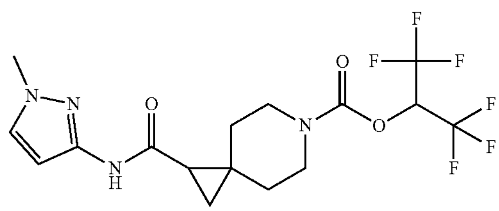 | | |
| 126 | 1,1,1,3,3,3-hexafluoro-propan-2-yl (R or S)-1-((1-methyl-1H-pyrazol-3-yl)carbamoyl)-6-azaspiro[2.5]octane-6-carboxylate peak 1 | 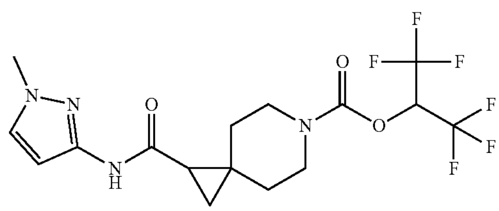 | δ 8.33 (s, 1H), 6.65 (s, 1H), 5.85-5.71 (m, 1H), 3.83 (s, 3H), 3.70-3.42 (m, 4H), 1.92-1.76 (m, 2H), 1.61-1.44 (m, 3H), 1.43-1.32 (m, 1H), 1.06-0.93 (m, 1H) | 429 |
| 127 | 1,1,1,3,3,3-hexafluoro-propan-2-yl (R or S)-1-((1-methyl-1H-pyrazol-3-yl)carbamoyl)-6-azaspiro[2.5]octane-6-carboxylate peak 2 | 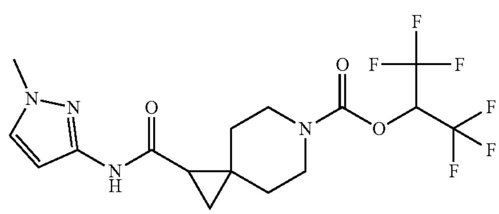 | δ 8.26 (d, J = 9.3 Hz, 1H), 6.65 (d, J = 2.3 Hz, 1H), 5.84-5.72 (m, 1H), 3.84 (s, 3H), 3.62-3.59 (m, 2H), 3.58-3.43 (m, 2H), 1.91-1.80 (m, 2H), 1.57-1.48 (m, 3H), 1.41-1.33 (m, 1H), 1.04-0.96 (m, 1H) | 429 |
| 128 | 1,1,1,3,3,3-hexafluoro-propan-2-yl (±)1-(thiazol-5-ylcarbamoyl)-6-azaspiro[2.5]octane-6-carboxylate | 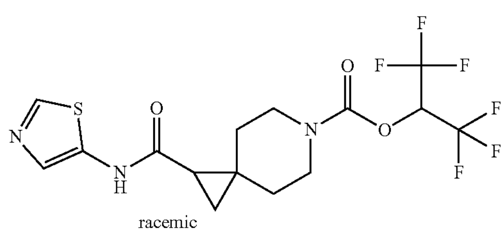 [SMILES: O=C(Nc1cncs1)C1CC12CCN(C(=O)OC(C(F)(F)F)C(F)(F)F)CC2] | | |
| 129 | 1,1,1,3,3,3-hexafluoro-propan-2-yl (R or S)-1-(thiazol-5-ylcarbamoyl)-6-azaspiro[2.5]octane-6-carboxylate peak 1 | 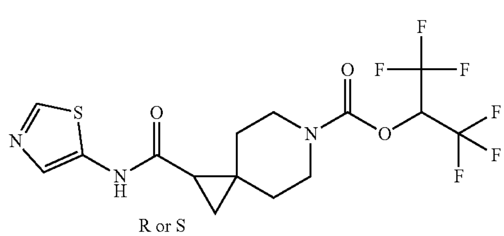 [SMILES: O=C(Nc1cncs1)C1CC12CCN(C(=O)OC(C(F)(F)F)C(F)(F)F)CC2] | δ 9.79 (s, 1H), 8.56 (s, 1H), 8.17-7.59 (m, 1H), 5.77(s, 1H), 3.98-3.24 (m, 4H), 2.01-1.79 (m, 2H), 1.75-1.38 (m, 4H), 1.12 (s, 1H) | 431 |

-continued

| Ex | Name | Structure | NMR (¹H NMR, 300 MHz or 400 MHz, Chloroform-d unless otherwise noted) | MS [M + H]⁺ |
|---|---|---|---|---|
| 130 | 1,1,1,3,3,3-hexafluoro-propan-2-yl (R or S)-1-(thiazol-5-ylcarbamoyl)-6-azaspiro[2.5]octane-6-carboxylate peak 2 | R or S | δ 9.45 (s, 1H), 8.50 (s, 1H), 7.75 (s, 1H), 5.87-5.68 (m, 1H), 3.77-3.67 (m, 1H), 3.59-3.44 (m, 3H), 1.97-1.76 (m, 2H), 1.73-1.59 (m, 2H), 1.49-1.40 (m, 2H), 1.16-1.08 (m, 1H) | 431 |
| 131 | 1,1,1,3,3,3-hexafluoro-propan-2-yl (±)1-((4-methyltetra-hydro-2H-pyran-4-yl)carbamoyl)-6-azaspiro[2.5]octane-6-carboxylate | racemic | | |
| 132 | 1,1,1,3,3,3-hexafluoro-propan-2-yl (R or S)-1-((4-methyl-tetrahydro-2H-pyran-4-yl)carbamoyl)-6-azaspiro[2.5]octane-6-carboxylate peak 1 | R or S | δ 5.84-5.68 (m, 1H), 5.40-5.32 (m, 1H), 3.78-3.46 (m, 8H), 2.16-2.05 (m,1H), 2.03-1.93 (m, 1H), 1.83-1.69 (m, 4H), 1.65-1.52 (m, 1H), 1.50-1.43 (m, 4H), 1.43-1.31 (m, 1H), 1.24-1.18 (m, 1H), 0.86-0.73 (m, 1H) | 447 |
| 133 | 1,1,1,3,3,3-hexafluoro-propan-2-yl (R or S)-1-((4-methyltetrahydro-2H-pyran-4-yl)carbamoyl)-6-azaspiro[2.5]octane-6-carboxylate peak 2 | R or S | δ 5.84-5.68 (m, 1H), 5.40-5.32 (m, 1H), 3.78-3.46 (m, 8H), 2.16-2.05 (m,1H), 2.03-1.93 (m, 1H), 1.83-1.69 (m, 4H), 1.65-1.52 (m, 1H), 1.50-1.43 (m, 4H), 1.43-1.31 (m, 1H), 1.24-1.18 (m, 1H), 0.86-0.73 (m, 1H) | 447 |
| 134 | 1,1,1,3,3,3-hexafluoropropan-2-yl (±)1-((1-methyl-1H-pyrazol-5-yl)carbamoyl)-6-azaspiro[2.5]octane-6-carboxylate | racemic | | |
| 135 | 1,1,1,3,3,3-hexafluoro-propan-2-yl (R or S)-1-((1-methyl-1H-pyrazol-5-yl)carbamoyl)-6-azaspiro[2.5]octane-6-carboxylate peak 1 | R or S | (DMSO-d₆) δ 10.15 (s, 1H), 7.30 (d, J = 1.9 Hz, 1H), 6.64-6.51 (m, 1H), 6.16 (d, J = 2.0 Hz, 1H), 3.66 (s, 3H), 3.63-3.44 (m, 3H), 3.31-3.23 (m, 1H), 1.93-1.82 (m, 1H), 1.77-1.57 (m, 2H), 1.56-1.35 (m, 2H), 1.15-1.05 (m, 1H), 1.03-0.91 (m, 1H) | 429 |

| Ex | Name | Structure | NMR (¹H NMR, 300 MHz or 400 MHz, Chloroform-d unless otherwise noted) | MS [M + H]⁺ |
|---|---|---|---|---|
| 136 | 1,1,1,3,3,3-hexafluoropropan-2-yl (R or S)-1-((1-methyl-1H-pyrazol-5-yl)carbamoyl)-6-azaspiro[2.5]octane-6-carboxylate peak 2 | R or S | (DMSO-d₆) δ10.15 (s, 1H), 7.30 (d, J = 1.9 Hz, 1H), 6.63-6.53 (m, 1H), 6.16 (d, J = 2.0 Hz, 1H), 3.66 (s, 3H), 3.62-3.41 (m, 3H), 3.32-3.24 (m, 1H), 1.92-1.83 (m, 1H), 1.75-1.56 (m, 2H), 1.55-1.39 (m, 2H), 1.14-1.06 (m, 1H), 1.01-0.94 (m, 1H) | 429 |
| 137 | 1,1,1,3,3,3-hexafluoropropan-2-yl (±)1-(thiazol-2-ylcarbamoyl)-6-azaspiro[2.5]octane-6-carboxylate | racemic | | |
| 138 | 1,1,1,3,3,3-hexafluoropropan-2-yl (R or S)-1-(thiazol-2-ylcarbamoyl)-6-azaspiro[2.5]octane-6-carboxylate peak 1 | R or S | δ 12.0-11.89 (m, 1H), 7.47-7.37 (m, 1H), 7.08-6.99 (m, 1H), 5.84-5.69 (m, 1H), 3.74-3.65 (m, 1H), 3.62-3.46 (m, 3H), 2.02-1.75 (m, 3H), 1.76-1.46 (m, 3H), 1.23-1.06 (m, 1H) | 432 |
| 139 | 1,1,1,3,3,3-hexafluoropropan-2-yl (R or S)-1-(thiazol-2-ylcarbamoyl)-6-azaspiro[2.5]octane-6-carboxylate peak 2 | R or S | δ 12.0-11.89 (m, 1H), 7.47-7.37 (m, 1H), 7.08-6.99 (m, 1H), 5.84-5.69 (m, 1H), 3.74-3.65 (m, 1H), 3.62-3.46 (m, 3H), 2.02-1.75 (m, 3H), 1.76-1.46 (m, 3H), 1.23-1.06 (m, 1H) | 432 |
| 140 | 1,1,1,3,3,3-hexafluoropropan-2-yl (±)1-(phenylcarbamoyl)-6-azaspiro[2.5]octane-6-carboxylate | racemic | | |
| 141 | 1,1,1,3,3,3-hexafluoropropan-2-yl (S)-1-(phenylcarbamoyl)-6-azaspiro[2.5]octane-6-carboxylate peak 1 | S | δ 7.51 (d, J= 8.0 Hz, 2H), 7.45-7.30 (m, 3H), 7.20-7.05 (m, 1H), 5.92-5.68 (m, 1H), 3.94-3.37 (m, 4H), 1.99-1.83 (m, 2H), 1.74-1.56 (m, 1H), 1.56-1.42 (m, 2H), 1.43-1.33 (m, 1H), 1.10-0.95 (m, 1H) | 425 |

| Ex | Name | Structure | NMR (¹H NMR, 300 MHz or 400 MHz, Chloroform-d unless otherwise noted) | MS [M + H]⁺ |
|---|---|---|---|---|
| 142 | 1,1,1,3,3,3-hexafluoro-propan-2-yl (R)-1-(phenylcarbamoyl)-6-azaspiro[2.5]octane-6-carboxylate peak 2 | 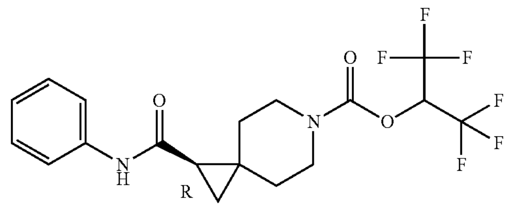 | δ 7.51 (d, J = 8.0 Hz, 2H), 7.43-7.31 (m, 3H), 7.20-7.07 (m, 1H), 5.90-5.72 (m, 1H), 3.96-3.28 (m, 4H), 2.01-1.84 (m, 2H), 1.79-1.56 (m, 1H), 1.53-1.44 (m, 1H), 1.43-1.33 (m, 1H), 1.11-0.94 (m, 1H) | 425 |
| 143 | 1,1,1,3,3,3-hexafluoro-propan-2-yl (±)1-(p-tolylcarbamoyl)-6-azaspiro[2.5]octane-6-carboxylate | 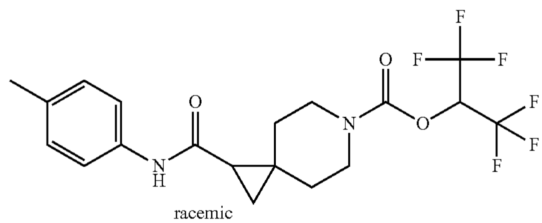 [SMILES: Cc1ccc(NC(=O)C2CC23CCN(C(=O)OC(C(F)(F)F)C(F)(F)F)CC3)cc1] | | |
| 144 | 1,1,1,3,3,3-hexafluoro-propan-2-yl (R or S)-1-(p-tolylcarbamoyl)-6-azaspiro[2.5]octane-6-carboxylate peak 1 | 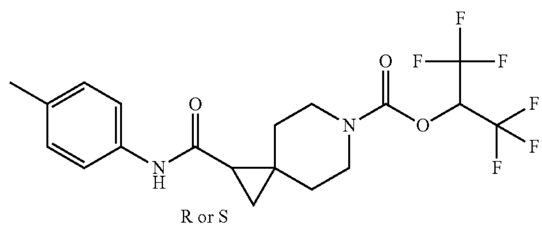 [SMILES: Cc1ccc(NC(=O)C2CC23CCN(C(=O)OC(C(F)(F)F)C(F)(F)F)CC3)cc1] | δ 7.45-7.35 (m, 2H), 7.32-7.29 (m, 1H), 7.17-7.12 (m, 2H), 5.84-5.74 (m, 1H), 3.74-3.65 (m, 1H), 3.63-3.47 (m, 3H), 2.36-2.32 (m, 3H), 1.93-1.83 (m, 2H), 1.66-1.55 (m, 1H), 1.53-1.46 (m, 2H), 1.41-1.34 (m, 1H), 1.01-0.96 (m, 1H) | 439 |
| 145 | 1,1,1,3,3,3-hexafluoro-propan-2-yl (R or S)-1-(p-tolylcarbamoyl)-6-azaspiro[2.5]octane-6-carboxylate peak 2 | 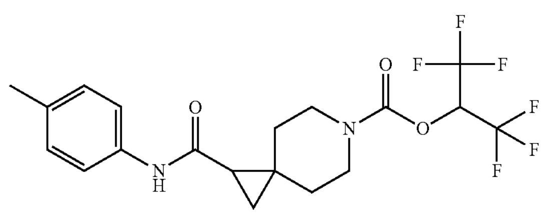 | δ 7.45-7.35 (m, 2H), 7.32-7.29 (m, 1H), 7.17-7.12 (m, 2H), 5.84-5.74 (m, 1H), 3.74-3.65 (m, 1H), 3.63-3.47 (m, 3H), 2.36-2.32 (m, 3H), 1.93-1.83 (m, 2H), 1.66-1.55 (m, 1H), 1.53-1.46 (m, 2H), 1.41-1.34 (m, 1H), 1.01-0.96 (m, 1H) | 439 |
| 146 | 1,1,1,3,3,3-hexafluoro-propan-2-yl (±)1-((3-fluorophenyl)carbamoyl)-6-azaspiro[2.5]octane-6-carboxylate | 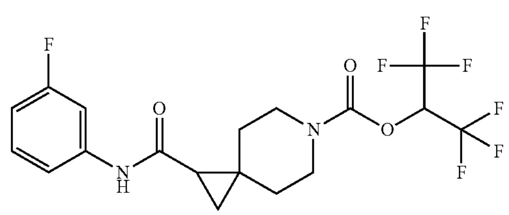 | | |
| 147 | 1,1,1,3,3,3-hexafluoro-propan-2-yl (R or S)-1-((3-fluorophenyl)carbamoyl)-6-azaspiro[2.5]octane-6-carboxylate peak 1 | 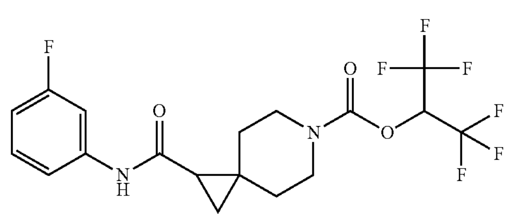 | δ 7.55-7.39 (m, 2H), 7.33-7.25 (m, 1H), 7.20-7.08 (m, 1H), 6.89-6.75 (m, 1H), 5.85-5.67 (m, 1H), 3.76-3.41 (m, 4H), 1.90-1.80 (m, 2H), 1.70-1.57 (m, 1H), 1.54-1.44 (m, 2H), 1.41-1.36 (m, 1H), 1.13-0.90 (m, 1H) | 443 |

| Ex | Name | Structure | NMR (¹H NMR, 300 MHz or 400 MHz, Chloroform-d unless otherwise noted) | MS [M + H]⁺ |
|---|---|---|---|---|
| 148 | 1,1,1,3,3,3-hexafluoro-propan-2-yl (R or S)-1-((3-fluorophenyl)car-bamoyl)-6-azaspiro[2.5]octane-6-carboxylate peak 2 | *R or S* | δ 7.55-7.39 (m, 2H), 7.33-7.25 (m, 1H), 7.20-7.08 (m, 1H), 6.89-6.75 (m, 1H), 5.85-5.67 (m, 1H), 3.76-3.41 (m, 4H), 1.90-1.80 (m, 2H), 1.70-1.57 (m, 1H), 1.54-1.44 (m, 2H), 1.41-1.36 (m, 1H), 1.13-0.90 (m, 1H) | 443 |
| 149 | 1,1,1,3,3,3-hexafluoro-propan-2-yl (±)1-(benzylcar-bamoyl)-6-azaspiro[2.5]octane-6-carboxylate | racemic | | |
| 150 | 1,1,1,3,3,3-hexafluoro-propan-2-yl (S)-1-(benzylcar-bamoyl)-6-aza-spiro[2.5]octane-6-carboxylate peak 1 | *S* | δ 7.37 (dd, J = 7.8, 6.1 Hz, 2H), 7.34-7.29 (m, 3H), 5.92 (s, 1H), 5.85-5.71 (m, 1H), 4.48 (d, J = 4.9 Hz, 2H), 3.70-3.45 (m, 4H), 1.94-1.74 (m, 2H), 1.62-1.35 (m, 3H), 1.34-1.28 (m, 1H), 1.04-0.87 (m, 1H) | 439 |
| 151 | 1,1,1,3,3,3-hexafluoro-propan-2-yl (R)-1-(benzylcar-bamoyl)-6-aza-spiro[2.5]octane-6-carboxylate peak 2 | *R* | δ 7.36 (d, J = 7.1 Hz, 2H), 7.34-7.29 (m, 3H), 5.92 (s, 1H), 5.84-5.71 (m, 1H), 4.48 (s, 2H), 3.75-3.30 (m, 4H), 2.01-1.75 (m, 2H), 1.62-1.27 (m, 4H), 0.98-0.85 (m, 1H) | 439 |
| 152 | 1,1,1,3,3,3-hexafluoro-propan-2-yl (±)1-((pyrimidin-5-ylmethyl)car-bamoyl)-6-aza-spiro[2.5]octane-6-carboxylate | racemic | | |
| 153 | 1,1,1,3,3,3-hexafluoro-propan-2-yl (R or S)-1-((pyrimidin-5-ylmethyl)car-bamoyl)-6-azaspiro[2.5]octane-6-carboxylate peak 1 | *R or S* | (DMSO-d₆) δ 9.08 (d, J = 3.1 Hz, 1H), 8.77-8.65 (m, 3H), 6.65-6.48 (m, 1H), 4.40-4.24 (m, 2H), 3.63-3.38 (m, 3H), 3.32-3.08 (m, 1H), 1.68-1.53 (m, 3H), 1.51-1.41 (m, 1H), 1.40-1.31 (m, 1H), 1.05-0.98 (dd, J = 5.4, 4.1 Hz, 1H), 0.87-0.79 (dd, J = 7.8, 3.9 Hz, 1H) | 441 |

| Ex | Name | Structure | NMR (¹H NMR, 300 MHz or 400 MHz, Chloroform-d unless otherwise noted) | MS [M + H]⁺ |
|---|---|---|---|---|
| 154 | 1,1,1,3,3,3-hexafluoropropan-2-yl (R or S)-1-((pyrimidin-5-ylmethyl)carbamoyl)-6-azaspiro[2.5]octane-6-carboxylate peak 2 | R or S | (DMSO-d₆) δ9.08 (d, J = 3.0 Hz, 1H), 8.74-8.68 (m, 3H), 6.62-6.50 (m, 1H), 4.40-4.24 (m, 2H), 3.59-3.40 (m, 3H), 3.22-3.11 (m, 1H), 1.70-1.52 (m, 3H), 1.51-1.42 (m, 1H), 1.43-1.29 (m, 1H), 1.04-0.98 (m, 1H), 0.86-0.80 (m, 1H) | 441 |
| 155 | 1,1,1,3,3,3-hexafluoropropan-2-yl (±)1-((pyridazin-3-ylmethyl)carbamoyl)-6-azaspiro[2.5]octane-6-carboxylate | racemic | | |
| 156 | 1,1,1,3,3,3-hexafluoropropan-2-yl (R or S)-1-((pyridazin-3-ylmethyl)carbamoyl)-6-azaspiro[2.5]octane-6-carboxylate peak 1 | R or S | δ 9.27-9.09 (m, 1H), 7.66-7.50 (m, 2H), 7.43-7.33 (m, 1H), 5.84-5.64 (m, 1H), 4.89-4.71 (m, 2H), 3.71-3.41 (m, 4H), 1.85-1.73 (m, 2H), 1.63-1.40 (m, 3H), 1.33-1.23 (m, 1H), 0.97-0.87 (m, 1H) | 441 |
| 157 | 1,1,1,3,3,3-hexafluoropropan-2-yl (1S)-1-(((2,3-dihydropyridazin-3-yl)methyl)carbamoyl)-6-azaspiro[2.5]octane-6-carboxylate peak 2 | R or S | δ 9.27-9.09 (m, 1H), 7.66-7.50 (m, 2H), 7.43-7.33 (m, 1H), 5.84-5.64 (m, 1H), 4.89-4.71 (m, 2H), 3.71-3.41 (m, 4H), 1.85-1.73 (m, 2H), 1.63-1.40 (m, 3H), 1.33-1.23 (m, 1H), 0.97-0.87 (m, 1H) | 441 |
| 158 | 1,1,1,3,3,3-hexafluoropropan-2-yl (±)1-((2-oxaspiro[3.3]heptan-6-yl)carbamoyl)-6-azaspiro[2.5]octane-6-carboxylate | racemic | | |
| 159 | 1,1,1,3,3,3-hexafluoropropan-2-yl (R or S)-1-((2-oxaspiro[3.3]heptan-6-yl)carbamoyl)-6-azaspiro[2.5]octane-6-carboxylate peak 1 | R or S | δ 5.86-5.69 (m, 1H), 4.47-4.18 (m, 2H), 4.12-4.02 (m, 1H), 3.73-3.57 (m, 5H) 3.54-3.44 (m, 1H), 2.55-2.26 (m, 2H), 1.91-1.66 (m, 5H), 1.60-1.46 (m, 2H), 1.33-1.19 (m, 1H), 0.98-0.77 (m, 1H) | 445 |

| Ex | Name | Structure | NMR (¹H NMR, 300 MHz or 400 MHz, Chloroform-d unless otherwise noted) | MS [M + H]⁺ |
|---|---|---|---|---|
| 160 | 1,1,1,3,3,3-hexafluoro-propan-2-yl (R or S)-1-((2-oxa-spiro[3.3]heptan-6-yl)carbamoyl)-6-aza-spiro[2.5]octane-6-carboxylate peak 2 | 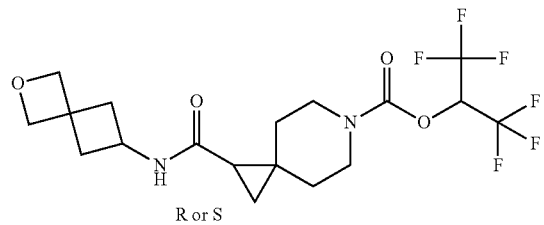 [SMILES: O=C(NC1CC2(COC2)C1)C1CC12CCN(C(=O)OC(C(F)(F)F)C(F)(F)F)CC2]<br>R or S | δ 5.86-5.69 (m, 1H), 4.47-4.18 (m, 2H), 4.12-4.02 (m, 1H), 3.73-3.57 (m, 5H) 3.54-3.44 (m, 1H), 2.55-2.26 (m, 2H), 1.91-1.66 (m, 5H), 1.60-1.46 (m, 2H), 1.33-1.19 (m, 1H), 0.98-0.77 (m, 1H) | 445 |
| 161 | 1,1,1,3,3,3-hexafluoro-propan-2-yl (±)1-((6-cyclopropyl-pyridin-3-yl)carbamoyl)-6-aza-spiro[2.5]octane-6-carboxylate | 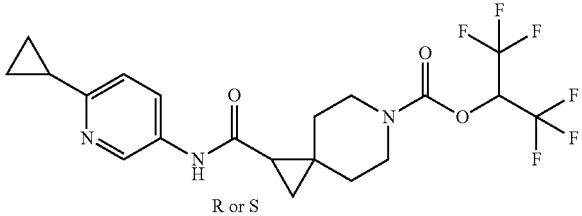 [SMILES: O=C(Nc1ccc(C2CC2)nc1)C1CC12CCN(C(=O)OC(C(F)(F)F)C(F)(F)F)CC2]<br>R or S | | |
| 162 | 1,1,1,3,3,3-hexafluoro-propan-2-yl (R)-1-((6-cyclopropyl-pyridin-3-yl)carbamoyl)-6-azaspiro[2.5]octane-6-carboxylate peak 1 | 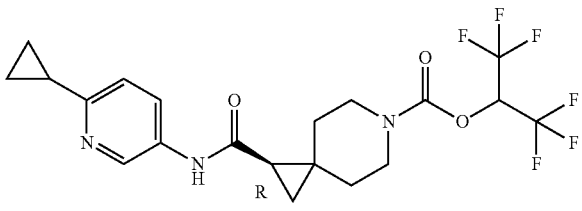<br>R | δ 8.41 (s, 1H), 8.10 (d, J = 8.5 Hz, 1H), 7.75 (s, 1H), 7.12 (d, J = 8.6 Hz, 1H), 5.84-5.72 (m, 1H), 3.78-3.45 (m, 4H), 2.12-2.01 (m, 1H), 1.92-1.80 (m, 2H), 1.70-1.55 (m, 2H), 1.53-1.42 (m, 1H), 1.42-1.35 (m, 1H), 1.07-0.94 (m, 5H) | 466 |
| 163 | 1,1,1,3,3,3-hexafluoro-propan-2-yl (S)-1-((6-cyclopropyl-pyridin-3-yl)carbamoyl)-6-azaspiro[2.5]octane-6-carboxylate peak 2 | 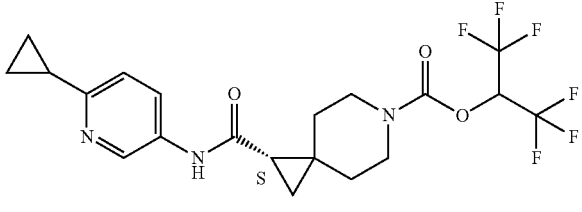<br>S | δ 8.43-8.35 (m, 1H), 8.10-8.03 (m, 1H), 7.73 (s, 1H), 7.11 (d, J = 8.5 Hz, 1H), 5.85-5.71 (m, 1H), 3.79-3.44 (m, 4H), 2.12-2.00 (m, 1H), 1.91-1.77 (m, 2H), 1.70-1.54 (m, 2H), 1.52-1.41 (m, 1H), 1.40-1.33 (m, 1H), 1.07-0.93 (m, 5H) | 466 |
| 164 | 1,1,1,3,3,3-hexafluoro-propan-2-yl (±)1-((6-isopropoxy-pyridin-3-yl)carbamoyl)-6-azaspiro[2.5]octane-6-carboxylate | 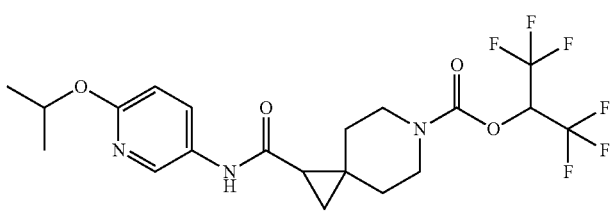<br>racemic | | |
| 165 | 1,1,1,3,3,3-hexafluoro-propan-2-yl (R or S)-1-((6-isopropoxy-pyridin-3-yl)carbamoyl)-6-azaspiro[2.5]octane-6-carboxylate peak 1 | 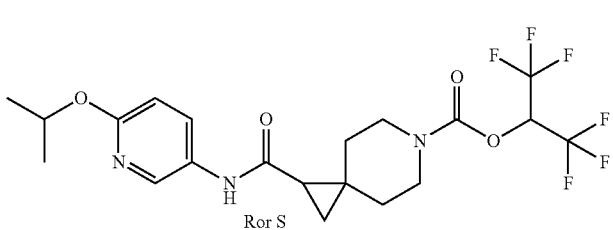<br>R or S | δ 8.16 (d, J = 2.6 Hz, 1H), 7.99-7.91 (m, 1H), 7.67- 7.47 (m, 1H), 6.70 (d, J = 8.9 Hz, 1H), 5.85-5.71 (m, 1H), 5.31-5.17 (m, 1H), 3.79-3.45 (m, 4H), 1.92-1.79 (m, 2H), 1.68-1.53 (m, 2H), 1.52-1.43 (m, 1H), 1.41-1.30 (m, 7H), 1.05-0.97 (m, 1H) | 484 |

| Ex | Name | Structure | NMR (¹H NMR, 300 MHz or 400 MHz, Chloroform-d unless otherwise noted) | MS [M + H]⁺ |
|---|---|---|---|---|
| 166 | 1,1,1,3,3,3-hexafluoro-propan-2-yl (R or S)-1-((6-isopropoxy-pyridin-3-yl)carbamoyl)-6-azaspiro[2.5]octane-6-carboxylate peak 2 | R or S | δ 8.17 (d, J = 2.8 Hz, 1H), 7.97 (d, J = 8.9 Hz, 1H), 7.66-7.46 (m, 1H), 6.71 (d, J = 8.9 Hz, 1H), 5.85-5.73 (m, 1H), 5.31-5.18 (m, 1H), 3.78-3.47 (m, 4H), 1.93-1.81 (m, 2H), 1.69-1.54 (m, 2H), 1.53-1.42 (m, 1H), 1.41-1.33 (m, 7H), 1.05-0.97 (m, 1H) | 484 |
| 167 | 1,1,1,3,3,3-hexafluoro-propan-2-yl (±)1-(((4-methyltetra-hydro-2H-pyran-4-yl)methyl)car-bamoyl)-6-azaspiro[2.5]octane-6-carboxylate | racemic | | |
| 168 | 1,1,1,3,3,3-hexafluoro-propan-2-yl (R or S)-1-(((4-methyltetra-hydro-2H-pyran-4-yl)methyl)car-bamoyl)-6-aza-spiro[2.5]octane-6-carboxylate peak 1 | R or S | δ 5.83-5.74 (m, 1H), 5.77-5.65 (m, 1H), 3.84-3.74 (m, 2H), 3.73-3.41 (m, 6H), 3.34-3.13 (m, 2H), 1.87-1.74 (m, 3H), 1.66-1.47 (m, 3H), 1.45-1.24 (m, 5H), 1.03 (s, 3H), 0.94-0.85 (m, 1H) | 461 |
| 169 | 1,1,1,3,3,3-hexafluoro-propan-2-yl (R or S)-1-(((4-methyltetra-hydro-2H-pyran-4-yl)methyl)car-bamoyl)-6-azaspiro[2.5]octane-6-carboxylate peak 2 | R or S | δ 5.84-5.74 (m, 1H), 5.78-5.66 (m, 1H), 3.85-3.75 (m, 2H), 3.74-3.41 (m, 6H), 3.34-3.12 (m, 2H), 1.86-1.74 (m, 3H), 1.66-1.51 (m, 3H), 1.48-1.24 (m, 5H), 1.03 (s, 3H), 0.93-0.85 (m, 1H) | 461 |
| 170 | 1,1,1,3,3,3-hexafluoro-propan-2-yl (±)1-((6-acetamido-pyridin-3-yl)carbamoyl)-6-azaspiro[2.5]octane-6-carboxylate | racemic | | |
| 171 | 1,1,1,3,3,3-hexafluoro-propan-2-yl (R or S)-1-((6-acetamido-pyridin-3-yl)carbamoyl)-6-azaspiro[2.5]octane-6-carboxylate peak 1 | R or S | δ 8.49 (d, J = 2.5 Hz, 1H), 8.45-8.30 (m, 1H) 8.15 (d, J = 8.9 Hz, 1H), 7.90 (d, J = 8.9 Hz, 1H), 7.77 (s, 1H), 5.85-5.73 (m, 1H), 3.78-3.67 (m, 1H), 3.65-3.44 (m, 3H), 2.23 (s, 3H), 1.95-1.77 (m, 2H), 1.70-1.54 (m, 2H), 1.52-1.43 (m, 1H), 1.42-1.35 (m, 1H), 1.07-0.98 (m, 1H) | 483 |

-continued

| Ex | Name | Structure | NMR (¹H NMR, 300 MHz or 400 MHz, Chloroform-d unless otherwise noted) | MS [M + H]⁺ |
|---|---|---|---|---|
| 172 | 1,1,1,3,3,3-hexafluoro-propan-2-yl (R or S)-1-((6-acetamido-pyridin-3-yl)carbamoyl)-6-azaspiro[2.5]octane-6-carboxylate peak 2 | R or S | δ 8.50 (d, J = 2.5 Hz, 1H), 8.43-8.29 (m, 1H) 8.15 (d, J = 8.9 Hz, 1H), 7.90 (d, J = 8.9 Hz, 1H), 7.82-7.78 (m, 1H), 5.84-5.72 (m, 1H), 3.79-3.67 (m, 1H), 3.65-3.45 (m, 3H), 2.23 (s, 3H), 1.96-1.76 (m, 2H), 1.70-1.55 (m, 2H), 1.53-1.43 (m, 1H), 1.42-1.34 (m, 1H), 1.08-0.99 (m, 1H) | 483 |
| 173 | 1,1,1,3,3,3-hexafluoro-propan-2-yl (±)1-((6-carbamoyl-pyridin-3-yl)carbamoyl)-6-azaspiro[2.5]octane-6-carboxylate | racemic | | |
| 174 | 1,1,1,3,3,3-hexafluoro-propan-2-yl (R)-1-((6-carbamoyl-pyridin-3-yl)carbamoyl)-6-azaspiro[2.5]octane-6-carboxylate peak 1 | R | δ 8.73 (s, 1H), 8.22 (s, 2H), 8.02 (s, 1H), 7.79 (s, 1H), 5.85-5.46 (m, 2H), 3.85-3.38 (m, 4H), 1.88 (s, 2H), 1.65 (s, 2H), 1.55-1.37 (m, 2H), 1.08 (s, 1H) | 469 |
| 175 | 1,1,1,3,3,3-hexafluoro-propan-2-yl (S)-1-((6-carbamoyl-pyridin-3-yl)carbamoyl)-6-azaspiro[2.5]octane-6-carboxylate peak 2 | S | δ 8.74 (s, 1H), 8.33-7.98 (m, 3H), 7.83 (s, 1H), 5.89-5.56 (m, 2H), 3.82-3.41 (m, 4H), 1.87 (s, 2H), 1.65 (s, 2H), 1.55-1.37 (m, 2H), 1.11-1.03 (m, 1H) | 469 |
| 176 | 1,1,1,3,3,3-hexafluoro-propan-2-yl (±)1-(isoxazol-3-ylcarbamoyl)-6-azaspiro[2.5]octane-6-carboxylate | racemic | | |
| 177 | 1,1,1,3,3,3-hexafluoro-propan-2-yl (R or S)-1-(isoxazol-3-ylcarbamoyl)-6-azaspiro[2.5]octane-6-carboxylate peak 1 | R or S | δ 10.30 (s, 1H), 8.30 (d, J = 1.7 Hz, 1H), 7.14 (s, 1H), 5.79-5.66 (m, 1H), 3.75-3.53 (m, 3H), 3.48-3.35 (m, 1H), 1.92-1.72 (m, 3H), 1.69-1.48 (m, 2H), 1.45-1.35 (m, 1H), 1.14-1.00 (m, 1H) | 416 |

| Ex | Name | Structure | NMR (¹H NMR, 300 MHz or 400 MHz, Chloroform-d unless otherwise noted) | MS [M + H]⁺ |
|---|---|---|---|---|
| 178 | 1,1,1,3,3,3-hexafluoro-propan-2-yl (R or S)-1-(isoxazol-3-ylcarbamoyl)-6-azaspiro[2.5]octane-6-carboxylate peak 2 | R or S | δ 10.39 (s, 1H), 8.30 (d, J = 1.8 Hz, 1H), 7.14 (s, 1H), 5.85-5.67 (m, 1H), 3.75-3.55 (m, 3H), 3.50-3.33 (m, 1H), 1.93-1.73 (m, 3H), 1.69-1.50 (m, 2H), 1.47-1.36 (m, 1H), 1.15-1.01 (m, 1H) | 416 |
| 179 | 1,1,1,3,3,3-hexafluoro-propan-2-yl (±)1-((6-(methylsulfon-amido)pyridin-3-yl)carbamoyl)-6-azaspiro[2.5]octane-6-carboxylate | racemic | | |
| 180 | 1,1,1,3,3,3-hexafluoro-propan-2-yl (R or S)-1-((6-(methylsulfon-amido)pyridin-3-yl)carbamoyl)-6-azaspiro[2.5]octane-6-carboxylate peak 1 | R or S | δ 10.02 (s, 1H), 8.41-8.31 (m, 1H), 8.28-8.13 (m, 1H), 7.76 (s, 1H), 7.40-7.32 (m, 1H), 5.87-5.69 (m, 1H), 3.80-3.68 (m, 1H), 3.66-3.45 (m, 3H), 3.15 (s, 3H), 1.92-1.79 (m, 2H), 1.69-1.63 (m, 1H), 1.60-1.57 (m, 1H), 1.54-1.44 (m, 1H), 1.43-1.36 (m, 1H), 1.09-1.00 (m, 1H) | 519 |
| 181 | 1,1,1,3,3,3-hexafluoro-propan-2-yl (R or S)-1-((6-(methylsulfon-amido)pyridin-3-yl)carbamoyl)-6-azaspiro[2.5]octane-6-carboxylate peak 2 | R or S | δ 9.89 (s, 1H), 8.44-8.30 (m, 1H), 8.27-8.13 (m, 1H), 7.72 (s, 1H), 7.39-7.31 (m, 1H), 5.87-5.72 (m, 1H), 3.83-3.69 (m, 1H), 3.64-3.43 (m, 3H), 3.15 (s, 3H), 1.94-1.80 (m, 2H), 1.70-1.62 (m, 2H), 1.61-1.57 (m, 1H), 1.54-1.44 (m, 1H), 1.42-1.38 (m, 1H), 1.12-0.96 (m, 1H) | 519 |
| 182 | (±)2-((5-(6-(((1,1,1,3,3,3-hexafluoro-propan-2-yl)oxy)car-bonyl)-6-aza-spiro[2.5]octane-1-carbox-amido)pyridin-2-yl)oxy)acetic acid | racemic | | |

| Ex | Name | Structure | NMR (¹H NMR, 300 MHz or 400 MHz, Chloroform-d unless otherwise noted) | MS [M + H]⁺ |
|---|---|---|---|---|
| 183 | (R or S)-2-((5-(6-(((1,1,1,3,3,3-hexafluoropropan-2-yl)oxy)carbonyl)-6-azaspiro[2.5]octane-1-carboxamido)pyridin-2-yl)oxy)acetic acid peak 1 | 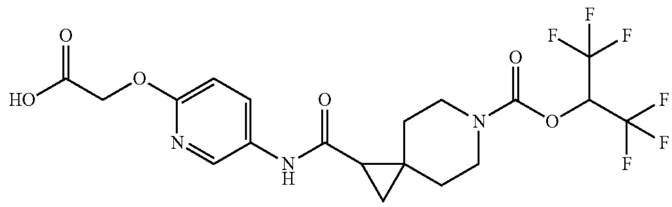 | (DMSO-d₆) δ 10.31 (s, 1H), 8.22 (d, J = 2.6 Hz, 1H), 7.88-7.78 (m, 1H), 6.75-6.67 (m, 1H), 6.59-6.45 (m, 1H), 4.46 (s, 2H), 3.59-3.58 (m, 1H), 3.55-3.52 (m, 1H), 3.33-3.18 (m, 2H), 1.79 (dd, J = 7.9, 5.4 Hz, 1H), 1.72-1.58 (m, 2H), 1.53-1.34 (m, 2H), 1.11-1.06 (m, 1H), 0.94-0.86 (m, 1H) | 500 |
| 184 | (R or S)-2-((5-(6-(((1,1,1,3,3,3-hexafluoropropan-2-yl)oxy)carbonyl)-6-azaspiro[2.5]octane-1-carboxamido)pyridin-2-yl)oxy)acetic acid peak 2 | 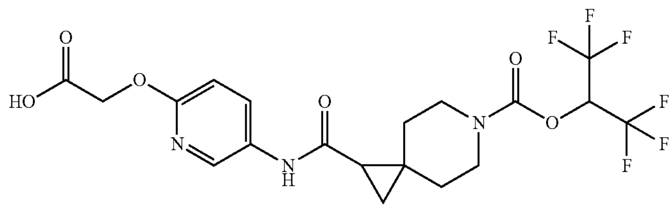 | (DMSO-d₆) δ 10.29 (s, 1H), 8.22 (d, J = 2.6 Hz, 1H), 7.85 (dd, J = 8.9, 2.7 Hz, 1H), 6.72 (d, J = 8.9 Hz, 1H), 6.62-6.46 (m, 1H), 4.46 (s, 2H), 3.61-3.55 (m, 3H), 3.35-3.23 (m, 2H), 1.79 (dd, J = 7.9, 5.4 Hz, 1H), 1.71-1.58 (m, 2H), 1.53-1.34 (m, 2H), 1.11-1.06 (m, 1H), 0.92 (dd, J = 7.9, 4.1 Hz, 1H) | 500 |
| 185 | 1,1,1,3,3,3-hexafluoropropan-2-yl (±)1-(3-cyclopropyl-5,6,7,8-tetrahydro-[1,2,4]triazolo[4,3-a]pyrazine-7-carbonyl)-6-azaspiro[2.5]octane-6-carboxylate | 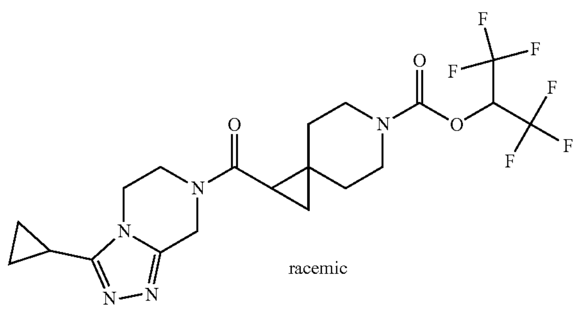 [SMILES: O=C(OC(C(F)(F)F)C(F)(F)F)N1CCC2(CC1)CC2C(=O)N1CCn2c(nnc2C2CC2)C1] | δ 5.79- 5.71 (m, 1H), 5.17-4.81 (m, 2H), 4.23-3.90 (m, 4H), 3.88-3.77 (m, 1H), 3.60-3.49 (m, 1H), 3.42-3.31 (m, 2H), 1.80-1.68 (m, 3H), 1.56 (br, 2H), 1.38 (br, 2H), 1.25-1.07 (m, 4H), 0.98-0.89 (m, 1H) | 496 |
| 186 | 1,1,1,3,3,3-hexafluoropropan-2-yl (±)1-(5,6,7,8-tetrahydroimidazo[1,2-a]pyrazine-7-carbonyl)-6-azaspiro[2.5]octane-6-carboxylate | 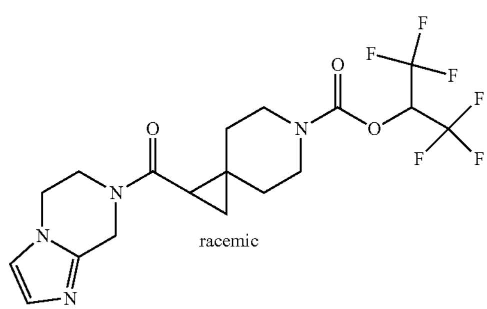 [SMILES: O=C(OC(C(F)(F)F)C(F)(F)F)N1CCC2(CC1)CC2C(=O)N1CCn2ccnc2C1] | δ 7.05 (s, 1H), 6.89 (s, 1H), 5.78-5.70 (m, 1H), 4.98-4.76 (m, 2H), 4.24 (br, 1H), 4.22-3.99 (m, 2H), 3.89 (br, 1H), 3.86-3.84 (m, 1H), 3.46-3.29 (m, 3H), 1.80-1.70 (m, 2H), 1.55-1.49 (m, 2H), 1.51-1.30 (m, 2H), 0.95-0.90 (m, 1H) | 455 |
| 187 | 1,1,1,3,3,3-hexafluoropropan-2-yl (±)1-(5,6,7,8-tetrahydropyrido[3,4-d]pyrimidine-7-carbonyl)-6-azaspiro[2.5]octane-6-carboxylate | 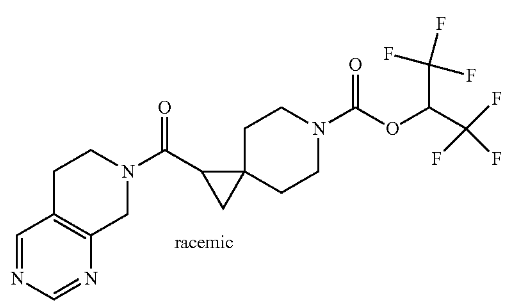 [SMILES: O=C(OC(C(F)(F)F)C(F)(F)F)N1CCC2(CC1)CC2C(=O)N1CCc2cncnc2C1] | □ 9.04 (s, 1H), 8.58 (s, 1H), 5.78-5.71 (m, 1H), 5.00-4.66 (m, 2H), 4.16-4.04 (m, 1H), 3.84-3.46 (m, 3H), 3.40-3.30 (m, 2H), 2.92-2.84 (m, 2H), 1.81-1.74 (m, 3H), 1.53-1.49 (m, 1H), 1.40 (d, J = 7.2 Hz, 2H), 0.94-0.90 (m, 1H) | 467 |

| Ex | Name | Structure | NMR (¹H NMR, 300 MHz or 400 MHz, Chloroform-d unless otherwise noted) | MS [M + H]⁺ |
|---|---|---|---|---|
| 188 | 1,1,1,3,3,3-hexafluoro-propan-2-yl (±)1-(methyl(pyridazin-3-yl)carbamoyl)-6-aza-spiro[2.5]octane-6-carboxylate | racemic | δ 9.07 (s, 1H), 7.76-7.74 (m, 1H), 7.55-7.52 (m, 1H), 5.81-5.75 (m, 1H), 3.83-3.72 (m, 2H), 3.65 (s, 3H), 3.54-3.44 (m, 2H), 1.87-1.78 (m, 1H), 1.74-1.57 (m, 3H), 1.47-1.38 (m, 2H), 0.91 (br, 1H) | 441 |
| 189 | 1,1,1,3,3,3-hexafluoro-propan-2-yl (±)1-((6-cyanopyridin-3-yl)carbamoyl)-6-aza-spiro[2.5]octane-6-carboxylate | racemic | (DMSO-d₆) δ 10.94-10.79 (m, 1H), 8.91-8.77 (m, 1H), 8.36-8.16 (m, 1H), 8.08-7.88 (m, 1H), 6.66-6.46 (m, 1H), 3.66-3.44 (m, 3H), 3.32-3.24 (m, 1H), 1.94-1.82 (m, 1H), 1.74-1.43 (m, 4H), 1.19-0.95 (m, 2H) | 451 |

Example 190—II. Biological Evaluation

Compounds were tested to assess their MAGL activity using the following in vitro and in vivo assays.

In Vitro Competitive Activity-Based Protein Profiling

PC3 human cell membrane proteomes (50 μL, 2.0 mg/mL total protein concentration) were preincubated with varying concentrations of inhibitors at 37° C. After 30 min, the ABPP probe JW912-Bodipy (1.0 μL, 50 μM in DMSO) was added and the mixture was incubated for 30 min at room temperature. Reactions were quenched with SDS loading buffer (15 μL-4×) and run on SDS-PAGE. Following gel imaging, serine hydrolase activity was determined by measuring fluorescent intensity of gel bands corresponding to MAGL using ImageJ 1.43u software. Intensities were converted to percent enzyme activity by normalizing to DMSO controls. IC50 values were determined by fitting percent enzyme activities to a non-linear regression, 4-parameter, sigmoidal dose response function in Prism GraphPad.

In Vitro Competitive Substrate Hydrolysis Enzyme Activity Assay

HEK293 cell lysates expressing recombinant human MAGL enzyme and 4-nitrophenyl acetate (pNPA) substrate were diluted separately in 50 mM HEPES (pH 7.0) containing 200 mM KCl and 1 mM EDTA. Lysates (50 μL, ~1.2 μg total protein) were preincubated with varying concentrations of inhibitors at 25° C. After 30 min, 2×pNPA substrate (50 μL, 2.5 mM) was added and the rate of substrate turnover was monitored by measuring the increase in absorbance at wavelength 405 nm for 20 minutes at 25° C. using a Biotek Neo2 plate reader. The mean velocity was converted to percent enzyme activity following background subtraction and normalization to DMSO controls. IC50 values were determined by fitting percent enzyme activities to a non-linear regression, 4-parameter, sigmoidal dose response function in Prism GraphPad.

In Vivo

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 1.

TABLE 1

| Ex | MAGL % inh. 1 μM (human PC3) | MAGL IC$_{50}$ (μM) (human HEK293) | MAGL IC$_{50}$ (μM) (human PC3) | MAGL % inh. 5 mg/kg (mouse) |
|---|---|---|---|---|
| 2 | 100 | 0.00289 | 0.002 | 100 |
| 3 | 100 | 0.435 | 0.127 | |
| 5 | 100 | 0.553 | 0.18 | |
| 6 | 100 | 0.00826 | 0.0046 | 100 |
| 8 | | | 0.0657 | 100 |
| 9 | | | 0.727 | |
| 11 | 100 | 0.0993 | 0.032 | |
| 12 | 100 | 0.102 | | |
| 14 | | | 0.013 | |
| 15 | | | 1 | |
| 17 | 100 | 0.00421 | 0.001 | |
| 18 | 100 | 0.053 | 0.039 | |
| 20 | | | 0.029 | 0 |
| 21 | | | 0.317 | |
| 23 | | | 0.2 | |
| 24 | | | 0.0024 | 90 |
| 26 | | | 0.016 | |
| 27 | | | 0.056 | |
| 29 | | | 0.003 | |
| 30 | | | 0.39 | |
| 32 | | | 0.25 | |
| 33 | | | 0.0022 | |
| 34 | 100 | 0.148 | | |
| 36 | | | 0.0051 | 0 |
| 37 | | | 0.0011 | 25 |
| 39 | 90 | 0.319 | 0.29 | |
| 40 | 100 | 0.00343 | 0.0027 | 100 |
| 42 | 100 | 0.243 | | |
| 43 | 100 | 0.244 | 0.04 | 100 |
| 45 | 100 | 0.06 | 0.014 | |
| 46 | 100 | 0.133 | | |
| 48 | 100 | 0.139 | | |

TABLE 1-continued

| Ex | MAGL % inh. 1 µM (human PC3) | MAGL IC$_{50}$ (µM) (human HEK293) | MAGL IC$_{50}$ (µM) (human PC3) | MAGL % inh. 5 mg/kg (mouse) |
|---|---|---|---|---|
| 49 | 100 | 0.003 | | |
| 51 | 100 | 0.0232 | 0.0048 | |
| 52 | 100 | 0.155 | | |
| 54 | 100 | 0.111 | | |
| 55 | 100 | 0.028 | | |
| 57 | 100 | 0.00473 | 0.0017 | |
| 58 | 100 | 0.138 | 0.049 | |
| 60 | 100 | 0.0854 | 0.036 | |
| 61 | 75 | 0.684 | | |
| 63 | 100 | 0.0169 | 0.007 | |
| 64 | 100 | 0.103 | | |
| 66 | 100 | 0.00102 | 0.0042 | |
| 67 | 100 | 0.0485 | | |
| 69 | 100 | 0.0136 | | |
| 70 | 75 | 0.985 | | |
| 72 | 100 | 0.00617 | | |
| 73 | 100 | 0.0003 | | |
| 75 | 100 | 0.00911 | | |
| 76 | 100 | 0.00241 | 0.0035 | |
| 78 | 100 | 0.00299 | 0.008 | |
| 79 | 50 | 0.851 | | |
| 81 | 100 | 0.000864 | 0.00087 | 25 |
| 82 | 100 | 0.118 | | |
| 84 | 100 | 0.0101 | 0.0089 | |
| 85 | 100 | 0.167 | 0.099 | |
| 87 | 100 | 0.463 | 0.2 | |
| 88 | 100 | 0.0718 | 0.0325 | |
| 90 | 100 | 0.00579 | 0.0047 | |
| 91 | 100 | 0.00599 | 0.0037 | |
| 93 | 100 | 0.00284 | | |
| 94 | 100 | 0.00323 | 0.0051 | |
| 96 | 100 | 0.0489 | 0.0193 | 100 |
| 97 | 90 | 1.38 | 0.2 | |
| 99 | 100 | 0.00552 | 0.0097 | |
| 100 | 75 | 0.736 | | |
| 102 | | | 0.15 | |
| 103 | | | 0.0033 | 50 |
| 105 | | | 0.1 | |
| 106 | | | 0.001 | 0 |
| 108 | | | 0.013 | 75 |
| 109 | | | 0.57 | |
| 111 | | | 0.074 | |
| 112 | | | 0.0042 | 75 |
| 114 | | | 2.6 | |
| 115 | | | 0.56 | |
| 117 | | | 0.0047 | 100 |
| 118 | | | 0.29 | |
| 120 | | | 0.3 | |
| 121 | | | 0.42 | |
| 123 | | | 0.16 | |
| 124 | | | 0.67 | |
| 126 | | | 0.23 | |
| 127 | | | 0.019 | 75 |
| 129 | | | 0.012 | 50 |
| 130 | | | 0.27 | |
| 132 | | | 0.027 | 100 |
| 133 | | | 1.6 | |
| 135 | | | 0.015 | 100 |
| 136 | | | 0.34 | |
| 138 | | | 0.001 | 75 |
| 139 | | | 0.11 | |
| 141 | | | 0.00091 | |
| 142 | | | 0.13 | |
| 144 | | | 0.0052 | |
| 145 | | | 0.27 | |
| 147 | | | 0.0018 | |
| 148 | | | 0.091 | |
| 150 | | | 0.0031 | |
| 151 | | | 0.031 | |
| 153 | | | 0.077 | |
| 154 | | | 0.86 | |
| 156 | | | 0.45 | |
| 157 | | | 0.23 | |
| 159 | | | 0.043 | |
| 160 | | | 0.59 | |
| 162 | | | 0.16 | |
| 163 | | | 0.001 | |
| 165 | | | 0.0014 | |
| 166 | | | 0.13 | |
| 168 | | | 0.0074 | |
| 169 | | | 0.21 | |
| 171 | | | 0.0025 | |
| 172 | | | 0.13 | |
| 174 | | | 0.22 | |
| 175 | | | 0.0014 | |
| 177 | | | 0.29 | |
| 178 | | | 0.0027 | |
| 180 | | | 0.28 | |
| 181 | | | 0.0305 | |
| 183 | | | 0.39 (rat) | |
| 184 | | | 1.4 | |
| 185 | 90 | 0.862 | 0.4 | |
| 186 | 100 | 0.168 | | |
| 187 | 100 | 0.143 | 0.11 | |
| 188 | 100 | 0.249 | 0.12 | |
| 189 | | | 0.0033 (rat) | |

Example 191—Effects of Acute Treatment in the Rat Formalin Paw Model of Inflammatory Pain In the rat formalin paw model formalin is administered into the right hand paw of a rat in order to induce pain (observed by hind limb licking duration and frequency). Test compounds are administered in order to evaluate their efficacy in reducing the frequency of hind limb licking, which is suggested to translate into an alleviation in pain such as acute and/or chronic pain in patients.

Experimental Protocol:

Male Sprague Dawley rats were divided into three cohorts to enable testing in the Laboras™ equipment to be carried out over three days in a balanced design to give treatment groups of 10. On the day of the study, male Sprague Dawley rats were weighed, tail marked and dosed orally with vehicle, test compound (0.1, 0.3, 0.6, 1, 3 or 10 mg/kg) or pregabalin (30 mg/kg) 4 h pre-test using a 5 mL/kg dosing volume. For Example 6 the vehicle used was 0.5% methylcellulose in water and for Example 8 the vehicle used was 20% HP-b-CD. Up to six animals were dosed at a time. After 4 h, rats received an intraplantar injection of 50 µL of a 2.5% v/v formalin solution into the right hind paw. Rats were immediately placed into the Laboras™ cages and data acquisition started. The primary measures recorded by Laboras™ for the formalin paw model are hind limb licking duration and frequency. Locomotion is also reported as maximum speed, average speed when moving or over the whole-time bin and distance travelled. After 40 min, when data acquisition was complete, rats were removed from the cages.

On removal from the test cages, rats were anaesthetised with the gaseous anaesthetic isoflu-rane (5% v/v isoflurane in oxygen) and blood samples were collected by cardiac puncture. Brains were then removed, rinsed in phosphate buffered saline (PBS), hemi-sected and frozen separately in liquid nitrogen.

Data Analysis/Statistics:

Data were analysed with Statistica software (TIBCO, USA version 11.1). All data are expressed as means±standard error of the mean (sem) to one decimal place. Data are presented as total activity between 0 and 10 minutes (early phase) and between 10 and 30 minutes (delayed inflammatory phase), as well as the time course data in 5 min time bins for the full 40 minutes of data acquisition. Time course data were analysed by repeated measures analysis of variance (ANOVA) followed by one-way ANOVAs at each time point and subsequent Dunnett's post hoc tests. The early and delayed inflammatory phases of these data were analysed with one-way ANOVAs and Dunnett's post hoc tests. Outliers are defined as values falling more than two standard deviations from the mean and have been excluded for the 0-10 min and the 10-30 min data as well as the time course data. The level of significance was set at $p<0.05$.

Figure 2:
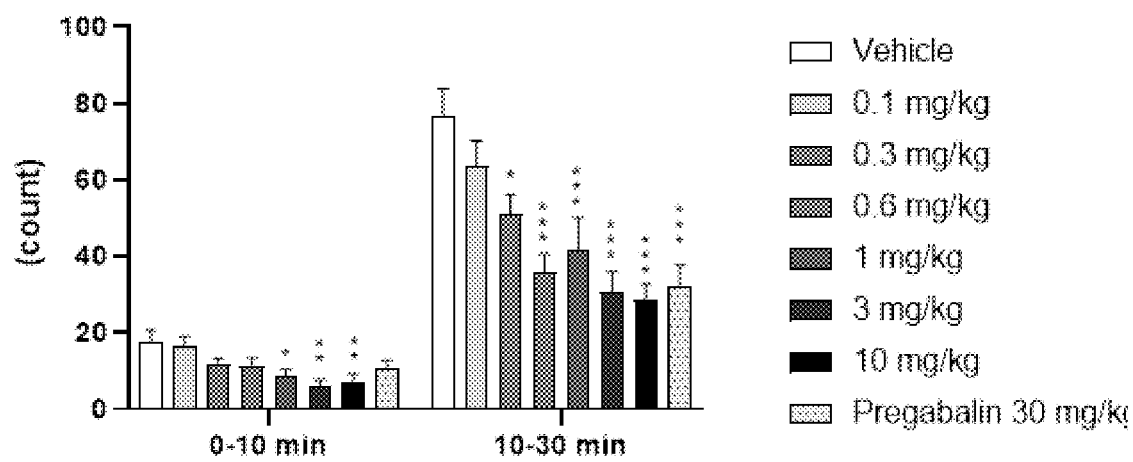
FIG. 2 Anti-nociceptive effects of Example 8 in the rat formalin model; y-axis: count—hind limb licking frequency; x-axis: time period (min). Significance level for post-hoc comparisons (relative to the vehicle group) are indicated: $*p<0.05$, $p<0.01$, $*p<0.001$.

As shown in FIG. 1, administration of Example 6 at 0.6 mg/kg, 3 mg/kg and 10 mg/kg showed statistically significant reduction in the measure of spontaneous pain (hind limb licking frequency) in the early and/or late phases of the test. As shown in FIG. 2, administration of Example 8 at 1 mg/kg, 3 mg/kg and 10 mg/kg showed statistically significant reduction in the measure of spontaneous pain (hind limb licking frequency) in both early and late phases of the test and Example 8 additionally at 0.3 mg/kg and 0.6 mg/kg demonstrated a statistically significant reduction in the measure of spontaneous pain in the late phase.

Example 192—Assessment of the Effect of Compounds of the Invention in the Maximal Electroshock Seizure Threshold (MEST) Model in the Rat Experimental Protocol:

In the MEST model, a low-intensity electrical current of high frequency and short duration is applied to induce tonic convulsions. The MEST test allows identification of anticonvulsant activity of compounds which may be useful in treatment of generalized seizures.

Animals were randomly assigned to vehicle, compound treatment or Lamotrigine dose groups. Animals were dosed at 5 mL/kg according to treatment groups (n=12 or 16/group), with either vehicle (0.5% MC) p.o. for Example 6, vehicle (10% HP-b-CD) for Example 8, test compound at 10 mg/kg p.o. 240 min pre-treatment time, or Lamotrigine p.o. 360 min pre-treatment time.

Rats were individually assessed for production of a tonic hind limb extensor seizure following a single corneally delivered electroshock of 0.3 second duration, using an 'up and down method' of shock titration (Kimball A W et al., 1957). Thus, the first rat within a treatment group was given a shock at the expected or estimated CC50 current (current producing tonic hind limb extensor seizures in 50% of animals). For subsequent animals, the stimulus intensity was lowered or raised in log $0.06:10^\Lambda$ (1+x*0,06) mA intervals if the preceding rat did or did not show tonic hind limb extension, respectively. This procedure was continued for all rats within a treatment group. Induction of seizure was measured as an all-or-nothing effect scored as either present (+) or absent (0) for each animal.

The data for each treatment group were recorded as the number of +'s and 0's at each current level employed and this information was then used to calculate the CC50 value (current required for 50% of the animals to show tonic hind limb extension)±standard error according to the method of Kimball et al. (1957). Drug effects were calculated as % change in CC50 from the vehicle control group.

Statistical Analysis:

Significant differences between drug-treated animals and controls were assessed according to Litchfield and Wilcoxon (1949) or One-Way ANOVA followed by Dunnett's multiple comparisons test.

Figure 3:
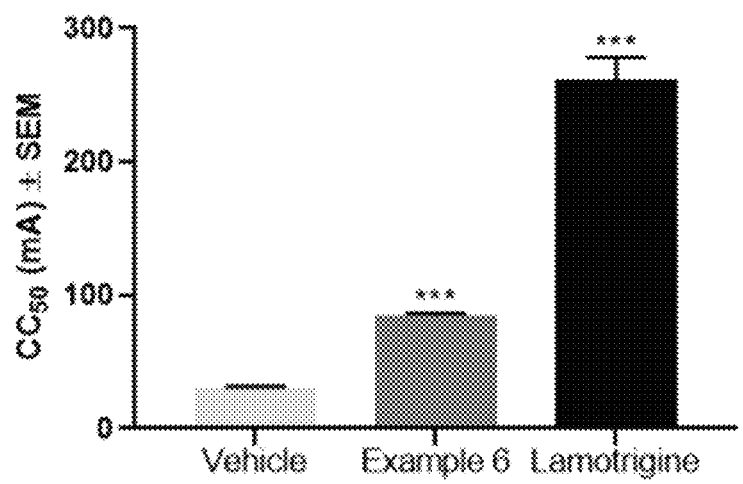
FIG. 3 Effect of Example 6 in the MEST model; y-axis: Estimated seizure threshold ($CC_{50}$) current (mA); Significance level for post-hoc comparisons (relative to the vehicle group) are indicated: $***p<0.001$.
Figure 4:
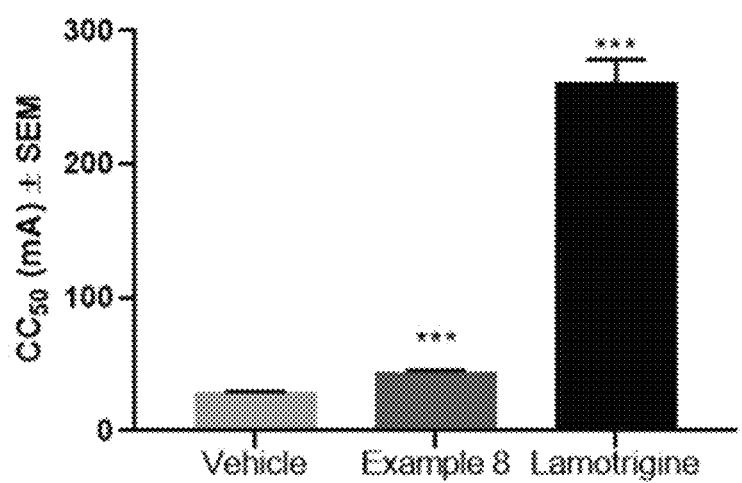
FIG. 4 Effect of Example 8 in the MEST model; y-axis: Estimated seizure threshold ($CC_{50}$) current (mA); Significance level for post-hoc comparisons (relative to the vehicle group) are indicated: $***p<0.001$.
Figure 5:
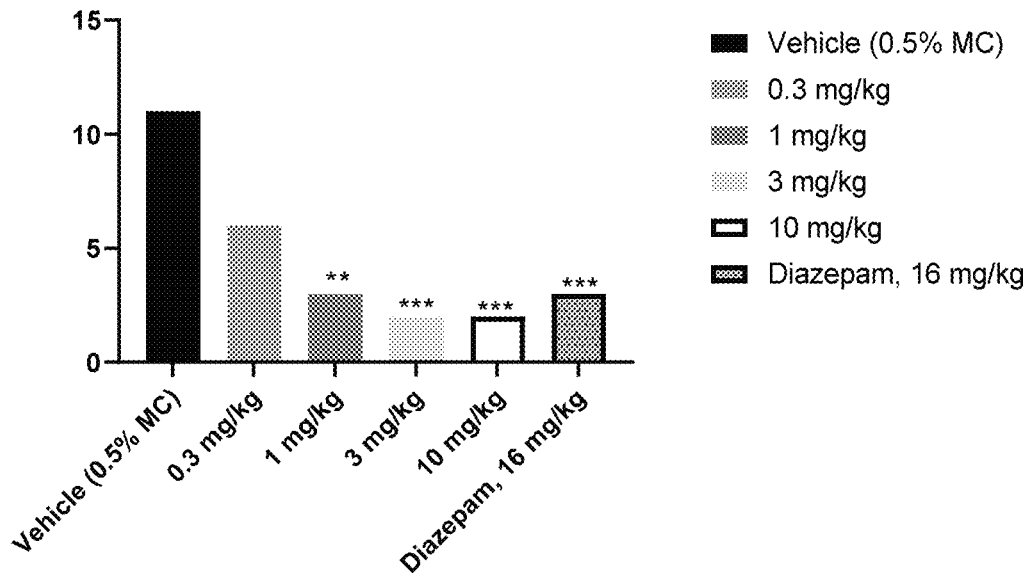
FIG. 5 Effect of Example 6 in the Kainic Acid Seizure Model; y-axis; count—number of animals from groups of 12 showing forelimb clonus. Significance level for post-hoc comparisons (relative to the vehicle group) are indicated: $<0.01$, $*<0.001$.
Figure 6:
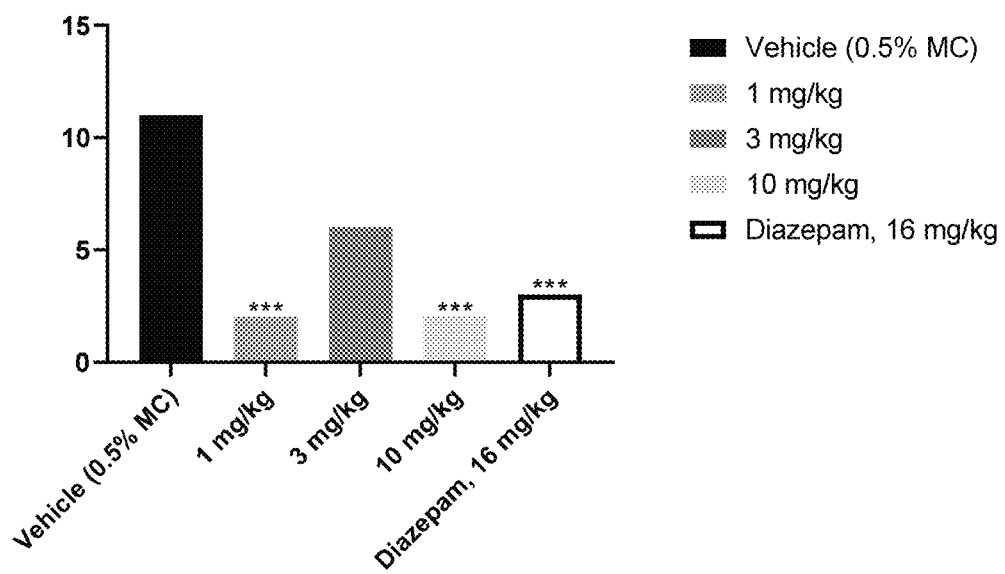
FIG. 6 Effect of Example 8 in the Kainic Acid Seizure Model; y-axis; count—number of animals from groups of 12 showing forelimb clonus. Significance level for post-hoc comparisons (relative to the vehicle group) are indicated: $***<0.001$.

Results:

The results suggest the presence of anticonvulsant activity with Example 6 and Example 8 at 10 mg/kg in the MEST in Rat (FIG. 3 and FIG. 4, respectively).

Example 193—Evaluation of Test Compound for Anticonvulsant Activity in the Kainic Acid Seizure Model in the Rat Kainic acid is an analog of the excitatory neurotransmitter, glutamate and acts as an agonist of kainic acid receptors. After systemic injection, kainic acid induces prolonged excitatory responses with many of the features of human temporal lobe epilepsy.

Experimental Protocol:

The method, which detects anticonvulsant activity related to a glutamatergic mechanism, follows that described by Ben-Ari et al (Neuroscience, 6, 1361-1391, 1981).

Rats, placed in individual Plexiglas cages (33×21×18 cm), are injected with kainic acid (20 mg/kg i.p.). The occurrences of the following symptoms are noted over a 120-minute period 30 minutes after kainic acid injection: forelimb clonus, rearings and rearings with falling, clonic convulsions, tonic convulsions and death. The presence of each symptom and the latencies to the first appearance of the symptoms are measured. The number of forelimb clonus is counted.

12 rats are studied per group. The test is performed partially blind.

The test substances will be evaluated at multiple doses, administered p.o. 240 minutes before the test, and compared with the corresponding vehicle control group (Group 2, administered with 10% HP-b-CD in distilled water, p.o. 240 minutes before the test).

Example 6 was evaluated at 0.3, 1, 3 and 10 mg/kg, and Example 8 was evaluated at 1, 3 and 10 mg/kg, administered p.o. 4 hours before the test, and compared with a vehicle control group (administered with 10% HP-b-CD, p.o. 4 hours before the test).

Diazepam (16 mg/kg) used as reference substance, was administered p.o. 60 minutes before the test (0.5% HP-b-CD) and was compared with vehicle controls.

Data Analysis/Statistics:

Quantitative data (latencies) with the test substance was analyzed by comparing treated groups with vehicle control using Kruskal-Wallis test followed by Mann-Whitney U test. Quantitative data with the reference substance will be analysed using Mann-Whitney U test.

Quantal data (frequencies) were analyzed by comparing treated groups with vehicle control using Fisher's Exact Probability tests.

The results suggest clear anticonvulsant effects for Example 6 over the dose-range 0.3-10 mg/kg and Example 8 over the dose-range 1-10 mg/kg in the kainic acid seizure test in the rat. The magnitude of the effects for Example 6 and Example 8 compounds at middle-high doses were close to those observed with the reference substance, Diazepam.

Example 194—Rat Kp

Brain disposition was evaluated in male Sprague-Dawley rats (n=3, standard body weight). Briefly, test compound was formulated as a simple suspension, in 0.5% HPMC in water, then administered by oral gavage (5 mg/kg, 5 mL/kg). Four hours post dosing, rats were sacrificed, and terminal blood and brain samples were taken. Blood was obtained via cardiac puncture (0.1 mL) and was added into 0.4 mL $CH_3CN$ for precipitation immediately. The samples were stored at $-75+/-15°$ C. prior to analysis. Brain tissue samples were collected after animals were fully exsanguinated, and the tissues were washed with cold saline quickly. After sectioning, brain sections were immediately frozen in liquid nitrogen and stored at $-75+/-15°$ C. prior to analysis. Blood and brain samples were analyzed by LC/MS/MS using an optimized analytical method. Concentrations of test compound in blood and brain were quantified against matrix matched calibration standards. The total blood, plasma, and brain concentration data are presented in Table 2 alongside the calculated brain $K_p$ (total brain concentration:total plasma concentration ratio), the calculated brain $k_{p,uu}$ (unbound brain concentration:unbound plasma concentration ratio), the free fractions in rat plasma and brain, and the in vitro rat blood to plasma distribution profile. The total plasma concentration data were calculated from the total blood concentration data using rat blood to plasma ratio which was measured in vitro (1 µM test compound). For $k_{p,uu}$ determination, the free fraction in rat plasma and brain homogenate were measured in vitro by standard equilibrium dialysis (1 µM test compound and 6 h equilibration against buffer pH 7.4; for rat plasma analysis, 100 mM stock solution of diisopropyl fluorophosphate was added to the pre-warmed rat plasma prior to adding test article).

TABLE 2

Total concentrations, brain $K_p$ and $K_{p,uu}$ are presented (mean, stdev from n = 3 rats)

| Ex | Total blood concentration (mM) | Total plasma concentration (mM) | Total brain concentration (mM) | Brain $K_p$ | Brain $K_{p,uu}$ | Rat plasma free fraction | Rat brain free fraction | Rat blood to plasma ratio |
|---|---|---|---|---|---|---|---|---|
| 2 | 0.049 | 0.066 | 0.199 uM | 3.01 | 0.925 | 0.078 | 0.024 | 0.833 |
| 6 | 0.415 | 0.576 | 1.78 uM | 3.09 | 2.25 | 0.055 | 0.040 | 0.72 |
| 8 | 0.119 | 0.124 | 0.255 uM | 2.06 | 0.801 | 0.427 | 0.167 | 0.96 |

Example 195—Solubility (kinetic)

The kinetic solubility of test articles was determined in PBS at pH 2.0 and pH 7.4 in duplicate. A stock solution of test compound in DMSO (10 mM) was incubated at RT for 2 hours with shaking at 1,100 RPM. The sample was then filtered using a vacuum manifold, diluted, and analyzed by LC-MS/MS. Chromatographic conditions: Phenomenex Synergi 4µ Hydro-PR 80A column (2.0×30 mm) coupled with pre-guard column; mobile phase=0.1% formic acid in acetonitrile and 0.1% formic acid in water; flowrate=0.65 mL/min; column temperature=40° C.; injection volume: 3 µL.

| Time (min) | 0 | 0.8 | 1.1 | 1.2 | 1.4 |
|---|---|---|---|---|---|
| % A | 5 | 100 | 100 | 5 | 5 |

Mass conditions: Turbo spray ion source; ESI ionization model; MRM scan type; Collison gas=6 L/min; Curtain gas=30 L/min; Nebulize gas=50 L/min; Auxiliary gas=50 L/min; Temperature=500 degrees C.; Ion spray voltage=+ 5500 v (positive MRM).

The filtered solution was analyzed and quantified against a standard of known concentration in DMSO using UPLC coupled with mass spectral peak identification and quantitation. Solubility values of the test articles were calculated using Microsoft Excel as follows (DF is the dilution factor):

$$[Sample] = \frac{AREA_{Sample} \times INJ\ VOL_{Std} \times DF_{Sample} \times [STD]}{AREA_{Std} \times INJ\ VOL_{Sample}}$$

The kinetic solubility data are presented in Table 3.

TABLE 3

Kinetic solubility at pH 2 and pH 7.4

| Ex | pH 2 Solubility (µM) | pH 7.4 Solubility (µM) |
|---|---|---|
| 2 | 30.34 | 188.64 |
| 6 | 240.44 | 106.34 |
| 8 | 308.09 | 256.47 |
| 17 |  | 0.07 |
| 20 |  | 309.76 |
| 24 |  | 197.25 |
| 29 |  | 8.63 |
| 40 | 163.13 | 100.48 |
| 43 |  | 233.41 |
| 60 |  | 258.78 |
| 66 |  | 8.74 |
| 76 |  | 1.33 |

TABLE 3-continued

Kinetic solubility at pH 2 and pH 7.4

| Ex | pH 2 Solubility (µM) | pH 7.4 Solubility (µM) |
|---|---|---|
| 78 | 16.97 | 12.57 |
| 81 |  | 130.5 |
| 90 | 32.98 |  |
| 96 |  | 236.99 |
| 99 |  | 28.53 |
| 112 | 185.13 | 108.74 |
| 117 |  | 250.82 |
| 127 | 275.38 | 291.87 |
| 181 |  | 295.59 |

Example 196—Solubility (Thermodynamic)

The thermodynamic solubility of test article was determined in PBS at pH 7.4 in duplicate. The test article (1.5 mg) in PBS was incubated for 24 hours at RT with shaking at 1100 rpm. Sample was then filtered using a vacuum manifold, diluted, and analyzed by LC-MS/MS. Chromatographic conditions: Phenomenex Synergi 4µ Hydro-PR 80A column (2.0×30 mm) coupled with pre-guard column;

mobile phase=0.1% formic acid in acetonitrile and 0.1% formic acid in water; flowrate=0.65 mL/min; column temperature=40 degrees C.; injection volume: 10 μL.

Mobile phase: 0.1% formic acid in acetonitrile (A) and 0.1% formic acid in water (B)

| Time (min) | 0 | 0.3 | 0.8 | 1.1 | 1.2 | 1.4 |
|---|---|---|---|---|---|---|
| %A | 5 | 5 | 100 | 100 | 5 | 5 |

Mass conditions: Turbo spray ion source; ESI ionization model; MRM scan type; Collison gas=6 L/min; Curtain gas=30 L/min; Nebulize gas=50 L/min; Auxiliary gas=50 L/min; Temperature=500 degrees C.; Ion spray voltage=+ 5500 v (positive MRM).

The filtered solution was analyzed and quantified against a standard of known concentration in DMSO using UPLC coupled with mass spectral peak identification and quantitation. Solubility values of the test articles were calculated using Microsoft Excel as follows (DF is the dilution factor):

$$[Sample] = \frac{AREA_{Sample} \times INJ\ VOL_{Std} \times DF_{Sample} \times [STD]}{AREA_{Std} \times INJ\ VOL_{Sample}}$$

The thermodynamic solubility data are presented in Table 4.

TABLE 4

| | Thermodynamic solubility at pH 7.4 |
|---|---|
| Ex | pH 7.4 Solubility (mg/mL) |
| 2 | 0.0918 |
| 6 | 0.0715 |
| 8 | 0.6064 |

Example 197—In Vitro Human Hepatocyte Stability

The metabolic stability of test articles (1 μM) in commercially sourced, pooled donor, cryopreserved human hepatocytes (0.5×10⁶ cells/mL) was determined in duplicate. The $CL_{int}$ reactions (250 μL) were initiated by addition of test compound. Aliquots (25 μL) were taken at 0, 15, 30, 45, 60, 90, 120 and 240 minutes and then protein crashed with ice-cold acetonitrile containing internal standard then centrifuged (3220 g for 25 minutes). Supernatant was used for LC-MS/MS analysis. The in vitro half-life (in vitro t1/2) was determined from the slope value: in vitro $t_{1/2}$=−0.693/k. Conversion of the in vitro $t_{1/2}$ (in min) into the scale-up unbound intrinsic clearance (Scaled-up unbound CLint, in mL/min/kg) was done using the following equation (mean of duplicate determinations), with data shown in Table 5: Scaled-up unbound CLint=kV/N×scaling factor. V=incubation volume (0.25 mL); N=number of hepatocytes per well (0.125×10⁵ cells). Scaling factors for in vivo intrinsic clearance prediction are listed below:

| Species | Hepatocyte concentration (10⁶ cells/g liver) | Liver weight (g liver/kg body weight) | Scaling Factor |
|---|---|---|---|
| Human | 99 | 25.7 | 2544.3 |

TABLE 5

| | Scaled-up unbound CL_int |
|---|---|
| Ex | Scaled-up unbound CLint (mL/min/kg) |
| 2 | 34.8 |
| 6 | 5.79 |
| 8 | 7.75 |
| 20 | 0.85 |
| 24 | 11.9 |
| 29 | 32.74 |
| 40 | 43.25 |
| 96 | 17.09 |
| 112 | 9.59 |
| 117 | 20.55 |
| 127 | 9.51 |
| 129 | 53.56 |
| 132 | 44.18 |
| 135 | 16.79 |
| 138 | 40.48 |
| 150 | 88.79 |
| 168 | 61.36 |
| 181 | 1.94 |

The invention claimed is:

1. A compound of Formula (I):

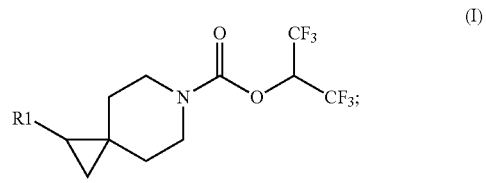

wherein:

R1 is selected from —C(O)NHR2;

R2 is selected from phenyl; 5- or 6-membered heteroaryl, wherein one or two heteroatoms are independently selected from N, O and S; 6-membered heterocycle, wherein one or two heteroatoms are independently selected from N and O; $C_3$-$C_7$ cycloalkyl; and 7 membered bicyclic heterocycle, wherein one or two heteroatoms are independently selected from N and O; and wherein each phenyl; 5- or 6-membered heteroaryl; 6-membered heterocycle; $C_3$-$C_7$ cycloalkyl; or 7-membered bicyclic heterocycle is unsubstituted or substituted with 1 or 2 substituents independently selected from halogen, $C_1$-$C_3$ alkyl, $C_1$-$C_3$ haloalkyl, $C_3$-$C_6$ cycloalkyl, $C_1$-$C_3$ alkoxy, cyano, —NHC(O)CH₃, —C(O)NH₂, —C(O)NHCH₃, —NHSO₂CH₃, —P(O) (CH₃)₂, —OCH₂COOH, and 5-membered heteroaryl having one or two heteroatoms independently selected from N and O;

or a pharmaceutically acceptable salt thereof.

2. The compound of claim 1, having the structure of Formula (Ia):

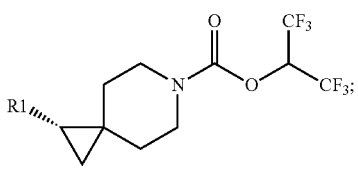

(Ia)

wherein:
R1 is selected from —C(O)NHR2;
R2 is selected from phenyl; 5- or 6-membered heteroaryl, wherein one or two heteroatoms are independently selected from N, O and S; 6-membered heterocycle, wherein one or two heteroatoms are independently selected from N and O; $C_3$-$C_7$ cycloalkyl; and 7 membered bicyclic heterocycle, wherein one or two heteroatoms are independently selected from N and O; and
wherein each phenyl; 5- or 6-membered heteroaryl; 6-membered heterocycle; $C_3$-$C_7$ cycloalkyl; or 7-membered bicyclic heterocycle is unsubstituted or substituted with 1 or 2 substituents independently selected from halogen, $C_1$-$C_3$ alkyl, $C_1$-$C_3$ haloalkyl, $C_3$-$C_6$ cycloalkyl, $C_1$-$C_3$ alkoxy, cyano, —NHC(O)$CH_3$, —C(O)$NH_2$, —C(O)$NHCH_3$, —$NHSO_2CH_3$, —P(O)($CH_3$)$_2$, —$OCH_2COOH$, and 5-membered heteroaryl having one or two heteroatoms independently selected from N and O;
or a pharmaceutically acceptable salt thereof.

3. The compound of claim 1, or a pharmaceutically acceptable salt thereof, wherein R2 is a 5- or 6-membered heteroaryl selected from the group consisting of pyridinyl, pyrazinyl, pyridazinyl, pyrimidyl, pyrazolyl, thiazolyl, and isoxazolyl, wherein the 5- or 6-membered heteroaryl is unsubstituted or substituted with 1 substituent selected from the group consisting of halogen, $C_1$-$C_3$ alkyl, $C_1$-$C_3$ haloalkyl, cyclopropyl, $C_1$-$C_3$ alkoxy, cyano, —NHC(O)$CH_3$, —C(O)$NH_2$, —C(O)$NHCH_3$, —$NHSO_2CH_3$, —P(O)($CH_3$)$_2$, —$OCH_2COOH$, and 5 membered heteroaryl having 1 or 2 heteroatoms selected independently from N and 0.

4. The compound of claim 1, or a pharmaceutically acceptable salt thereof, wherein R2 is a 6-membered heterocycle selected from the group consisting of tetrahydro-2H-pyran-4-yl, piperazinyl, and piperidinyl, wherein the 6-membered heterocycle is unsubstituted or substituted with 1 substituent selected from the group consisting of $C_1$-$C_3$ alkyl, $C_3$-$C_6$ cycloalkyl, and cyano.

5. The compound of claim 1, or a pharmaceutically acceptable salt thereof, wherein R2 is a 6-membered heterocycle selected from the group consisting of tetrahydro-2H-pyran-4-yl, piperazinyl, and piperidinyl, wherein the 6-membered heterocycle is unsubstituted.

6. The compound of claim 1, or a pharmaceutically acceptable salt thereof, wherein R2 is a 6-membered heterocycle selected from the group consisting of tetrahydro-2H-pyran-4-yl, piperazinyl, and piperidinyl, wherein the 6-membered heterocycle is substituted with 1 substituent selected from the group consisting of $C_1$-$C_3$ alkyl, $C_3$-$C_6$ cycloalkyl, and cyano.

7. The compound of claim 1, wherein the compound is selected from the group consisting of:
1,1,1,3,3,3-hexafluoropropan-2-yl (±)1-(pyridin-3-ylcarbamoyl)-6-azaspiro[2.5]octane-6-carboxylate;
1,1,1,3,3,3-hexafluoropropan-2-yl (±)1-(pyridazin-3-yl-carbamoyl)-6-azaspiro[2.5]octane-6-carboxylate;
1,1,1,3,3,3-hexafluoropropan-2-yl (±)1-(isoxazol-4-ylcarbamoyl)-6-azaspiro[2.5]octane-6-carboxylate;
1,1,1,3,3,3-hexafluoropropan-2-yl (±)1-((2-(trifluoromethyl)pyrimidin-4-yl)carbamoyl)-6-azaspiro[2.5]octane-6-carboxylate;
1,1,1,3,3,3-hexafluoropropan-2-yl (±)1-((6-(dimethylphosphoryl)pyridin-3-yl)carbamoyl)-6-azaspiro[2.5]octane-6-carboxylate;
1,1,1,3,3,3-hexafluoropropan-2-yl (±)1-(pyridin-4-ylcarbamoyl)-6-azaspiro[2.5]octane-6-carboxylate;
1,1,1,3,3,3-hexafluoropropan-2-yl (±)1-((6-(1H-pyrazol-1-yl)pyridin-3-yl)carbamoyl)-6-azaspiro[2.5]octane-6-carboxylate;
1,1,1,3,3,3-hexafluoropropan-2-yl (±)1-((6-(methylcarbamoyl)pyridin-3-yl)carbamoyl)-6-azaspiro[2.5]octane-6-carboxylate;
1,1,1,3,3,3-hexafluoropropan-2-yl (±)1-((6-methoxypyridin-3-yl)carbamoyl)-6-azaspiro[2.5]octane-6-carboxylate;
1,1,1,3,3,3-hexafluoropropan-2-yl (±)1-((5-fluoropyridin-3-yl)carbamoyl)-6-azaspiro[2.5]octane-6-carboxylate;
1,1,1,3,3,3-hexafluoropropan-2-yl (±)1-(pyridin-2-ylcarbamoyl)-6-azaspiro[2.5]octane-6-carboxylate;
1,1,1,3,3,3-hexafluoropropan-2-yl (±)1-(2-(trifluoromethyl)-5,6,7,8-tetrahydroimidazo[1,2-a]pyrazine-7-carbonyl)-6-azaspiro[2.5]octane-6-carboxylate;
1,1,1,3,3,3-hexafluoropropan-2-yl (±)1-(pyrazin-2-ylcarbamoyl)-6-azaspiro[2.5]octane-6-carboxylate;
1,1,1,3,3,3-hexafluoropropan-2-yl (±)1-((5-chloropyridin-3-yl)carbamoyl)-6-azaspiro[2.5]octane-6-carboxylate;
1,1,1,3,3,3-hexafluoropropan-2-yl (±)1-((2-methylpyridin-3-yl)carbamoyl)-6-azaspiro[2.5]octane-6-carboxylate;
1,1,1,3,3,3-hexafluoropropan-2-yl (±)1-((6-(trifluoromethyl)pyridin-2-yl)carbamoyl)-6-azaspiro[2.5]octane-6-carboxylate;
1,1,1,3,3,3-hexafluoropropan-2-yl (±)1-((6-(trifluoromethyl)pyridin-3-yl)carbamoyl)-6-azaspiro[2.5]octane-6-carboxylate;
1,1,1,3,3,3-hexafluoropropan-2-yl (±)1-((6-methylpyridin-3-yl)carbamoyl)-6-azaspiro[2.5]octane-6-carboxylate;
1,1,1,3,3,3-hexafluoropropan-2-yl (±)1-((2-(trifluoromethyl)pyridin-3-yl)carbamoyl)-6-azaspiro[2.5]octane-6-carboxylate;
1,1,1,3,3,3-hexafluoropropan-2-yl (±)1-(pyrimidin-5-ylcarbamoyl)-6-azaspiro[2.5]octane-6-carboxylate;
1,1,1,3,3,3-hexafluoropropan-2-yl (±)1-((2-(trifluoromethyl)pyrimidin-5-yl)carbamoyl)-6-azaspiro[2.5]octane-6-carboxylate;
1,1,1,3,3,3-hexafluoropropan-2-yl (±)1-((2-methylpyrimidin-5-yl)carbamoyl)-6-azaspiro[2.5]octane-6-carboxylate;
1,1,1,3,3,3-hexafluoropropan-2-yl (±)1-((6-methylpyridazin-3-yl)carbamoyl)-6-azaspiro[2.5]octane-6-carboxylate;
1,1,1,3,3,3-hexafluoropropan-2-yl (±)1-(pyridazin-4-ylcarbamoyl)-6-azaspiro[2.5]octane-6-carboxylate;
1,1,1,3,3,3-hexafluoropropan-2-yl (±)1-((5-methylpyrazin-2-yl)carbamoyl)-6-azaspiro[2.5]octane-6-carboxylate;
1,1,1,3,3,3-hexafluoropropan-2-yl (±)1-((1-methylpiperidin-4-yl)carbamoyl)-6-azaspiro[2.5]octane-6-carboxylate;
1,1,1,3,3,3-hexafluoropropan-2-yl (±)1-(morpholine-4-carbonyl)-6-azaspiro[2.5]octane-6-carboxylate;

1,1,1,3,3,3-hexafluoropropan-2-yl (±)1-(4-cyanopiperidine-1-carbonyl)-6-azaspiro[2.5]octane-6-carboxylate;
1,1,1,3,3,3-hexafluoropropan-2-yl (±)1-((1-methyl-1H-pyrazol-3-yl)carbamoyl)-6-azaspiro[2.5]octane-6-carboxylate;
1,1,1,3,3,3-hexafluoropropan-2-yl (±)1-(thiazol-5-ylcarbamoyl)-6-azaspiro[2.5]octane-6-carboxylate;
1,1,1,3,3,3-hexafluoropropan-2-yl (±)1-(4-methyltetrahydro-2H-pyran-4-yl)carbamoyl)-6-azaspiro[2.5]octane-6-carboxylate;
1,1,1,3,3,3-hexafluoropropan-2-yl (±)1-((1-methyl-1H-pyrazol-5-yl)carbamoyl)-6-azaspiro[2.5]octane-6-carboxylate;
1,1,1,3,3,3-hexafluoropropan-2-yl (±)1-(thiazol-2-ylcarbamoyl)-6-azaspiro[2.5]octane-6-carboxylate;
1,1,1,3,3,3-hexafluoropropan-2-yl (±)1-(phenylcarbamoyl)-6-azaspiro[2.5]octane-6-carboxylate;
1,1,1,3,3,3-hexafluoropropan-2-yl (±)1-(p-tolylcarbamoyl)-6-azaspiro[2.5]octane-6-carboxylate;
1,1,1,3,3,3-hexafluoropropan-2-yl (±)-1-((3-fluorophenyl)carbamoyl)-6-azaspiro[2.5]octane-6-carboxylate:
1,1,1,3,3,3-hexafluoropropan-2-yl (±)1-((2-oxaspiro[3.3]heptan-6-yl)carbamoyl)-6-azaspiro[2.5]octane-6-carboxylate;
1,1,1,3,3,3-hexafluoropropan-2-yl (±)-1-((6-cyclopropylpyridin-3-yl)carbamoyl)-6-azaspiro[2.5]octane-6-carboxylate;
1,1,1,3,3,3-hexafluoropropan-2-yl (±)1-((6-isopropoxypyridin-3-yl)carbamoyl)-6-azaspiro[2.5]octane-6-carboxylate;
1,1,1,3,3,3-hexafluoropropan-2-yl (±)1-((6-acetamidopyridin-3-yl)carbamoyl)-6-azaspiro[2.5]octane-6-carboxylate;
1,1,1,3,3,3-hexafluoropropan-2-yl (±)1-((6-carbamoylpyridin-3-yl)carbamoyl)-6-azaspiro[2.5]octane-6-carboxylate;
1,1,1,3,3,3-hexafluoropropan-2-yl (±)1-(isoxazol-3-ylcarbamoyl)-6-azaspiro[2.5]octane-6-carboxylate;
1,1,1,3,3,3-hexafluoropropan-2-yl (±)1-((6-(methylsulfonamido)pyridin-3-yl)carbamoyl)-6-azaspiro[2.5]octane-6-carboxylate;
(±)2-((5-(6-(((1,1,1,3,3,3-hexafluoropropan-2-yl)oxy)carbonyl)-6-azaspiro[2.5]octane-1-carboxamido)pyridin-2-yl)oxy)acetic acid; and
1,1,1,3,3,3-hexafluoropropan-2-yl (±)1-((6-cyanopyridin-3-yl)carbamoyl)-6-azaspiro[2.5]octane-6-carboxylate;
or a pharmaceutically acceptable salt thereof.

8. The compound of claim 1, wherein the compound is selected from the group consisting of:
1,1,1,3,3,3-hexafluoropropan-2-yl (R)-1-(pyridin-3-ylcarbamoyl)-6-azaspiro[2.5]octane-6-carboxylate;
1,1,1,3,3,3-hexafluoropropan-2-yl (S)-1-(pyridin-3-ylcarbamoyl)-6-azaspiro[2.5]octane-6-carboxylate;
1,1,1,3,3,3-hexafluoropropan-2-yl (R)-1-(pyridazin-3-yl-carbamoyl)-6-azaspiro[2.5]octane-6-carboxylate;
1,1,1,3,3,3-hexafluoropropan-2-yl (S)-1-(pyridazin-3-yl-carbamoyl)-6-azaspiro[2.5]octane-6-carboxylate;
1,1,1,3,3,3-hexafluoropropan-2-yl (R)-1-(isoxazol-4-ylcarbamoyl)-6-azaspiro[2.5]octane-6-carboxylate;
1,1,1,3,3,3-hexafluoropropan-2-yl (S)-1-(isoxazol-4-yl-carbamoyl)-6-azaspiro[2.5]octane-6-carboxylate;
1,1,1,3,3,3-hexafluoropropan-2-yl (R)-1-((2-(trifluoromethyl)pyrimidin-4-yl)carbamoyl)-6-azaspiro[2.5]octane-6-carboxylate;
1,1,1,3,3,3-hexafluoropropan-2-yl (S)-1-((2-(trifluoromethyl)pyrimidin-4-yl)carbamoyl)-6-azaspiro[2.5]octane-6-carboxylate;
1,1,1,3,3,3-hexafluoropropan-2-yl (R)-1-((6-methoxypyridin-3-yl)carbamoyl)-6-azaspiro[2.5]octane-6-carboxylate;
1,1,1,3,3,3-hexafluoropropan-2-yl (S)-1-((6-methoxypyridin-3-yl)carbamoyl)-6-azaspiro[2.5]octane-6-carboxylate;
1,1,1,3,3,3-hexafluoropropan-2-yl (R)-1-((6-methylpyridazin-3-yl)carbamoyl)-6-azaspiro[2.5]octane-6-carboxylate;
1,1,1,3,3,3-hexafluoropropan-2-yl (S)-1-((6-methylpyridazin-3-yl)carbamoyl)-6-azaspiro[2.5]octane-6-carboxylate;
1,1,1,3,3,3-hexafluoropropan-2-yl (R)-1-(((tetrahydro-2H-pyran-4-yl)methyl)carbamoyl)-6-azaspiro[2.5]octane-6-carboxylate;
1,1,1,3,3,3-hexafluoropropan-2-yl (S)-1-(((tetrahydro-2H-pyran-4-yl)methyl)carbamoyl)-6-azaspiro[2.5]octane-6-carboxylate;
1,1,1,3,3,3-hexafluoropropan-2-yl (R)-1-(phenylcarbamoyl)-6-azaspiro[2.5]octane-6-carboxylate;
1,1,1,3,3,3-hexafluoropropan-2-yl (S)-1-(phenylcarbamoyl)-6-azaspiro[2.5]octane-6-carboxylate;
1,1,1,3,3,3-hexafluoropropan-2-yl (R)-1-((6-cyclopropylpyridin-3-yl)carbamoyl)-6-azaspiro[2.5]octane-6-carboxylate;
1,1,1,3,3,3-hexafluoropropan-2-yl (S)-1-((6-cyclopropylpyridin-3-yl)carbamoyl)-6-azaspiro[2.5]octane-6-carboxylate;
1,1,1,3,3,3-hexafluoropropan-2-yl (R)-1-((6-carbamoylpyridin-3-yl)carbamoyl)-6-azaspiro[2.5]octane-6-carboxylate; and
1,1,1,3,3,3-hexafluoropropan-2-yl (S)-1-((6-carbamoylpyridin-3-yl)carbamoyl)-6-azaspiro[2.5]octane-6-carboxylate;
or a pharmaceutically acceptable salt thereof.

9. The compound of claim 1 that is 1,1,1,3,3,3-hexafluoropropan-2-yl (S)-1-(pyridin-3-ylcarbamoyl)-6-azaspiro[2.5]octane-6-carboxylate, or a pharmaceutically acceptable salt thereof.

10. The compound of claim 1 that is 1,1,1,3,3,3-hexafluoropropan-2-yl (S)-1-(pyridazin-3-ylcarbamoyl)-6-azaspiro[2.5]octane-6-carboxylate, or a pharmaceutically acceptable salt thereof.

11. The compound of claim 1 that is 1,1,1,3,3,3-hexafluoropropan-2-yl (S)-1-(isoxazol-4-ylcarbamoyl)-6-azaspiro[2.5]octane-6-carboxylate, or a pharmaceutically acceptable salt thereof.

12. A pharmaceutical composition comprising the compound of claim 1, or a pharmaceutically acceptable salt thereof, and one or more pharmaceutically acceptable carriers or diluents.

* * * * *